US008796330B2

(12) United States Patent
Déziel et al.

(10) Patent No.: US 8,796,330 B2
(45) Date of Patent: Aug. 5, 2014

(54) INHIBITORS OF HISTONE DEACETYLASE AND PRODRUGS THEREOF

(75) Inventors: Robert Déziel, Mount-Royal (CA); Alain Ajamian, Montreal (CA)

(73) Assignee: Methylgene Inc. (CA)

( * ) Notice: Subject to any disclaimer, the term of this patent is extended or adjusted under 35 U.S.C. 154(b) by 712 days.

(21) Appl. No.: 11/959,204

(22) Filed: Dec. 18, 2007

(65) Prior Publication Data

US 2008/0146623 A1    Jun. 19, 2008

Related U.S. Application Data

(60) Provisional application No. 60/870,768, filed on Dec. 19, 2006.

(51) Int. Cl.
| | |
|---|---|
| A61K 31/21 | (2006.01) |
| A61K 31/7028 | (2006.01) |
| A61K 31/4196 | (2006.01) |
| A61K 31/4425 | (2006.01) |
| C07C 259/06 | (2006.01) |

(52) U.S. Cl.
USPC ........... 514/507; 514/383; 514/356; 514/358; 562/621; 546/347; 548/268.6

(58) Field of Classification Search
USPC ......... 514/357, 617, 604, 443, 507, 383, 356, 514/358; 564/161, 91; 549/55; 546/337, 546/347; 435/184; 562/621; 548/268.6
See application file for complete search history.

(56) References Cited

U.S. PATENT DOCUMENTS

| | | | |
|---|---|---|---|
| 3,479,396 A | 11/1969 | Buu-Hoi et al. | |
| 4,035,376 A | 7/1977 | Janssen et al. | |
| 4,439,519 A | 3/1984 | Ohki et al. | |
| 4,792,560 A | 12/1988 | Huang | |
| 5,804,601 A | 9/1998 | Kato et al. | |
| 5,891,916 A | 4/1999 | Kato et al. | |
| 6,407,235 B1 | 6/2002 | Alanine et al. | |
| 6,541,661 B1* | 4/2003 | Delorme et al. | 560/318 |
| 6,545,131 B1 | 4/2003 | Isaacs et al. | |
| 6,653,309 B1 | 11/2003 | Saunders et al. | |
| 6,855,702 B2 | 2/2005 | Venit et al. | |
| 7,115,573 B2 | 10/2006 | Pickford et al. | |
| 2002/0142955 A1 | 10/2002 | Dubois et al. | |
| 2004/0019017 A1 | 1/2004 | Mortimore et al. | |
| 2004/0167174 A1 | 8/2004 | Man et al. | |
| 2005/0131018 A1* | 6/2005 | Sendzik | 514/312 |
| 2005/0137141 A1 | 6/2005 | Hilfinger | |
| 2006/0135594 A1 | 6/2006 | Fraley et al. | |
| 2006/0166903 A1 | 7/2006 | Morimoto et al. | |
| 2007/0197550 A1* | 8/2007 | Georgopapadakou et al. | 514/254.07 |
| 2008/0139673 A1* | 6/2008 | Hu et al. | 514/789 |
| 2008/0146623 A1 | 6/2008 | Deziel et al. | |

FOREIGN PATENT DOCUMENTS

| | | |
|---|---|---|
| EP | 0 196 674 A2 | 10/1986 |
| EP | 0 847 992 A1 | 9/1996 |
| EP | 1541549 A1 | 6/2005 |
| JP | 11-302173 A | 11/1999 |
| WO | 00/69819 A1 | 11/2000 |
| WO | 01/38322 A1 | 5/2001 |
| WO | 01/70675 | 9/2001 |
| WO | 2004080423 A2 | 9/2004 |
| WO | 2004113336 A1 | 12/2004 |
| WO | 2005055928 A2 | 6/2005 |
| WO | 2005/097747 A1 | 10/2005 |
| WO | 2006/017214 A2 | 2/2006 |
| WO | 2006075888 A1 | 7/2006 |
| WO | 2006099416 A1 | 9/2006 |

OTHER PUBLICATIONS

Nagarajan et al. Indian Journal of Chemistry, Section B, Organic Chemistry, 1991, 30B (2), 222-229.*
Chhaya, P. N. et al., "Acid-Catalyzed Reactions of Ortho-Substituted Benzohydroxamic Acids in Polyphosphoric Acid (PPA)", J. Org. Chem, 1986, vol. 51, 4458-4460.
Bouchain, G. et al., "Novel Hydroxamate and Anilide Derivatives as Potent Histone Deacetylase Inhibitors: Synthesis and Antiproliferative Evaluation", Current Medicinal Chemistry, 2003, vol. 10, 2359-2372.
Moradei, O. et al., "Histone Deacetylase Inhibitors: Latest Developments, Trends and Prospects", Curr. Med. Chem.-Anti-Cancer Agents, 2005, vol. 5, 529-560.
Hua DH, Tamura M, Egi M, et al., Antiprotozal activities of symmetrical bishydroxamic acids, Bioorg Med Chem, Oct. 1, 2003, 4357-61; 11(20), Department of Chemistry, Kansas State University, Manhattan, KS, USA.
Kwasi A. Ohemeng, et al., Novel Bishydroxamic Acids as 5-Lipoxygenase Inhibitors, Bioorg Med Chem 1994, pp. 187-193, vol. 2 No. 3, Discovery Research, The R. W. Johnson Pharmaceutical Research Institute, Rariton, NJ, USA.
XP002672206, Database Caplus, Chemical Abstracts Service, Columbus, Ohio, Guillaumel et al., "Synthesis of 3-chloroindolinones from variously substituted beta-nitrostyrenes", retrieved from STN database accession No. 1981-424707, Journal of Heterocyclic Chemistry, 1980, 17(7), 1531-1536.
XP002672207, Database Caplus, Chemical Abstracts Service, Columbus, Ohio, Eckstein; Z., "Synthesis of 6-methoxybenzoxazolone", retrieved from STN Database accession No. 1962-456227, Przemysl Chemiczny, 1962, 41(2), 66-68.
XP002672208, Database CA, Chemical Abstracts Service, Columbus, Ohio, Deliwala et al., "Chemotherapy of tuberculosis. V. Synthesis of some N4-acyl-N1-arylsulfanilhydroxamides", retrieved from STN Database accession No. 1951-36112, Proceedings-Indian Academy of Sciences, 1950, Section A, 31A, 183-186.

(Continued)

*Primary Examiner* — Sreeni Padmanabhan
*Assistant Examiner* — Irina Neagu
(74) *Attorney, Agent, or Firm* — McDonnell Boehnen Hulbert & Berghoff LLP

(57) ABSTRACT

The invention relates to the inhibition of histone deacetylase. The invention provides compounds, prodrugs thereof, and methods for inhibiting histone deacetylase enzymatic activity. The invention also provides compositions and methods for treating cell proliferative diseases and conditions.

3 Claims, No Drawings

(56) References Cited

OTHER PUBLICATIONS

XP002672209, Database CA, Chemical Abstracts Service, Columbus, Ohio, Moore et al., "Substituted sulfanilamides. III. N4-Acyl-N1-hydroxy derivatives", retrieved from STN Database accession No. 1940-43200, Journal of the American Chemical Society, 1940, vol. 62, 2097-2099.

XP002672210, Database CA, Chemical Abstracts Service, Columbus, Ohio, "Insecticidal N-benzoyl-N-pyridyloxyphenylureas," retrieved from STN Database accession No. 1986:5782, Jun. 19, 1985.

XP002672211, Database CA, Chemical Abstracts Service, Columbus, Ohio, Samizo et al., "Preparation of benzothiazin-3-ones as matrix metalloprotease inhibitors and prodrugs for treatment of joint disease, cancer metastasis, inflammation and periodontitis," retrieved from STN Database accession No. 2002:344919, May 9, 2002.

European Search Report dated Apr. 11, 2012 for Application No. 07855542.2.

Suzuki, T. et al., "Synthesis and Histone Deacetylase Inhibitory Activity of New Benzamide Derivatives", J. Med. Chem., 1999, vol. 42, 3001-3003.

XP002162157; Database Beilstein, Beilstein Informationssysteme GmbH.; Aug. 1, 2008.

XP002162158; Database Beilstein, Beilstein Informationssysteme GmbH.; Aug. 1, 2008.

XP002162159; Database Beilstein, Beilstein Informationssysteme GmbH; Aug. 1, 2008.

XP002162160; Database Beilstein, Beilstein Informationssysteme GmbH.; Aug. 1, 2008.

XP002162161; Database Beilstein, Beilstein Informationssysteme GmbH.; Aug. 1, 2008.

Unpublished 2013 manuscript by Augenbraun et al. entitled, "Fluconazole and MGCD290 in vulvo vaginal candidiasis (VVC): Results from a randomized phase II study", 2 pages.; 2013.

Han, Jeung-Whan, et al., "Apicidin, a Histone Deacetylase Inhibitor, Inhibits Proliferation of Tumor Cells via Induction of p21 WAF1/CIP1 and Gelsolin," Nov. 1, 2000, Cancer Research, 60, pp. 6068-6074.

Davie, James R., "Inhibition of Histone Deacetylase Activity by Butyrate 1,2," The Journal of Nutrition, 2003, pp. 2485S-2493S.

Price, Christopher P., et al., "Dissecting the Behavior of a Promiscuous Solvate Former," Angew. Chem. Int. ed. 2006, 45, pp. 2062-2066.

Datta, Sharmistha, et al., "Crystal Structures of Drugs: Advances in Determination, Prediction and Engineering," Nature Reviews, vol. 3, Jan. 2004, pp. 42-57.

Hilfiker, Rolf, "Polymorphism in the Pharmaceutical Industry," 2006, pp. 215-223.

Wolff, Manfred E., "Burger's Medicinal Chemistry and drug Discovery," Fifth Ed., vol. 1: Principles and Practice, John Wiley & sons, 1995, 975-977.

Banker, Gilbert S., et al., "Modem Pharmaceutics," Marcel Dekker, New York, 1996, p. 451, p. 596.

West, Anthony R., "Solid State Chemistry and its Applications," Wiley, New York, 1988, pp. 358, p. 365.

Smith et al., "Histone Deacetylase Inhibitors Enhance *Candida albicans* Sensitivity to Azoles and Related Antifungals: Correlation with Reduction in CDR and ERG Upregulation," Antimicrobial Agents and Chemotherapy, 46 (11):3532-3539 (2002).

Vazquez, J.A., "Combination Antifungal Therapy Against Candida species: The New Frontier—Are We There Yet?" Medical Mycology, 41(5): 355-368 (2003).

Csordas, Adam, "On the Biological Role of Histone Acetylation," Biochem. J., 265:23-38 (1990), Feb. 7, 2014.

Taunton et al., "A Mammalian Histone Deacetylase Related to the Yeast Transcriptional Regulator Rpd3p," Science, 272:408-411 (1996).

Yang et al., "Class II Histone Deacetylases: From Sequence to Function, Regulation, and Clinical Implication," Molecular and Cellular Biol., 25(8):2873-2884 (2005).

Trojer et al., "Histone Deacetylase in Fungi: Novel Members, New Facts," Nuc. Acids. Res., 31(571):3971-3981 (2003).

Cress et al., "Histone Deacetylases, Transcriptional, Control and Cancer," Journal of Cell. Phys., 184:1-16 (2000).

Huck Hui Ng and Adrian Bird, "Histone Deacetylases: Silencer for Hire," TIBS, 121-126 (2000).

Nagnaghi-Jaulin et al., "Histone Acetylation and the Control of the Cell Cycle," Prog. Cell Cycle Res., 4:41-47 (2000).

Richon et al., "A Class of Hybrid Polar Inducers of Transformed Cell Differentiation Inhibits Histone Deacetylases," Proc. Natl. Acad. Sci. USA, 95:3003-3007 (1998).

Yoshida et al., "Potent and Specific Inhibition of Mammalian Histone Deacetylase Both In Vivo and In Vitro by Trichostatin A," Journal of Biol. Chem., 265(28):17174-17179 (1990).

Yoshida et al., "Reversible Arrest of Proliferation of Rat 3Y1 Fibroblasts in Both the G1 and G2 Phases by Trichostatin A," Exp. Cell. Res., 177:122-131 (1988).

Finnin et al., "Structures of a Histone Deacetylase Homologue Bound to the TSA and SAHA Inhibitors," Nature, 401:188-193 (1999).

Georgopapadakou, Nafsika H., "Antifungals: Mechanism of Action and, Resistance, Established and Novel Drugs," Curr. Opin. Micro. Biology, 1:547-557 (1988).

Kaur et al., "Functional Genomic Analysis of Fluconazole, Susceptibility in the Pathogenic Yeast *Candida glabrata*: Roles of Calcium Signaling and Mitochondria," AntiMicrob. Agents and Chemo., 48(5):1600-1613 (2004).

Tekaia et al., "*Aspergillus Fumigatus*: Saprophyte or Pathogen?," Curr. Opin. Microbiol., 8:385-392 (2005).

Jean-Paul Latge, "*Aspergillus Fumigatus* and Aspergillosis," Clinical Microb. Reviews, 12(2):310-350 (1999).

Henry et al., "Upregulation of ERG Genes in Candida Species by Azoles and Other Sterol Biosynthesis Inhibitors," Antimicrob. Agents and Chemother., 44(10):2693-2700 (2000).

Song et al., "The *Candida Albicans* Lanosterol 14-a-Demethylas (ERG 11) Gene Promoter is Maximally Induced After Prolonged Growth with Antifungal Drugs," Antimicrob. Agents and Chemother., 48(4):1136-1144 (2004).

Franzusoff et al., "Localization of Components Involved in Protein Transport and Processing Through Yeast Golgi Apparatus," The Journal of Cell Biol., 112(1):27-37 (1991).

De Ruijter et al., "The Novel Histone Deacetylase Inhibitor BL1521 Inhibits. Proliferation and Induces Apoptosis in Neuroblastoma Cells," Biochem. Pharmacol., 68:1279-1288 (2004).

Weidner et al., "Development of a Homologous Transformation System for the Human Pathogenic Fungus *Aspergillus Fumigatus* Based on the pyrG Gene Encoding Orotidine 5Wonophosphate Decarboxylase," Curr. Genet., 33:378-385 (1998).

Turnidge et al., "The Postantibiotic Effect of Antifungal Agents Against Common Pathogenic Yeasts", J. Antimicrob. Chemother., 34:83-92 (1994).

Vermitsky, et al.,"Azole Resistance in *Candida glabrata*: Coordinate Upregulation of Multidrug Transporters and Evidence for a Pdr1-Like Transcription Factor," Antimicrob. Agents and Chemother., 48(10):3773-3781 (2004).

Clark et al., "Correlation Between Rhodamine 123 Accumulation and Azole Sensitivity in Candida Species: Possible Role for Drug Efflux in Drug Resistance," 40(2):419-425 (1996).

Arthington-Skaggs et al., "Quantitation of Ergosterol Content: Novel Method for Determination of Fluconazole Susceptibility of *Candida albicans*," J. of Clin. Microbiol., 37(10):3332-3337 (1999).

Sanguinetti, et al., "Mechanisms of Azole Resistance in Clinical Isolates of *Candida glabrata* Collected During a Hospital Survey of Antifungal Resistance," Antimicrob, Agents and Chemother, 49(2):668-679 (2005).

(56) References Cited

OTHER PUBLICATIONS

Samizo, Fumio et al., "Preparation of benzothiazin-3-ones as matrix metalloprotease inhibitors and prodrugs fro treatment of joint disease, cancer, metastasis, inflammation and peridontitis", Chemical Abstracts Service, STN Database, Columbus Ohio, U.S.; retrieved from STN Database accession No. 2002:344919, May 9, 2002.

Moradei, O., et al., "Histone Deacetylase Inhibitors: Latest Developments, Trends and Prospects" Current Medicinal Chemistry, Anti-Cancer Agents, Bentham Science Publishers, vol. 5, No. 5, 2005, pp. 529-560, Hilversum, NL.

Bouchain Giliane et al., "Novel Hydroxamate and Anilide Derivatives as Potent Histone Deacetylase Inhibitors: Synthesis and Antiproliferative Evaluation", Current Medicinal Chemistry, Bentham Science Publishers, vol. 10, No. 22, 2003, pp. 2359-2372.

Chhaya P. N., et al., "Acid-Catalyzed Reactions of Ortho-Substited Benzohdroxamic Acids in Polyphosphoric Acid" Journal of Organic Chemistry, vol. 51, No. 23. 1986, pp. 4458-4460, U.S.

* cited by examiner

INHIBITORS OF HISTONE DEACETYLASE AND PRODRUGS THEREOF

CROSS-REFERENCE TO RELATED APPLICATIONS

This application claims the benefit of priority of U.S. Application No. 60/870,768, filed Dec. 19, 2006.

BACKGROUND OF THE INVENTION

1. Field of the Invention

This invention relates to the inhibition of histone deacetylase. More particularly, the invention relates to compounds and prodrugs thereof that inhibit, histone deacetylase enzymatic activity. The invention also relates to methods of inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23-38 (1990) teaches that histones are subject to posttranslational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science*, 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA*, 96: 4868-4873 (1999), teaches that HDACs may be divided into two classes, the first represented by yeast Rpd3-like proteins, and the second represented by yeast Hda1-like proteins.

Histone deacetylases play an important role in gene regulation in mammalian cells. Gray and Ekstrom, *Expr. Cell. Res.* 262: 75-83 (2001); Zhou et al., *Proc. Natl. Acad. Sci. USA* 98: 10572-10577 (2001); Kao et al. *J. Biol. Chem.* 277: 187-193 (2002) and Gao et al. *J. Biol. Chem.* 277: 25748-25755 (2002) teach that there are 11 members of the histone deacetylase (HDAC) family. Another family of deacetylases involved in gene expression is the Sir2 family. Gray and Ekstrom, supra, teach that there are seven members of the Sir2 family in humans.

Class I human histone deacetylases include HDAC1, HDAC2, HDAC3 and HDAC8. The Class I enzymes are expressed in a wide variety of tissues and are reported to be localized in the nucleus. Class II human histone deacetylases include HDAC4, HDAC5, HDAC6, HDAC7, HDAC9 and HDAC10. The Class II enzymes have been described as limited in tissue distribution and they can shuttle between the nucleus and the cytoplasm. The Class II enzymes are further divided into Class IIa (HDAC4, HDAC5, HDAC7 and HDAC9) and Class IIb (HDAC6 and HDAC10). Recent classifications place HDAC11 in a class of its own.

Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, and by a synthetic compound, suberoylanilide hydroxamic acid (SAHA). Yoshida and Beppu, *Exper. Cell Res.*, 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188-193 (1999), teaches that TSA and SAHA inhibit cell growth, induce terminal differentiation, and prevent the formation of tumors in mice.

U.S. Pat. No. RE39850, incorporated herein by reference, discloses compounds that inhibit HDAC activity for intervening in cell cycle regulation and therapeutic potential in the treatment of cell proliferative diseases or conditions. However, these compounds can exhibit poor bioavailability, thereby limiting their therapeutic potential. It is therefore desirable to also prepare bioavailable analogs of such active compounds.

SUMMARY OF THE INVENTION

The invention provides compounds, prodrugs and methods for treating diseases or conditions ameliorated by modulating HDAC activity, such as cell proliferative diseases, or fungal infection, by administering such prodrugs. In particular, the invention provides prodrug inhibitors of histone deacetylase enzymatic activity. These prodrugs are cleavable (e.g., hydrolysable) in a mammalian cell, a plant cell or fungal pathogen cell. Thus, also included within the scope of the present invention are products of the cleaved prodrugs, which include novel hydroxamate based compounds. For the purpose of clarity, a "prodrug compound" or "prodrug" of the present invention is intended to mean a non-cleaved compound as defined by Formula (1), (2) and (3). A "cleavage product" of the prodrug is intended to mean a prodrug compound from which the prodrug moiety has been removed.

In a first aspect, therefore, the invention provides prodrugs of inhibitors of histone deacetylase, the prodrugs having the formula (1):

$$\text{Cy-}L^1\text{-Ar}\text{—}Y^1\text{—C(O)—N(}R^x\text{)—Z} \quad (1)$$

and pharmaceutically acceptable salts thereof, wherein

Cy is —H, cycloalkyl, aryl, heteroaryl, or heterocyclyl, any of which may be optionally substituted;

$L^1$ is —$(CH_2)_m$—W—, where m is 0, 1, 2, 3, or 4, and W is selected from the group consisting of —C(O)NH—, —S(O)$_2$NH—, —NHC(O)—, —NHS(O)$_2$—, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted;

Z is —R$^{20}$, —O—R$^{20}$, —R$^{21}$, or

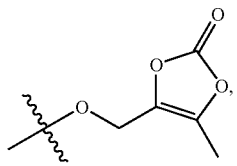

wherein —R$^{20}$ is selected from the group consisting of —C(O)—R$^{10}$, —C(O)O—R$^{10}$, —R$^{11}$, —CH(R$^{12}$)—O—C(O)—R$^{10}$, —C(O)—C[(R$^{10}$)(R$^{10'}$)]$_{1-4}$—NH(R$^{13}$), —S(O$_2$)R$^{10}$, —P(O)(OR$^{10}$)(OR$^{10}$), —C(O)—(CH$_2$)$_n$—CH(OH)—CH$_2$—O—R$^{10}$, —C(O)—O—(CH$_2$)$_n$—CH(OH)—CH$_2$—O—R$^{10}$ and —C(O)—(CH$_2$)$_n$—C(O)OR$^{10}$, —C(O)—(CH$_2$)$_{1-4}$—C(OH)(COOR$^{10}$)—(CH$_2$)$_{1-4}$—COOR$^{10}$, —C(O)-[C(R$^{14}$)(R$^{14}$)]$_{1-4}$—P(O)(OH)(OH), —C(O)—(CH$_2$)$_{1-4}$—N(R$^{14}$)—C[=N(R$^{10'}$)]-N(R$^{10'}$)(R$^{10'}$), —C(O)—(CH$_2$)—CH(OH)—(CH$_2$)—N(CH$_3$)(CH$_3$), —C(O)—CH(NH$_2$)—(CH$_2$)$_{1-6}$—COOH (preferably —C(O)—CH(NH$_2$)—(CH$_2$)—COOH), provided that the N to which Z is bound is not directly bonded to two O atoms; and further provided that (a) when Z is —R$^{20}$ then R$^x$ is —OH, and (b) when Z is —OR$^{20}$ then R$^x$ is —H;

R$^x$ is H or —OH;

or

R$^x$ is absent and R$^{20}$ forms an optionally substituted heterocyclic ring with the N to which it is attached;

n is 0, 1, 2, 3, or 4, preferably 1, 2, 3, or 4;

each R$^{10}$ is independently selected from the group consisting of hydrogen, optionally substituted C$_1$-C$_{20}$ alkyl, optionally substituted C$_2$-C$_{20}$ alkenyl, optionally substituted C$_2$-C$_{20}$ alkynyl, optionally substituted C$_1$-C$_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynyl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);

each R$^{10'}$ is independently hydrogen or C$_{1-6}$alkyl, or R$^{10}$ and R$^{10'}$ together with the carbon atom to which they are attached form an optionally substituted spirocycloalkyl;

R$^{21}$ is a sugar or -amino acid-R$^3$, wherein R$^{13}$ is covalently bound to the N-terminus;

R$^{11}$ is selected from the group consisting of hydrogen, optionally substituted heterocycloalkyl, optionally substituted aryl, and optionally substituted heteroaryl;

R$^{12}$ is selected from hydrogen or alkyl; and

R$^{13}$ is selected from the group consisting of hydrogen, —C(O)—CH[N(R$^{10'}$)(R$^{10'}$)]-C$_1$-C$_6$alkyl, —C(O)—CH[N(R$^{10'}$)(R$^{10'}$)]-C$_1$-C$_6$alkyl-N(R$^{10'}$)(R$^{10'}$), —C(O)—CH[N(R$^{10'}$)(R$^{10'}$)]-C$_1$-C$_6$alkyl-aryl, —C(O)—CH[N(R$^{10'}$)(R$^{10'}$)]-C$_1$-C$_6$alkyl-heteroaryl, —C(O)-aryl, —C(O)-heteroaryl, an amino protecting group, and R$^{10}$; and each R$^{14}$ is independently selected from the group consisting of H, C$_1$-C$_6$alkyl and cycloalkyl, or two R$^4$, together with the atom to which they are attached, form a cycloalkyl.

In a second embodiment, the invention provides prodrugs of inhibitors of histone deacetylase, the prodrugs having the formula (2):

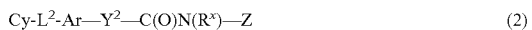

Cy-L$^2$-Ar—Y$^2$—C(O)N(R$^x$)—Z     (2)

and pharmaceutically acceptable salts thereof, wherein

Cy is H or is cycloalkyl, aryl, heteroaryl, or heterocyclyl, any of which may be optionally substituted, provided that Cy is not a (spirocycloalkyl)heterocyclyl;

L$^2$ is C$_1$-C$_6$ saturated alkylene, C$_2$-C$_6$ alkenylene or C$_2$-C$_6$ alkynylene, wherein the alkylene or alkenylene optionally may be substituted, and wherein one or two of the carbon atoms of the alkylene is optionally replaced by a heteroatomic moiety independently selected from the group consisting of O; NR', R' being alkyl, acyl, or hydrogen; S; S(O); or S(O)$_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

Y$^2$ is a chemical bond or a straight- or branched-chain saturated alkylene, which may be optionally substituted, provided that the alkylene is not substituted with a substituent of the formula —C(O)R wherein R comprises an α-amino acyl moiety;

R$^x$ is H or —OH;

Z is —R$^{20}$, —O—R$^{20}$, —R$^{21}$, or

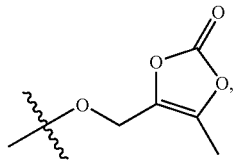

wherein —R$^{20}$ is selected from the group consisting of —C(O)—R$^{10}$, —C(O)O—R$^{10}$, —R$^{11}$, —CH(R$^{12}$)—O—C(O)—R$^{10}$, —C(O)—C[(R$^{10}$)(R$^{10'}$)]$_{1-4}$—NH(R$^3$), —S(O$_2$)R$^{10}$, —P(O)(OR$^{10}$)(OR$^{10}$), —C(O)—(CH$_2$)$_n$—CH(OH)—CH$_2$—O—R$^{10}$, —C(O)—(CH$_2$)$_{1-4}$—C(OH)(COOR$^{10}$)—(CH$_2$)$_{1-4}$—COOR$^{10}$, —C(O)-[C(R$^{14}$)(R$^{14}$)]$_{1-4}$—P(O)(OH)(OH), —C(O)—(CH$_2$)$_{1-4}$—N(R$^{14}$)—C[=N(R$^{10'}$)]-N(R$^{10'}$)(R$^{10'}$), —C(O)—(CH$_2$)—CH(OH)—(CH$_2$)—N(CH$_3$)(CH$_3$), —C(O)—CH(NH$_2$)—(CH$_2$)$_{1-6}$—COOH (preferably —C(O)—CH(NH$_2$)—(CH$_2$)—COOH), —C(O)—O—(CH$_2$)$_n$—CH(OH)—CH$_2$—O—R$^{10}$ and —C(O)—(CH$_2$)$_n$—C(O)OR$^{10}$, provided that the N to which Z is bound is not directly bonded to two O atoms; and further provided that (a) when Z is —R$^{20}$ then R$^x$ is —OH, and (b) when Z is —OR$^{20}$ then R$^x$ is —H;

or

R$^x$ is absent and R$^{20}$ forms an optionally substituted heterocyclic ring with the N to which it is attached;

n is 0, 1, 2, 3, or 4, preferably 1, 2, 3, or 4;

each R$^{10}$ is independently selected from the group consisting of hydrogen, optionally substituted C$_1$-C$_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynyl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);

each $R^{10'}$ is independently hydrogen or $C_{1-6}$alkyl, or
$R^{10}$ and $R^{10'}$ together with the carbon atom to which they are attached form an optionally substituted spirocycloalkyl;
$R^{21}$ is a sugar or -amino acid-$R^{13}$, wherein $R^{13}$ is covalently bound to the N-terminus;
$R^{11}$ is selected from the group consisting of hydrogen, optionally substituted heterocycloalkyl, optionally substituted aryl, and optionally substituted heteroaryl;
$R^{12}$ is selected from hydrogen or alkyl; and
$R^{13}$ is selected from the group consisting of hydrogen, —C(O)—CH[N($R^{10'}$)($R^{10'}$)]-$C_1$-$C_6$alkyl, —C(O)—CH[N($R^{10'}$)($R^{10'}$)]-$C_1$-$C_6$alkyl-N($R^{10'}$)($R^{10'}$), —C(O)—CH[N($R^{10'}$)($R^{10'}$)]-$C_1$-$C_6$alkyl-aryl, —C(O)—CH[N($R^{10'}$)($R^{10'}$)]-$C_1$-$C_6$alkyl-heteroaryl, —C(O)-aryl, —C(O)-heteroaryl, an amino protecting group, and $R^{10}$; and
each $R^{14}$ is independently selected from the group consisting of H, $C_1$-$C_6$alkyl and cycloalkyl, or two $R^{14}$, together with the atom to which they are attached, form a cycloalkyl.

In a third embodiment, the invention provides prodrugs of inhibitors of histone deacetylase, the prodrugs having the formula (3):

$$\text{Cy-L}^3\text{-Ar}—Y^3—C(O)N(R^x)—Z \quad (3)$$

and pharmaceutically acceptable salts thereof, wherein
Cy is —H, cycloalkyl, aryl, heteroaryl, or heterocyclyl, any of which may be optionally substituted, provided that Cy is not a (spirocycloalkyl)heterocyclyl;
$L^3$ is selected from the group consisting of
(a) —($CH_2$)$_m$—W—, where m is 0, 1, 2, 3, or 4, and W is selected from the group consisting of —C(O)NH—, —S(O)$_2$NH—, —NHC(O)—, —NHS(O)$_2$—, and —NH—C(O)—NH—; and
(b) $C_1$-$C_6$ alkylene or $C_2$-$C_6$ alkenylene, wherein the alkylene or alkenylene optionally may be substituted, and wherein one of the carbon atoms of the alkylene optionally may be replaced by O; NR', R' being alkyl, acyl, or hydrogen; S; S(O); or S(O)$_2$;
Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl;
$R^x$ is H or —OH;
Z is —$R^{20}$, —O—$R^{20}$, —$R^{21}$, or

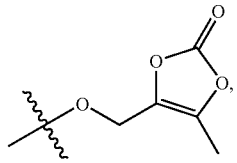

wherein —$R^{20}$ is selected from the group consisting of —C(O)—$R^{10}$, —C(O)O—$R^{10}$, —$R^{11}$, —CH($R^{12}$)—O—C(O)—$R^{10}$, —C(O)—C[($R^{10}$)($R^{10'}$)]$_{1-4}$—NH($R^{13}$), —S(O$_2$)$R^{10}$, —P(O)(O$R^{10}$)(O$R^{10}$), —C(O)—($CH_2$)$_n$—CH(OH)—$CH_2$—O—$R^{10}$, —C(O)—($CH_2$)$_{1-4}$—C(OH)(COO$R^{10}$)—($CH_2$)$_{1-4}$—COO$R^{10}$, —C(O)-[C($R^{14}$)($R^{14}$)]$_{1-4}$—P(O)(OH)(OH), —C(O)—($CH_2$)$_{1-4}$—N($R^{14}$)—C[=N($R^{10'}$)]-N($R^{10'}$)($R^{10'}$), —C(O)—($CH_2$)—CH(OH)—($CH_2$)—N($CH_3$)($CH_3$), —C(O)—CH($NH_2$)—($CH_2$)$_{1-6}$—COOH (preferably —C(O)—CH($NH_2$)—($CH_2$)—COOH), —C(O)—O—($CH_2$)$_n$—CH(OH)—$CH_2$—O—$R^{10}$ and —C(O)—($CH_2$)$_n$—C(O)O$R^{10}$, provided that the N to which Z is bound is not directly bonded to two O atoms; and further provided that (a) when Z is —$R^{20}$ then $R^x$ is —OH, and (b) when Z is —O$R^{20}$ then $R^x$ is —H;

or $R^x$ is absent and $R^{20}$ forms an optionally substituted heterocyclic ring with the N to which it is attached;
n is 0, 1, 2, or 4, preferably 1, 2, 3, or 4;
each $R^{10}$ is independently selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynyl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);
each $R^{10'}$ is independently hydrogen or $C_{1-6}$alkyl, or
$R^{10}$ and $R^{10'}$ together with the carbon atom to which they are attached form an optionally substituted spirocycloalkyl;
$R^{21}$ is a sugar or -amino acid-$R^{13}$, wherein $R^{13}$ is covalently bound to the N-terminus;

$R^{11}$ is selected from the group consisting of hydrogen, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, —C(O)—CH[N($R^{10'}$)($R^{10'}$)]-$C_1$-$C_6$alkyl, —C(O)—CH[N($R^{10'}$)($R^{10'}$)]-$C_1$-$C_6$alkyl-N($R^{10'}$)($R^{10'}$), —C(O)—CH[N($R^{10'}$)($R^{10'}$)]-$C_1$-$C_6$alkyl-aryl, —C(O)—CH[N($R^{10'}$)($R^{10'}$)]-$C_1$-$C_6$alkyl-heteroaryl, —C(O)-aryl, —C(O)-heteroaryl, an amino protecting group, and $R^{10}$; and each $R^{14}$ is independently selected from the group consisting of H, $C_1$-$C_6$alkyl and cycloalkyl, or two $R^{14}$, together with the atom to which they are attached, form a cycloalkyl.

DETAILED DESCRIPTION OF THE PREFERRED EMBODIMENTS

The invention provides prodrugs, cleavage products thereof, and methods for inhibiting histone deacetylase enzymatic activity. The invention also provides compositions and methods for treating diseases or conditions ameliorated by modulating HDAC activity, such as cell proliferative diseases and conditions, and fungal infection. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:

Unless otherwise indicated by context, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11. In some other preferred embodiments, the histone deacetylase is derived from a protozoal or fungal source. Preferred fungi include, but are not limited to *Saccharomyces cerevisiae, Candida* spp. (such as *C. albicans, C. glabrata, C. tropicalis, C. parapsilosis, C. krusei, C. lusitaniae, C. dubliniensis*), *Aspergillus* spp. (such as *A. fumigatus, A. flavus, A. niger, A. terreus*), *Fusarium* spp., *Paecilomyces lilacinus, Rhizopus arrhizus* and *Coccidioides immitis*. In certain preferred embodiments, the histone deacetylase is a fungal HDAC including, but not limited to Rpd3, Hos1, Hos2, Hda1, Hos3, Sir2, Hst, and homologs thereof. In preferred embodiments, a cleavage product of a prodrug compound of the present invention shows synergistic activity with an antifungal agent against a fungal species, preferably at concentrations of inhibitor not toxic to mammalian cells. Preferably such antifungal agents are azole antifungal agents (a large number of active antifungal agents have an azole functionality as part of their structure; such an antifungal agent is generally referred to as an "antifungal azole", an "azole antifungal agent" or an "azole"). Such combinations, and compositions thereof, can be used to selectively treat fungal infection.

The term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus.

Preferred antifungal agents are ergosterol synthesis inhibitors, and include, but are not limited to azoles and phenpropimorph. Other antifungal agents include, but are not limited to terbinafine. Preferred azoles include imidazoles and triazoles. Further preferred antifungal agents include, but are not limited to, ketoconazole, itroconazole, fluconazole, voriconazole, posaconazole, ravuconazole and miconazole. Like azoles, phenpropimorph is an ergosterol synthesis inhibitor, but acts on the ergosterol reductase (ERG24) step of the synthesis pathway. Terbinafine, is also an ergosterol inhibitor, but acts on the squalene eposidase (ERG1) step.

The term "histone deacetylase inhibitor" or "inhibitor of histone deacetylase" is used to identify a compound having a structure as defined herein, which is capable of interacting with a histone deacetylase and inhibiting its enzymatic activity. Inhibiting histone deacetylase enzymatic activity means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect. In certain preferred embodiments of the present invention, cleavage (e.g., hydrolysis) of the prodrug releases a compound (a cleavage (e.g., hydrolyzation) product) which is an inhibitor of histone deacetylase that is more active against a fungal histone decetylase than against a mammalian histone deacetylase. In certain preferred embodiments of the present invention, the inhibitor of histone deacetylase is specific for a fungal histone deacetylase.

The terms "treating", "treatment", or the like, as used herein covers the treatment of a disease-state in an animal and includes at least one of: (i) preventing the disease-state from occurring, in particular, when such animal is predisposed to the disease-state but has not yet developed symptoms of having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In a preferred embodiment the terms "treating", "treatment", or the like, covers the treatment of a disease-state in an animal and includes at least one of (ii), (iii) and (iv) above. In a preferred embodiment of the present invention the animal is a mammal, preferably a primate, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$—$C_m$" heterocyclyl or "$C_n$—$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" is intended to mean a straight or branched chain aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

The term "heteroalkyl" is intended to mean a saturated or unsaturated, straight or branched chain aliphatic group, wherein one or more carbon atoms in the chain are independently replaced by a heteroatom selected from the group consisting of O, $S(O)_{0-2}$, N and $N(R^{33})$.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is $(C_1$-$C_6)$alk$(C_6$-$C_{10})$aryl, including, without limitation, benzyl, phenethyl, and naphthylmethyl. For simplicity, when written as "aralkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl), and xanthenyl.

Aromatic polycycles include, but are not limited to, bicyclic and tricyclic fused ring systems, including for example naphthyl.

Non-aromatic polycycles include, but are not limited to, bicyclic and tricyclic fused ring systems where each ring can be 4-9 membered and each ring can containing zero, 1 or more double and/or triple bonds. Suitable examples of non-aromatic polycycles include, but are not limited to, decalin, octahydroindene, perhydrobenzocycloheptene and perhydrobenzo-[f]-azulene.

Polyheteroaryl groups include bicyclic and tricyclic fused rings systems where each ring can independently be 5 or 6 membered and contain one or more heteroatom, for example, 1, 2, 3 or 4 heteroatoms, independently chosen from O, N and S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like.

Non-aromatic polyheterocyclic groups include but are not limited to bicyclic and tricyclic ring systems where each ring can be 4-9 membered, contain one or more heteratom, for example 1, 2, 3 or 4 heteratoms, independently chosen from O, N and S, and contain zero, or one or more C—C double or triple bonds. Suitable examples of non-aromatic polyheterocycles include but are not limited to, hexitol, cis-perhydrocyclohepta[b]pyridinyl, decahydro-benzo[f][1,4]oxazepinyl, 2,8-dioxabicyclo[3.3.0]octane, hexahydro-thieno[3,2-b] thiophene, perhydropyrrolo[3,2-b]pyrrole, perhydronaphthyridine, perhydrop-1H-dicyclopenta[b,e]pyran.

Mixed aryl and non-aryl polyheterocycle groups include but are not limited to bicyclic and tricyclic fused ring systems where each ring can be 4-9 membered, contain one or more heteroatom independently chosen from O, N and S and at least one of the rings must be aromatic. Suitable examples of mixed aryl and non-aryl polyheteorcycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydropyrido[2,3-b][1,4]diazepin-4-one, 1,2,3,4,6,11-hexhydrobenzo[b]pyrido[2,3-e][1,4]diazepine-5-one, methylenedioxyphenyl, bis-methylenedioxyphenyl, 1,2,3,4-tetrahydronaphthalene, dibenzosuberane dihydroanthracene and 9H-fluorene.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkyl-carbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33a})_s$—$NR^{30}R^{31}$, wherein s is from 0 (in which case the nitrogen is directly bonded to the moiety that is substituted) to 6, $R^{32}$ and $R^{33a}$ are each independently hydrogen, halo, hydroxyl or $C_1$-$C_4$alkyl, and $R^{30}$ and $R^{31}$ are each independently hydrogen, cyano, oxo, hydroxyl, —$C_1$-$C_8$ alkyl, $C_1$-$C_8$ heteroalkyl, $C_1$-$C_8$ alkenyl, carboxamido, $C_1$-$C_3$ alkyl-carboxamido, carboxamido-$C_1$-$C_3$ alkyl, amidino, $C_2$-$C_8$hydroxyalkyl, $C_1$-$C_3$ alkylaryl, aryl-$C_1$-$C_3$ alkyl, $C_1$-$C_3$ alkylheteroaryl, heteroaryl-$C_1$-$C_3$ alkyl, $C_1$-$C_3$ alkylheterocyclyl, heterocyclyl-$C_1$-$C_3$ alkyl $C_1$-$C_3$ alkylcycloalkyl, cycloalkyl-$C_1$-$C_3$ alkyl, $C_2$-$C_8$ alkoxy, $C_2$-$C_8$ alkoxy-$C_1$-$C_4$alkyl, $C_1$-$C_8$ alkoxycarbonyl, aryloxycarbonyl, aryl-$C_1$-$C_3$ alkoxycarbonyl, heteroaryloxycarbonyl, heteroaryl-$C_1$-$C_3$ alkoxycarbonyl, $C_1$-$C_8$ acyl, $C_0$-$C_8$ alkyl-carbonyl, aryl-$C_0$-$C_8$ alkyl-carbonyl, heteroaryl-$C_0$-$C_8$ alkyl-carbonyl, cycloalkyl-$C_0$-$C_8$ alkyl-carbonyl, $C_0$-$C_8$ alkyl-NH-carbonyl, aryl-$C_0$-$C_8$ alkyl-NH-carbonyl, heteroaryl-$C_0$-$C_8$ alkyl-NH-carbonyl, cycloalkyl-$C_0$-$C_8$ alkyl-NH-carbonyl, $C_0$-$C_8$ alkyl-O-carbonyl, aryl-$C_0$-

$C_8$ alkyl-O-carbonyl, heteroaryl-$C_0$-$C_8$ alkyl-O-carbonyl, cycloalkyl-$C_0$-$C_8$ alkyl-O-carbonyl, $C_1$-$C_8$ alkylsulfonyl, arylalkylsulfonyl, arylsulfonyl, heteroarylalkylsulfonyl, heteroarylsulfonyl, $C_1$-$C_8$ alkyl-NH-sulfonyl, arylalkyl-NH-sulfonyl, aryl-NH-sulfonyl, heteroarylalkyl-NH-sulfonyl, heteroaryl-NH-sulfonylaroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$ alkyl-, heteroaryl-$C_1$-$C_3$ alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —CO—$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^3$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyloctyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are unsubstituted.

In other preferred embodiments, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing more than one Cl), cyano, nitro, alkyl, cycloalkyl, alkenyl, cycloalkenyl, alkynyl, heterocycle, aryl, —$OR^1$, —$SR^u$, —S(=O)$R^y$, —S(=O)$_2R^y$, —P(=O)$_2R^y$, —S(=O)$_2OR^y$, —P(=O)$_2OR^y$, —NR'R$^w$, —NR$^v$S(=O)$_2R^y$, —NR$^v$P(=O)$_2R^y$, —S(=O)$_2$NR'R$^w$, —P(=O)$_2$NR'R$^w$, —C(=O)$OR^y$, —C(=O)$R^u$, —C(=O)NR'R$^w$, —OC(=O)$R^u$, OC(=O)NR'R$^w$, NR'C(=O)$OR^y$, —NR$^{xx}$C(=O)NR'R$^w$, —NR$^{xx}$S(=O)$_2$NR'R$^w$, —NR$^{xx}$P(=O)$_2$NR'R$^w$, —NR$^v$C(=O)$R^u$ or —NR$^v$P(=O)$_2R^y$, wherein $R^w$ is hydrogen, alkyl, cycloalkyl, alkenyl, cycloalkenyl, alkynyl, heterocycle or aryl; $R^v$, $R^w$ and $R^{xx}$ are independently hydrogen, alkyl, cycloalkyl, heterocycle or aryl, or said $R^v$ and $R^w$ together with the N to which they are bonded optionally form a heterocycle; and $R^y$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cylic substituents at any available point or points of attachement, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In a preferred embodiment, a heterocyclic group is substituted on carbon, nitrogen and/or sulfur at one or more positions. Preferred substituents on nitrogen include, but are not limited to N-oxide, alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quaternized.

Especially preferred substituents on alkyl groups include halogen and hydroxy.

Especially preferred substituents on ring groups, such as aryl, heteroaryl, cycloalkyl and heterocyclyl, include halogen, alkoxy and alkyl.

Preferred substituents on aromatic polycycles include, but are not limited to, oxo, $C_1$-$C_6$alkyl, cycloalkylalkyl (e.g. cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR^{aa}$, such as alkoxy, wherein $R^{aa}$ is selected from the group consisting of H, $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_{0-6}Z^aR^{bb}$, wherein $Z^a$ is selected from the group consisting of O, $NR^{cc}$, S and S(O), and $R^{bb}$ is selected from the group consisting of H, $C_1$-$C_6$alkyl, $C_4$-$C_9$cycloalkyl, $C_4$-$C_9$heterocycloalkyl, $C_4$-$C_9$heterocycloalkylalkyl, aryl, mixed aryl and non-aryl polycycle, heteroaryl, arylalkyl, (e.g. benzyl), and heteroarylalkyl (e.g. pyridylmethyl); and $R^{cc}$ is selected from the group consisting of H, $C_1$-$C_6$alkyl, $C_4$-$C_9$cycloalkyl, $C_4$-$C_9$heterocycloalkyl, aryl, heteroaryl, arylalkyl (e.g. benzyl), heteroarylalkyl (e.g. pyridylmethyl) and amino acyl.

Preferred substituents on non-aromatic polycycles include, but are not limited to, oxo, $C_3$-$C_9$cycloalkyl, such as cyclopropyl, cyclobutyl, cyclopentyl, cyclohexyl and the like. Unless otherwise noted, non-aromatic polycycle substituents include both unsubstituted cycloalkyl groups and cycloalkyl groups that are substituted by one or more suitable substituents, including but not limited to, $C_1$-$C_6$alkyl, oxo, halo, hydroxy, aminoalkyl, oxyalkyl, alkylamino and $OR^{aa}$, such as alkoxy. Preferred substituents for such cycloalkyl groups include halo, hydroxy, alkoxy, oxyalkyl, alkylamino and aminoalkyl.

Preferred substituents on carbon atoms of polyheteroaryl groups include but are not limited to, straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino, $OR^{aa}$ (for example alkoxy), and a substituent of the formula —O—$(CH_2CH$=$CH(CH_3)(CH_2))_{1-3}H$. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example by N-oxide or $R^{cc}$. Preferred substituents on nitrogen atoms include H, $C_1$-$C_4$alkyl, acyl, aminoacyl and sulfonyl. Preferably sulfur atoms are unsubstituted. Preferred substituents on sulfur atoms include but are not limited to oxo and lower alkyl.

Preferred substituents on carbon atoms of non-aromatic polyheterocyclic groups include but are not limited to straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino and $OR^{aa}$, for example alkoxy. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example, N-oxide or $R^{cc}$. Preferred N substituents include H, $C_1$-$C_4$ alkyl, acyl, aminoacyl and sulfonyl. Preferably, sulfur atoms are unsubstituted. Preferred S substituents include oxo and lower alkyl.

Preferred substituents on mixed aryl and non-aryl polyheterocycle groups include, but are not limited to, nitro or as described above for non-aromatic polycycle groups. Preferred substituents on carbon atoms include, but are not limited to, —N—OH, =N—OH, optionally substituted alkyl, unsaturation (i.e., there are one or more double or triple C—C bonds), oxo, acyl, cycloalkyl, halo, oxyalkyl, alkylamino, aminoalkyl, acylamino and $OR^{aa}$, for example alkoxy. Preferably substitutions on nitrogen atoms include, for example, N-oxide or $R^{cc}$. Preferred N substituents include H, $C_{1-4}$alkyl, acyl aminoacyl and sulfonyl. Preferably sulfur atoms are unsubstituted. Preferred S substituents include oxo and lower alkyl.

A "halohydrocarbyl" is a hydrocarbyl moiety in which from one to all hydrogens have been replaced with one or more halo.

The term "halogen" or "halo" is intended to mean chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" is intended to mean a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

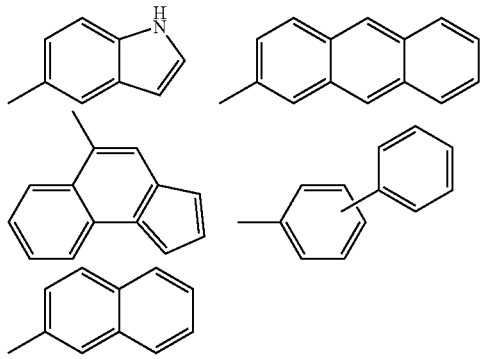

An "unsubstituted" moiety (e.g., unsubstituted cycloalkyl, unsubstituted heteroaryl, etc.) means that moiety as defined above that does not have an optional substituent. Thus, for example, "unsubstituted aryl" does not include phenyl substituted with a halo.

As used herein, "an amino protecting group" refers to any functional group commonly used to protect an α-amino group. Suitable amino protecting groups include, but are not limited to, t-butyloxycarbonyl, isoamyloxycarbonyl, o-nitrophenylsulfenyl, fluoroenylmethyloxycarbonyl, o-nitropyridinylsulfenyl and biphenylpropyloxycarbonyl.

An "amino acid residue" refers to any residue of a natural or unnatural amino acid, non-limiting examples of which are residues of alanine, arginine, asparagine, aspartic acid, cysteine, homocysteine, glutamine, glutamic acid, isoleucine, norleucine, glycine, phenylglycine, leucine, histidine, methionine, lysine, phenylalanine, homophenylalanine, ornithine, praline, serine, homoserine, valine, norvaline, threonine, tryptophane, tyrosine and the like. With the exception of glycine, all amino acids may be in the D-, L- or D,L-form.

The term "radical" is intended to mean a chemical moiety comprising one or more unpaired electrons.

Some compounds of the invention may have one or more chiral centers and/or geometric isomeric centers (E- and Z-isomers), and it is to be understood that the invention encompasses all such optical, diastereoisomers and geometric isomers. The invention also comprises all tautomeric forms of the compounds disclosed herein.

All of the compounds in this application were named using Chemdraw Ultra version 9 or 10, which are available through Cambridgesoft.co, 100 Cambridge Park Drive, Cambridge, Mass. 02140.

Compounds

In a first aspect, the invention provides prodrugs of inhibitors of histone deacetylase, the prodrugs having the formula (1):

$$Cy-L^1-Ar-Y^1-C(O)-N(R^x)-Z \qquad (1)$$

and pharmaceutically acceptable salts thereof, wherein

Cy is —H, cycloalkyl, aryl, heteroaryl, or heterocyclyl, any of which may be optionally substituted;

$L^1$ is —(CH$_2$)$_m$—W—, where m is 0, 1, 2, 3, or 4, and W is selected from the group consisting of —C(O)NH—, —S(O)$_2$NH—, —NHC(O)—, —NHS(O)$_2$—, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted;

$R^x$ is H or —OH;

Z is —R$^{20}$, —O—R$^{20}$, —R$^{21}$, or

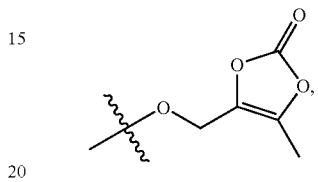

wherein —R$^{20}$ is selected from the group consisting of —C(O)—R$^{10}$, —C(O)O—R$^{10}$, —R$^{10}$, —CH(R$^{12}$)—O—C(O)—R$^{10}$, —C(O)—C[(R$^{10}$)(R$^{10'}$)]$_{1-4}$—NH(R$^{13}$), —S(O$_2$)R$^{10}$, —P(O)(OR$^{10}$)(OR$^{10'}$), —C(O)—(CH$_2$)$_n$—CH(OH)—CH$_2$—O—R$^{10}$, —C(O)—(CH$_2$)$_{1-4}$—C(OH)(COOR$^{10}$)—(CH$_2$)$_{1-4}$—COOR$^{10}$, —C(O)-[C(R$^{14}$)(R$^{14}$)]$_{1-4}$—P(O)(OH)(OH), —C(O)—(CH$_2$)$_{1-4}$—N(R$^{14}$)—C[=N(R$^{10'}$)]-N(R$^{10'}$)(R$^{10'}$), —C(O)—(CH$_2$)—CH(OH)—(CH$_2$)—N(CH$_3$)(CH$_3$), —C(O)—CH(NH$_2$)—(CH$_2$)$_{1-6}$—COOH (preferably —C(O)—CH(NH$_2$)—(CH$_2$)—COOH), —C(O)—O—(CH$_2$)$_n$—CH(OH)—CH$_2$—O—R$^{10}$ and —C(O)—(CH$_2$)$_n$—C(O)OR$^{10}$, provided that the N to which Z is bound is not directly bonded to two O atoms and further provided that (a) when Z is —R$^{20}$ then R$^x$ is —OH, and (b) when Z is —OR$^{20}$ then R$^x$ is —H; or $R^x$ is absent and R$^{20}$ forms an optionally substituted heterocyclic ring with the N to which it is attached;

n is 0, 1, 2, 3, or 4, preferably 1, 2, 3, or 4;

each R$^{10}$ is independently selected from the group consisting of hydrogen, optionally substituted C$_1$-C$_{20}$ alkyl, optionally substituted C$_2$-C$_{20}$ alkenyl, optionally substituted C$_2$-C$_{20}$ alkynyl, optionally substituted C$_1$-C$_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynyl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);

each $R^{10'}$ is independently hydrogen or $C_{1-6}$alkyl, or $R^{10}$ and $R^{10'}$ together with the carbon atom to which they are attached form an optionally substituted spirocycloalkyl;

$R^{21}$ is a sugar or -amino acid-$R^{13}$, wherein $R^{13}$ is covalently bound to the N-terminus;

$R^{11}$ is selected from the group consisting of hydrogen, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, —C(O)—CH[N($R^{10'}$)($R^{10'}$)]-$C_1$-$C_6$alkyl, —C(O)—CH[N($R^{10'}$)($R^{10'}$)]-$C_1$-$C_6$alkyl-N($R^{10'}$)($R^{10'}$), —C(O)—CH[N($R^{10'}$)($R^{10'}$)]-$C_1$-$C_6$alkyl-aryl, —C(O)—CH[N($R^{10'}$)($R^{10'}$)]-$C_1$-$C_6$alkyl-heteroaryl, —C(O)-aryl, —C(O)-heteroaryl, an amino protecting group, and $R^{10}$; and each $R^{14}$ is independently selected from the group consisting of H, $C_1$-$C_6$ alkyl and cycloalkyl, or two $R^{14}$, together with the atom to which they are attached, form a cycloalkyl.

In certain preferred embodiments, Cy is $C_6$-$C_{14}$ aryl, more preferably $C_6$-$C_{10}$ aryl, and most preferably phenyl or naphthyl, any of which may be optionally substituted. In certain other preferred embodiments, Cy is heteroaryl. In some preferred embodiments, the heteroaryl group is selected from the group consisting of thienyl, benzothienyl, furyl, benzofuryl, quinolyl, isoquinolyl, and thiazolyl, any of which may be optionally substituted. In certain particularly preferred embodiments, Cy is selected from the group consisting of phenyl, naphthyl, thienyl, benzothienyl, and quinolyl, any of which may be optionally substituted. In certain other preferred embodiments, Cy is phenyl, pyridine or indole, more preferably phenyl or indole. In certain preferred embodiments, Cy is substituted with one or more substituents selected from the group consisting of trihaloalkyl (preferably trifluoroalkyl), halogen, CN, amidine, sulfone, alkylsulfone, imidate and alkylimidate. In certain preferred embodiments, Cy is phenyl substituted with one or more substituents selected from the group consisting of trihaloalkyl (preferably trifluoroalkyl), halogen, CN, amidine, sulfone, alkylsulfone, imidate and alkylimidate, preferably selected from the group consisting of trihaloalkyl (preferably trifluoroalkyl) and halogen.

$L^1$ is —$(CH_2)_m$—W—, where m is 0, 1, 2, 3, or 4, and W is selected from the group consisting of —C(O)NH—, —S(O)$_2$NH—, —NHC(O)—, —NHS(O)$_2$—, and —NHC(O)—NH—. Preferably, m is 0, 1, or 2, more preferably 0 or 1.

Preferably, Ar is $C_6$-$C_{14}$ arylene, more preferably $C_6$-$C_{10}$ arylene, any of which may be additionally substituted. In certain preferred embodiments, Ar is phenylene, preferably 4-phenylene. In some preferred embodiments, the phenylene is fused to an aryl or heteroaryl ring, or to a saturated or partially unsaturated cycloalkyl or heterocyclic ring, any of which groups also may be optionally substituted.

$Y^1$ is a chemical bond or is a straight- or branched-chain alkylene, which may be optionally substituted. In some preferred embodiments, $Y^1$ is a chemical bond, and the group —C(O)NH-Z is directly attached to Ar. In some other preferred embodiments, $Y^1$ is alkylene, preferably saturated alkylene. Preferably, the saturated alkylene is $C_1$-$C_8$ alkylene, more preferably $C_1$-$C_6$ alkylene, still more preferably $C_1$-$C_3$ alkylene, and yet still more preferably $C_1$-$C_2$ alkylene, any of which may be optionally substituted. In some particularly preferred embodiments, $Y^1$ is methylene.

Substituted alkyl, aryl, heterocyclyl, and heteroaryl groups have one or more, preferably between one and about three, more preferably one or two substituents, which are preferably selected from the group consisting of $C_1$-$C_6$ alkyl, preferably $C_1$-$C_4$ alkyl; halo, preferably Cl, Br, or F; haloalkyl, preferably (halo)$_{1-5}$($C_1$-$C_6$)alkyl, more preferably (halo)$_{1-5}$($C_1$-$C_3$) alkyl, and most preferably $CF_3$; $C_1$-$C_6$ alkoxy, preferably methoxy, ethoxy, or benzyloxy; $C_6$-$C_{10}$ aryloxy, preferably phenoxy; $C_1$-$C_6$ alkoxycarbonyl, preferably $C_1$-$C_3$ alkoxycarbonyl, most preferably carbomethoxy or carboethoxy; $C_6$-$C_{10}$ aryl, preferably phenyl; ($C_6$-$C_{10}$)ar($C_1$-$C_6$)alkyl, preferably ($C_6$-$C_{10}$)ar($C_1$-$C_3$)alkyl, more preferably benzyl, naphthylmethyl or phenethyl; hydroxy($C_1$-$C_6$)alkyl, preferably hydroxy($C_1$-$C_3$)alkyl, more preferably hydroxymethyl; amino($C_1$-$C_6$)alkyl, preferably amino($C_1$-$C_3$)alkyl, more preferably aminomethyl; ($C_1$-$C_6$)alkylamino, preferably methylamino, ethylamino, or propylamino; di-($C_1$-$C_6$)alkylamino, preferably dimethylamino or diethylamino; ($C_1$-$C_6$) alkylcarbamoyl, preferably methylcarbamoyl, dimethylcarbamoyl, or benzylcarbamoyl; ($C_6$-$C_{10}$)arylcarbamoyl, preferably phenylcarbamoyl; ($C_1$-$C_6$)alkaneacylamino, preferably acetylamino; ($C_6$-$C_{10}$)areneacylamino, preferably benzoylamino; ($C_1$-$C_6$)alkanesulfonyl, preferably methanesulfonyl; ($C_1$-$C_6$)alkanesulfonamido, preferably methanesulfonamido; ($C_6$-$C_{10}$)arenesulfonyl, preferably benzenesulfonyl or toluenesulfonyl; ($C_6$-$C_{10}$)arenesulfonamido, preferably benzenesulfonyl or toluenesulfonyl; ($C_6$-$C_{10}$)ar($C_1$-$C_6$)alkylsulfonamido, preferably benzylsulfonamido; $C_1$-$C_6$ alkylcarbonyl, preferably $C_1$-$C_3$ alkylcarbonyl, more preferably acetyl; ($C_1$-$C_6$)acyloxy, preferably acetoxy; cyano; amino; carboxy; hydroxy; ureido; and nitro. One or more carbon atoms of an alkyl, cycloalkyl, or heterocyclyl group may also be optionally substituted with an oxo group.

In some particularly preferred embodiments, Cy is a phenyl, naphthyl, thienyl, benzothienyl, or quinolyl moiety which is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$) alkyl, halo, nitro, hydroxy, $C_1$-$C_6$ alkoxy, $C_1$-$C_6$ alkoxycarbonyl, carboxy, and amino.

In some preferred embodiments, Z is —O—C(O)—$R^{10}$, —O—C(O)-[C($R^{10'}$)($R^{10'}$)]$_{1-4}$—NH($R^{13}$) or —O$R^{11}$.

In some preferred embodiments, the amino acid is an L-amino acid.

In certain preferred embodiments, the sugar residue is a saccharide selected from the group consisting of glucose, galactose, mannose, gulose, idose, talose, allose, altrose, fructose, rhamnose, ribose and xylose.

In a second embodiment, the invention provides prodrugs of inhibitors of histone deacetylase, the prodrugs represented by formula (2):

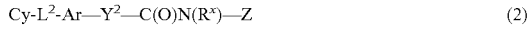

Cy-$L^2$-Ar—$Y^2$—C(O)N($R^x$)—Z (2)

and pharmaceutically acceptable salts thereof, wherein

Cy is H, cycloalkyl, aryl, heteroaryl, or heterocyclyl, any of which may be optionally substituted, provided that Cy is not a (spirocycloalkyl)heterocyclyl;

$L^2$ is $C_1$-$C_6$ saturated alkylene or $C_2$-$C_6$ alkenylene, wherein the alkylene or alkenylene optionally may be substituted, and wherein one or two of the carbon atoms of the alkylene is optionally replaced by a heteroatomic moiety independently selected from the group consisting of O; NR', R' being alkyl, acyl, or hydrogen; S; S(O); or S(O)$_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an α-amino acyl moiety;

$R^x$ is H or —OH;

Z is —$R^{20}$, —O—$R^{20}$, —$R^{21}$, or

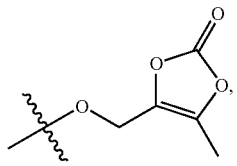

wherein —$R^{20}$ is selected from the group consisting of —C(O)—$R^{10}$, —C(O)O—$R^{11}$, —$R^{10}$, —CH($R^{12}$)—O—C(O)—$R^{10}$, —C(O)—C[($R^{10}$)($R^{10'}$)]$_{1-4}$—NH($R^{13}$), —S(O$_2$)$R^{10}$, —P(O)(O$R^{10}$)(O$R^{10}$), —C(O)—(CH$_2$)$_{14}$—C(OH)(COO$R^{10}$)—(CH$_2$)$_{1-4}$—COO$R^{10}$, —C(O)-[C($R^{14}$)($R^{14}$)]$_{1-4}$—P(O)(OH)(OH), —C(O)—(CH$_2$)$_{1-4}$—N($R^{14}$)—C[=N($R^{10'}$)]-N($R^{10'}$)($R^{10'}$), —C(O)—(CH$_2$)—CH(OH)—(CH$_2$)—N(CH$_3$)(CH$_3$), —C(O)—CH(NH$_2$)—(CH$_2$)$_{1-6}$—COOH (preferably —C(O)—CH(NH$_2$)—(CH$_2$)—COOH), —C(O)—(CH$_2$)$_n$—CH(OH)—CH$_2$—O—$R^{10}$, —C(O)—O—(CH$_2$)$_n$—CH(OH)—CH$_2$—O—$R^{10}$ and —C(O)—(CH$_2$)$_n$—C(O)O$R^{10}$, provided that the N to which Z is bound is not directly bonded to two O atoms; and further provided that (a) when Z is —$R^{20}$ then $R^x$ is —OH, and (b) when Z is —O$R^{20}$ then $R^x$ is —H; or $R^x$ is absent and $R^{20}$ forms an optionally substituted heterocyclic ring with the N to which it is attached;

n is 0, 1, 2, 3, or 4, preferably 1, 2, 3, or 4;

each $R^{10}$ is independently selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynyl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);

each $R^{10'}$ is independently hydrogen or $C_{1-6}$alkyl, or $R^{10}$ and $R^{10'}$ together with the carbon atom to which they are attached form an optionally substituted spirocycloalkyl;

$R^{21}$ is a sugar or -amino acid-$R^3$, wherein $R^{13}$ is covalently bound to the N-terminus;

$R^{11}$ is selected from the group consisting of hydrogen, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, —C(O)—CH[N($R^{10'}$)($R^{10'}$)]-$C_1$-$C_6$alkyl, —C(O)—CH[N($R^{10'}$)($R^{10'}$)]-$C_1$-$C_6$alkyl-N($R^{10'}$)($R^{10'}$), —C(O)—CH[N($R^{10'}$)($R^{10'}$)]-$C_1$-$C_6$alkyl-aryl, —C(O)—CH[N($R^{10'}$)($R^{10'}$)]-$C_1$-$C_6$alkyl-heteroaryl, —C(O)-aryl, —C(O)-heteroaryl, an amino protecting group, and $R^{10}$; and each $R^{14}$ is independently selected from the group consisting of H, $C_1$-$C_6$alkyl and cycloalkyl, or two R together with the atom to which they are attached, form a cycloalkyl.

Preferred substituents Cy, Ar, and Z according to this aspect of the invention are as defined above for the first embodiment. Preferred substituents of $Y^2$ are as defined above for $Y^1$. In some preferred embodiments, $L^2$ is saturated $C_1$-$C_8$ alkylene, more preferably $C_1$-$C_6$ alkylene, still more preferably $C_1$-$C_4$ alkylene, any of which groups may be optionally substituted. In some other preferred embodiments, $L^2$ is $C_2$-$C_8$ alkenylene, more preferably $C_2$-$C_6$ alkenylene, and still more preferably $C_2$-$C_4$ alkenylene, any of which groups may be optionally substituted. The alkylene or alkenylene group may be substituted at one or more carbon positions with a substituent preferably selected from the list of preferred substituents recited above. More preferably, $L^2$ is substituted at one or two positions with a substituent independently selected from the group consisting of $C_1$-$C_6$ alkyl, $C_6$-$C_{10}$ aryl, amino, oxo, hydroxy, $C_1$-$C_4$ alkoxy, and $C_6$-$C_{10}$ aryloxy. In some particularly preferred embodiments, the alkylene or alkenylene group is substituted with one or two oxo or hydroxy groups.

In some preferred embodiments, $L^1$ is $C_1$-$C_6$ saturated alkylene, wherein on of the carbon atoms of the saturated alkylene is replaced by a heteroatom moiety selected from the group consisting of O; NR', R' being alkyl, acyl, or hydrogen; S; S(O); or S(O)$_2$. Preferably, the carbon atom adjacent to Cy is replaced by a heteroatom moiety. In some particularly preferred embodiments, $L^1$ is selected from the group consisting of —S—(CH$_2$)$_2$—, —S(O)—(CH$_2$)$_2$—, —S(O)$_2$—(CH$_2$)$_2$—, —S—(CH$_2$)$_3$—, —S(O)—(CH$_2$)$_3$—, and —S(O)$_2$—(CH$_2$)$_3$—.

In some preferred embodiments, Z is —O—C(O)—$R^{10}$, —O—C(O)-[C($R^{10}$)($R^{10}$)]$_{1-4}$—NH($R^{13}$) or —O$R^{11}$. Even more preferred embodiments of compound (2) are:

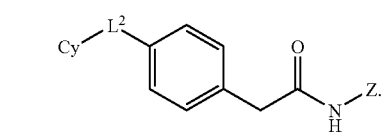

In a third embodiment, the invention provides prodrugs of inhibitors of histone deacetylase, the prodrugs represented by formula (3):

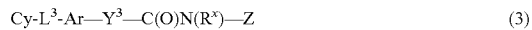

and pharmaceutically acceptable salts thereof, wherein

Cy is —H, cycloalkyl, aryl, heteroaryl, or heterocyclyl, any of which may be optionally substituted, provided that Cy is not a (spirocycloalkyl)heterocyclyl;

$L^3$ is selected from the group consisting of
  (a) —$(CH_2)_m$—W—, where m is 0, 1, 2, 3, or 4, and W is selected from the group consisting of —C(O)NH—, —S(O)$_2$NH—, —NHC(O)—, —NHS(O)$_2$—, and —NH—C(O)—NH—; and
  (b) $C_1$-$C_6$ alkylene or $C_2$-$C_6$ alkenylene, wherein the alkylene or alkenylene optionally may be substituted, and wherein one of the carbon atoms of the alkylene optionally may be replaced by O; NR', R' being alkyl, acyl, or hydrogen; S; S(O); or S(O)$_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl;

$R^x$ is H or —OH;

Z is —$R^{20}$, —O—$R^{20}$, —$R^{21}$, or

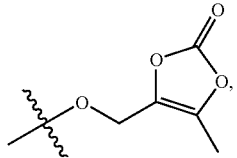

wherein —$R^{20}$ is selected from the group consisting of —C(O)—$R^{10}$, —C(O)O—$R^{10}$, —$R^{10}$, —CH($R^{12}$)—O—C(O)—$R^{10}$, —C(O)—$(CH_2)_{1-4}$—C(OH)(COOR$^{10}$)—$(CH_2)_{1-4}$—COOR$^{10}$, —C(O)-[C($R^{14}$)($R^{14}$)]$_{1-4}$—P(O)(OH)(OH), —C(O)—$(CH_2)_{1-4}$—N($R^{14}$)—C[=N($R^{10'}$)]-N($R^{10'}$)($R^{10'}$), —C(O)—$(CH_2)$—CH(OH)—$(CH_2)$—N(CH$_3$)(CH$_3$), —C(O)—CH(NH$_2$)—$(CH_2)_{1-6}$—COOH (preferably —C(O)—CH(NH$_2$)—$(CH_2)$—COOH), —C(O)—C[($R^{10}$)($R^{10'}$)]$_{1-4}$—NH($R^{13}$), —S(O$_2$)$R^{10}$, —P(O)(O$R^{10}$)(O$R^{10'}$), —C(O)—$(CH_2)_n$—CH(OH)—$CH_2$—O—$R^{10}$, —C(O)—O—$(CH_2)_n$—CH(OH)—$CH_2$—O—$R^{10}$ and —C(O)—$(CH_2)_n$—C(O)O$R^{10}$, provided that the N to which Z is bound is not directly bonded to two O atoms; and further provided that (a) when Z is —$R^{20}$ then $R^x$ is —OH, and (b) when Z is —O$R^{20}$ then $R^x$ is —H; or $R^x$ is absent and $R^{20}$ forms an optionally substituted heterocyclic ring with the N to which it is attached;

n is 0, 1, 2, 3, or 4, preferably 1, 2, 3, or 4;

each $R^{10}$ is independently selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynl, optionally substituted heteroarylalkynyl, optionally substituted alkylcycloalkyl, optionally substituted alkylheterocycloalkyl, optionally substituted alkylaryl, optionally substituted alkylheteroaryl, optionally substituted alkenylcycloalkyl, optionally substituted alkenylheterocycloalkyl, optionally substituted alkenylaryl, optionally substituted alkenylheteroaryl, optionally substituted alkynylcycloalkyl, optionally substituted alkynylheterocycloalkyl, optionally substituted alkynylary, optionally substituted alkynylheteroaryl, a sugar residue, and an amino acid residue (preferably bonded through the carboxy terminus of the amino acid);

each $R^{10'}$ is independently hydrogen or $C_{1-6}$alkyl, or $R^{10}$ and $R^{10'}$ together with the carbon atom to which they are attached form an optionally substituted spirocycloalkyl;

$R^{21}$ is a sugar or -amino acid-$R^{13}$, wherein $R^{13}$ is covalently bound to the N-terminus;

$R^{11}$ is selected from the group consisting of hydrogen, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, —C(O)—CH[N($R^{10'}$)($R^{10'}$)]-$C_1$-$C_6$alkyl, —C(O)—CH[N($R^{10'}$)($R^{10'}$)]-$C_1$-$C_6$alkyl-N($R^{10'}$)($R^{10'}$), —C(O)—CH[N($R^{10'}$)($R^{10'}$)]-$C_1$-$C_6$alkyl-aryl, —C(O)—CH[N($R^{10'}$)($R^{10'}$)]-$C_1$-$C_6$alkyl-heteroaryl, —C(O)-aryl, —C(O)-heteroaryl, an amino protecting group, and $R^{10}$; and each $R^{14}$ is independently selected from the group consisting of H, $C_1$-$C_6$alkyl and cycloalkyl, or two R together with the atom to which they are attached, form a cycloalkyl.

Preferred substituents Cy, Ar, and Z according to this aspect of the invention are as defined above for the first embodiment. Preferred substituents $L^3$ are as defined above for $L^1$ or $L^2$ Preferably, $Y^3$ is $C_2$ alkenylene or $C_2$ alkynylene, wherein one or both carbon atoms of the alkenylene optionally may be substituted with $C_1$-$C_6$ alkyl, $C_6$-$C_{10}$ aryl, $(C_1$-$C_6$)alk($C_6$-$C_{10}$)aryl, or $(C_6$-$C_{10}$)ar($C_1$-$C_6$)alkyl. More preferably, $Y^3$ is $C_2$ alkenylene or $C_2$ alkynylene, wherein one or both carbon atoms of the alkenylene optionally may be substituted with $C_1$-$C_4$ alkyl, $C_6$-$C_{10}$ aryl, $(C_1$-$C_4$)alk($C_6$-$C_{10}$)aryl, or $(C_6$-$C_{10}$)ar($C_1$-$C_4$)alkyl. Still more preferably, $Y^3$ is selected from the group consisting of —C≡C—, —CH=CH—, —C(CH$_3$)=CH—, and —CH=C(CH$_3$)—.

In a preferred embodiment of the compounds of formulae (1), (2), and (3), Z is selected from the group consisting of —O—C(O)—$(CH_2)_{1-4}$—C(OH)(COOR$^{10}$)—$(CH_2)_{1-4}$—COOR$^{10}$, —O—C(O)-[C($R^{14}$)($R^{14}$)]$_{1-4}$—P(O)(OH)(OH), —O—C(O)—$(CH_2)_{1-4}$—N($R^{14}$)—C[=N($R^{10'}$)]-N($R^{10'}$)($R^{10'}$), —O—C(O)—$(CH_2)$—CH(OH)—$(CH_2)$—N(CH$_3$)(CH$_3$), —O—C(O)—CH(NH$_2$)—$(CH_2)_{1-6}$—COOH, preferably —O—C(O)—CH(NH$_2$)—$(CH_2)$—COOH.

In a preferred embodiment of the compounds of formulae (1), (2), and (3), Z is selected from the group consisting of —O—C(O)—$(CH_2)$—C(OH)(COOH)—$(CH_2)$—COOH, —O—C(O)—$CH_2$—P(O)(OH)(OH), —O—C(O)—$(CH_2)$—N(CH$_3$)—C(=NH)—NH$_2$, —O—C(O)—$(CH_2)$—CH(OH)—$(CH_2)$—N(CH$_3$)(CH$_3$), —O—C(O)—CH(NH$_2$)—$(CH_2)$—COOH.

In some preferred embodiments, Z is —O—C(O)—$R^{10}$, —O—C(O)-[C($R^{10}$)($R^{10'}$)]$_{1-4}$—NH($R^{13}$) or —O$R^{11}$.

In some preferred embodiments of the prodrugs of inhibitors of histone deacetylase, of formulae (1), (2), and (3), Z is —O—$R^{20}$ wherein $R^{20}$ is —C(O)—C$R^{10}R^{10'}$—NH($R^{13}$), $R^{13}$ and $R^{10'}$ are H, and $R^{10}$ is $C_1$-$C_6$-alkyl or an amino acid side chain, or $R^{10}$ and $R^{10'}$ together with the carbon to which they are linked form $C_3$-$C_6$ cycloalkyl.

Naturally-occurring or non-naturally occurring amino acids are used to prepare the prodrugs of the invention. In particular, standard amino acids suitable as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine and proline. Particularly preferred are L-amino acids. Optionally an included amino acid is an α-, β-, or γ-amino acid. Also, naturally-occurring, non-standard amino acids can be utilized in the compositions and methods of the invention. For example, in addition to the standard naturally occurring amino acids commonly found in proteins, naturally occurring amino acids also illustratively include 4-hydroxyproline, gamma.-carboxyglutamic acid, selenocysteine, desmosine, 6-N-methyllysine, epsilon.-N,N,N-trimethyllysine, 3-methylhistidine, O-phosphoserine, 5-hydroxylysine, epsilon.-N-acetyllysine, omega.-N-methylarginine, N-acetylserine, gamma.-aminobutyric acid, citrulline, ornithine, azaserine, homocysteine, beta.-cyanoalanine and S-adenosylmethionine. Non-naturally occurring amino acids include phenyl glycine, meta-tyrosine, para-amino phenylalanine, 3-(3-pyridyl)-L-alanine-, 4-(trifluoromethyl)-D-phenylalanine, and the like.

In other embodiments, the prodrugs of inhibitors of histone deacetylase of the invention comprise those of formulae (1), (2) and (3) as defined above, except that $R^{20}$ of Z is described in U.S. Pat. No. 4,443,435 (incorporated by reference in its entirety) as comprising —CH($R^{130}$)—X—C(O)—$R^{131}$ wherein X is O, S, or $NR^{132}$;

$R^{131}$ is
(a) straight or branched chain alkyl having from 1 to 20 carbon atoms especially methyl, ethyl, isopropyl, t-butyl, pentyl or hexyl;
(b) aryl having from 6 to 10 carbon atoms especially phenyl, substituted pentyl or naphthalene;
(c) cycloalkyl having from 3 to 8 carbon atoms especially cyclopentyl, or cyclohexyl;
(d) alkenyl having from 2-20 carbon atoms especially $C_{2-6}$ alkenyl such as vinyl, allyl, or butenyl;
(e) cycloalkenyl having from 5 to 8 carbon atoms especially cyclopentenyl or cyclohexenyl;
(f) alkynyl having from 2 to 20 carbon atoms especially $C_{2-6}$ alkynyl for example, ethynyl, propynyl or hexynyl;
(g) aralkyl, alkaryl, aralkenyl, aralkynyl, alkenylaryl or alkynylaryl wherein alkyl, aryl, alkenyl and alkynyl are as previously defined;
(h) lower alkoxycarbonyl especially $C_{1-6}$ alkoxycarbonyl such as methoxycarbonyl, ethoxycarbonyl, t-butoxycarbonyl and cyclopentoxycarbonyl;
(i) carboxyalkyl or alkanoyloxyalkyl especially carboxy-$C_{1-6}$ alkyl such as formyloxymethyl and formyloxypropyl; or $C_{1-6}$ (alkylcarboxyalkyl) such as acetoxymethyl, n-propanoyloxyethyl and pentanoyloxybutyl;
(j) saturated or unsaturated monoheterocyclic or polyheterocyclic, or fused heterocyclic, either directly bonded to the carbonyl function or linked thereto via an alkylene bridge, containing from 1 to 3 of any one or more of the heteroatoms N, S or O in each heterocyclic ring thereof and each such ring being from 3- to 8-membered; and
(k) mono- or polysubstituted derivatives of the above, each of said substituents being selected from the group consisting of lower alkyl; lower alkoxy; lower alkanoyl; lower alkanoyloxy; halo especially bromo, chloro, or fluoro; haloloweralkyl especially fluoro, chloro or bromoloweralkyl such as trifluoromethyl and 1-chloropropyl; cyano; carbethoxy; loweralkylthio, especially $C_{1-6}$ loweralkylthio such as methylthio, ethylthio and n-propylthio; nitro; carboxyl; amino; loweralkylamino especially $C_{1-6}$ alkylamino, for example, methylamino, ethylamino and n-butylamino; diloweralkylamino especially di($C_{1-6}$ loweralkyl)amino such as N,N-dimethylamino, N,N-diethylamino and N,N-dihexylamino; carbamyl; loweralkylcarbamyl especially $C_{1-6}$ alkylcarbamyl such as methylcarbamyl and ethyl carbamoyl; and $R^{133}$—X—C(O)-phenyl-, wherein $R^{133}$ is hydrogen or alkyl having from 1 to 10 carbons;

$R^{130}$ is hydrogen, (b) $R^{131}$, lower alkanoyl, cyano, haloloweralkyl, carbamyl, loweralkylcarbamyl, or diloweralkylcarbamyl, —$CH_2ONO_2$, or —$CH_2OCOR^{131}$;

$R^{132}$ is hydrogen or lower alkyl; and further wherein $R^{131}$ and $R^{130}$ may be taken together to form a ring cyclizing moiety selected from the group consisting of:

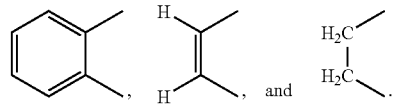

In other embodiments, the prodrugs of inhibitors of histone deacetylase of the invention comprise those of formulae (1), (2) and (3) as defined above, except that $R^{20}$ of Z is described in U.S. Pat. No. 6,407,235 (incorporated by reference in its entirety) as comprising:

a) —C(O)($CH_2$)$_m$C(O)$OR^{40}$, wherein m is 1, 2, 3 or 4,

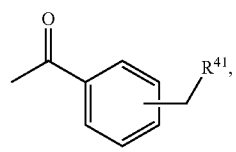

b)

wherein $R^{41}$ is —N($R^{42}$)($R^{43}$) and $R^{42}$ and $R^{43}$ are hydrogen or lower alkyl, or is a five or six member heterocyclyl or heteroaryl optionally substituted by lower alkyl, or c) —C(O)($CH_2$)NHC(O)($CH_2$)N($R^{42}$)($R^{43}$).

In other embodiments, the prodrugs of inhibitors of histone deacetylase of the invention comprise those of formulae (1), (2) and (3) as defined above, except that $R^{20}$ of Z is described in U.S. Pat. No. 6,545,131 (incorporated by reference in its entirety) as comprising: CO—(CH=CH)$_{n1}$—($CH_2$)$_{n2}$—Ar—$NH_2$, —CO—($CH_2$)$_{n2}$—(CH=CH)$_{n1}$—Ar—$NH_2$, CO—($CH_2$)$_{n2}$—(CH=CH)$_{n1}$—CO—NH—Ar—$NH_2$ and CO—(CH=CH)$_{n1}$—($CH_2$)$_{n2}$—CO—NH—Ar—$NH_2$ and substituted variations thereof, where n1 and n2 are from 0 to 5, Ar is a substituted or unsubstituted aryl group. In some preferred embodiments, Z is CO—($CH_2$)$_{n3}$—$NH_2$, where n3 is from 0 to 15, preferably 3-15, and also preferably 6-12. Particularly preferred substituent groups within this class are 6-aminohexanoyl, 7-aminoheptanoyl, 8-aminooctanoyl, 9-aminononanoyl, 10-aminodecanoyl, 11-aminoundecanoyl, and 12-aminododecanoyl. These substituents are generally synthesized from the corresponding amino acids, 6-aminohexanoic acid, and so forth. The amino acids are N-terminal protected by standard methods, for example Boc protection. Dicyclohexylcarbodiimide (DCCl)-promoted coupling of the N-terminal protected substituent to thapsigargin, followed by standard deprotection reactions produces primary amine-containing thapsigargin analogs.

In other embodiments, the prodrugs of inhibitors of histone deacetylase of the invention comprise those of formulae (1), (2) and (3) as defined above, except that $R^{20}$ of Z is described in U.S. Pat. No. 7,115,573 (incorporated by reference in its entirety) as comprising:

(1) an oligopeptide of the formula $(AA)_n$-$AA^3$-$AA^2$-$AA^1$, wherein: each AA independently represents an amino acid, n is 0 or 1, and when n is 1, then $(AA)_n$ is $AA^4$ which represents any amino acid, $AA^3$ represents isoleucine, $AA^2$ represents any amino acid, and $AA^1$ represents any amino acid, (2) a stabilizing group, and (3) optionally, a linker group not cleavable by a trouase, such as TOP (described in greater detail below)

wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the compound by enzymes present in whole blood, and wherein the compound is cleavable by an enzyme associated with the target cell, the enzyme associated with the target cell being other than TOP (Thimet oligopeptidase). The compound preferably includes an oligopeptide that is resistant to cleavage by a trouase, particularly TOP, i.e., resistant to cleavage under physiological conditions. The optionally present linker group that is not cleavable by a trouase is not cleavable under physiological conditions.

The typical orientation of these portions of the prodrug is as follows: (stabilizing group)-(oligopeptide)-(optional linker group)-(therapeutic agent).

Direct linkage of two portions of the prodrug means a covalent bond exists between the two portions. The stabilizing group and the oligopeptide are therefore directly linked via a covalent chemical bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Thus, typically, the oligopeptide is covalently bound to the linker group which, in turn, is covalently bound to the therapeutic agent.

In an alternative embodiment, the orientation of the prodrug may be reversed so that a stabilizing group is attached to the oligopeptide at the C-terminus and the therapeutic agent is directly or indirectly linked to the N-terminus of the oligopeptide. Thus, in an alternative embodiment, the first attachment site of the oligopeptide may be the C-terminus of the oligopeptide and the second attachment site by the oligopeptide may be the N-terminus of the oligopeptide. The linker group may optimally be present between the therapeutic agent and the oligopeptide. The alternative embodiment of the prodrug of the invention functions in the same manner as does the primary embodiment.

The stabilizing group typically protects the prodrug from cleavage by proteinases and peptidases present in blood, blood serum, and normal tissue. Particularly, since the stabilizing group caps the N-terminus of the oligopeptide, and is therefore sometimes referred to as an N-cap or N-block, it serves to ward against peptidases to which the prodrug may otherwise be susceptible. A stabilizing group that hinders cleavage of the oligopeptide by enzymes present in whole blood is chosen from the following:

(1) other than an amino acid, or (2) an amino acid that is either (i) a non-genetically-encoded amino acid or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with succinic acid and adipic acid being most preferred. Other examples of useful N-caps in the prodrug compound of the invention include diglycolic acid, fumaric acid, naphthalene dicarboxylic acid, pyroglutamic acid, acetic acid, 1- or 2-, naphthylcarboxylic acid, 1,8-naphthyl dicarboxylic acid, aconitic acid, carboxycinnamic acid, triazole dicarboxylic acid, gluconic acid, 4-carboxyphenyl boronic acid, a $(PEG)_n$-analog such as polyethylene glycolic acid, butane disulfonic acid, maleic acid, nipecotic acid, and isonipecotic acid.

Further, a non-genetically encoded amino acid such as one of the following may also be used as the stabilizing group: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

A linker group between the oligopeptide and the therapeutic agent may be advantageous for reasons such as the following: 1. As a spacer for steric considerations in order to facilitate enzymatic release of the $AA^1$ amino acid or other enzymatic activation steps. 2. To provide an appropriate attachment chemistry between the therapeutic agent and the oligopeptide. 3. To improve the synthetic process of making the prodrug conjugate (e.g., by pre-derivitizing the therapeutic agent or oligopeptide with the linker group before conjugation to enhance yield or specificity.) 4. To improve physical properties of the prodrug. 5. To provide an additional mechanism for intracellular release of the drug.

Linker structures are dictated by the required functionality. Examples of potential linker chemistries are hydrazide, ester, ether, and sulfhydryl. Amino caproic acid is an example of a bifunctional linker group. When amino caproic acid is used as part of the linker group, it is not counted as an amino acid in the numbering scheme of the oligopeptide.

The oligopeptide moiety is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by TOP. Test compounds resistant to cleavage by TOP are selected. The resulting conjugate may also be tested for stability in whole blood. Test compounds stable in whole blood are selected.

The combination of oligopeptide, stabilizing group, and optional linker of U.S. Pat. No. 7,115,573 is further described in US 2002-0142955, also incorporated herein by reference.

In other embodiments, the prodrugs of inhibitors of histone deacetylase of the invention comprise those of formulae (1), (2) and (3) as defined above, except that $R^{20}$ of Z is described in US 2004-0019017 A1 (incorporated by reference in its entirety and which describes caspase inhibitor prodrugs), as comprising:

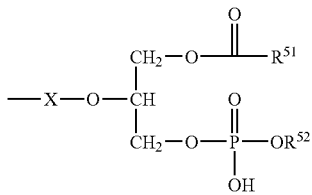

wherein $R^{51}$ is a saturated or unsaturated, straight-chain or branched, substituted or unsubstituted alkyl of 2 to 30, preferably 2 to 24, carbon atoms;

$R^{52}$ is H or a phospholipid head group, preferably choline;

X is a direct covalent bond or a group $C(O)LR^{53}$ wherein L is a saturated or unsaturated, straight-chain or branched, substituted or unsubstituted alkyl having from 2 to 15 carbon atoms, which optionally includes cyclic elements, and is optionally interrupted by one or more atoms selected from the group consisting of oxygen, sulfur and $N(R^{54})$; $R^{53}$ is selected from the group consisting of O, S and $N(R^{54})$, wherein $R^{54}$ is H or a saturated or unsaturated alkyl having 1 to 6 carbon atoms.

In other embodiments, the prodrugs of inhibitors of histone deacetylase of the invention comprise those of formulae (1), (2) and (3) as defined above, except that $R^{20}$ of Z is the Y moiety described in U.S. Pat. No. 7,115,573 (incorporated by reference in its entirety).

In other embodiments, the prodrugs of inhibitors of histone deacetylase of the invention comprise those of formulae (1), (2) and (3) as defined above, except that $R^{20}$ of Z is described in US 2006-0166903 A1 (incorporated by reference in its entirety, as comprising-X-L-O—P(O)(O$^-$)—O—CH$_2$—CH$_2$—N(CH$_3$)$_3{}^+$, wherein X and L are as described in US 2006-0166903A1.

In other embodiments, the prodrugs of inhibitors of histone deacetylase of the invention comprise those of formulae (1), (2) and (3) as defined above, except Z is one of the cleavable prodrug moieties described in U.S. Pat. No. 6,855,702, US 2005-0137141, and US 2006-0135594, all hereby incorporated by reference in their entirety.

In other embodiments, the prodrugs of inhibitors of histone deacetylase of the invention comprise those of formulae (1), (2) and (3) as defined above, wherein
Cy is optionally substituted aryl, preferably optionally substituted phenyl;
Ar is optionally substituted aryl, preferably optionally substituted phenyl;
$R^x$ is H or OH; and
Z is —O—$R^{20}$ or $R^{21}$.

In other embodiments, the prodrugs of inhibitors of histone deacetylase of the invention comprise those of formulae (1), (2) and (3) as defined above, wherein
Cy is optionally substituted aryl, preferably optionally substituted phenyl;
Ar is optionally substituted aryl, preferably optionally substituted phenyl;
$R^x$ is H or OH; and
Z is —O—$R^{20}$ or $R^{21}$, wherein
$R^{20}$ is —C(O)—C[($R^{10}$)($R^{10'}$)]$_{1-4}$—NH($R^{13}$) or —C(O)—$R^{10}$.

In a preferred embodiment of the present invention, the prodrugs of inhibitors of histone deacetylase comprise those of formula (2).

In other embodiments, the prodrugs of inhibitors of histone deacetylase of the invention comprise those of formulae (2) as defined above, wherein
Cy is optionally substituted aryl, preferably optionally substituted phenyl;
Ar is optionally substituted aryl, preferably optionally substituted phenyl;
$R^x$ is H or OH; and
Z is —O—$R^{20}$ or $R^{21}$.

In other embodiments, the prodrugs of inhibitors of histone deacetylase of the invention comprise those of formulae (2) as defined above, wherein
Cy is optionally substituted aryl, preferably optionally substituted phenyl;
Ar is optionally substituted aryl, preferably optionally substituted phenyl;
$R^x$ is H or OH; and
Z is —O—$R^{20}$ or $R^{21}$, wherein
$R^{20}$ is —C(O)—C[($R^{10}$)($R^{10'}$)]$_{1-4}$—NH($R^{13}$) or —C(O)—$R^{10}$.

In other embodiments, the prodrugs of inhibitors of histone deacetylase of the invention comprise those of formulae (2) as defined above, wherein
Cy is optionally substituted aryl, preferably optionally substituted phenyl, wherein the substituents are preferably selected from the group consisting of —$CF_3$, halo, heterocyclyl and fused heterocyclyl;
$L^2$ is saturated $C_3$alkyl or $C_4$alkyl, preferably unsubstituted;
Ar is optionally substituted aryl, preferably optionally substituted phenyl;
$Y^2$ is $C_1$alkyl or $C_2$alkyl, preferably $C_1$alkyl, optionally substituted;
$R^x$ is H or OH, preferably H;
Z is —O—$R^{20}$ or $R^{21}$;
$R^{20}$ is —C(O)—C[($R^{10}$)($R^{10'}$)]$_{1-4}$—NH($R^{13}$) or —C(O)—$R^{10}$;
each $R^{10}$ is independently selected from the group consisting of H, optionally substituted alkyl, optionally substituted-alkylphenyl, optionally substituted-alkylheteroaryl and optionally substituted heteroaryl;
each $R^{10'}$ is independently H or alkyl; or
$R^{10}$ and $R^{10'}$ together with the atom to which they are attached form a $C_3$ or $C_4$spirocycloalkyl, preferably a $C_3$spirocycloalkyl;
$R^{13}$ is selected from the group consisting of H, —C(O)—CH[N($R^{10}$)($R^{10'}$)]-$C_1$-$C_6$alkyl-N($R^{10}$)($R^{10'}$), —C(O)-heteroaryl, —C(O)-aryl, —C(O)—CH[N($R^{10}$)($R^{10'}$)]-$C_1$-$C_6$alkyl, —C(O)—CH[N($R^{10}$)($R^{10'}$)]-$C_1$-$C_6$alkyl-aryl and —C(O)—CH[N($R^{10}$)($R^{10'}$)]-$C_1$-$C_6$alkyl-heteroaryl; and
$R^{21}$ is amino acid-$R^{13}$ (preferably the amino acid is lysine or arginine).

In other embodiments, the prodrugs of inhibitors of histone deacetylase of the invention comprise those of formulae (2) as defined above, wherein
Cy is optionally substituted aryl, preferably optionally substituted phenyl, wherein the substituents are preferably selected from the group consisting of —$CF_3$, halo, heterocyclyl and fused heterocyclyl;
$L^2$ is saturated $C_3$alkyl or $C_4$alkyl, preferably unsubstituted;
Ar is optionally substituted aryl, preferably optionally substituted phenyl;

$Y^2$ is $C_1$alkyl or $C_2$alkyl, preferably $C_1$alkyl, optionally substituted;

$R^x$ is H or OH, preferably H;

Z is —O—$R^{20}$;

$R^{20}$ is —C(O)—C[($R^{10}$)($R^{10'}$)]$_{1-4}$—NH($R^{13}$), preferably —C(O)—C[($R^{10}$)($R^{10'}$)]$_{1-2}$—NH($R^{13}$), more preferably —C(O)—C[($R^{10}$)($R^{10'}$)]—NH($R^{13}$);

each $R^{10}$ is independently selected from the group consisting of H, optionally substituted alkyl and optionally substituted-alkylphenyl;

each $R^{10'}$ is independently H or alkyl; or $R^{10}$ and $R^{10'}$ together with the atom to which they are attached form a $C_3$ or $C_4$spirocycloalkyl, preferably a $C_3$spirocycloalkyl; and $R^{13}$ is H.

In other embodiments, the prodrugs of inhibitors of histone deacetylase of the invention comprise those of formulae (2) as defined above, wherein Cy is optionally substituted aryl, preferably optionally substituted phenyl, wherein the substituents are preferably selected from the group consisting of —$CF_3$, halo, heterocyclyl and fused heterocyclyl;

$L^2$ is saturated $C_3$alkyl or $C_4$alkyl, preferably unsubstituted;

Ar is optionally substituted aryl, preferably optionally substituted phenyl;

$Y^2$ is $C_1$alkyl or $C_2$alkyl, preferably $C_1$alkyl, optionally substituted;

$R^x$ is H or OH, preferably H;

Z is $R^{21}$;

$R^{21}$ is amino acid-$R^{13}$ (preferably the amino acid is lysine or arginine); and $R^{13}$ is H.

In other embodiments, the prodrugs of inhibitors of histone deacetylase of the invention comprise those of formulae (2) as defined above, wherein Cy is optionally substituted aryl, preferably optionally substituted phenyl, wherein the substituents are preferably selected from the group consisting of —$CF_3$, halo, heterocyclyl and fused heterocyclyl;

$L^2$ is saturated $C_3$alkyl or $C_4$alkyl, preferably unsubstituted;

Ar is optionally substituted aryl, preferably optionally substituted phenyl;

$Y^2$ is $C_1$alkyl or $C_2$alkyl, preferably $C_1$alkyl, optionally substituted;

$R^x$ is H or OH, preferably H;

Z is —O—$R^{20}$;

$R^{20}$ is —C(O)—$R^{10}$; and $R^{10}$ is selected from the group consisting of optionally substituted alkyl, optionally substituted-alkylphenyl, optionally substituted-alkylheteroaryl and optionally substituted heteroaryl.

In other embodiments, the prodrugs of inhibitors of histone deacetylase of the invention comprise those of formulae (2) as defined above, wherein Cy is optionally substituted aryl, preferably optionally substituted phenyl, wherein the substituents are preferably selected from the group consisting of —$CF_3$, halo, heterocyclyl and fused heterocyclyl;

$L^2$ is saturated $C_3$alkyl or $C_4$alkyl, preferably unsubstituted;

Ar is optionally substituted aryl, preferably optionally substituted phenyl;

$Y^2$ is $C_1$alkyl or $C_2$alkyl, preferably $C_1$alkyl, optionally substituted;

$R^x$ is H or OH, preferably H;

Z is —O—R $R^{20}$ is —C(O)—C[($R^{10}$)($R^{10'}$)]—NH($R^{13}$), wherein $R^{10}$ and $R^{10'}$ together with the atom to which they are attached form a $C_3$ or $C_4$spirocycloalkyl, preferably a $C_3$spirocycloalkyl; and $R^{13}$ is selected from the group consisting of H, —C(O)—CH[N($R^{10}$)($R^{10'}$)]-$C_1$-$C_6$alkyl-N($R^{10}$)($R^{10'}$), —C(O)-heteroaryl, —C(O)-aryl, —C(O)—CH[N($R^{10}$)($R^{10'}$)]-$C_1$-$C_6$alkyl, —C(O)—CH[N($R^{10}$)($R^{10'}$)]-$C_1$-$C_6$alkyl-aryl and —C(O)—CH[N($R^{10}$)($R^{10'}$)]-$C_1$-$C_6$alkyl-heteroaryl, wherein $R^{10}$ and $R^{10'}$ are each independently selected from H and $C_1$-$C_6$alkyl, preferably H.

Preferred prodrugs of the invention include those in Table A:

TABLE A

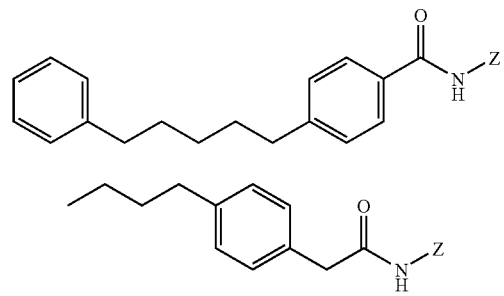

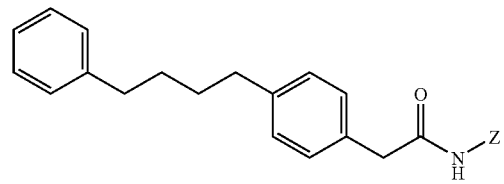

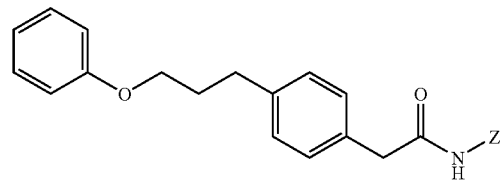

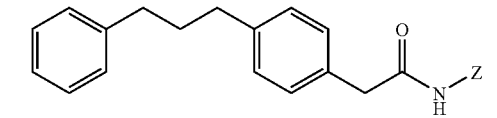

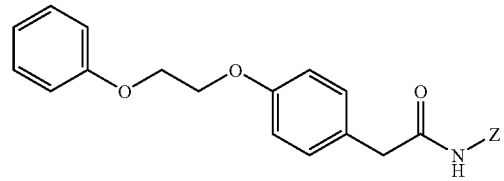

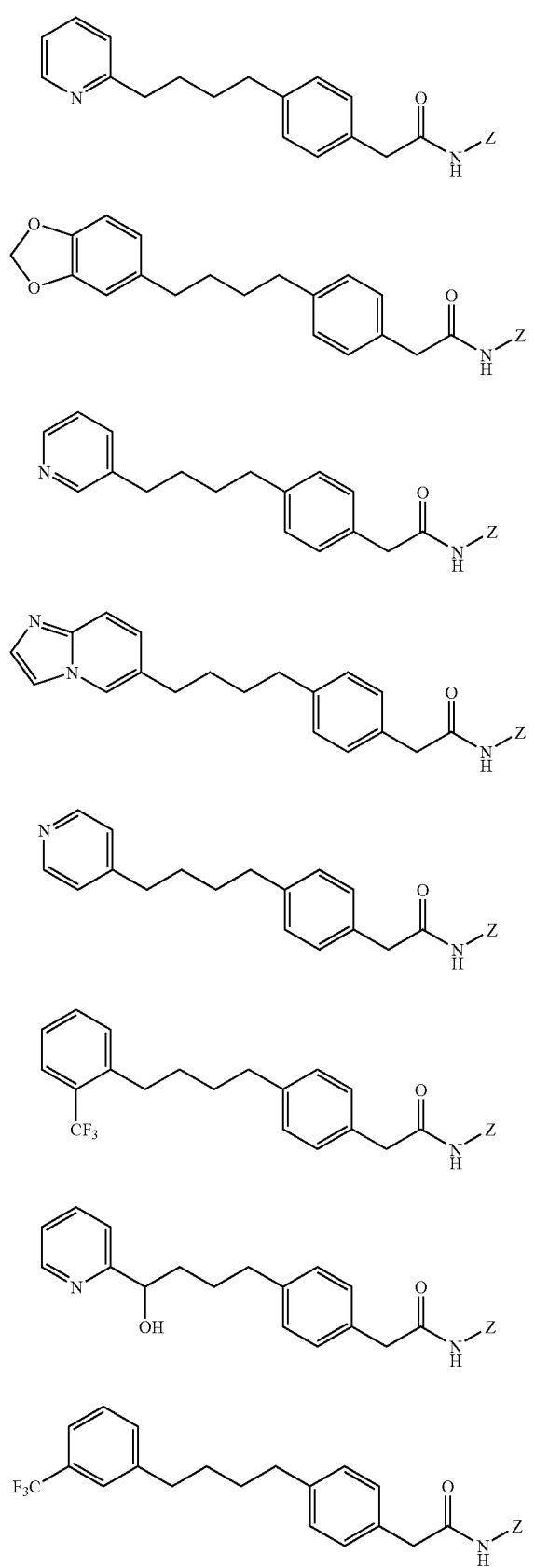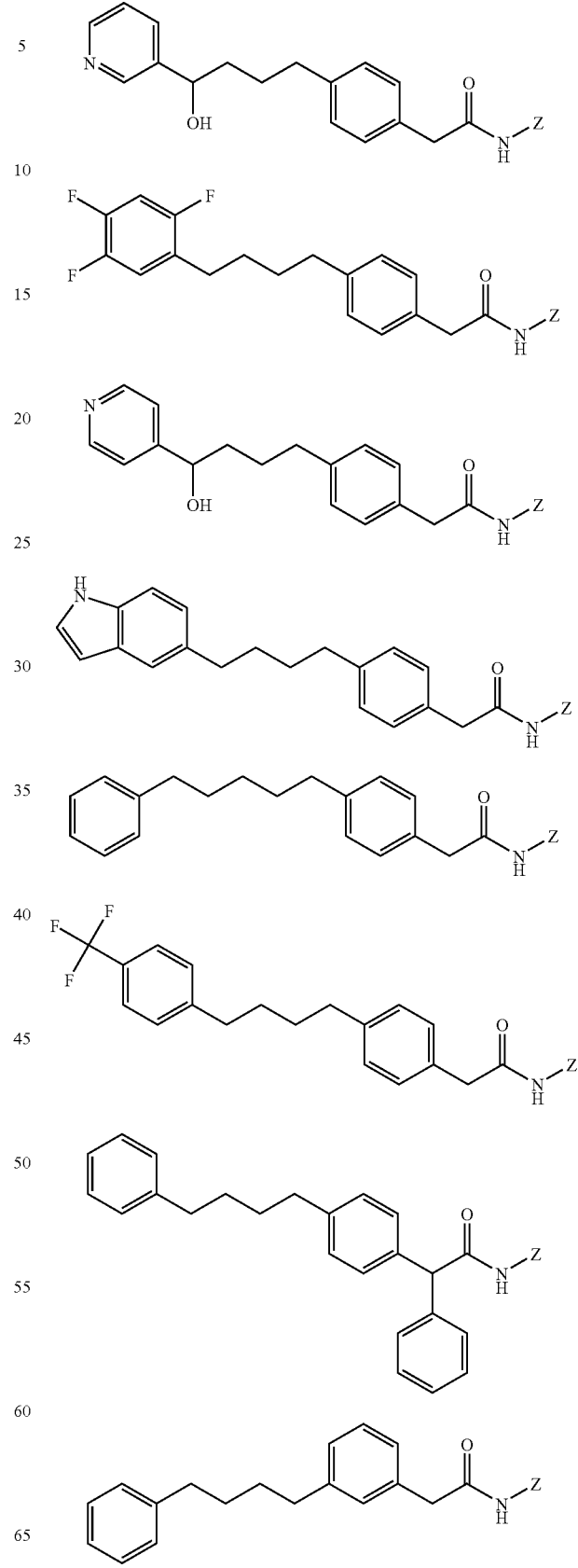

TABLE A-continued

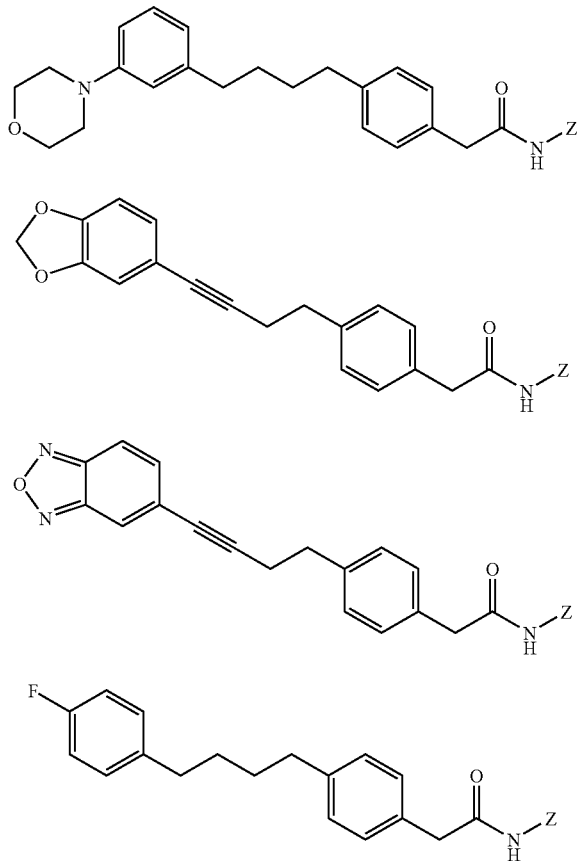

Preferred prodrug compounds of the invention are cleavable (e.g., hydrolysable) in mammalian and/or fungal pathogen cells into compounds (cleavage products) in which Z in formulae (1), (2), and (3) is —OH. Such cleavage products are active histone deacetylase inhibitors. Thus, according to another aspect, the invention provides compounds of formulae (1), (2), and (3) as defined above (and pharmaceutically acceptable salts thereof) with the exception that Z is —OH. Among the preferred cleavage compounds are those with structure:

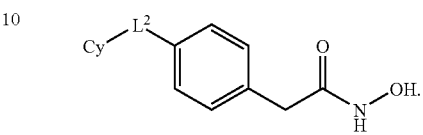

Preferred cleavage products of the prodrug compounds of the invention include those in Table A in which Z is —OH.

All compounds of the invention, whether prodrug or corresponding cleavage product, can be racemic or diastereomerically or enantiomerically enriched. In addition, compounds of the invention, whether prodrug or corresponding cleavage product, can be in the form of a hydrate, solvate, pharmaceutically acceptable salt, and/or complex.

Synthesis

Compounds of formula Cy-$L^1$-Ar—$Y^1$—C(O)—NH—O—H, wherein $L^1$ is —S(O)$_2$NH—, preferably may be prepared according to the synthetic routes depicted in Schemes 1-5. Accordingly, in certain preferred embodiments, compounds I are preferably prepared according to the general synthetic route depicted in Scheme 1. Thus, a sulfonyl chloride (II) is treated with an amine (III) in a solvent such as methylene chloride in the presence of an organic base such as triethylamine. Treatment of the crude product with a base such as sodium methoxide in an alcoholic solvent such as methanol effects cleavage of any dialkylated material and affords the sulfonamide (IV). Hydrolysis of the ester function in IV can be effected by treatment with a hydroxide base, such as lithium hydroxide, in a solvent mixture such as tetrahydrofuran and methanol to afford the corresponding acid (V).

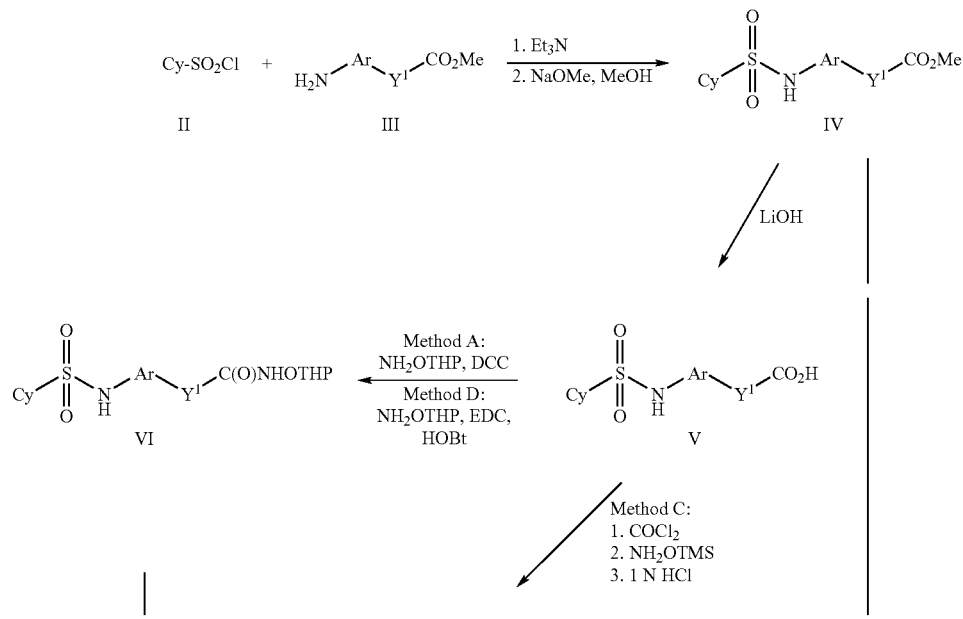

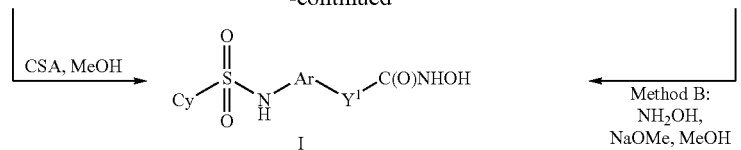

In some embodiments, conversion of the acid V to the hydroxamic acid I may be accomplished by coupling V with a protected hydroxylamine, such as tetrahydropyranylhydroxylamine (NH$_2$OTHP), to afford the protected hydroxamate VI, followed by acidic hydrolysis of VI to provide the hydroxamic acid I. The coupling reaction is preferably accomplished with the coupling reagent dicyclohexylcarbodiimide (DCC) in a solvent such as methylene chloride (Method A) or with the coupling reagent 1-(3-dimethylaminopropyl)-3-ethylcarbodiimide in presence of N-hydroxy benzotriazole in an aprotic solvent such as dimethylformamide (Method D). Other coupling reagents are known in the art and may also be used for this reaction. Hydrolysis of VI is preferably effected by treatment with an organic acid such as camphorsulfonic acid in a protic solvent such as methanol.

Alternatively, in some other embodiments, acid V is converted to the corresponding acid chloride, preferably by treatment with oxalic chloride, followed by the addition of a protected hydroxylamine such as O-trimethylsilylhydroxylamine in a solvent such as methylene chloride, which then provides the hydroxylamine I upon workup (Method C).

In still other embodiments, the ester IV is preferably treated with hydroxylamine in a solvent such as methanol in the presence of a base such as sodium methoxide to furnish the hydroxylamine I directly (Method B).

SCHEME 2

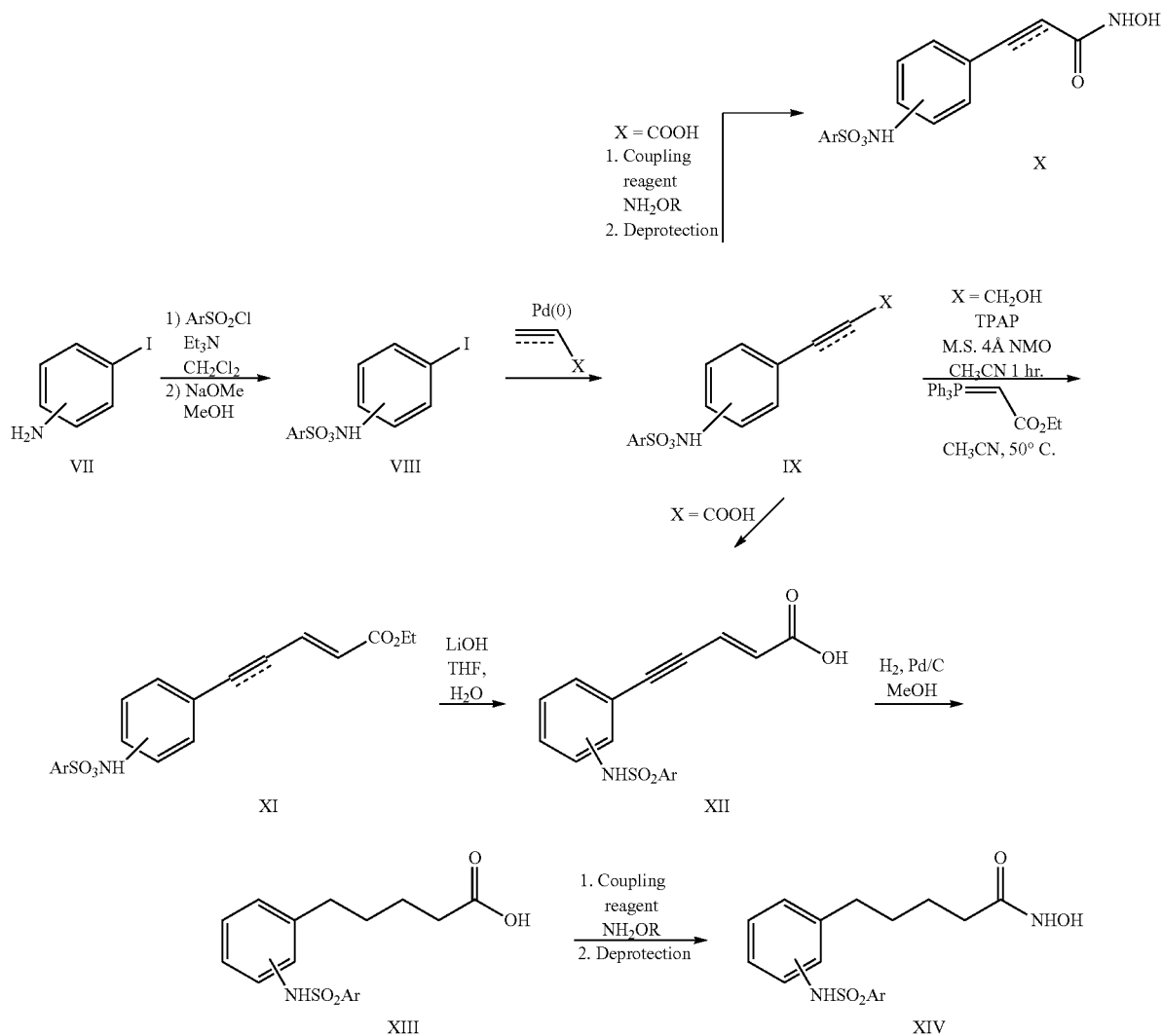

Compounds of formula X and XIV preferably are prepared according to the general procedure outlined in Scheme 2. Thus, an aminoaryl halide (VII) is treated with a sulfonyl chloride in presence of a base such as triethylamine, followed by treatment with an alkoxide base, to furnish the sulfonamide VIII. One of skill in the art will recognize that reverse sulfonamide analogs can be readily prepared by an analogous procedure, treating a haloarenesulfonyl halide with an arylamine.

Compound VIII is coupled with a terminal acetylene or olefinic compound in the presence of a palladium catalyst such as tetrakis(triphenylphosphine)palladium(0) in a solvent such as pyrrolidine to afford IX.

Oxidation of the compound of formula IX (X=CH$_2$OH), followed by homologation of the resulting aldehyde using a Wittig type reagent such as carbethoxymethylenetriphenylphosphorane in a solvent such as acetonitrile, gives the compound of formula XI. Basic hydrolysis of XI, such as by treatment with lithium hydroxide in a mixture of THF and water, provides the acid XII. Hydrogenation of XII may preferably be performed over a palladium catalyst such as Pd/C in a protic solvent such as methanol to afford the saturated acid XIII. Coupling of the acid XIII with an O-protected hydroxylamine such as O-tetrahydropyranylhydroxylamine is effected by treatment with a coupling reagent such as 1-(3-dimethylaminopropyl)-3-ethylcarbodiimide in the presence of N-hydroxybenzotriazole (HOBT), or N,N-dicyclohexylcarbodiimide (DCC), in a solvent such as DMF, followed by deprotection to furnish the compound of general formula XIV.

The acid IX, wherein X=COOH, may be coupled directly with an O-protected hydroxylamine such as O-tetrahydropyranylhydroxylamine, followed by deprotection of the hydroxy protecting group to furnish the hydroxamic acid X.

Compounds of formula Cy-L$^1$-Ar—Y$^1$—C(O)—NH—O—H, wherein L$^1$ is —C(O)NH—, preferably may be prepared according to the synthetic routes analogous to those depicted in Schemes 1-2, substituting acid chloride starting materials for the sulfonyl chloride starting materials in those Schemes.

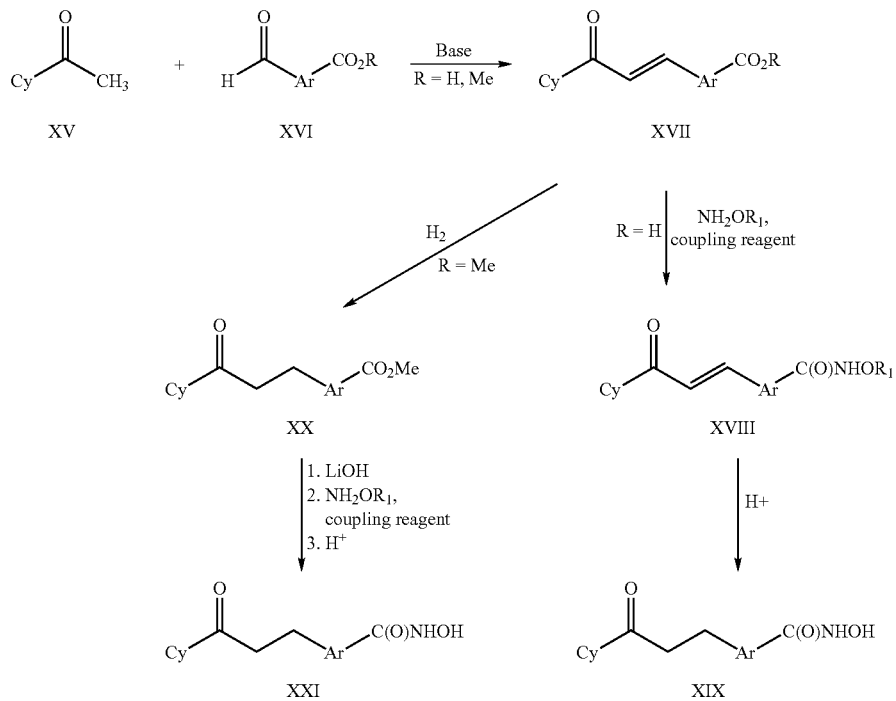

Scheme 3

Compounds of the formula Cy-L$^2$-Ar—Y$^2$—C(O)—NH—O—H are preferably prepared according to the synthetic routes outlined in Schemes 3-5. Accordingly, in certain preferred embodiments, compounds of formulae XIX and XXI (L$^2$=—C(O)—CH=CH— or —C(O)—CH$_2$CH$_2$—) preferably are prepared according to the route described in Scheme 3. Thus, a substituted aryl acetophenone (XV) is treated with an aryl aldehyde (XVI) in a protic solvent such as methanol in the presence of a base such as sodium methoxide to afford the enone XVII.

The acid substituent of XVII (R=H) is coupled with an O-protected hydroxylamine such as O-tetrahydropyranylhydroxylamine (R$_1$=tetrahydropyranyl) to afford the O-protected-N-hydroxybenzamide XVIII. The coupling reaction is preferably performed by treating the acid and hydroxylamine with dicyclohexylcarbodiimide in a solvent such as methylene chloride or with 1-(3-dimethylaminopropyl)-3-ethylcarbodiimide in the presence of N-hydroxybenzotriazole in a solvent such as dimethylformamide. Other coupling reagents are known in the art and may also be used in this reaction. O-Deprotection is accomplished by treatment of XVIII with an acid such as camphorsulfonic acid in a solvent such as methanol to afford the hydroxamic acid XIX (L$^2$=—C(O)—CH=CH—).

Saturated compounds of formula XXI (L=—C(O)—CH$_2$CH$_2$—) are preferably prepared by hydrogenation of XVII (R=Me) over a palladium catalyst, such as 10% Pd/C, in a solvent such as methanol-tetrahydrofuran. Basic hydrolysis of the resultant product XIX with lithium hydroxide, followed by N-hydroxy amide formation and acid hydrolysis as described above, then affords the hydroxamic acid XXI.

Scheme 4

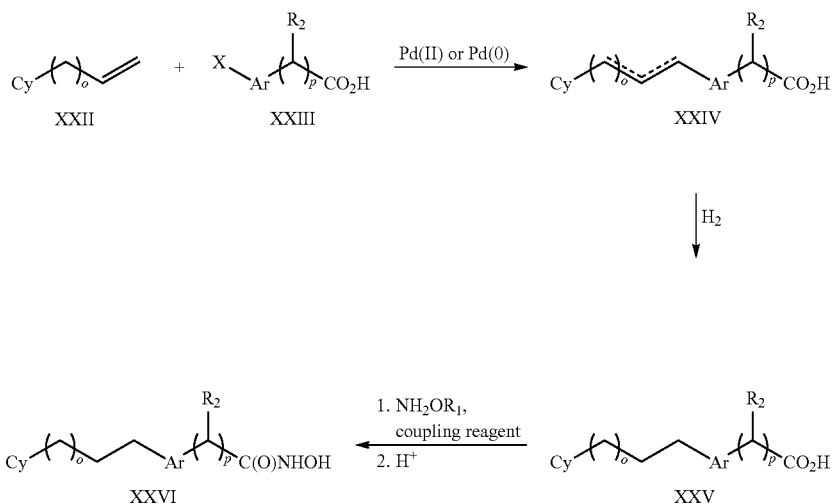

Compounds of formula XXVI ($L^2$=—$(CH_2)_{o+2}$—) are preferably prepared by the general procedures described in Schemes 4 and 5. Thus, in some embodiments, a terminal olefin (XXII) is coupled with an aryl halide (XXIII) in the presence of a catalytic amount of a palladium source, such as palladium acetate or tris(dibenzylideneacetone)dipalladium (0), a phosphine, such as triphenylphosphine, and a base, such as triethylamine, in a solvent such as acetonitrile to afford the coupled product XXIV. Hydrogenation, followed by N-hydroxyamide formation and acid hydrolysis, as described above, affords the hydroxamic acid XXVI.

Scheme 5

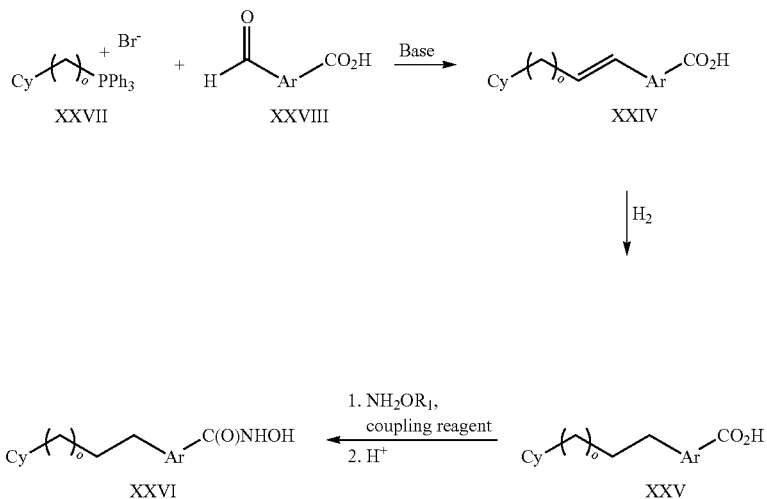

Alternatively, in some other embodiments, a phosphonium salt of formula XXVII is treated with an aryl aldehyde of formula XXVIII in the presence of base, such as lithium hexamethyldisilazide, in a solvent, such as tetrahydrofuran, to produce the compound XXIV. Hydrogenation, followed by N-hydroxyamide formation and acidic hydrolysis, then affords the compounds XXVI.

Scheme 6

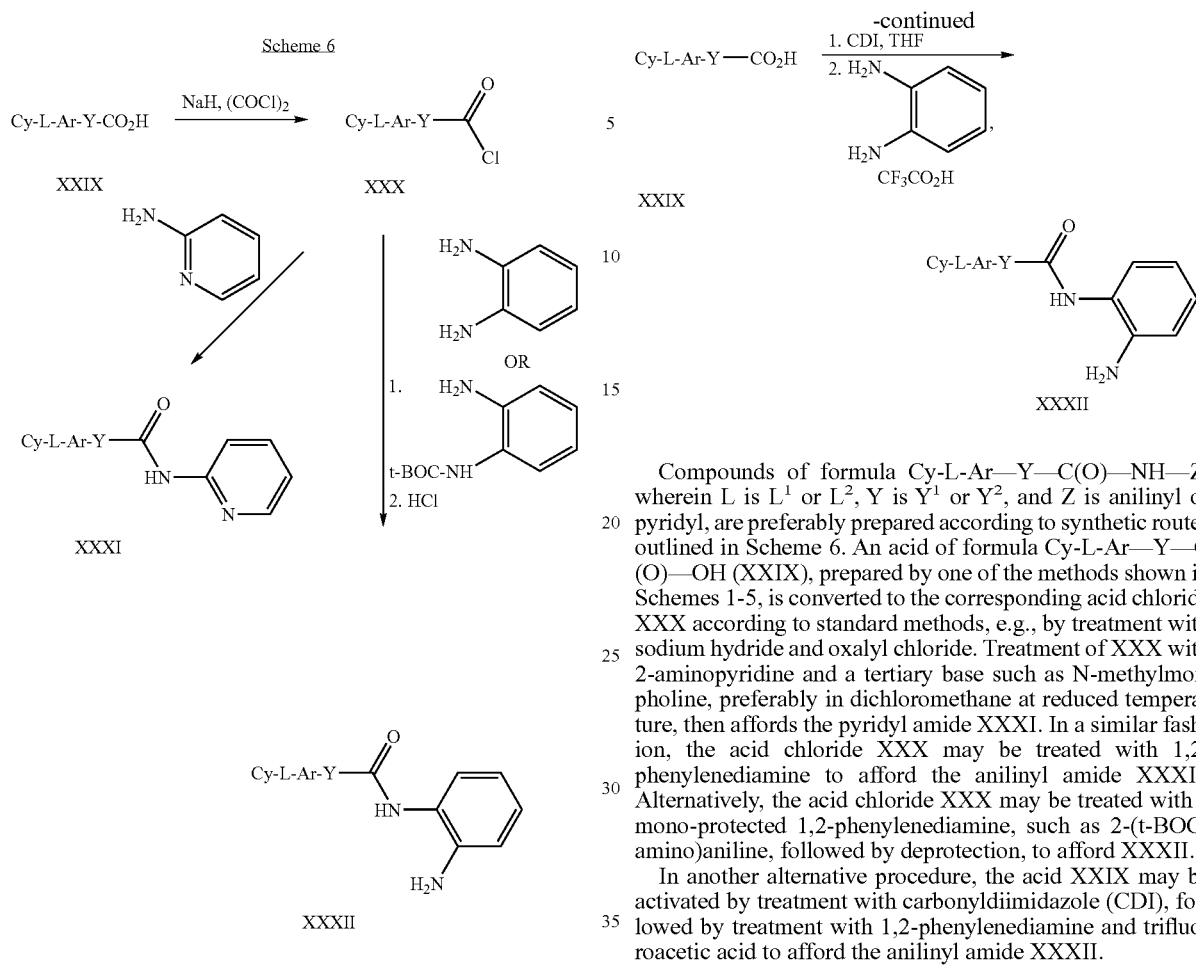

Compounds of formula Cy-L-Ar—Y—C(O)—NH—Z, wherein L is $L^1$ or $L^2$, Y is $Y^1$ or $Y^2$, and Z is anilinyl or pyridyl, are preferably prepared according to synthetic routes outlined in Scheme 6. An acid of formula Cy-L-Ar—Y—C(O)—OH (XXIX), prepared by one of the methods shown in Schemes 1-5, is converted to the corresponding acid chloride XXX according to standard methods, e.g., by treatment with sodium hydride and oxalyl chloride. Treatment of XXX with 2-aminopyridine and a tertiary base such as N-methylmorpholine, preferably in dichloromethane at reduced temperature, then affords the pyridyl amide XXXI. In a similar fashion, the acid chloride XXX may be treated with 1,2-phenylenediamine to afford the anilinyl amide XXXII. Alternatively, the acid chloride XXX may be treated with a mono-protected 1,2-phenylenediamine, such as 2-(t-BOC-amino)aniline, followed by deprotection, to afford XXXII.

In another alternative procedure, the acid XXIX may be activated by treatment with carbonyldiimidazole (CDI), followed by treatment with 1,2-phenylenediamine and trifluoroacetic acid to afford the anilinyl amide XXXII.

Scheme 7

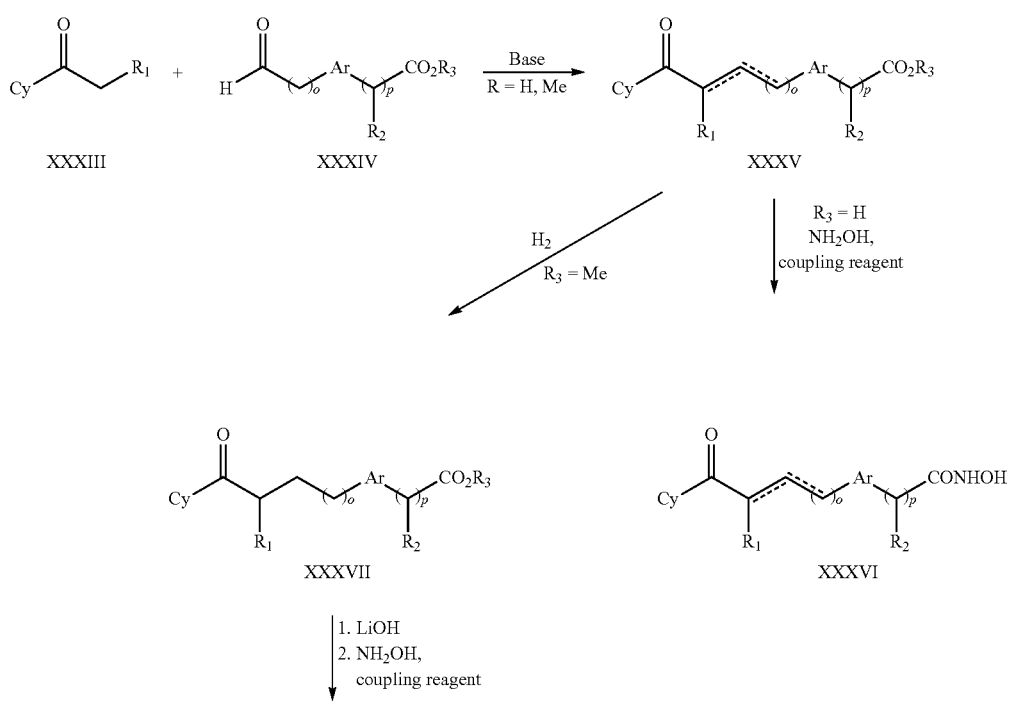

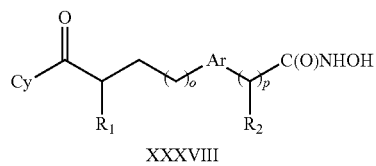

XXXVIII

Compounds of formula XXXVIII (L²=—C(O)-alkylene-) preferably are prepared according to the general procedure depicted in Scheme 7. Thus, Aldol condensation of ketone XXXIII (R₁=H or alkyl) with aldehyde XXXIV affords the adduct XXXV. The adduct XXXV may be directly converted to the corresponding hydroxamic acid XXXVI, or may first undergo hydrogenation to afford the saturated compound XXVII and then be converted to the hydroxamic acid XXX-VIII.

the corresponding sulfone, which is conveniently isolated after conversion to the methyl ester by treatment with diazomethane. Ester hydrolysis then affords the acid XLII, which is converted to the hydroxamic acid XLIII according to any of the procedures described above. The sulfide XL¹ also may be converted directly to the corresponding hydroxamic acid XLIV, which then may be selectively oxidized to the sulfoxide XLV, for example, by treatment with hydrogen peroxide and tellurium dioxide.

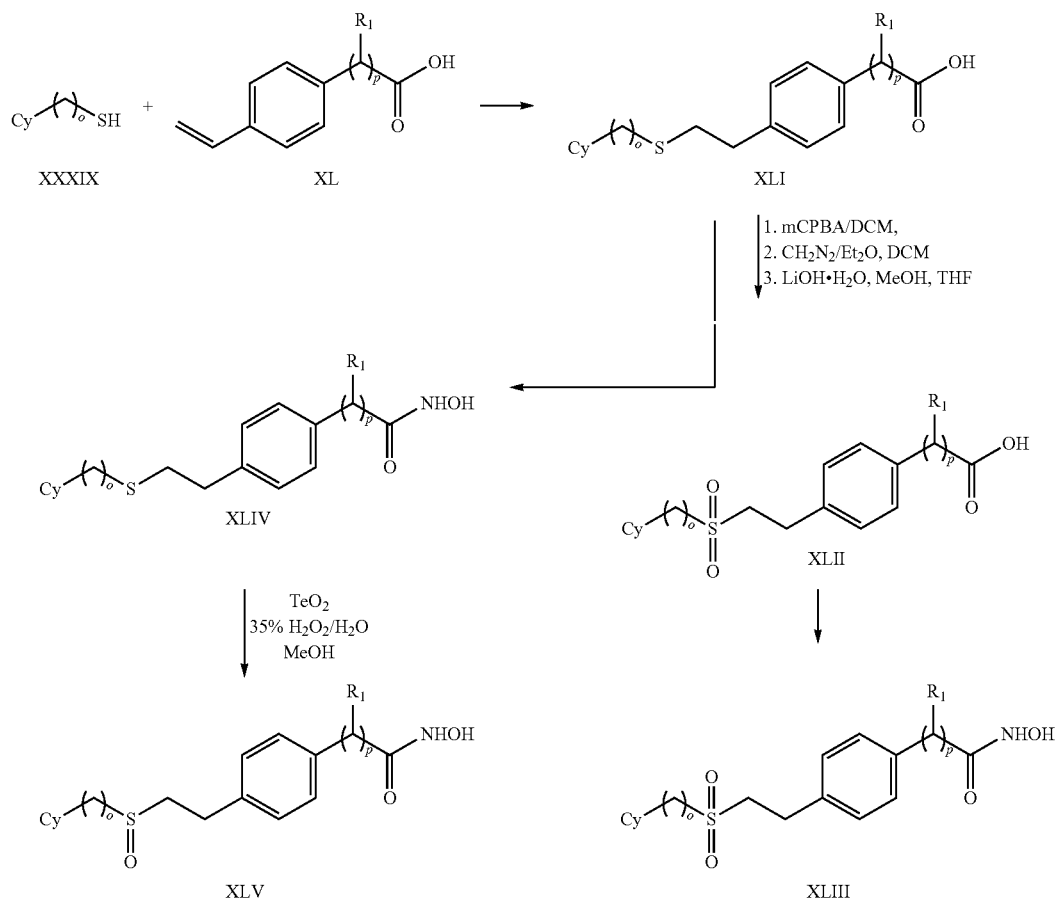

Scheme 8

Compounds of formula Cy-L²-Ar—Y²—C(O)—NH—O—H, wherein one of the carbon atoms in L is replaced with S, S(O), or S(O)₂ preferably are prepared according to the general procedure outlined in Scheme 8. Thus, thiol XXXIX is added to olefin XL to produce XL¹. The reaction is preferably conducted in the presence of a radical initiator such as 2,2'-azobisisobutyronitrile (AIBN) or 1,1'-azobis(cyclohexanecarbonitrile) (VAZO™). Sulfide oxidation, preferably by treatment with m-chloroperbenzoic acid (mCPBA), affords Alternatively, compounds of Cy-L²-Ar—Y²—C(O)—NH—O—H can be prepared according to Scheme 9. In Scheme 9, haloaryl acetic acid XLVI is esterified, by, for example, treatment with HCl in dioxane in the presence of an alcohol such as methanol, to afford acetate XLVII. Paladium coupling of acetate XLVII with alkyne XLVIII with, for example (Ph₃P)₄Pd in DME and diethylamine in the presence of CuI, produces XLVIX, which is subsequently reduced under H₂ and, for example, Pd/C in methanol, to afford XLVX. N-hydroxyamide formation and acid hydrolysis, as described above, then leads to XLVXI.

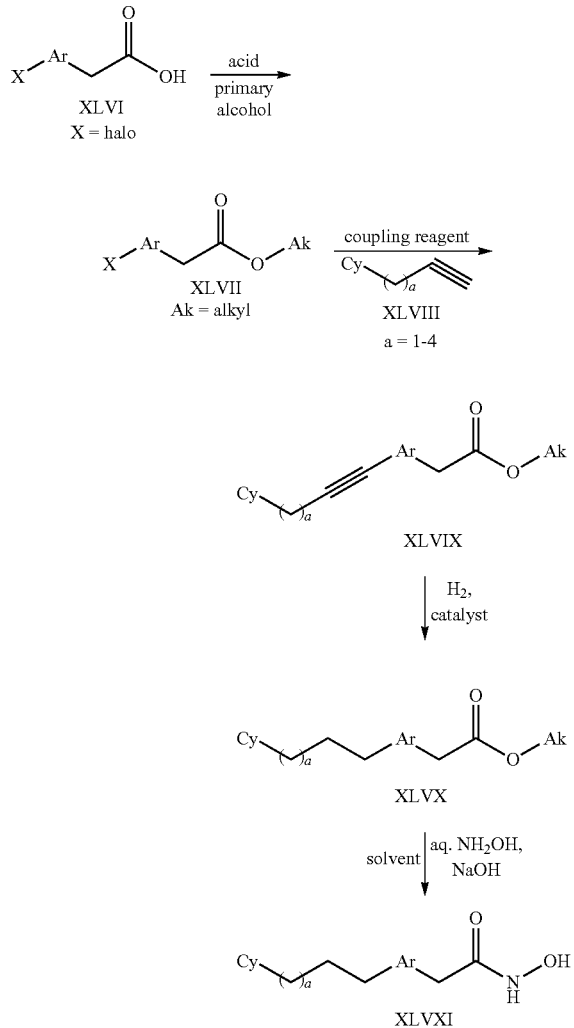

Compounds of formulas (1)-(3) can be prepared as depicted in Scheme 10. XLVXI is treated with an amino acid XLVXII under standard peptide coupling conditions, such as, for example, EDC and HOBt in DMF, to afford the protected acetamide XLVXIII, which is subsequently deprotected to yield the prodrug XLVXIV.

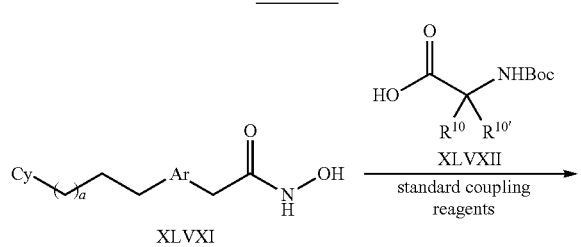

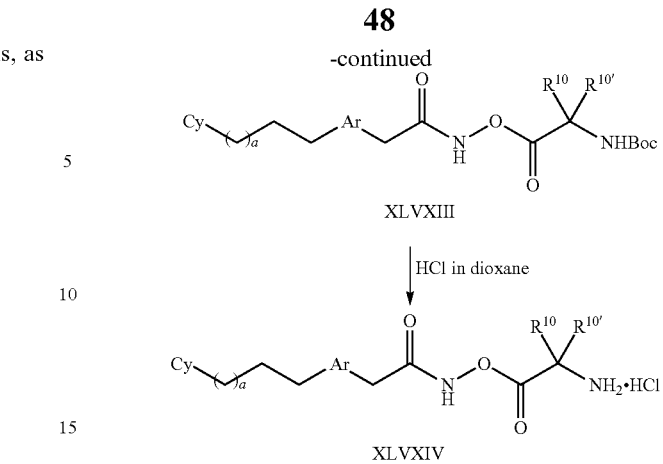

Other compounds of formula (1)-(3) can be prepared by methods known by those skilled in the art. Examples of such methods can be found in U.S. Pat. Nos. 4,443,435; 6,407,235; 6,545,131; 6,855,702; 7,115,573; United States Patent Application Nos. US 2002-0142955, US 2004-0019017, US 2005-0137141, US 2006-0135594, US 2006-0166903 and international publication WO 2005/097747, all of which are incorporated herein by reference.

Pharmaceutical Compositions

In a second aspect, the invention provides pharmaceutical compositions comprising a prodrug of an inhibitor of histone deacetylase represented by any one of formulae (1)-(3) and a pharmaceutically acceptable carrier, excipient, or diluent. Compounds of the invention (whether a prodrug or a hydrolzyation product) or compositions thereof may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention (whether a prodrug or a hydrolzyation product) or compositions thereof are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g. *Remington's Pharmaceutical Sciences*, 18th Edition, ed. A. Gennaro, Mack Publishing Co., Easton, Pa., 1990.

Inhibition of Histone Deacetylase

In a third aspect, the invention provides a method of inhibiting histone deacetylase in a cell, comprising contacting a cell in which inhibition of histone deacetylase is desired with a prodrug of an inhibitor of histone deacetylase according to any of formulas (1)-(3).

Measurement of the enzymatic activity of a histone deacetylase can be achieved using known methodologies. For example, Yoshida et al., *J. Biol. Chem.*, 265: 17174-17179 (1990), describes the assessment of histone deacetylase enzymatic activity by the detection of acetylated histones in trichostatin A treated cells. Taunton et al., *Science*, 272: 408-

411 (1996), similarly describes methods to measure histone deacetylase enzymatic activity using endogenous and recombinant HDAC-1. Both of these references are hereby incorporated by reference in their entirety.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, HDAC-8, HDAC-9, HDAC-10, and HDAC-11). As discussed below, certain particularly preferred histone deacetylase inhibitors are those that interact with and reduce the enzymatic activity of a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer, or other appropriate method (which may depend on the cell type being counted) known to those of skill in the art. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the prodrug of the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, a cleavage (e.g., hydrolyzation) product of a prodrug of an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For example, the hydrolyzation products of the prodrugs of histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such a synchronization of cultured cells may also be useful for testing the efficacy of a new transfection protocol, where transfection efficiency varies and is dependent upon the particular cell cycle phase of the cell to be transfected. Use of the prodrugs of histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the cleavage product of a prodrug of a histone deacetylase inhibitor of the invention induces cell differentiation in the contacted cell. Thus, a neoplastic cell, when contacted with a prodrug of an inhibitor of histone deacetylase of the invention may be induced to differentiate, resulting in the production of a daughter cell that is phylogenetically more advanced than the contacted cell. In certain other preferred embodiments, the contacted cell is a fungal cell.

In some preferred embodiments, the contacted cell is in an animal. Thus, the invention provides a method for treating a cell proliferative disease or condition in an animal, or treating a fungal infection, comprising administering to an animal in need of such treatment a therapeutically effective amount of a prodrug of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a prodrug of a histone deacetylase inhibitor of the invention.

It is contemplated that some cleavage products of the prodrugs of the invention have inhibitory activity against a histone deacetylase from a protozoal source. Thus, the invention also provides a method for treating or preventing a protozoal disease or infection, comprising administering to an animal in need of such treatment a therapeutically effective amount of a prodrug of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a prodrug of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal.

In certain particularly preferred embodiments, prodrugs of the invention are administered intravenously in a hospital setting. In certain other preferred embodiments, administration may preferably be by the oral route.

When administered systemically, the prodrug of an histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (i.e., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. Antisense oligonucleotides according to this aspect of the invention, when directed to mammalian HDAC, are complementary to regions of RNA or double-stranded DNA that encode HDAC-1, HDAC-2, HDAC-3, HDAC-4, HDAC-5, HDAC-6, HDAC7, HDAC-8, HDAC-9, HDAC-10 and/or HDAC-11.

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1-6 saturated or unsaturated carbon atoms, or with an —O-aryl or allyl group having 2-6 carbon atoms, wherein such alkyl, aryl or allyl group may be unsubstituted or may be substituted, e.g. with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group. The term "oligonucleotide" also encompasses linked nucleic acid and peptide nucleic acid.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof (see e.g. Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active by quantitating the mRNA encoding a product of the gene, or in a Western blotting analysis assay for the product of the gene, or in an activity assay for an enzymatically active gene product, or in a soft agar growth assay, or in a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g. Pon, R. T. (1993) Methods in Molec. Biol. 20: 465-496).

Particularly, preferred oligonucleotides have nucleotide sequences of from about 13 to about 35 nucleotides which include the nucleotide sequences shown in Tables 1-3. Yet additional particularly preferred oligonucleotides have nucleotide sequences of from about 15 to about 26 nucleotides of the nucleotide sequences shown in Tables 1-3.

TABLE 1

| SEQ ID NO. | SEQUENCE | TARGET (**) |
|---|---|---|
| 1 | 5'-GAG ACA GCA GCA CCA GCG GG-3' | 17-36 |
| 2 | 5'-ATG ACC GAG TGG GAG ACA GC-3' | 21-49 |
| 3 | 5'-GGA TGA CCG AGT GGG AGA CA-3' | 31-50 |

TABLE 1-continued

| SEQ ID NO. | SEQUENCE | TARGET (**) |
|---|---|---|
| 4 | 5'-CAG GAT GAC CGA GTG GGA GA-3' | 33-52 |
| 5 | 5'-TGT GTT CTC AGG ATG ACC GA-3' | 41-60 |
| 6 | 5'-GAG TGA CAG AGA CGC TCA GG-3' | 62-81 |
| 7 | 5'-TTC TGG CTT CTC CTC CTT GG-3' | 1504-1523 |
| 8 | 5'-CTT GAC CTC CTC CTT GAC CC-3' | 1531-1550 |
| 9 | 5'-GGA AGC CAG AGC TGG AGA GG-3' | 1565-1584 |
| 10 | 5'-GAA ACG TGA GGG ACT CAG CA-3' | 1585-1604 |
| 11 | 5'-CCG TCG TAG TAG TAA CAG ACT TT-3' | 138-160 |
| 12 | 5'-TGT CCA TAA TAG TAA TTT CCA A-3' | 166-187 |
| 13 | 5'-CAG CAA ATT ATG AGT CAT GCG GAT TC-3' | 211-236 |

(**) target reference numbering is in accordance with HDAC-1, GenBank Accession Number U50079.

TABLE 2

| SEQ ID NO. | SEQUENCE | TARGET (***) |
|---|---|---|
| 14 | 5'-CTC C-TT GAC T-GT ACG C-CA TG-3' | 1-20 |
| 15 | 5'-TGC T-GC TGC T-GC TGC T-GC CG-3' | 121-141 |
| 16 | 5'-CCT C-CT GCT G-CT GCT G-CT GC-3' | 132-152 |
| 17 | 5'-CCG T-CG TAG T-AG TAG C-AG ACT T-T-3' | 138-160 |
| 18 | 5'-TGT C-CA TAA T-AA TAA T-TT CCA A-3' | 166-187 |
| 19 | 5'-CAG C-AA GTT A-TG GGT C-AT GCG G-AT TC-3' | 211-236 |
| 20 | 5'-GGT T-CC TTT G-GT ATC T-GT TT-3' | 1605-1625 |

(***) target reference numbering is in accordance with HDAC-2, GenBank Accession Number U31814.

TABLE 3

| SEQ ID NO. | SEQUENCE | TARGET (***) |
|---|---|---|
| 21 | 5'-GCT GCC TGC CGT GCC CAC CC-3' | 514-533 |

(***) target reference numbering is in accordance with HDAC-4.

The following examples are intended to further illustrate certain preferred embodiments of the invention, and are not intended to limit the scope of the invention.

EXAMPLES

Preparation of Amines

Methyl-3-aminophenylacetate (1)

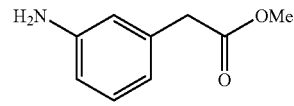 [SMILES: COC(=O)Cc1cccc(N)c1]

To a solution of 3-aminophenylacetic acid (3 g, 19.85 mmol) in methanol (50 mL) at room temperature was added HCl conc. (37%, 7.5 mL). The mixture was stirred 6 h at room temperature then treated with a saturated aqueous solution of NaHCO$_3$. The solvent was removed under reduced pressure then the aqueous phase was extracted several times with CH$_2$Cl$_2$. The combined organic extracts were dried over (MgSO$_4$) and evaporated. The crude mixture was purified by flash chromatography using hexane/AcOEt (1:1) yielding 1 as a yellow oil (3.06 g, 79%).

$^1$H NMR: (300 MHz, CDCl$_3$): δ 7.10 (t, J=8 Hz, 1H), 6.68-6.58 (m, 3H), 3.69-3.65 (m, 5H), 3.53 (s, 2H).

Methyl-4-aminophenyl benzoate (2)

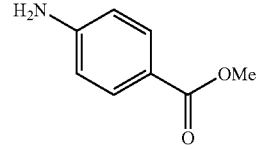 [SMILES: COC(=O)c1ccc(N)cc1]

To a solution of 4-aminobenzoic acid (10 g, 72.92 mmol) in methanol (200 mL) at room temperature was added HCl conc. (37%, 25 mL). The solution mixture was heated overnight at 70° C. Once the solution was clear (completed) the reaction was treated with a saturated aqueous solution of NaHCO$_3$ and Na$_2$CO$_3$ powder until pH 9. The solvent was then evaporated under reduced pressure and the aqueous phase was extracted several times with AcOEt. The combined organic extracts were dried over (MgSO$_4$) and evaporated. The crude product 2 (9.30 g 85%) was obtained as a beige solid and was clean enough to use without further purification.

$^1$H NMR: (300 MHz, CDCl$_3$): δ 7.85 (d, J=8 Hz, 2H), 6.63 (d, J=8 Hz, 2H), 4.04 (broad s. 2H), 3.85 (s. 3H).

Methyl-4-aminophenylacetate (3)

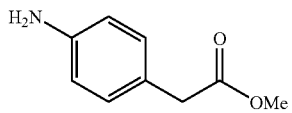 [SMILES: COC(=O)Cc1ccc(N)cc1]

To a solution of 4-aminophenylacetic acid (10 g, 66.2 mmol) in methanol (150 mL) at room temperature was added HCl conc. (37% 25 mL). The mixture became yellow and was stirred overnight. The reaction mixture was then quenched with a saturated aqueous solution of NaHCO$_3$. The methanol was evaporated under reduced pressure and the aqueous layer was extracted several times with AcOEt. The combined organic extracts were dried over (MgSO$_4$) and evaporated. The crude residue was purified by flash chromatography using hexane/AcOEt (4:1) as solvent mixture yielding 3 as a yellow oil (9.44 g, 74%).

$^1$H NMR: (300 MHz, CDCl$_3$): δ 7.05 (d, J=10 Hz, 2H), 6.65 (d, J=10 Hz, 2H), 3.65 (s, 3H), 3.63 (broad s, 2H), 3.51 (s, 2H).

Example 1

2-[4-benzo[b]thiophene-2-sulfonylamino)-phenyl]-N-hydroxy-acetamide (4)

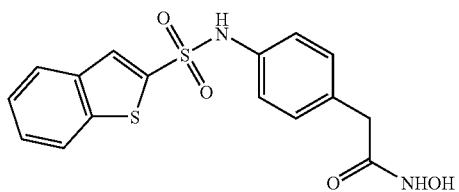

Step 1: Methyl-2-[4-benzo[b]thiophene-2-sulfonylamino)-phenyl]-acetate (5)

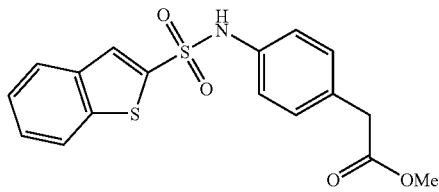 [SMILES: COC(=O)Cc1ccc(NS(=O)(=O)c2cc3ccccc3s2)cc1]

To a solution of 3 (500 mg, 2.56 mmol), in CH$_2$Cl$_2$ (8 mL) at room temperature were added Et$_3$N (712 μμL, 5.12 mmol) followed by 2-benzothiophenesulfonyl chloride (712 mg, 3.07 mmol). The mixture was stirred overnight at room temperature then quenched with a saturated aqueous solution of NaHCO$_3$. The phases were separated and the aqueous layer was extracted several times with CH$_2$Cl$_2$. The combined organic extracts were dried over (MgSO$_4$) and evaporated. The mixture of the mono and bis alkylated products were dissolved in methanol (~8 mL) and NaOMe was added (691 mg, 12.8 mmol). The resulting mixture was heated at 60° C. for 30 min the HCl 1N was added until pH 2. Then a saturated aqueous solution of NaHCO$_3$ was added until pH 7-8. The solvent was evaporated under reduced pressure and the aqueous layer was extracted several times with CH$_2$Cl$_2$. The combined organic extracts were dried over (MgSO$_4$) and evaporated. The residue was purified by flash chromatography using toluene/AcOEt 7:3 as solvent mixture and a second flash chromatography using CH$_2$Cl$_2$/acetone 98:2 as solvent yielding the title compound 5 as yellowish powder (487 mg, 53%).

$^1$H NMR: (300 MHz, CDCl$_3$): δ 7.80 (d, J=8 Hz, 2H), 7.75 (s, 1H), 7.44 (m, 2H), 7.14 (m, 4H), 6.79 (broad s, 1H) 3.67 (s, 3H), 3.56 (s, 2H)

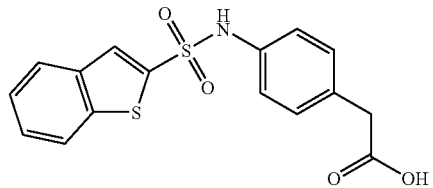 [SMILES: O=C(O)Cc1ccc(NS(=O)(=O)c2cc3ccccc3s2)cc1]

Step 2: 2-[4-benzo[b]thiophene-2-sulfonylamino)-phenyl]-acetic acid (6)

To a solution of 5 from step 1 (451 mg, 1.25 mmol) in a solvent mixture of THF (20 mL) and H$_2$O (20 mL) at room temperature was added LiOH (524 mg, 12.5 mmol). The mixture was stirred for 2 h at room temperature and then was treated with a saturated aqueous solution of NH$_4$Cl. The resulting solution was extracted several times with AcOEt. The combined organic extracts were dried over (MgSO$_4$). The crude residue was then purified by flash chromatography using CH$_2$Cl$_2$/MeOH (9:1) as solvent mixture yielding the title compound 6 as white solid (404 mg, 93%).

$^1$H NMR: (300 MHz, DMSO-d$_6$): δ 8.03 (d, J=8 Hz, 1H), 7.97 (d, J=7 Hz, 1H), 7.92 (s, 1H), 7.50-7.45 (m, 2H), 7.13-7.06 (m, 4H), 3.44 (s, 2H).

Step 3: 2-[4-benzo[b]thiophene-2-sulfonylamino)-phenyl]-N-hydroxy-acetamide (4)

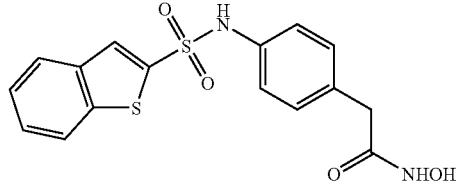

Method A:

To a solution of 6 (150 mg, 0.432 mmol) in a solvent mixture of CH$_2$Cl$_2$ (10 mL) and THF (5 mL) was added at room temperature 1,3-dicyclohexylcarbodiimide (DCC, 116 mg, 0.563 mmol). The reaction mixture was stirred 30 min at room temperature then NH$_2$OTHP (76 mg, 0.650 mmol) and dimethylaminopyridine (DMAP, 5 mg) were added. The solution was stirred over night at room temperature and the solvents were evaporated under reduced pressure. The crude material was purified by flash chromatography using CH$_2$Cl$_2$/MeOH (9:1) as solvent. The residue was dissolved in MeOH (~10 mL) and 10-camphorsulfonic acid (CSA, 100 mg, 0.432 mmol) was added. The mixture was stirred at room temperature overnight then treated with a saturated aqueous solution of NaHCO$_3$. The solvent was evaporated under reduced pressure and the aqueous phase was extracted several times with CH$_2$Cl$_2$ (3×) and AcOEt (3×). The combined organic extracts were dried over (MgSO$_4$) and evaporated. The crude product was purified by preparative high pressure liquid chromatography on reversed phase silica gel using a gradient of water/CH$_3$CN (10-65%) yielding the title compound 4 as yellowish solid (70 mg, 45%).

$^1$H NMR (300 MHz, CD$_3$OD): δ 7.92-7.88 (m, 2H), 7.80 (s, 1H), 7.50-7.45 (m, 2H), 7.23-7.16 (m, 4H) 3.35 (s, 2H).

Except where otherwise indicated, the following compounds were prepared by procedures analogous to those described in Example 1, but substituting the sulfonyl chloride indicated for 2-benzothiophenesulfonyl chloride in step 1.

Example 2

2-[4-(2-nitrobenzenesulfonylamino)-phenyl]-N-hydroxy-acetamide (7)

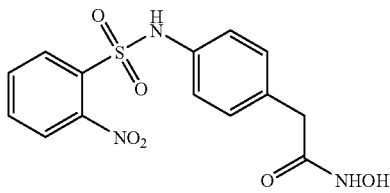

Sulfonyl chloride: 2-nitrobenzenesulfonyl chloride

Yield: Step 1: 82%

Yield: Step 2: 99%

Yield: Step 3: 19%

$^1$H NMR (300 MHz, DMSO-$d_6$); δ 10.59 (s, 1H); 8.78 (s, 1H); 7.94 (s, 2H), 7.81 (s, 2H), 7.20-7.02 (m, 4H); 3.13 (s, 2H).

Example 3

2-[4-(2,5-dichlorobenzenesulfonylamino)-phenyl]-N-hydroxy-acetamide (8)

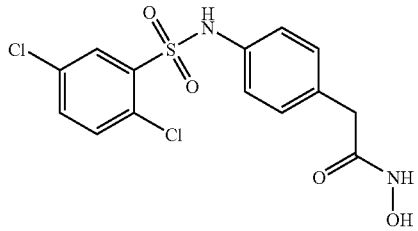 [SMILES: O=C(Cc1ccc(NS(=O)(=O)c2cc(Cl)ccc2Cl)cc1)NO]

Sulfonyl Chloride: 2,5-Dichlorobenzenesulfonyl chloride

Yield: Step 1: 66%

Yield: Step 2: 96%

Yield: Step 3: 66%

$^1$H NMR (300 MHz, DMSO-$d_6$); δ 10.68 (s, 1H), 8.88 (s, 1H), 7.95 (s, 1H), 7.67 (s, 2H); 7.13 (d, 2H, J=8 Hz), 7.02 (d, 2H, J=8 Hz), 3.16 (s, 2H)

Example 4

2-[4-(4-methylbenzenesulfonylamino)-phenyl]-N-hydroxy-acetamide (9)

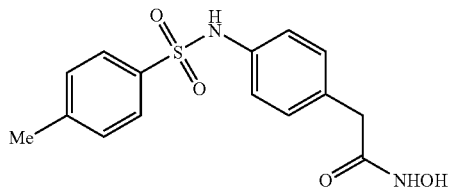

Sulfonyl Chloride: 4-methylbenzenesulfonyl chloride

Step 1: Yield 100%

Step 2: 2-[4-(4-methylbenzenesulfonylamino)-phenyl]-N-hydroxy-acetamide (9)

Method B:

To a solution of methyl-2-[4-(4-methylbenzenesulfonylamino)]phenylacetate (459 mg, 1.44 mmol) in methanol (10 mL), at room temperature were added hydroxylamine hydrochloride (200 mg, 2.88 mmol) followed by sodium methoxide (389 mg, 7.19 mmol). The resulting mixture was heated overnight at 60° C. then treated with HCl (1N) until pH 2. The solvent was evaporated under reduced pressure then the aqueous phase was extracted several times with $CH_2Cl_2$. The combined organic extracts were dried over ($MgSO_4$) then evaporated. The crude mixture was purified by flash chromatography using $CH_2Cl_2$/MeOH (9:1) as solvent mixture yielding the title compound 9 (244 mg, 53%) as a white powder.

$^1$H NMR (300 MHz, acetone-$d_6$); δ 7.68 (d, J=8 Hz, 2H); 7.29 (d, J=8 Hz, 2H), 7.15 (br. s, 4H), 3.33 (s, 2H, $CH_2$), 2.33 (s, 3H, $CH_3$).

The following compounds were prepared following procedures analogous to those described in Example 1, step 1, and Example 4, step 2 (Method B), but substituting the sulfonyl chloride indicated for 2-benzothiophenesulfonyl chloride in step 1.

Example 5

2-[4-(3-trifluoromethylbenzenesulfonylamino)-phenyl]-N-hydroxy acetamide (10)

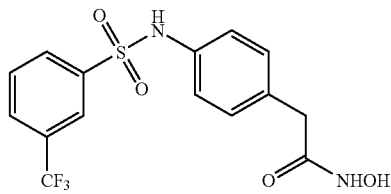

Sulfonyl Chloride: 3-trifluoromethylbenzenesulfonyl chloride

Yield: Step 1: 70%

Yield: Step 2: 49%

$^1$H NMR (300 MHz, acetone-$d_6$); δ=8.09 (s, 1H), 8.05 (d, 1H, J=8 Hz), 7.95 (d, 1H, J=8 Hz); 7.77 (t, 1H, J=8 Hz); 7.21 (d, 2H, J=8 Hz), 7.13 (d, 2H, J=8 Hz); 3.35 (s, 2H, $CH_2$)

Example 6

2-[4-(tert-butylsulfonylamino)-phenyl]-N-hydroxy-acetamide (11)

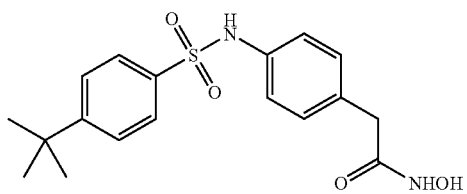

Sulfonyl chloride: 4-tert-butylsulfonyl chloride

Yield: Step 1: 76%
Yield: Step 2: 40%
$^1$H NMR (300 MHz, acetone-$d_6$); δ 7.75 (d, 2H, J=9 Hz), 7.56 (d, 2H, J=9 Hz); 7.17 (s, 4H); 3.34 (s, 2H), 1.29 (s, 9H)

The following compound was prepared following procedures analogous to those described in Example 1, steps 1-2, substituting the sulfonyl chloride indicated for 2-benzothiophenesulfonyl chloride in step 1, followed by hydroxamic acid formation using Method C

Example 7

2-[2-(naphthylsulfonylamino)-phenyl]-N-hydroxy-acetamide (12)

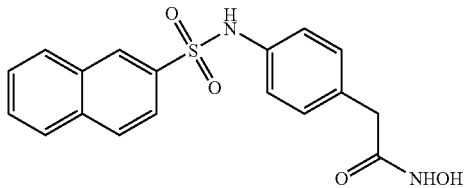

Sulfonyl Chloride: 2-naphthylsulfonyl chloride

Yield: Step 1: 100%
Yield: Step 2: 100%
Step 3: 2-[2-(naphthylsulfonylamino)-phenyl]-N-hydroxy-acetamide (12)
Method C:

To a solution of 2-[2-(naphthylsulfonylamino)]-phenylacetic acid (191 mg, 563 mmol) in $CH_2Cl_2$ (20 mL) at room temperature were added DMF (1 drop) followed by $(COCl)_2$ (250 μL, 2.81 mmol). The mixture became yellow and solidification appeared. The reaction was stirred 90 min at room temperature then $(COCl)_2$ was added until no bubbling (~1 mL). Then the solvents were evaporated under reduced pressure. The crude material was dissolved in $CH_2Cl_2$ and TMSONH$_2$ (3 mL) was added to the solution. The reaction was exothermic and the resulting mixture was stirred 2 h at room temperature then treated with HCl (1N) until pH 2. The phases were separated and the aqueous layer was extracted several times with $CH_2Cl_2$. The combined organic extracts were dried over (MgSO$_4$) then evaporated. The crude compound was purified 3 times by flash chromatography using $CH_2Cl_2$/MeOH (9:1) as solvent mixture then another purification using preparative high pressure liquid chromatography using reversed phase chromatography with a gradient of water/$CH_3CN$ (10-70%) yielding the title compound 12 as a white powder (29 mg, 15%).

$^1$H NMR (300 MHz, acetone-$d_6$); δ 9.13 (s, 1H), 8.42 (s, 1H), 8.08-7.97 (m, 3H), 7.82 (dd, 1H, J=9 Hz, 1.5 Hz), 7.70-7.63 (m, 2H), 7.21-7.14 (m, 4H), 3.50 (s, 2H)

The following compound was prepared following procedures analogous to those described in Example 1, steps 1-2, substituting the indicated sulfonyl chloride and amine indicated for 2-benzothiophenesulfonyl chloride and 3 in step 1, followed by hydroxamic acid formation using Method D.

Example 8

N-hydroxy-[4-benzo[b]thiophene-2-sulfonylamino)-phenyl]-benzamide (13)

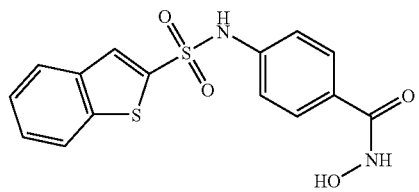 [SMILES: O=C(NO)c1ccc(NS(=O)(=O)c2cc3ccccc3s2)cc1]

Sulfonyl Chloride: 2-Benzothiophenesulfonyl chloride

Amine: Methyl-4-aminobenzoate (2)
Yield: Step 1: 80%
Yield: Step 2: 69%
Step 3: N-hydroxy-[4-benzo[b]thiophene-2-sulfonylamino)-phenyl]-benzamide (13)
Method D:

To a solution of 2-[4-benzo[b]thiophene-2-sulfonylamino] benzoic acid (300 mg, 90 mmol) in DMF (20 mL) at room temperature were added 1-(3-dimethyl-aminopropyl)-3-ethylcarbodiimide hydrochloride (EDC, 207 mg, 1.08 mmol), and 1-Hydroxybenzotriazole hydrate (HOBT, 182 mg, 1.35 mmol). The mixture was stirred 20 min. at room temperature then NH$_2$OTHP (158 mg, 1.35 mmol) was added. The resulting mixture was heated at 50° C. for 24 h then stirred at room temperature for 24 h. The DMF solvent was evaporated under reduced pressure and the residue was dissolved in $CH_2Cl_2$ and washed with brine or a saturated aqueous solution of NaHCO$_3$. The combined organic extracts were dried over (MgSO$_4$) then condensed. The crude compound was purified by flash chromatography using $CH_2Cl_2$/MeOH (9:1) as solvent mixture. The residue was then dissolved in methanol (20 mL) then 10-camphorsulfonic acid (CSA, 100 mg, 45 mmol) was added. The mixture was stirred 2 h at room temperature then the solvents were evaporated under reduced pressure at room temperature to avoid thermal decomposition. The crude was purified by flash chromatography using $CH_2Cl_2$/MeOH (9:1) as solvent mixture. A second purification was performed using a preparative high pressure liquid chromatography using a gradient of water/$CH_3CN$ (10-85%) as solvent giving the title compound 13 as a red solid (212 mg, 68%).

¹H NMR (300 MHz, acetone-d₆); δ 10.69 (s, 1H), 9.70 (s, 1H); 8.01-7.97 (m, 3H), 7.77 (d, 2H, J=9 Hz); 7.55-7.39 (m, 4H).

Example 9

2-[3-benzo[b]thiopene-2-sulfonylamino)-phenyl]N-hydroxy-acetamide (14)

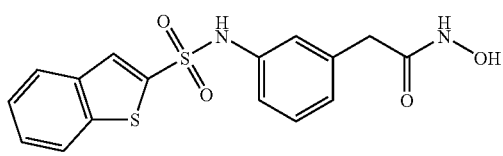 [SMILES: O=C(Cc1cccc(NS(=O)(=O)c2cc3ccccc3s2)c1)NO]

Sulfonyl Chloride: 2-Benzothiophenesulfonyl chloride

Amine: Methyl-3-aminophenyl acetate (1)

Yield: Step 1: 88%

Yield: Step 2: 89%

Yield: Step 3: 32%

¹H NMR (300 MHz, Acetoned₆); δ 10.20 (s, 1H), 7.99-7.95 (m, 3H), 7.53-7.43 (m, 2H), 7.35 (s, 1H), 7.21-7.17 (m, 2H), 7.06-7.03 (m, 1H), 3.38 (s, 2H)

Example 10

2-[4-(3,4-dichlorobenzenesulfonylamino)-phenyl]-N-hydroxy-acetamide (15)

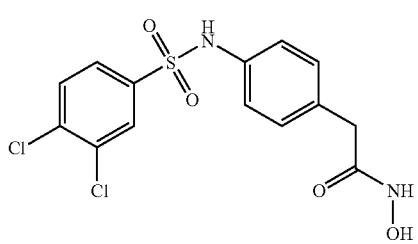 [SMILES: O=C(Cc1ccc(NS(=O)(=O)c2ccc(Cl)c(Cl)c2)cc1)NO]

Sulfonyl Chloride: 3,4-Dichlorobenzenesulfonyl chloride

Yield: Step 1: 80%

Yield: Step 2: 67%

Yield: Step 3: 81%

¹H NMR (300 MHz, acetone-d₆); δ 10.12 (s, 1H), 9.15 (s, 1H), 7.92 (s, 1H), 7.74-7.71 (m, 2H), 7.23 (d, 2H, J=9 Hz), 7.14 (d, 2H, J=9 Hz), 3.36 (s, 2H)

Example 11

2-[4-(2-Thiophenesulfonylamino)-phenyl]-N-hydroxy-acetamide (16)

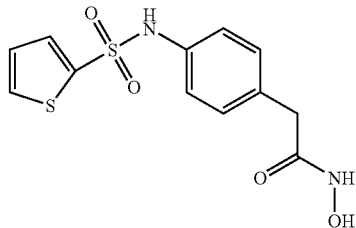 [SMILES: O=C(Cc1ccc(NS(=O)(=O)c2cccs2)cc1)NO]

Sulfonyl Chloride: 2-Thiophenesulfonyl chloride

Yield: Step 1: 84%

Yield: Step 2: 83%

Yield: Step 3: 9%

¹H NMR (300 MHz, acetone-d₆); δ 7.78 (s, 1H), 7.53 (s, 1H), 7.21 (s, 4H), 7.09 (s, 1H), 3.37 (s, 2H)

Example 12

2-[4-(3-nitrobenzenesulfonylamino)-phenyl]-N-hydroxy-acetamide (17)

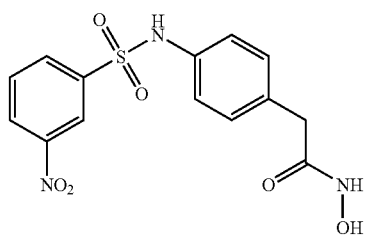 [SMILES: O=C(Cc1ccc(NS(=O)(=O)c2cccc([N+](=O)[O-])c2)cc1)NO]

Sulfonyl Chloride: 3-Nitrobenzenesulfonyl Chloride

Yield: Step 1: 47%

Yield: Step 2: 34%

Yield: Step 3: 16%

¹H NMR (300 MHz, acetone-d₆); δ 9.31 (s, 1H), 8.59 (s, 1H), 8.45 (d, 1H, J=8 Hz), 8.16 (d, 1H, J=8 Hz), 7.85 (t, 1H, J=8 Hz), 7.20-7.14 (m, 4H), 3.35 (s, 2H)

Example 13

2-[4-(8-quinolinesulfonylamino)-phenyl]-N-hydroxy-acetamide (18)

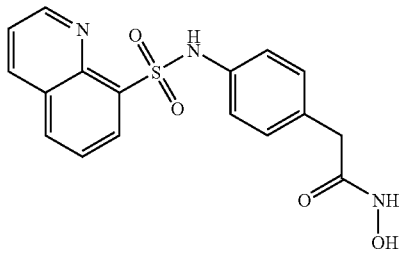 [SMILES: O=C(Cc1ccc(NS(=O)(=O)c2cccc3cccnc23)cc1)NO]

Sulfonyl Chloride: 8-quinolinesulfonyl chloride

Yield: Step 1: 83%
Yield: Step 2: 78%
Yield: Step 3: 42%
$^1$H NMR (300 MHz, acetone-$d_6$); δ 9.17 (s, 1H), 8.50 (d, 1H, J=8 Hz), 8.33 (d, 1H, J=8 Hz), 8.21 (d, 1H, J=8 Hz), 7.71-7.68 (m, 3H), 7.05 (broad s., 4H), 3.22 (s, 2H)

Example 14

2-[4-(4-bromobenzenesulfonylamino)-phenyl]-N-hydroxy-acetamide (19)

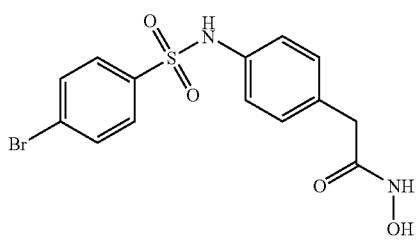 [SMILES: O=C(Cc1ccc(NS(=O)(=O)c2ccc(Br)cc2)cc1)NO]

Sulfonyl Chloride: 4-Bromobenzenesulfonyl chloride

Yield: Step 1: 80%
Yield: Step 2: 81%
Yield: Step 3: 48%
$^1$H NMR (300 MHz, acetone-$d_6$); δ 9.17 (s, 1H), 7.72 (s, 4H), 7.19-7.14 (m, 4H), 3.35 (s, 2H)

Example 15

N-Hydroxy-5-[3-benzenesulfonylamino)-phenyl]-pentanamide (26)

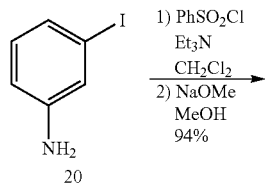

1) PhSO$_2$Cl
Et$_3$N
CH$_2$Cl$_2$
2) NaOMe
MeOH
94%

-continued

Pd(PPh$_3$)$_4$
pyrrolidine
rt 1 hr.

21 → 22 (99%)

TPAP
M.S. 4Å NMO
CH$_3$CN 1 hr.

Ph$_3$P=CHCO$_2$Et
CH$_3$CN, 50° C.
36%

23

LiOH
THF, H$_2$O
88%

24

H$_2$, Pd/C
MeOH

25

1. NH$_2$OTHP
EDC, HOBt
DMF
2. CSA, MeOH

26
Example 15

Step 1: 3-(benzenesulfonylamino)-phenyl iodide (21)

To a solution of 3-iodoaniline (5 g, 22.8 mmol), in CH$_2$Cl$_2$ (100 mL), were added at room temperature Et$_3$N (6.97 mL) followed by benzenesulfonyl chloride (5.84 mL). The mixture was stirred 4 h then a white precipitate was formed. A saturated aqueous solution of NaHCO$_3$ was added and the phases were separated. The aqueous layer was extracted several times with CH$_2$Cl$_2$ and the combined extracts were dried over (MgSO$_4$) then evaporated. The crude mixture was dissolved in MeOH (100 mL) and NaOMe (6 g), was added and the mixture was heated 1 h at 60° C. The solution became clear with time and HCl (1N) was added. The solvent was evaporated under reduced pressure then the aqueous phase was extracted several times with $CH_2Cl_2$. The combined organic extracts were dried over ($MgSO_4$) and evaporated. The crude material was purified by flash chromatography using (100% $CH_2Cl_2$) as solvent yielding the title compound 21 (7.68 g, 94%) as yellow solid.

$^1$H NMR: (300 MHz, $CDCl_3$): δ 7.82-7.78 (m, 2H), 7.60-7.55 (m, 1H), 7.50-7.42 (m, 4H), 7.10-7.06 (m, 1H), 6.96 (t, J=8 Hz, 1H), 6.87 (broad s, 1H).

Step 2: 3-(benzenesulfonylamino)-phenyl-propargylic alcohol (22)

To a solution of 21 (500 mg, 1.39 mmol) in pyrrolidine (5 mL) at room temperature was added $Pd(PPh_3)_4$ (80 mg, 0.069 mmol), followed by CuI (26 mg, 0.139 mmol). The mixture was stirred until complete dissolution. Propargylic alcohol (162 μL, 2.78 mmol) was added and stirred 6 h at room temperature. Then the solution was treated with a saturated aqueous solution of $NH_4Cl$ and extracted several times with AcOEt. The combined organic extracts were dried over ($MgSO_4$) then evaporated. The residue was purified by flash chromatography using hexane/AcOEt (1:1) as solvent mixture yielding 22 (395 mg, 99%) as yellow solid.

$^1$H NMR: (300 MHz, $CDCl_3$): δ 7.79-7.76 (m, 2H), 7.55-7.52 (m, 1H), 7.45 (t, J=8 Hz, 2H), 7.19-7.15 (m, 3H), 7.07-7.03 (m, 1H), 4.47 (s, 2H).

Step 3: 5-[3-(benzenesulfonylamino)-phenyl]-4-yn-2-pentenoate (23)

To a solution of 22 (2.75 g, 9.58 mmol) in $CH_3CN$ (150 mL) at room temperature were added 4-methylmorpholine N-oxide (NMO, 1.68 g, 14.37 mmol) followed by tetrapropylammonium perruthenate (TPAP, 336 mg, 958 mmol). The mixture was stirred at room temperature 3 h, and then filtrated through a Celite pad with a fritted glass funnel. To the filtrate carbethoxymethylenetriphenyl-phosphorane (6.66 g, 19.16 mmol) was added and the resulting solution was stirred 3 h at room temperature. The solvent was evaporated and the residue was dissolved in $CH_2Cl_2$ and washed with a saturated aqueous solution of $NH_4Cl$. The aqueous layer was extracted several times with $CH_2Cl_2$ then the combined organic extract were dried over ($MgSO_4$) and evaporated. The crude material was purified by flash chromatography using hexane/AcOEt (1:1) as solvent mixture giving 23 (1.21 g, 36%) as yellow oil.

$^1$H NMR: (300 MHz, $CDCl_3$): δ 7.81 (d, J=8 Hz, 2H), 7.56-7.43 (m, 3H), 7.26-7.21 (m, 3H), 7.13-7.11 (m, 1H), 6.93 (d, J=16 Hz, 1H), 6.29 (d, J=16 Hz, 1H), 4.24 (q, J=7 Hz, 2H), 1.31 (t, J=7 Hz, 3H).

Step 4: 5-[3-(benzenesulfonylamino)-phenyl]-4-yn-2-pentenic acid (24)

To a solution of 23 (888 mg, 2.50 mmol) in a solvent mixture of THF (10 mL) and water (10 mL) at room temperature was added LiOH (1.04 g, 25.01 mmol). The resulting mixture was heated 2 h at 60° C. and treated with HCl (1N) until pH 2. The phases were separated and the aqueous layer was extracted several times with AcOEt. The combined organic extracts were dried over ($MgSO_4$) then evaporated. The crude residue was purified by flash chromatography using $CH_2Cl_2$/MeOH (9:1) as solvent mixture yielding 24 (712 mg, 88%), as white solid.

$^1$H NMR: (300 MHz, DMSO-$d_6$): δ 7.78-7.76 (m, 2H), 7.75-7.53 (m, 3H), 7.33-7.27 (m, 1H), 7.19-7.16 (m, 3H), 6.89 (d, J=16 Hz, 1H), 6.33 (d, J=16 Hz, 1H).

Step 5: 5-[3-(benzenesulfonylamino)-phenyl]-pentanoic acid (25)

To a solution 24 (100 mg, 306 mmol), in MeOH (6 mL) at room temperature was added a solution of Pd/C (10%, 20 mg, 1 mL MeOH). The reaction mixture was degassed and purged several times with $H_2$ gas with a final pressure of 60 psi. The mixture was stirred 2 h at room temperature then the resulting solution was filtrated over a silica gel pad with a fritted glass funnel. The solvent was evaporated yielding 25 (68 mg, 96%) and it was used directly for the next step without further purification.

$^1$H NMR: (300 MHz, acetone-$d_6$): δ 7.81-7.78 (m, 2H), 7.56-7.46 (m, 3H), 7.11-7.01 (m, 3H), 6.87 (d, J=8 Hz, 1H), 2.49 (broad s, 2H), 2.25 (broad s, 2H), 1.52 (broad s, 4H)

Step 6: N-Hydroxy-5-[3-benzenesulfonylamino)-phenyl]-pentanamide (26)

To a solution of 25 (100 mg, 300 mmol) in DMF (10 mL) at room temperature were added 1-(3-dimethylaminopropyl)-3-ethyl-carbodiimide hydrochloride (EDC, 69 mg, 320 mmol), and 1-hydroxybenzotriazole hydrate (HOBT, 61 mg, 45 mmol). The mixture was stirred 20 min. at room temperature then $NH_2OTHP$ (53 mg, 45 mmol) was added. The resulting mixture was heated overnight at 50° C. The DMF solvent was evaporated under reduced pressure and the residue was dissolved in $CH_2Cl_2$ and washed with brine or a saturated aqueous solution of $NaHCO_3$. The combined organic extracts were dried over ($MgSO_4$) then evaporated. The crude compound was purified by flash chromatography using hexane/acetone (7:3) as solvent mixture. The residue was then dissolved in MeOH (20 mL) then 10-camphorsulfonic acid (CSA, 35 mg, 150 mmol) was added. The mixture was stirred 2 h at room temperature then the solvents were evaporated under reduced pressure at room temperature to avoid thermal decomposition. The crude mixture was purified by flash chromatography using $CH_2Cl_2$/MeOH (9:1) as solvent mixture giving 26 as a yellowish solid (62 mg, 60%).

$^1$H NMR: (300 MHz, acetone-$d_6$): δ=7.80-7.78 (m, 2H), 7.56-7.52 (m, 3H), 7.13-6.89 (m, 4H), 2.52 (broad s, 2H), 2.10 (broad s, 2H), 1.53 (broad s, 4H)

Example 16

N-Hydroxy-5-[4-(benzenesulfonylamino)-phenyl]-4-yn-2-pentanamide (32)

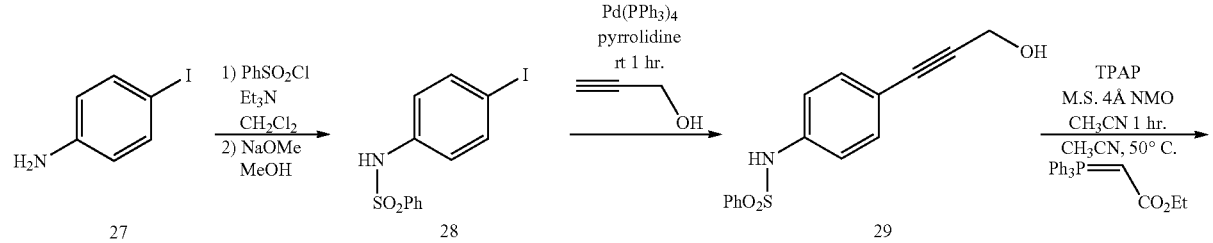

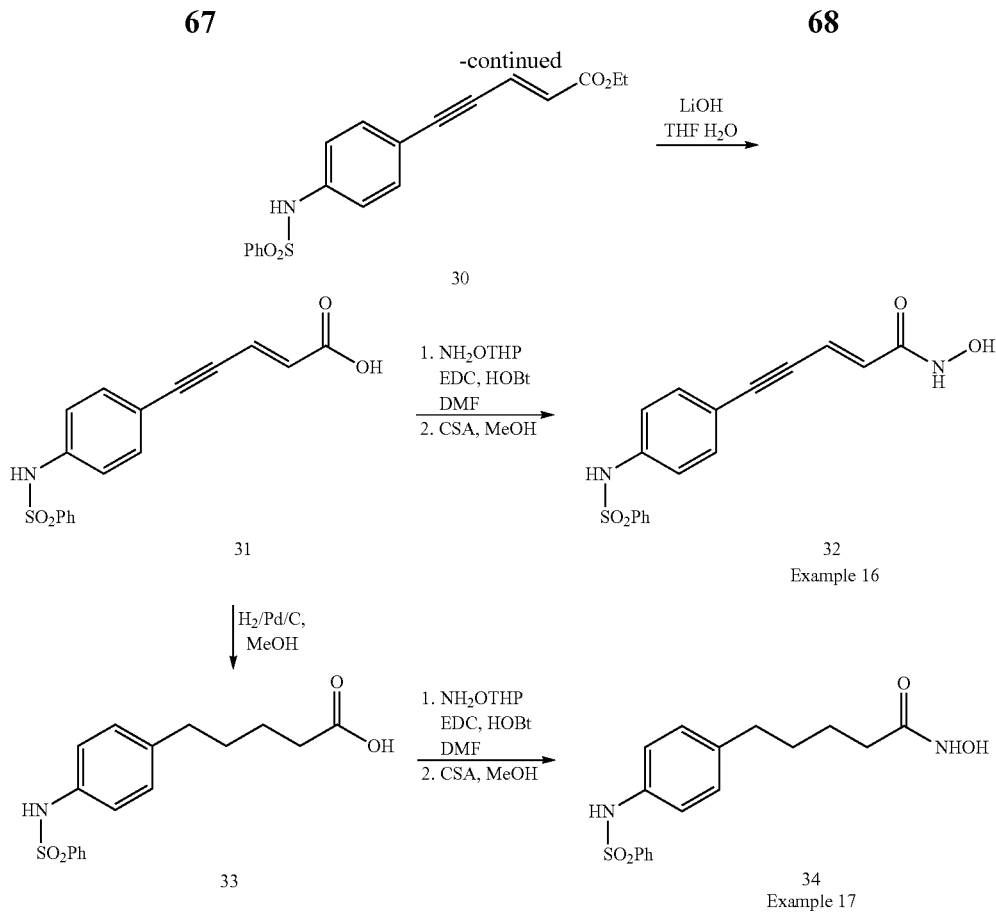

Step 1: 4-(benzenesulfonylamino)-phenyl iodide (28)
Compound 28 was prepared using the procedure described in Example 15, step 1, but substituting 4-iodoaniline for 3-iodoaniline.
Yield: 97%
$^1$H NMR: (300 MHz, CDCl$_3$): δ 9.15 (broad s, 1H), 7.82 (d, J=8 Hz, 2H), 7.68-7.51 (m, 5H), 7.05 (d, J=8 Hz, 2H).

Step 2: 4-(benzenesulfonylamino)-phenyl-propargylic alcohol (29)
Compound 29 was prepared using the procedure described in Example 15, step 2 but substituting compound 21 for compound 28.
Yield: 61%
$^1$H NMR: (300 MHz, acetone-d$_6$): δ 7.83-7.80 (m, 2H), 7.62-7.51 (m, 3H), 7.30 (d, J=8 Hz, 2H), 7.21 (d, J=8 Hz, 2H), 4.36 (s, 2H), 2.80 (broad s, 2H).

Step 3: 5-[4-(benzenesulfonylamino)-phenyl]-4-yn-2-pentenoate (30)
Compound 30 was prepared using the procedure described in Example 15, step 3 but substituting compound 22 for compound 29
Yield: 16%
$^1$H NMR: (300 MHz, CDCl$_3$): δ 7.81-7.78 (m, 2H), 7.59-7.43 (m, 3H), 7.34 (d, J=8 Hz, 2H), 7.05 (d, J=8 Hz, 2H), 6.93 (d, J=16 Hz, 1H), 6.26 (d, J=16 Hz, 1H), 4.23 (q, J=7 Hz, 2H), 1.30 (t, J=7 Hz, 3H).

Step 4: 5-[4-(benzenesulfonylamino)-phenyl]-4-yn-2-pentenic acid (31)
Compound 31 was prepared using the procedure described in Example 15 step 4 but substituting compound 23 for compound 30

Yield: 92%
$^1$H NMR: (300 MHz, acetone-d$_6$): δ 7.87-7.84 (m, 2H), 7.62 (m, 3H), 7.42 (d, J=8 Hz, 2H), 7.28 (d, J=8 Hz, 2H), 6.94 (d, J=16 Hz, 1H), 6.29 (d, J=16 Hz, 1H).

Step 5: N-hydroxy-5-[4-(benzenesulfonylamino)-phenyl]-4-yn-2-pentanamide (32)
Compound 32 was prepared using the procedure described in Example 15 step 6 but substituting compound 25 for compound 31
Yield: 78%
$^1$H NMR: (300 MHz, acetone-d$_6$): δ 7.84 (broad s, 2H), 7.60-7.55 (m, 3H), 7.38-7.30 (m, 4H), 6.84 (d, J=16 Hz, 1H), 6.40 (d, J=16 Hz, 1H).

Example 17

N-Hydroxy-5-[4-benzenesulfonylamino)-phenyl]-pentanamide (34)

Step 1: 5-[4-(benzenesulfonylamino)-phenyl]-pentanoic acid (33)
Compound 33 was prepared using the procedure described in Example 15 step 5 but substituting compound 24 for compound 31.
Yield: 100%
$^1$H NMR: (300 MHz, acetone-d$_6$): δ=7.78-7.75 (m, 2H), 7.56-7.46 (m, 3H), 7.16-7.05 (m, 4H), 2.52 (broad s, 2H), 2.29-2.25 (m, 2H), 1.56 (broad s, 4H).

Step 2: N-Hydroxy-5-[4-benzenesulfonylamino)-phenyl]-pentanamide (34)
Compound 34 was prepared using the procedure described in Example 15 step 6 but substituting compound 25 for compound 33.

Yield: 62%

$^1$H NMR: (300 MHz, acetone-$d_6$): δ 7.78-7.75 (m, 2H), 7.59-7.51 (m, 3H), 7.09 (broad s, 4H), 2.85 (broad s, 1H), 2.53 (broad s, 2H), 2.05 (broad s, 2H), 1.56 (broad s, 4H).

Example 18

N-Hydroxy-3-[4-(benzenesulfonylamino)-phenyl]-2-propenamide (36)

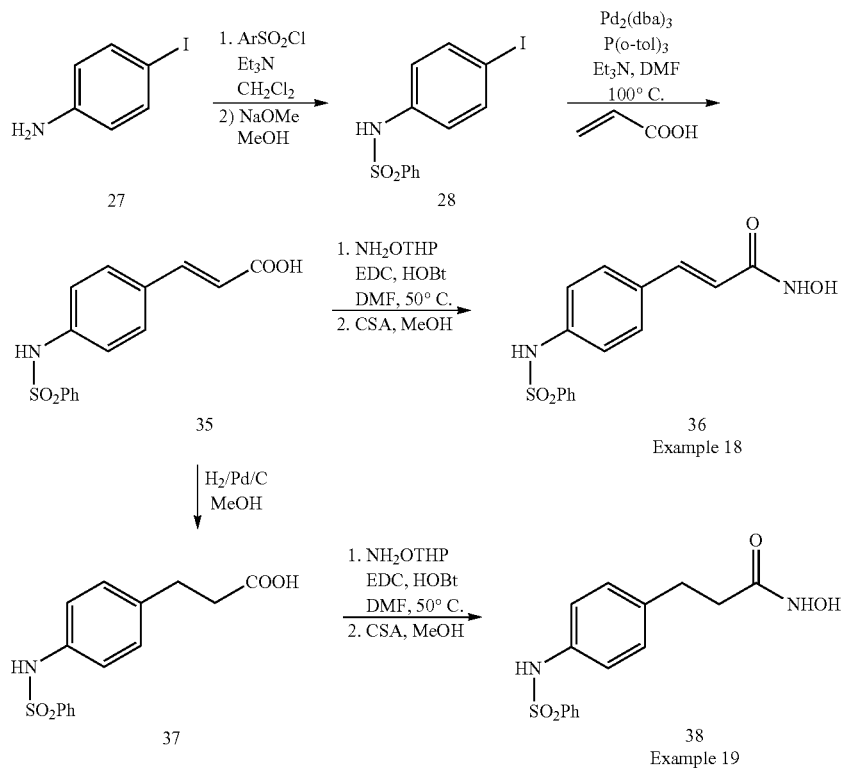

Step 1: 3-[4-(benzenesulfonylamino)-phenyl]-2-propenoic acid (35)

To a solution of 28 (500 mg, 1.39 mmol), in DMF (10 mL) at room temperature were added tris(dibenzylideneacetone)dipalladium(0) (Pd$_2$(dba)$_3$; 38 mg, 1.67 mmol), tri-o-tolylphosphine (P(o-tol)$_3$, 25 mg, 0.83 mmol), Et$_3$N (483 μμL, 3.48 mmol) and finally acrylic acid (84 μμL, 1.67 mmol). The resulting solution was degassed and purged several times with N$_2$ then heated overnight at 100° C. The solution was filtrated through a Celite pad with a fritted glass funnel then the filtrate was evaporated. The residue was purified by flash chromatography using CH$_2$Cl$_2$/MeOH (95:5) as solvent mixture yielding the title compound 35 (415 mg, 99%) as yellowish solid.

$^1$H NMR: (300 MHz, acetone-$d_6$): δ 7.88-7.85 (m, 2H), 7.62-7.55 (m, 6H), 7.29 (d, J=9 Hz, 2H), 6.41 (d, J=16 Hz, 1H), 2.95 (s, 1H), 2.79 (s, 1H).

Step 2: N-Hydroxy-3-[4-(benzenesulfonylamino)-phenyl]-2-propenamide (36)

To a solution of 35 (200 mg, 0.660 mmol) in DMF (10 mL) at room temperature were added 1-(3-Dimethylaminopropyl)-3-ethyl-carbodiimide hydrochloride (EDCI, 151 mg, 0.79 mmol), and 1-Hydroxybenzotriazole hydrate (HOBT, 134 mg, 0.99 mmol). The mixture was stirred 20 min. at room temperature then NH$_2$OTHP (116 mg, 0.99 mmol) was added. The resulting mixture was heated at 50° C. for 24 h then the DMF solvent was evaporated under reduced pressure and the residue was dissolved in CH$_2$Cl$_2$, washed with a saturated aqueous solution of NaHCO$_3$. The combined organic extracts were dried over (MgSO$_4$) then condensed. The crude compound was purified by flash chromatography using Hexane/acetone (7:3) as solvent mixture. The residue was then dissolved in MeOH (10 mL) then 10-camphorsulfonic acid (CSA, 77 mg, 0.33 mmol) was added. The mixture was stirred 2 h at room temperature then the solvents were evaporated under reduced pressure at room temperature to avoid thermal decomposition. The crude product was purified by flash chromatography using CH$_2$Cl$_2$/MeOH (9:1) as solvent mixture giving compound 36 (116 mg, 55%) as a orange solid.

$^1$H NMR: (300 MHz, acetone-$d_6$): δ 7.85-7.83 (m, 2H), 7.64-7.47 (m, 6H), 7.26 (d, J=8 Hz, 2H), 6.48 (m, 1H), 2.82 (s, 1H), 2.79 (s, 1H).

Example 19

N-Hydroxy-3-[4-(benzenesulfonylamino)-phenyl]-2-propanamide (38)

Step 1: 3-[4-(benzenesulfonylamino)-phenyl]-2-propionic acid (37)

To a solution of 35 (350 mg, 1.16 mmol) in MeOH (15 mL) at room temperature was added a solution of Pd/C 10% (50 mg. in MeOH ~3 mL). Then the resulting solution was purged several times with H$_2$ with a final pressure of 60 psi. The solution was stirred 4 h then filtrated through a Celite pad with a fritted glass funnel. The filtrate was evaporated and the residue compound 37 was pure enough to use for the next step without further purification.

¹H NMR: (300 MHz, acetone-d₆): δ 8.92 (broad s, 1H), 7.79-7.76 (m, 2H), 7.60-7.47 (m, 3H), 7.12 (s, 4H), 3.32 (s, 1H), 2.81 (t, J=8 Hz, 2H), 2.53 (t, J=8 Hz, 2H).

Step 2: N-Hydroxy-3-[4-(benzenesulfonylamino)-phenyl]-2-propanamide (38)

To a solution of 37 (1.16 mmol) in DMF (10 mL) at room temperature were added 1-(3-Dimethylaminopropyl)-3-ethyl-carbodiimide hydrochloride (EDC, 266 mg, 1.39 mmol), and 1-Hydroxybenzotriazole hydrate (HOBT, 235 mg, 1.74 mmol). The mixture was stirred 20 min. at room temperature then NH₂OTHP (204 mg, 1.74 mmol) was added. The resulting mixture was heated at 50° C. for 24 h then the DMF solvent was condensed under reduced pressure and the residue was dissolved in CH₂Cl₂, washed with a saturated aqueous solution of NaHCO₃. The combined organic extracts were dried over (MgSO₄) then evaporated. The crude compound was purified by flash chromatography using Hexane/acetone (7:3) as solvent mixture. The residue was then dissolved in MeOH (10 mL) then 10-camphorsulfonic acid (CSA, 135 mg, 0.58 mmol) was added. The mixture was stirred 2 h at room temperature then the solvents were evaporated under reduced pressure at room temperature to avoid thermal decomposition. The crude was purified by flash chromatography using CH₂Cl₂/MeOH (9:1) as solvent mixture giving the title compound 38 (237 mg, 64%, for the last 3 steps) as a yellow solid.

¹H NMR: (300 MHz, acetone-d₆): δ 8.91 (broad s, 1H), 7.78-7.76 (m, 2H), 7.57-7.51 (m, 3H), 7.10 (broad s, 4H), 2.82 (broad s, 2H), 2.34 (broad s, 2H), 1.07 (s, 1H), 0.85 (s, 1H).

Example 20

N-Hydroxy-4-[4-(benzenesulfonylamino)-phenyl]-butanamide (42)

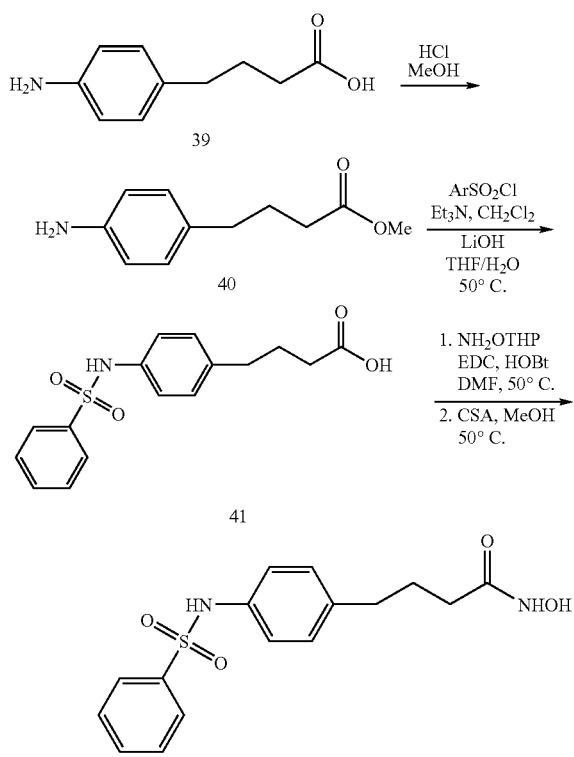

42
Example 20

Step 1: Methyl-4-(4-aminophenyl)-butanoate (40)

To a solution of 4-(4-aminophenyl)-butyric acid (5 g, 27.90 mmol) in MeOH (100 mL) at room temperature was added HCl conc. (37% 15 mL). The resulting mixture was stirred overnight at 50° C. then treated with a saturated aqueous solution NaHCO₃ and Na₂CO₃ solid until pH 9. The solvent was evaporated under reduced pressure then the aqueous phase was extracted several times with CH₂Cl₂. The crude material was purified by flash chromatography using CH₂Cl₂/MeOH as solvent mixture yielding 40 (4.93 g, 91%) as orange solid.

¹H NMR: (300 MHz, acetone-d₆): δ 6.89 (d, J=8 Hz, 2H), 6.59 (d, J=8 Hz, 2H), 4.40 (broad s, 1H), 3.60 (s, 3H), 2.48 (t, J=7 Hz, 2H), 2.28 (t, J=7 Hz, 2H), 1.82 (qt, J=7 Hz, 2H).

Step 2: 4-[4-(benzenesulfonylamino)-phenyl]-butyric acid (41)

To a solution of 40 (500 mg, 2.59 mmol) in CH₂Cl₂ at room temperature were added Et₃N (901 µµL, 6.48 mmol) followed by benzenesulfonyl chloride (661 µL, 5.18 mmol). The mixture was stirred overnight at room temperature then treated with a saturated aqueous solution of NH₄Cl. The phases were separated and the organic layer was extracted several times with CH₂Cl₂. The combined organic extracts were dried over (MgSO₄) then evaporated under reduced pressure. The residue was dissolved in a solvent mixture of THF (25 mL) and water (25 mL) then LiOH (1.08 g, 25.9 mmol) was added. The mixture was heated at 50° C. for 1 h then treated with HCl (1N) until pH2. The phases were separated and the aqueous layer was extracted several times with AcOEt. The combined organic extracts were dried over (MgSO₄) then evaporated. The crude was purified by flash chromatography using CH₂Cl₂/MeOH (95:5) as solvent mixture yielding 41 (800 mg, 96%) as a white solid ¹H NMR: (300 MHz, CDCl₃): δ 8.82 (1H, s broad), 7.77-7.74 (2H, m), 7.55-50 (1H, m), 7.44-7.39 (2H, m), 7.05-6.97 (4H, m), 2.58 (2H, t, J=7 Hz), 2.31 (2H, t, J=7 Hz), 2.17 (1H, s), 1.94-1.84 (2H, m).

Step 3: N-Hydroxy-4-[4-(benzenesulfonylamino)-phenyl]-butanamide (42)

To a solution 41 (800 mg, 2.59 mmol) in DMF (20 mL) at room temperature were added 1-(3-Dimethylaminopropyl)-3-ethyl-carbodiimide hydrochloride (EDC, 593 mg, 3.12 mmol), and 1-Hydroxybenzotriazole hydrate (HOBT, 524 mg, 3.89 mmol). The mixture was stirred 20 min. at room temperature then NH₂OTHP (455 mg, 3.89 mmol) was added. The resulting mixture was heated at 50° C. for 24 h then the DMF solvent was evaporated under reduced pressure and the residue was dissolved in CH₂Cl₂, washed with a saturated aqueous solution of NaHCO₃. The combined organic extracts were dried over (MgSO₄) then evaporated. The crude compound was purified by flash chromatography using Hexane/acetone (7:3) as solvent mixture. The residue was then dissolved in MeOH (30 mL) then 10-camphorsulfonic acid (CSA, 300 mg, 1.30 mmol) was added. The mixture was stirred 2 h at 50° C. then the solvents were condensed under reduced pressure at room temperature to avoid thermal decomposition. The crude was purified by flash chromatography using CH₂Cl₂/MeOH (9:1) as solvent mixture giving the title compound 42 (115 mg, 13%) as a yellowish solid.

¹H NMR: (300 MHz, CDCl₃): δ 7.79-7.76 (m, 2H), 7.61-7.48 (m, 3H), 7.13-7.05 (m, 4H), 2.83 (broad s, 1H), 2.53 (t, J=7 Hz, 2H), 2.14-2.04 (m, 2H), 1.83 (t, J=7 Hz, 2H).

Example 21

N-Hydroxy-4-(3-oxo-3-phenylpropenyl)-benzamide (45)

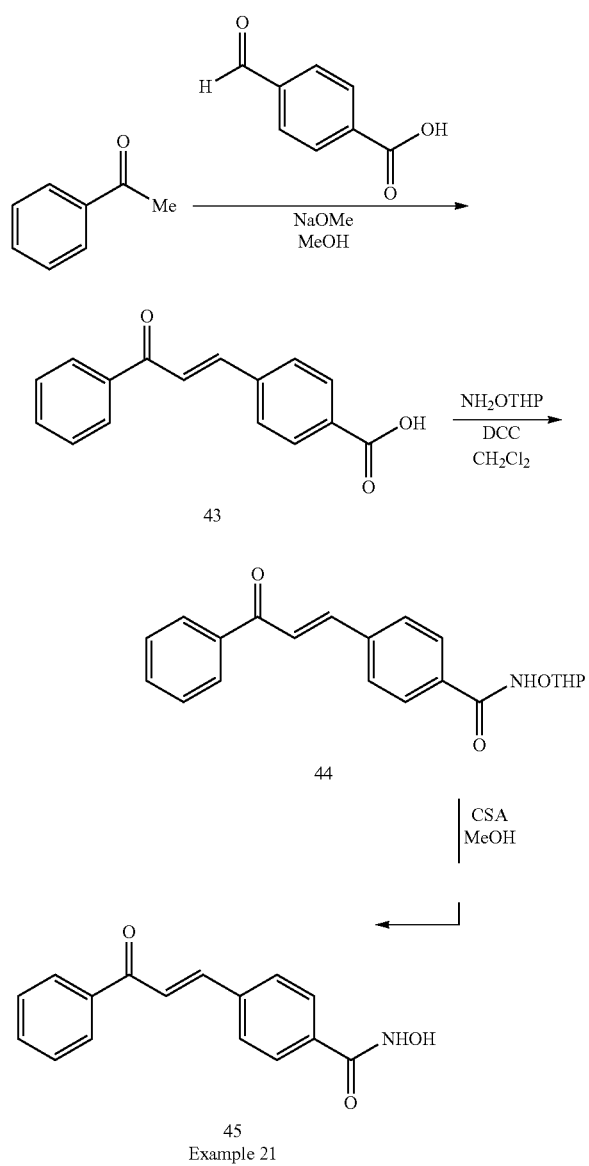

Example 21

Step 1: 4-(3-oxo-3-phenylpropenyl)-benzoic acid (43)

Sodium methoxide (1.8 g, 33.3 mmol) was added to a stirred suspension of 4-carboxybenzaldehyde (2.5 g, 16.6 mmol) and acetophenone (2.0 g uL, 16.6 mmol) in methanol (50 mL) at room temperature. The mixture was stirred at room temperature for 16 hours, and half of the volume of methanol was removed under reduced pressure. The mixture was poured into HCl 1M (50 mL) (until pH=2) and ethyl acetate was added. The separated aqueous layer was extracted with ethyl acetate (3×30 mL) dried (MgSO$_4$ anh.), filtered and evaporated. The residue was triturated with dichloromethane-hexanes (1:1) to afford 3 g of 43 (72% yield).

$^1$H NMR (300 MHz, CDCl$_3$); δ 7.50-7.87 (m, 7H), 8.04 (d, 2H, J=8 Hz), 8.16 (d, 2H, J=8 Hz)

Step 2: 4-(3-oxo-3-phenylpropenyl)-N—(O-tetrahydropyranyl)-benzamide (44)

The carboxylic acid 43 (260 mg, 1.0 mmol) was dissolved in anhydrous CH$_2$Cl$_2$ (10 mL) and DCC (256 mg, 1.2 mmol) followed by NH$_2$OTHP (145 mg, 1.2 mmol) were added. The mixture was allowed to stir at room temperature for 2 h. Added NH$_4$Cl sat. and extracted with EtOAc. The organic layer was dried over MgSO$_4$, filtered and the solvent was evaporated under vacuum. (Purification by column chromatography using 1% MeOH/CH$_2$Cl$_2$ give the title compound which was used directly in the next step.

Step 3: N-Hydroxy-4-(3-oxo-3-phenylpropenyl)-benzamide (45)

The protected hydroxamic acid 44 (234 mg, 0.67 mmol) was dissolved in MeOH (7 mL) then CSA (31 mg, 0.13 mmol) was added. The mixture was allowed to stir at reflux for 2 hours or until the reaction was complete by TLC. Added HCl 1N, extracted with EtOAc, dried the organic layer over anhydrous MgSO$_4$ and filtered. The solvent was evaporated under vacuum. Purification by column chromatography using 5% MeOH/CH$_2$Cl$_2$, gave the title compound.

$^1$H NMR (300 MHz, DMSO-d$_6$), δ 7.53-8.20 (m, 11H); 9.12 (br. s, 1H); 11.35 (br. s, 1H)

Example 22

N-Hydroxy-4-(3-oxo-3-phenylpropyl)-benzamide (50)

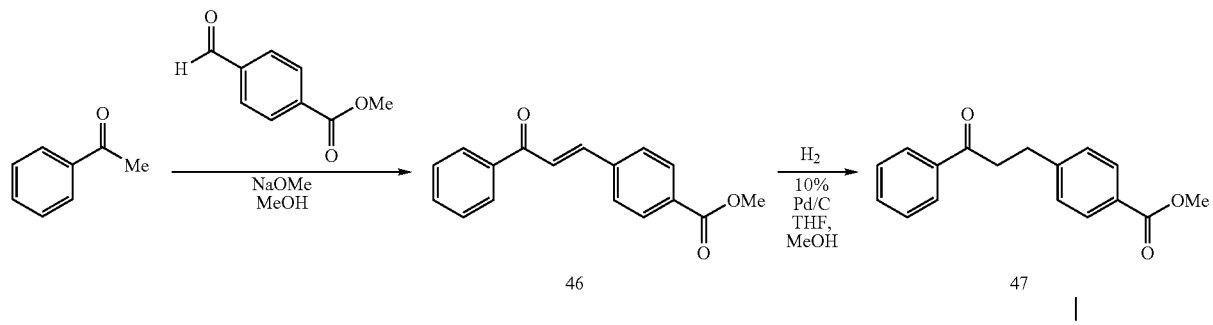

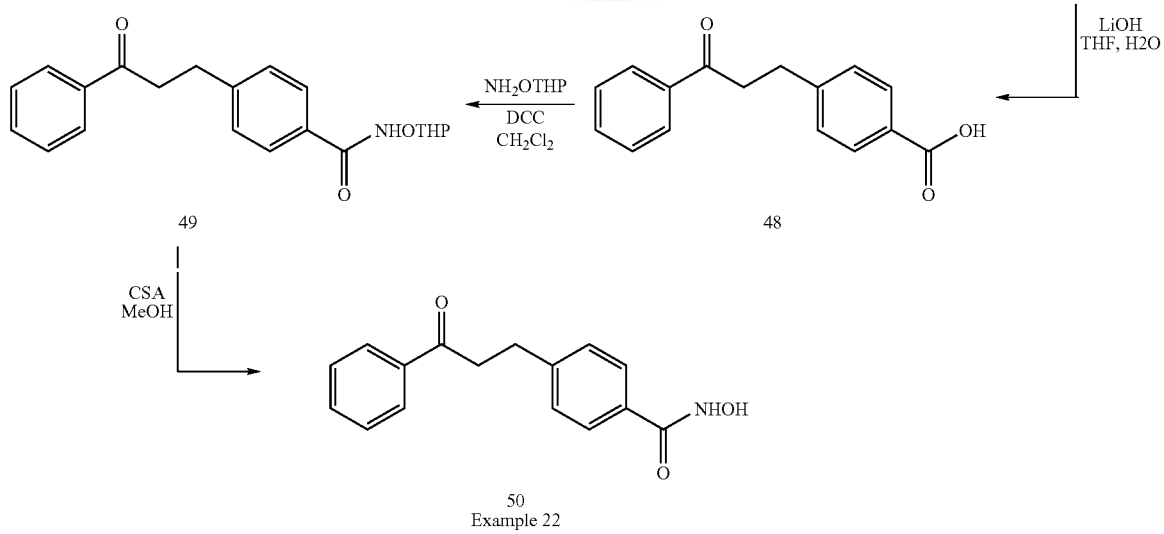

49

48

50
Example 22

Step 1: Methyl-4-(3-oxo-3-phenylpropenyl)-benzoate (46)

To 4-carbomethoxybenzaldehyde (79 mg, 0.48 mmol) and acetophenone (56 L, 0.48 mmol) in anhydrous methanol (1.6 mL), was added neat sodium methoxide (26 mg, 0.48 mmol). The mixture was stirred at room temperature overnight then heated to reflux for 1 hour, cooled down to room temperature and added HCl 1N and EtOAc. The layers were separated and the organic layer dried over anhydrous $MgSO_4$ and filtered. The solvent was evaporated under vacuum to afford a yellow solid, which was recrystallized from acetonitrile/water to give a pale yellow crystalline solid.

$^1$H NMR (300 MHz, $CDCl_3$); δ 3.95 (s, 3H), 7.50-8.12 (m, 11H)

Step 2: Methyl-4-(3-oxo-3-phenylpropyl)-benzoate (47)

The aromatic enone 46 (321 mg, 1.20 mmol) was dissolved in anhydrous THF (6 mL) and anhydrous MeOH (6 ml). Added 2 small scoops of Pd 10% on activated C, placed under an atmosphere of hydrogen and allowed to stir for 2 hours at room temperature. Purged with nitrogen, filtered through Celite and removed solvent by evaporation under vacuum. The benzylic alcohol is reoxidized to the ketone by the following procedure. The crude was taken back in anhydrous $CH_2Cl_2$ (10 mL), with 3 Å molecular sieves, TPAP (1 scoop) was added followed by NMO (212 mg, 1.8 mmol). Stirred at room temperature for 30 minutes and filtered through a plug of silica gel. Solvent was evaporated under vacuum and purified by column chromatography using 10% EtOAc/Hexane.

$^1$H NMR (300 MHz, $CDCl_3$); δ 3.14 (t, 2H), 3.34 (t, 2H), 3.90 (s, 3H), 7.30-7.60 (m, 6H), 7.92-7.99 (m, 4H).

Step 3: 4-(3-oxo-3-phenylpropyl)-benzoic acid (48)

To a solution of methyl ester 47 (195 mg, 0.73 mmol) in water/THF (1:1, 0.07M) was added LiOH (46 mg, 1.1 mmol). The resulting solution was stirred overnight at room temperature or until no starting material was detected by TLC. HCl 1N was added and the solution was extracted with EtOAc and the organic layer was dried over anhydrous $MgSO_4$. Filtration and evaporation of the solvent under vacuum followed by purification by column chromatography using 10% MeOH/ $CH_2Cl_2$, gave the title compound.

$^1$H NMR (300 MHz, $CDCl_3$); δ 3.16 (t, 2H), 3.36 (t, 2H), 7.33-7.60 (m, 5H), 7.93-8.06 (m, 4H).

Step 4: N-hydroxy-4-(3-oxo-3-phenylpropyl)-benzamide (50)

Following the procedure described in Example 21, Steps 2-3, but substituting compound 48 for carboxylic acid 4, the title compound was obtained.

$^1$H NMR (300 MHz, DMSO-$d_6$); δ 2.97 (t, 2H), 3.38 (t, 2H), 7.34 (d, 2H, J=8 Hz), 7.45-7.70 (m, 5H), 7.96 (dd, 2H, J=8 Hz, 1 Hz), 11.14 (br. s, 1H)

Example 23

N-Hydroxy-4-(3-oxo-3-phenyl-1-hydroxypropyl)-benzamide (53)

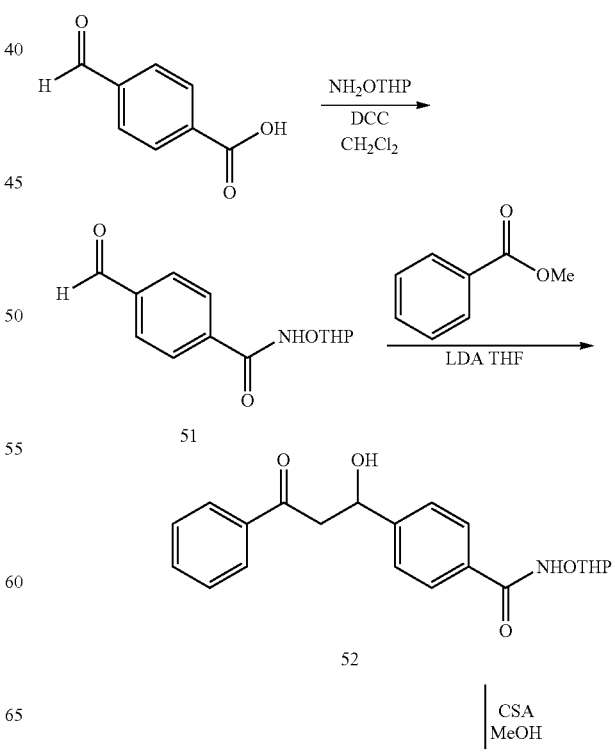

51

52

-continued

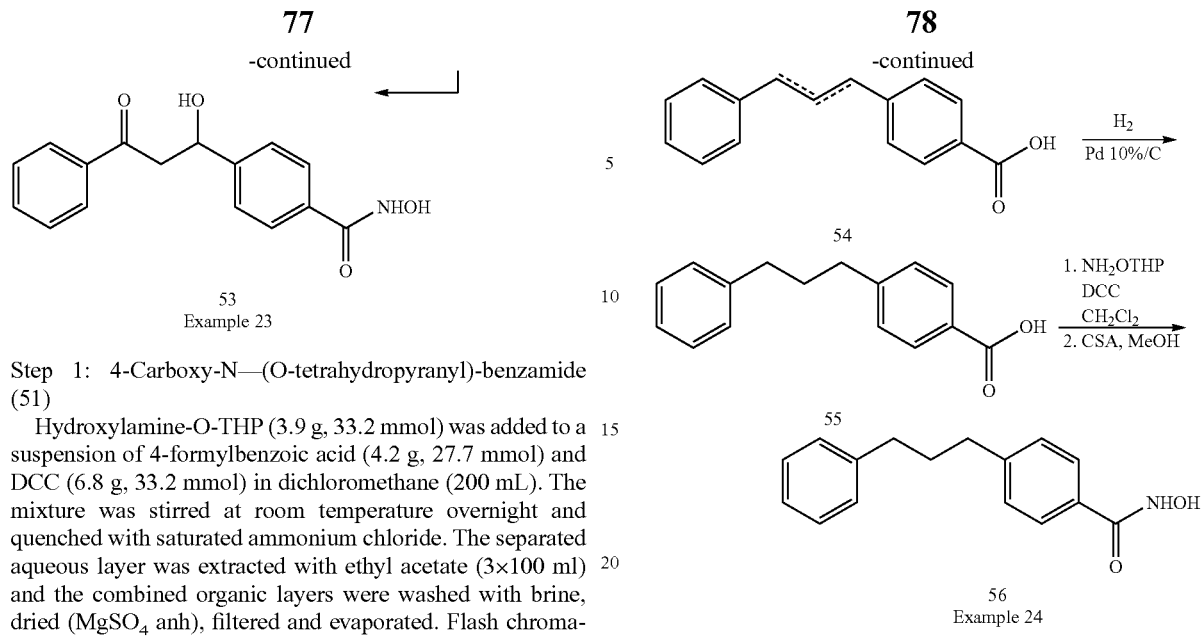

53
Example 23

Step 1: 4-Carboxy-N—(O-tetrahydropyranyl)-benzamide (51)

Hydroxylamine-O-THP (3.9 g, 33.2 mmol) was added to a suspension of 4-formylbenzoic acid (4.2 g, 27.7 mmol) and DCC (6.8 g, 33.2 mmol) in dichloromethane (200 mL). The mixture was stirred at room temperature overnight and quenched with saturated ammonium chloride. The separated aqueous layer was extracted with ethyl acetate (3×100 ml) and the combined organic layers were washed with brine, dried (MgSO$_4$ anh), filtered and evaporated. Flash chromatography of the residue (10% methanol in CH$_2$Cl$_2$), afforded (51).

$^1$H NMR (300 MHz, CDCl$_3$); δ ppm. 10.04 (s, 1H), 8.95 (s, 1H), 7.99 (d, 2H, J=7.0 Hz), 7.93 (d, 2H, J=7.0 Hz), 5.1 (s, 1H), 3.60 (m, 2H), 1.60 (m, 6H)

Step 2: 4-(3-oxo-3-phenyl-1-hydroxypropyl)-N—(O-tetrahydropyranyl)-benzamide (52)

n-BuLi (1.4M/hexane, 1.6 mL, 2.2 mmol) was added to a 0° C. solution of diisopropylamine (337 µL, 2.4 mmol) in anhydrous THF (15 mL). Stirred at 0° C. 10 minutes, then cooled to −78° C. Added acetophenone, then stirred 30 minutes at −78° C. Cannulated into a −78° C. solution of the aldehyde 9 (50 mg, 2.0 mmol) in anhydrous THF (10 mL). Stirred 3 hours at −78° C., then added NH$_4$Cl. Warmed to room temperature, extracted with EtOAc, dried over MgSO$_4$, filtered and evaporated solvent under vacuum. Purification by HPLC CH$_3$CN:H$_2$O: TFA 0.1%; 10-95% gave the title compound 52.

Step 3: N-Hydroxy-4-(3-oxo-3-phenyl-1-hydroxypropyl)-benzamide (53)

Following the same procedure as described in Example 21, Step 3, but substituting compound 52 for compound 44, the title compound was obtained.

$^1$H NMR (300 MHz, DMSO-d$_6$); δ 3.20 (dd, 1H, J=4 Hz, J=16 Hz), 3.42 (dd, 1H=16 Hz, 8 Hz), 5.20 (m, 1H), 7.44-8.18 (m, 9H), 11.15 (br. s, 1H), 11.32 (br. s, 1H)

Example 24

N-Hydroxy-4-(3-phenylpropyl)-benzamide (56)

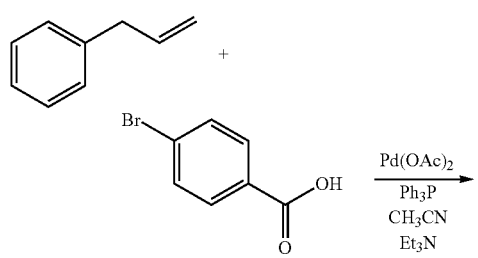

Step 1: 4-(3-phenylpropenyl)-benzoic acid/4-(3-phenyl-2-propenyl)-benzoic acid (54)

Allylbenzene (255 µµL, 1.9 mmol), 4-bromobenzoic acid (523 mg, 2.6 mmol), Et$_3$N (0.91 mL, 6.5 mmol), Palladium (II) Acetate (16 mg, 0.052 mmol), triphenylphosphine (60 mg, 0.21 mmol) and acetonitrile (5 mL) were stirred at reflux overnight in a round bottom flask. Added HCl 1N, extracted with EtOAc, dried the organic layer on anhydrous MgSO$_4$, filtered, evaporated solvent under vacuum. Purified by column chromatography using 10% MeOH/CH$_2$Cl$_2$ yielded 90 mg (14%) of mixture of two regioisomers 54. The mixture was then submitted for hydrogenation without further characterization.

Step 2: 4-(3-phenylpropyl)-benzoic acid (55)

A mixture of regioisomeric olefins 54 (100 mg, 0.42 mmol) and Pd 10% on C (10 mg) in methanol (4 mL) was vigorously stirred under H$_2$ atmosphere (14 psi). The mixture was stirred for 2 hours at room temperature, filtered through Celite and evaporated to afford 55 as an oil. Flash chromatography of the residue gave 55 (88 mg, 88%).

$^1$H NMR (300 MHz, CDCl$_3$); δ ppm 8.10 (d, 2H, J=8.0 Hz), 7.35 (m, 7H), 2.73 (m, 4H), 2.00 (m, 2H)

Step 3: N-Hydroxy-4-(3-phenylpropyl)-benzamide (56)

Following the same procedure as described in Example 21, Steps 2-3, but substituting compound 55 for compound 43, the title compound was obtained as a beige solid. (24 mg, 26% yield)

$^1$H NMR (300 MHz, CD$_3$OD); δ (ppm) 7.63 (d, 2H, J=8.0 Hz); 7.38-7.05 (m, 7H), 2.63 (m, 4H), 1.91 (m, 2H)

Example 25

N-Hydroxy-4-(4-phenylbutyl)-benzamide (61)

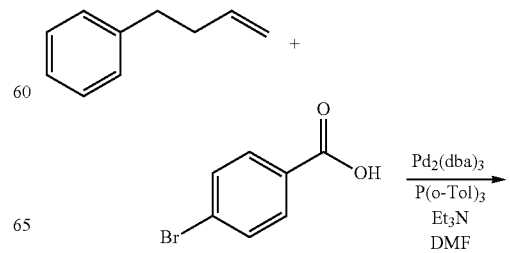

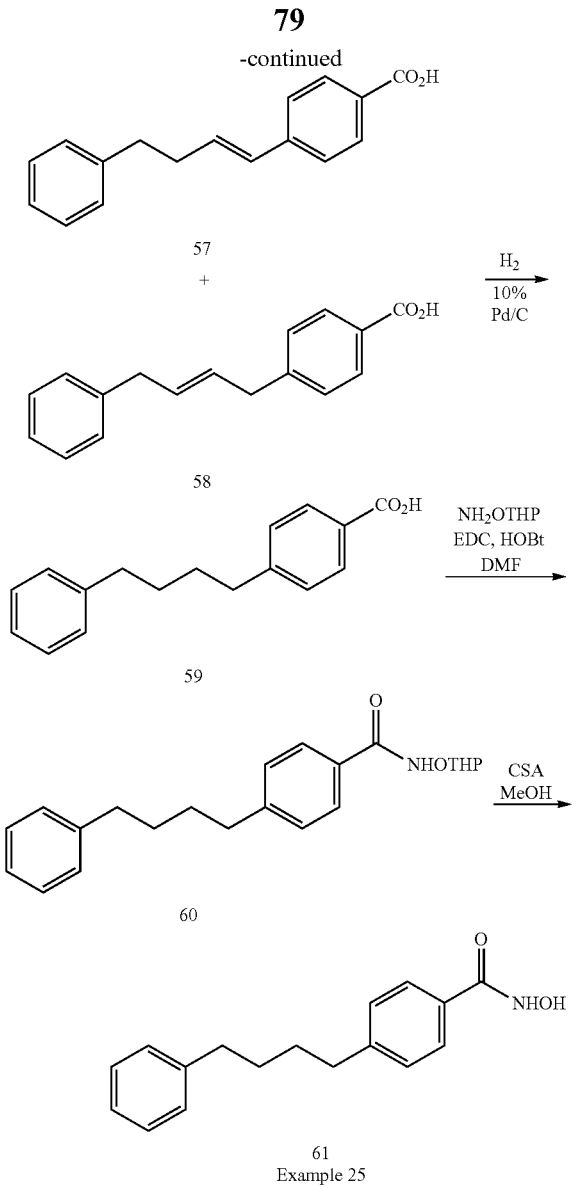

Example 25

Step 1: 4-(1-butenyl-4-phenyl)-benzoic acid/4-(2-butenyl-4-phenyl)-benzoic acid (57/58)

Under nitrogen atmosphere in a 25 mL round bottomed flask were mixed: 4-phenyl-1-butene (568 μL, 3.8 mmol), 4-bromobenzoic acid (634 mg, 3.2 mmol), tris(dibenzylideneacetone)dipalladium(0) (87 mg, 0.1 mmol), tri-o-tolylphosphine (58 mg, 0.2 mmol), triethylamine (1.1 mL, 7.9 mmol) in N,N-dimethylformamide (7 mL, 0.5 M solution). The mixture was stirred for 22 hours at 100° C. Then, the resulting suspension was cooled to room temperature, filtered through Celite and rinsed with ethyl acetate. The filtrate was acidified with 1N HCl, the phases were separated and the aqueous layer was extracted with ethyl acetate. The combined organic layers were washed with water, brine, dried over MgSO$_4$, filtered and concentrated. The resulting solid was triturated with hexane:dichloromethane (9:1) to give 367 mg (46%) of beige solid 57/58.

$^1$H NMR (300 MHz, (CD$_3$)$_2$CO): δ (ppm) 2.50-2.60 (m, 2H), 2.80 (t, 2H, J=9.0 Hz), 6.40-6.50 (m, 2H), 7.12-7.35 (m, 5H), 7.41 (d, 2H, J=9.0 Hz), 7.92 (d, 2H, J=9.0 Hz).

Step 2: 4-(4-phenylbutyl)-benzoic acid (59)

Following the procedure described in Example 24, Step 2, but substituting compound 57/58 for compounds 54, the title compound was obtained as a white solid in 92% yield.

$^1$H NMR (300 MHz, CD$_3$OD); δ (ppm) 1.60-1.75 (m, 4H), 2.65 (t, 2H, J=9.0 Hz), 2.72 (t, 2H, J=9.0 Hz), 7.12-7.30 (m, 5H), 7.33 (d, 2H, J=9.0 Hz), 7.96 (d, 2H, J=9.0 Hz)

Step 3: 4-(4-phenylbutyl)-N—(O-tetrahydropyranyl)-benzamide (60)

Under nitrogen atmosphere in a 25 mL round bottomed flask, to 4-(4-phenylbutyl)benzoic acid 59 (341 mg, 1.3 mmol) in 5 mL of N,N-dimethylformamide (0.3 M solution) was added the 1-(3-dimethylaminopropyl)-3-ethylcarbodiimide hydrochloride (308 mg, 1.6 mmol) and the 1-hydroxybenzotriazole hydrate (272 mg, 2.0 mmol) at room temperature. The mixture was stirred for 30 minutes then, the 2-(tetrahydropyranyl)hydroxylamine (235 mg, 2.0 mmol) was added and the mixture was stirred for 4 days. The N,N-dimethylformamide was removed under vacuum, the resulting oil was dissolved in ethyl acetate, washed with water and brine, dried over MgSO$_4$, filtered and concentrated to give 95% yield of crude title compound 60.

$^1$H NMR (300 MHz, CD$_3$OD); δ (ppm) 1.50-1.75 (m, 10H), 2.65 (t, 2H, J=9.0 Hz), 2.72 (t, 2H, J=9.0 Hz), 3.51 (d, 1H, J=15 Hz), 4.05 (t, 1H, J=15 Hz), 5.05 (s, 1H), 7.10-7.35 (m, 7H), 7.75 (d, 2H, J=9.0 Hz), 10.60 (s, 1H)

Step 4: N-Hydroxy-4-(4-phenylbutyl)-benzamide (61)

Under nitrogen atmosphere, to the crude oil in a 25 mL round bottomed flask, were added 5 mL of methyl alcohol (0.3 M solution) and camphorsulfonic acid (333 mg, 1.4 mmol). The mixture was stirred for 2 hours at room temperature. The methyl alcohol was removed under vacuum without heating and the resulting oil was purified by flash chromatography eluting methyl alcohol and dichloromethane (1:19). The solid was with hexane:dichloromethane (9:1) to give 212 mg (59%) of beige solid 61.

$^1$H NMR (300 MHz, (CD$_3$)$_2$CO): δ 1.66 (m, 4H), 2.65 (t, 2H, J=7.2 Hz), 2.70 (t, 2H, J=7.1 Hz), 7.15-7.31 (m, 7H), 7.75 (d, 2H, J=7.8 Hz), 8.18 (broad s, 1H), 10.68 (broad s, 1H).

$^{13}$C NMR (75.46 MHz, (CD$_3$)$_2$CO): δ 31.6 (t), 31.8 (t), 36.1 (t), 36.2 (t), 2×126.4 (d), 127.8 (d), 2×129.1 (d), 2×129.2 (d), 2×129.3 (d), 130.6 (s), 143.3 (s), 147.3 (s), 165.9 (s).

Example 26

N-Hydroxy-3-(3-phenylpropyl)-benzamide (64)

Step 1: 3-(3-phenylpropenyl)-benzoic acid (62)

Following the same procedure as described in Example 24, step 1, but substituting 4-bromobenzoic acid for 3-bromobenzoic acid, the title compound was obtained as mixture of olefins. The mixture was submitted to the next step without purification.

$^1$H NMR (300 MHz, CDCl$_3$); δ (ppm); 3.6 (dd, 2H, CH$_2$); 6.4 (dd, 2H, vinylic); 7.0-7.5 (m, 8H, CHAr); 8.0 (s, 1H, CHAr)

Step 2: 3-(3-phenylpropyl)-benzoic acid (63)

Following the same procedure as described in Example 24, Step 2, but substituting compound 62 for compound 54, the title compound was obtained in 52% yield and submitted to the next step without further purification.

$^1$H NMR (300 MHz, CDCl$_3$); δ (ppm): 2.0 (m, 2H, CH$_2$); 2.7 (m, 4H, 2CH$_2$); 7.0-7.4 (m, 8H, CHAr); 8.0 (s, 1H, CHAr)

Step 3: N-Hydroxy-3-(3-phenylpropyl)-benzamide (64)

Following the procedure described in Example 25, Step 3-4, but substituting compound 63 for compound 59, the title compound was obtained. Purification by flash chromatography using CH$_2$Cl$_2$:MeOH (9.5:0.5) gave compound 64 in 20% yield.

$^1$H NMR (300 MHz, DMSO-d$_6$); δ 1.8 (m, 2H, CH$_2$); 2.8 (m, 4H, CH$_2$); 7.0-7.4 (m, 7H, CHAr); 7.6 (s, CHAr); 9.0 (s, NH); 11.2 (s, OH)

Example 27

N-Hydroxy-3-(2-phenylethyl)-benzamide (68)

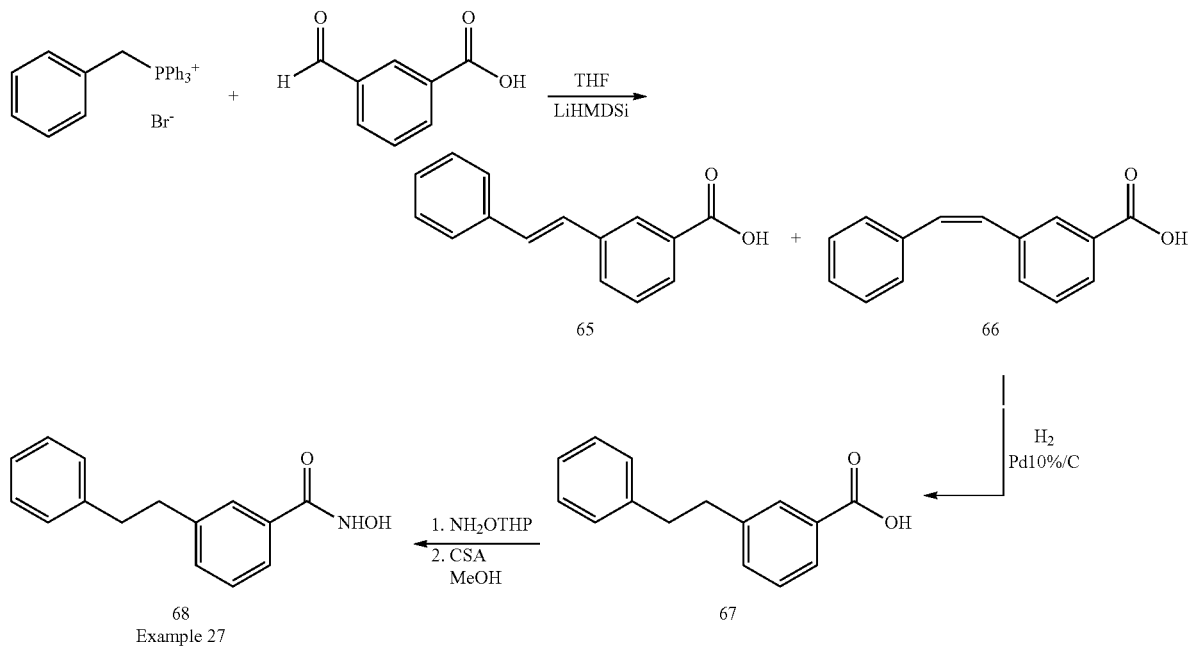

Step 1: 3-(2-phenylethenyl)-benzoic acid (65/66)

A 1.0 M solution of lithium bis(trimethylsilyl) amide (3.3 mL, 3.3 mmol) in THF was added to a stirred suspension of benzyltriphenylphosphonium bromide (1.44 g, 3.6 mmol) in THF (35 mL) at 0° C. The resulting orange solution was added via cannula to a mixture of 3-carboxybenzaldehyde (500 mg, 3.3 mmol) and lithium bis(trimethylsilyl)amide (3.3 mL, 3.3 mmol) in THF (10 mL). The mixture was stirred overnight at room temperature. A 1N solution of HCl (75 mL) and ethyl acetate (75 mL) were added and the separated aqueous layer was extracted with ethyl acetate (3×50 mL), dried (MgSO$_4$ anh.) filtered and evaporated. The residue was purified by HPLC (10:95 CH$_3$CN:H$_2$O, TFA 0.1%) to afford 130 mg of the title compound (17%)

$^1$H NMR (300 MHz, CDCl$_3$); δ (ppm) (1:1) E:Z mixture 8.22 (s, 1H), 7.98 (s, 1H), 7.90-7.10 (m, 16H), 6.70 (d, 1H, J=15.0 Hz), 6.62 (d, 1H, J=15.0 Hz)

Step 2: 3-(2-phenylethyl)-benzoic acid (67)

Following the same procedure as described in Example 24, Step 2, but substituting compounds 65/66 for compound 54, the title compound was obtained quantitatively.

$^1$H NMR (300 MHz, CDCl$_3$); δ (ppm) 2.98 (m, 4H); 7.30 (m, 7H); 7.99 (m, 2H)

Step 3: N-Hydroxy-3-(2-phenylethyl)-benzamide (68)

Following the same procedure as described in Example 25, Step 3 and 4, but substituting compound 67 for compound 59, the title compound was obtained in 22% yield.

$^1$H NMR (300 MHz, DMSO-d$_6$); δ (ppm) 2.82 (s, 4H); 7.03-7.08 (m, 8H); 7.62 (s, 1H); 8.98 (br. s, 1H); 11.15 (br. s, 1H)

Example 28

N-Hydroxy-4-(2-thiophenyl)-ethyl benzamide (70)

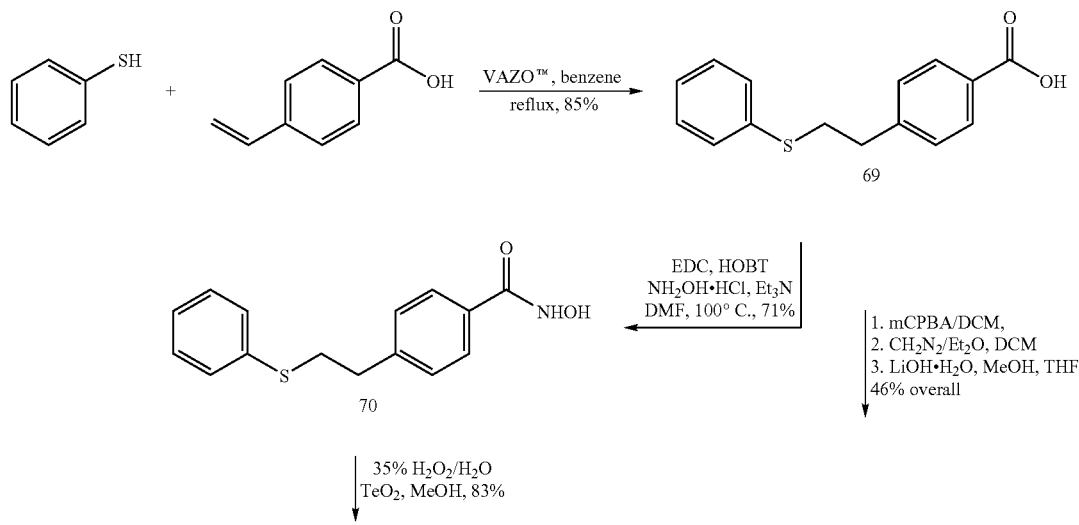

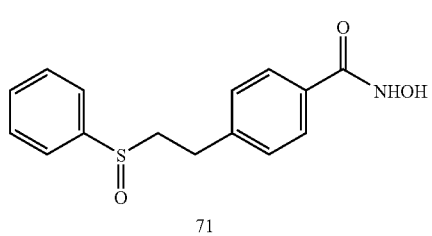

71

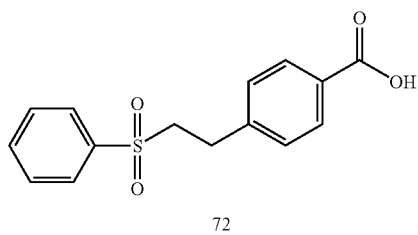

72

EDC, HOBT
NH$_2$OH·HCl, Et$_3$N
DMF, 100° C.

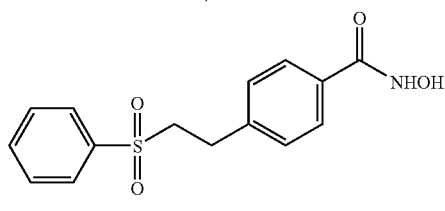

73

Step 1: 4-(2-thiophenyl)-ethyl benzoic acid (69)

According to the published procedure (Gareau et al., *Tet. Lett.,* 1994, 1837), under nitrogen atmosphere in a 50 mL round bottomed flask containing 4-vinylbenzoic acid (1.0 g, 6.75 mmoles) in 10 mL of benzene (0.7 M) was added benzenethiol (797 µL, 7.76 mmoles) followed by VAZO™ (Aldrich Chemical Company, 495 mg, 2.02 mmoles). The mixture was stirred for 12 hours at reflux. The resulting solution was cooled at room temperature and the solvent was evaporated under vacuo. The solid was purified by trituration using hexane and dichloromethane to afford 1.94 g (85%) of white solid.

$^1$H NMR (300 MHz, CDCl$_3$): δ 3.01 (t, 2H, J=8.4 Hz), 3.28 (dd, 2H, J=7.2, 7.8 Hz), 7.21 (tt, 1H, J=1.2, 7.2 Hz), 7.34 (t, 2H, J=8.1 Hz), 7.38-7.43 (m, 1H), 7.41 (d, 2H, J=8.4 Hz), 7.97 (d, 2H, J=8.1 Hz).

Step 2: N-Hydroxy-4-(2-thiophenyl)-ethyl benzamide (70)

Under nitrogen atmosphere in a 50 mL round bottomed flask containing 4-(2-thiophenyl)-ethyl benzoic acid (600 mg, 2.32 mmoles) in 12 mL of N,N-dimethyl-formamide (0.2 M) was added 1-(3-dimethylaminopropyl)-3-ethylcarbodiimide hydrochloride (579 mg, 3.02 mmoles) and 1-hydroxybenzotriazole hydrate (377 mg, 2.79 mmoles) at room temperature. The mixture was stirred 30 minutes then, hydroxylamine hydrochloride (242 mg, 3.48 mmoles) and triethylamine (971 µL, 6.97 mmoles) was added and the mixture was stirred for 12 hours at 50° C. The N,N-dimethylformamide was removed under vacuo and the resulting oil was dissolved in ethyl acetate, washed with water, saturated sodium hydrogen carbonate solution, water and brine. The organic layer was dried over anhydrous magnesium sulfate, filtered and concentrated under vacuo. The crude solid was purified by trituration using hexane and dichloromethane to afford 450 mg (71%) of a beige solid.

RP-HPLC (Hewlett-Packard 1100, column C18 HP 4.6× 250 mm, flow 1 mL/min, 10-95% CH$_3$CN/H$_2$O in 42 min with 0.1% TFA); Purity: 95.8% (220 nm), 93.2% (254 nm).

$^1$H NMR (300.072 MHz, (CD$_3$)$_2$CO): δ 2.98 (t, 2H, J=7.2 Hz), 3.26 (dd, 2H, J=6.6, 8.4 Hz), 7.21 (tt, 1H, J=1.5, 6.9 Hz), 7.31-7.42 (m, 6H), 7.77 (d, 2H, J=9.3 Hz), 8.08 (broad s, 1H), 10.69 (broad s, 1H).

$^{13}$C NMR (75.46 MHz, (CD$_3$)$_2$CO): δ 34.8 (t), 35.9 (t), 126.7 (d), 127.9 (d), 2×129.6 (d), 2×129.7 (d), 2×129.9 (d), 131.3 (s), 137.3 (s), 145.0 (s).

Elemental Analysis; Calc for C$_{15}$H$_{15}$O$_2$NS X 0.1H$_2$O: % C=75.31, % H=7.14, % N=5.17. Found: % C=75.2±0.1, % H=7.41±0.07, % N=5.17±0.01.

N-Hydroxy-4-(2-benzenesulfonyl)-ethyl benzamide (73)

Step 1: 4-(2-benzenesulfonyl)-ethyl benzoic acid (72)

Under nitrogen atmosphere in a 100 mL round bottomed flask containing 4-(2-thiophenyl)-ethyl benzoic acid (69) (600 mg, 2.32 mmoles) in 20 mL of dichloromethane (0.1 M) at 0° C. was added portionwise 3-chloroperbenzoic acid (Aldrich Chemical Co., 57-86% pure solid by, 2 g, 6.97 mmoles), as described by Nicolaou et al., *J. Am. Chem. Soc.,* 114: 8897 (1992). The mixture was allowed to reach room temperature and was stirred for 1 hour. Dimethyl sulfide (5 mL) was added, the mixture was diluted in dichloromethane and washed 3 times with water. The organic layer was dried over anhydrous magnesium sulfate, filtered and the solvent were evaporated in vacuo to afford 3 g of white solid. This mixture of 3-chlorobenzoic acid and the desired 4-(2-benzenesulfonyl)-ethyl benzoic acid was placed in a 125 mL Erlenmeyer flask, dissolved in 30 mL of dichloromethane and treated with an excess of freshly prepared diazomethane solution in diethyl ether (0.35 M). Nitrogen was bubbled to removed the excess of diazomethane and solvents were evaporated under vacuum. The resulting solid was purified by flash chromatography, eluting with 20% ethyl acetate: 80% hexane to afford 341.6 mg (48%) of the corresponding ester. Saponification of this ester was done using the same procedure as described in Example 1, step 2, to afford 312.4 mg (96%) of 4-(2-benzenesulfonyl)-ethyl benzoic acid (72)

$^1$H NMR (300 MHz, CDCl$_3$): δ 3.06-3.11 (m, 2H), 3.56-3.61 (m, 2H), 7.37 (d, 2H, J=8.4 Hz), 7.67 (tt, 2H, J=1.5, 7.2 Hz), 7.76 (tt, 1H, J=1.2, 7.5 Hz), 7.93 (d, 2H, J=8.7 Hz), 7.97 (dd, 2H, J=1.8, 6.9 Hz).

Step 2: N-Hydroxy-4-(2-benzenesulfonyl)-ethyl benzamide (73)

Following the procedure described for N-hydroxy-4-(2-thiophenyl)-ethyl benzamide, but substituting 4-(2-benzenesulfonyl)-ethyl benzoic acid for 4-(2-thiophenyl)-ethyl benzoic acid, the title compound was obtained as a beige solid.

RP-HPLC (Hewlett-Packard 1100, column C18 HP 4.6× 250 mm, flow 1 mL/min, 10-95% CH$_3$CN/H$_2$O in 42 min with 0.1% TFA); Purity: 98.8% (220 nm), 97.6% (254 nm).

$^1$H NMR (300.072 MHz, (CD$_3$)$_2$CO): δ 2.98 (t, 2H, J=7.2 Hz), 3.26 (dd, 2H, J=6.6, 8.4 Hz), 7.21 (tt, 1H, J=1.5, 6.9 Hz), 7.31-7.42 (m, 6H), 7.77 (d, 2H, J=9.3 Hz), 8.08 (broad s, 1H), 10.69 (broad s, 1H).

$^{13}$C NMR (75.46 MHz, (CD$_3$)$_2$CO): δ 25.2 (t), 34.3 (t), 55.6 (t), 128.0 (d), 2×128.8 (d), 129.4 (d), 2×130.2 (d), 131.1 (s), 134.5 (d), 140.7 (s), 145.5 (s), 165.8 (s).

N-Hydroxy-4-(2-benzenesulfoxide)-ethyl benzamide (71)

According to the procedure described by Van Der Borght et al., *J. Org. Chem.*, 65: 288 (2000), under a nitrogen atmosphere in a 10 mL round bottomed flask containing N-hydroxy-4-(2-thiophenyl)-ethyl benzamide (70) (50 mg, 0.18 mmol) in 2 mL of methanol (0.1 M) was added tellurium dioxide (3 mg, 0.018 mmol) followed by a solution 35% in water of hydrogen peroxide (32 μL, 0.36 mmol). The mixture was stirred for five days and then brine was added. The aqueous layer was extracted 3 times with ethyl acetate and the combined organic layers were dried over anhydrous magnesium sulfate, filtered and the solvent were evaporated under vacuo. The resulting solid (43.3 mg) was purified by trituration using acetonitrile to afford 10 mg (20%) of beige solid.

RP-HPLC (Hewlett-Packard 1100, column C18 HP 4.6× 250 mm, flow 1 mL/min, 10-95% CH$_3$CN/H$_2$O in 42 min with 0.1% TFA); Purity: 98.8% (220 nm), 97.9% (254 nm).

$^1$H NMR (300.072 MHz, (CD$_3$)$_2$CO): δ 2.76-2.91 (m, 1H), 3.00-3.29 (m, 3H), 7.34 (d, 2H, J=8.4 Hz), 7.55-7.62 (m, 3H), 7.70 (dd, 2H, J=1.5, 8.1 Hz), 7.76 (d, 2H, J=8.1 Hz), 8.08 (broad s, 1H), 10.70 (broad s, 1H).

$^{13}$C NMR (75.46 MHz, (CD$_3$)$_2$CO): δ 28.3 (t), 57.8 (t), 2×124.8 (d), 128.0 (d), 2×129.6 (d), 2×130.0 (d), 131.5 (d), 144.1 (s), 145.7 (s).

Example 29

N-Hydroxy-3-[4-(3-phenylpropyl)-phenyl]-propanamide (77)

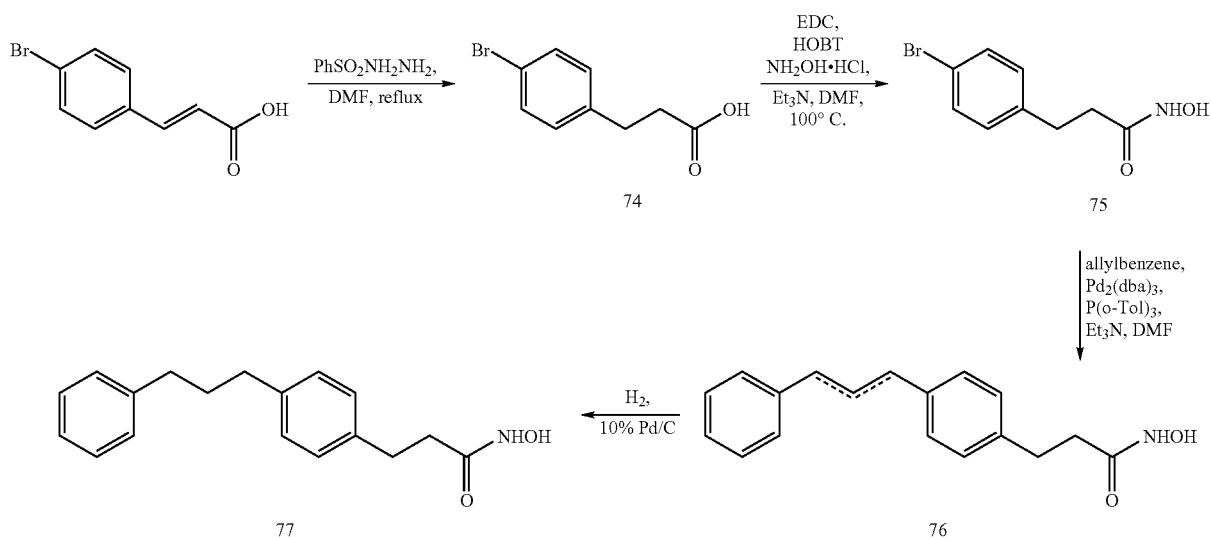

Step 1: 3-(4-bromophenyl)-propanoic acid (74)

Under nitrogen atmosphere in a 250 mL round bottomed flask containing 4-bromocinnamic acid (5.0 g, 22 mmoles) in 45 mL of N,N-dimethylformamide (0.5 M) was added benzenesulfonylhydrazide (7.6 g, 44 mmoles). The mixture was stirred at reflux for 12 hours. The solution was cooled at room temperature, aqueous saturated ammonium chloride was added and the aqueous layer was extracted with ethyl acetate 3 times. Combined organic layers were washed with water and brine, dried over anhydrous magnesium sulfate, filtered and concentrated under vacuo. The resulting solid was purified by flash chromatography eluting with 5% methanol: 95% dichloromethane to afford 3.66 g (73%) of beige solid.

$^1$H NMR (300 MHz, CDCl$_3$): δ 2.66 (t, 2H, J=7.5 Hz), 2.91 (d, 2H, J=7.5 Hz), 7.08 (d, 2H, J=8.4 Hz), 7.41 (d, 2H, J=8.4 Hz).

Step 2: N-Hydroxy-3-(4-bromophenyl)-propanamide (75)

Following a procedure analogous to that described for the preparation of 70, 1.54 g (39%) of the title compound was obtained.

$^1$H NMR (300 MHz, CDCl$_3$): δ 2.39 (t, 2H, J=7.8 Hz), 2.89 (d, 2H, J=7.2 Hz), 7.18 (d, 2H, J=8.1 Hz), 7.42 (d, 2H, J=8.7 Hz), 8.18 (broad s, 1H), 9.98 (broad s, 1H).

Step 3: N-Hydroxy-3-[4-(3-phenyl-1-propenyl)-phenyl]-propanamide and N-Hydroxy-3-[4-(3-phenyl-2-propenyl)-phenyl]-propanamide (76)

Following a procedure analogous to that described in Example 25, step 1, but substituting N-hydroxy-3-(4-bromophenyl)-propanamide (75) (250 mg, 1.02 mmol) for 4-bromobenzoic acid and allyl benzene (163 μL, 1.2 mmol) for 4-phenyl-1-butene, to yield 155.4 mg (54%) of the mixed title compounds.

¹H NMR (300 MHz, CDCl₃): δ 2.39 (m, 2H), 2.88 (t, 2H, J=8.4 Hz), 3.51 (t, 2H, J=8.1 Hz), 6.32-6.53 (m, 2H), 7.14-7.44 (m, 9H), 8.60 (broad s, 1H), 10.04 (broad s, 1H).

Step 4: N-Hydroxy-3[4-(3-phenylpropyl)-phenyl]-propanamide (77)

Following a procedure analogous to that described in Example 24, step 2, but substituting the mixture of N-hydroxy-3-[4-(3-phenyl-1-propenyl)-phenyl]-propanamide and N-hydroxy-3-[4-(3-phenyl-2-propenyl)-phenyl]-propanamide (155 mg, 0.55 mmol) for olefins 54, 155.4 mg (99%) of the title compound was obtained.

RP-HPLC: (Hewlett-Packard 1100, column C18 HP 4.6× 250 mm, flow 1 mL/min, 10-95% CH₃CN/H₂O in 42 min with 0.1% TFA); Purity: 99.9% (220 nm) (2 peaks but same compound proven by LCMS, 99.9% (254 nm). ¹H NMR (300.072 MHz, (CD₃)₂CO): δ 1.91 (quintuplet, 2H, J=8.1 Hz), 2.38 (t, 2H, J=7.8 Hz), 2.61 (q, 4H, J=9.6 Hz), 2.87 (t, 2H, J=7.2 Hz), 7.12-7.29 (m, 9H), 8.42 (broad s, 1H), 10.01 (broad s, 1H).

¹³C NMR (75.46 MHz, (CD₃)₂CO): δ 26.3 (t), 28.7 (t), 29.8 (t), 30.3 (t), 30.7 (t), 121.1 (d), 3×123.7 (d), 3×123.8 (d), 133.9 (s), 133.4 (s), 137.8 (s), 164.9 (s).

Elemental Analysis; Calc for C₁₈H₂₁O₂N X 0.1H₂O: % C=75.81, % H=7.49, % N=4.91. Found: % C=75.7±0.3, % H=7.54±0.02, % N=4.85±0.03.

Example 30

Step 1: Ethyl 3-(4-nitrophenyl)-2-isopropyl propanoate (78)

To a precooled solution of diisopropylamine (34.7 mmol) in THF (30 mL) under nitrogen was added dropwise a 1.0 M solution of n-butyllithium (33.3 mmol). The resulting light yellow solution was stirred at −78° C. over 30 minutes and transferred via canula to a precooled (−78° C.) solution of ethyl isovalerate (34.7 mmol) in THF (50 mL). The mixture was stirred at −78° C. over 1 hour and a 4-nitrobenzyl bromide (13.9 mmol) solution in THF (20 mL) at room temperature was transferred dropwise via canula to the enolate solution which turned deep red. The mixture was stirred over 15 minutes and the reaction was quenched with aqueous saturated ammonium chloride solution (NH₄Cl). The mixture was allowed to warm to room temperature over 1 hour and turned brown upon warming. It was poured into a large volume of saturated NH₄Cl solution and the layers were separated. The aqueous layer was extracted twice with diethyl ether and the combined organic layers were washed with brine, dried over magnesium sulfate and concentrated in vacuo. The residue was purified by flash chromatography on silica gel using ethyl acetate and hexanes (10:90) as the eluent, yielding 73% of the pure title compound 78 as a light yellow oil.

Step 2: Ethyl 3-(4-aminophenyl), 2-isopropyl propanoate (79)

To a hydrogen flushed (vacuum/H₂, 3 times) solution of 1 (1.88 mmol) in methanol (10 mL) was added 10% palladium on charcoal (0.018 mmol) previously quenched with methanol in a separate flask. The black heterogeneous resulting mixture was stirred at room temperature under hydrogen atmosphere (1 atm) over 20 hours. The hydrogen was then

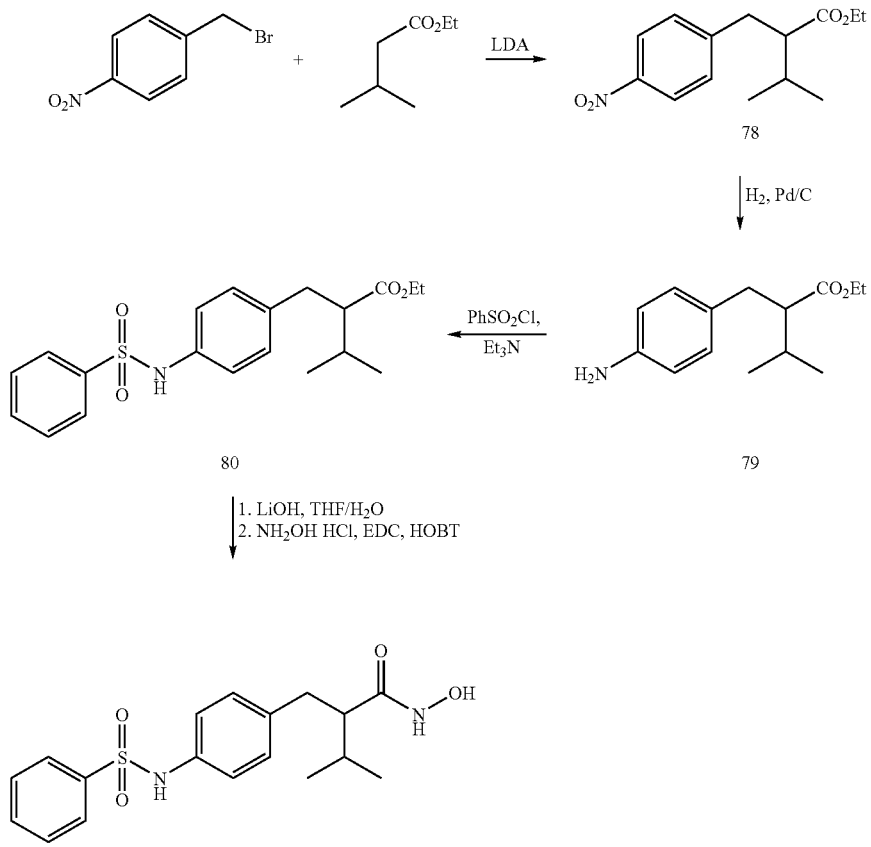

evacuated by vacuum and replaced with air. Then, the mixture was filtered through celite, rinsing with methanol while making sure the pad never gets dry. The filtrate was concentrated to a red oil. The residue was purified by flash chromatography on silica gel using ethyl acetate and hexanes (30:70) as the eluent, yielding 73% of the pure title compound 79 as a light red oil.

Steps 3-5: (81)

Compound 79 was coupled with benzenesulfonyl chloride in the presence of triethylamine according to the procedure described in Example 1, step 1, to afford the sulfonamide 80. Ester hydrolysis and coupling with hydroxylamine were then accomplished as described in Example 28 to afford the hydroxamic acid 81.

$^1$H NMR: (Acetone-$d_6$) δ (ppm): 9.76 (bs, 1H), 8.83 (bs, 1H), 7.74 (d, J=8.2 Hz, 2H), 7.59-7.49 (m, 3H), 7.04 (s, 4H), 2.83-2.73 (m, 3H), 1.83 (sext, J=6.9 Hz, 1H), 1.00 (d, J=6.9 Hz, 3H), 0.93 (d, J=6.9 Hz, 3H).

HRMS: 344.1195 ($M^+$-$H_2O$) (calc.); 344.1200±0.0010 (found).

Example 31

Compound 82 was obtained in good yield from commercially available bromoaminopyridine through a palladium catalyzed coupling with tert-butyl acrylate. Treatment of 82 with 4-phenylbenzenesulfonyl chloride afforded a mixture of sulfonamide 84 and bis-sulfonamide 83, which was converted to 84 upon chromatographic isolation followed by basic methanolysis. Acidic cleavage of the t-butyl ester was effected by treatment of 84 with aqueous formic acid and a tert-butyl cation scavenger to afford the acrylic acid 85 in quantitative yield. Finally, coupling of 85 with o-phenylenediamine in the presence of benzotriazol-1-yloxytris(dimethylamino)phosphonium hexafluorophosphate (BOP) afforded the anilide 86.

Data for 86:

$^1$H NMR: (300.07 MHz; $CD_3OD$): δ (ppm): 8.23 (d, J=1.9, 1H); 8.03 (bd, J=8.5; 2H); 7.96 (dd, J=1.9, 9.1; 1H); 7.76 (bd, J=8.5, 2H); 7.63 (dd, J=1.4, 8.2); 7.53 (J=15.5; 1H), 7.48-7.36 (m, 3H); 7.29 (d, J=9.1, 1H) 7.18 (dd, J=1.4, 8.0, 1H); 7.03 (dt, J=1.4, 7.8, 1H); 6.86 (d, J=1.4, 7.9, 1H) 6.76 (d, J=15.6, 1H) 6.75-6.69 (m, 1H); 4.85 (bs, 4H).

$^{13}$C NMR: (75.5 MHz; $CD_3OD$) δ (ppm): 166.4; 154.7; 146.9; 146.2; 143.1; 141.1; 140.6; 138.6; 137.9; 130.1; 129.5; 128.8; 128.5; 128.3; 126.7; 125.6; 125.0; 122.1; 120.8; 119.5; 118.6; 114.9

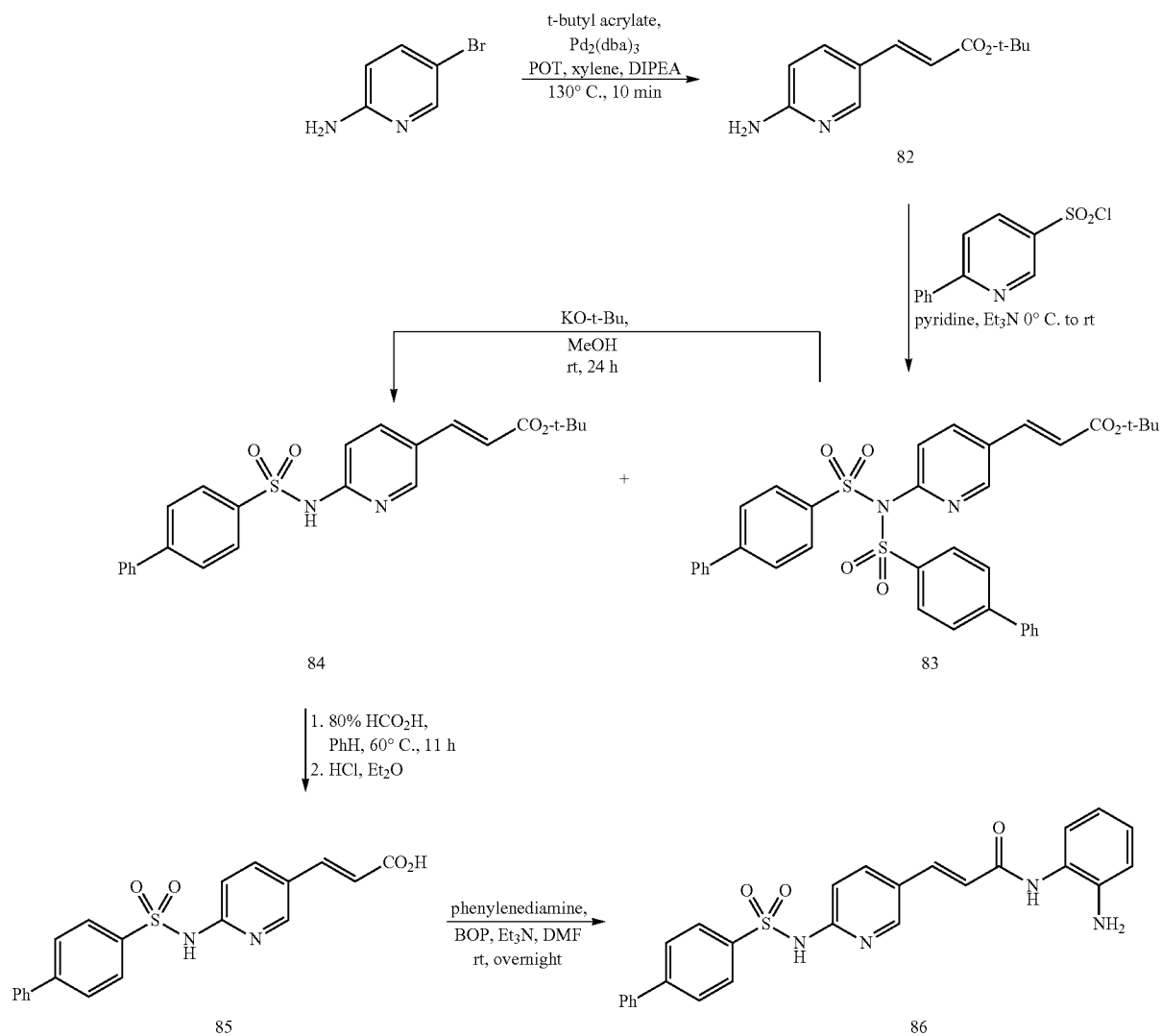

MS: calc for $C_{26}H_{22}O_3N_4S$: 470.556. found: 471.5 for [M+H] (low resolution MS).

By procedures analogous to those described in Examples 1-31 above, the following compounds were synthesized:

87

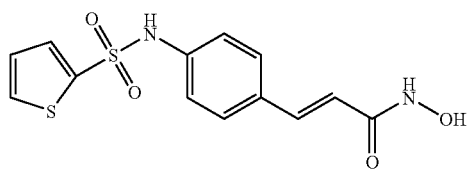

$^1$H NMR: (300 MHz, CD$_3$OD): δ=7.76-7.74 (1H, m), 7.58-7.48 (4H, m), 7.22 (2H, d, J=7.5 Hz), 7.10 (1H, t, J=5.1 Hz), 6.41 (1H, d broad, J=14.7 Hz).

88

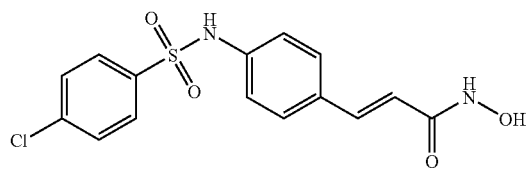

$^1$H NMR: (300 MHz, CD$_3$OD): δ=7.79 (2H, d, J=8.1 Hz), 7.56-7.46 (5H, m), 7.17 (2H, d, J=8.1 Hz), 6.39 (1H, d, J=15.9 Hz).

Analysis: $C_{15}H_{13}N_2O_4SCl$ X 0.1H$_2$O, X 0.3 TFA Found: C=48.26%, H=3.58%, N=6.97%, S=7.86%. Calc.: C=48.19%, H=3.50%, N=7.20%, S=8.25%

89

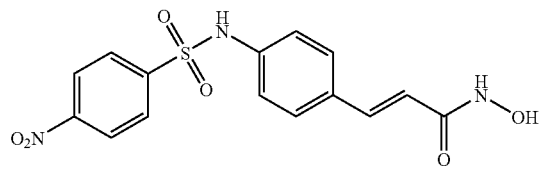

$^1$H NMR: (300 MHz, DMSO d$_6$): δ=10.85 (1H, s br), 10.70 (1H, s br), 8.99 (1H, s), 8.37 (2H, d, J=9 Hz), 8.01 (2H, d, J=9 Hz), 7.44 (2H, d, J=8.7 Hz), 7.33 (1H, d, J=15.3 Hz), 7.12 (2H, d, J=8.4 Hz), 6.31 (1H, d, J=15.9 Hz).

Analysis: $C_{15}H_{13}N_3O_6S$ X 0.4H$_2$O, X 0.3 TFA Found: C=46.39%, H=3.49%, N=10.44%, S=7.92%. Calc.: C=46.29%, H=3.51%, N=10.38%, S=7.92%.

90

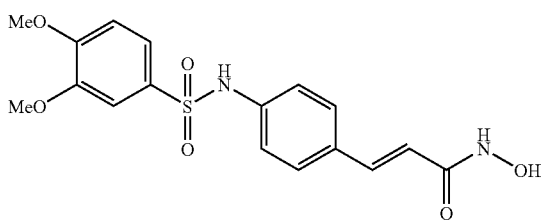

$^1$H NMR: (300 MHz, DMSO d$_6$): δ=10.70 (1H, s br), 10.33 (1H, s br), 8.99 (1H, s br), 7.44-7.26 (5H, m), 7.12 (2H, d, J=8.7 Hz), 7.06 (1H, d, J=8.4 Hz), 6.30 (1H, d, J=16.2 Hz), 3.78 (3H, s), 3.75 (3H, s)

Analysis: $C_{17}H_{18}N_2O_6S$ X 0.2H$_2$O Found: C=53.56%, H=5.03%, N=7.71%, S=8.01%. Calc.: C=53.45%, H=4.86%, N=7.33%, S=8.39%.

91

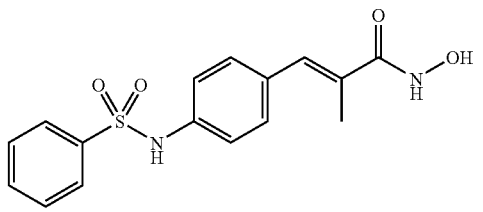

$^1$H NMR: (CD$_3$OD) δ (ppm): 7.78 (d, J=7.1 Hz, 1H), 7.56-7.45 (m, 3H), 7.24 (d, J=8.5 Hz, 2H), 7.12 (d, J=8.8 Hz, 2H), 7.06 (s, 1H), 2.00 (d, J=1.4 Hz, 3H).

$^{13}$C NMR: (CD$_3$OD) δ (ppm): 135.2, 132.9, 128.1, 127.7, 125.5, 124.6, 124.1, 122.3, 116.8, 115.6, 8.4.

92

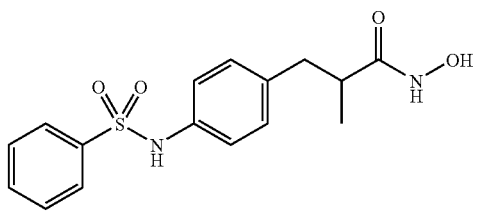

$^1$H NMR: (Acetone-d$_6$) δ (ppm): 9.86 (bs, 1H), 8.86 (bs, 1H), 7.83 (bs, 1H), 7.76 (d, J=6.7 Hz, 1H), 7.62-7.48 (m, 3H), 7.10-7.03 (m, 4H), 2.87-2.79 (m, 3H), 2.56-2.39 (m, 2H), 1.05 (d, J=6.6 Hz, 3H).

HRMS: 334.0987 (calc.); 334.0991±0.0010 (found)

93

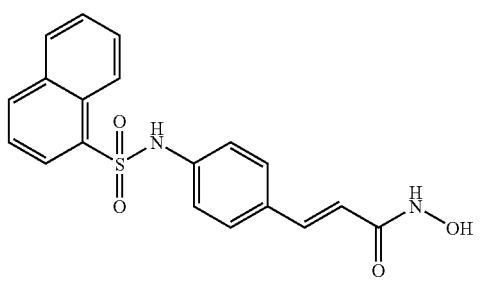

$^1$H NMR: (300 MHz, DMSO d$_6$): δ=10.94 (1H, s broad), 10.65 (1H, s broad), 8.95 (1H, s Broad), 8.73-8.71 (1H, m), 8.24-8.21 (2H, m), 8.05 (1H, m), 7.74-7.63 (3H, m), 7.33-7.23 (2H, m), 7.06-7.04 (2H, m), 6.24 (1H, d, J=15.3).

Analysis: $C_{19}H_{16}N_2O_4S$ X 0.5H$_2$O Found: C=60.31%, H=4.58%, N=7.43%. Calc.: C=60.46%, H=4.54%, N=7.42%

93

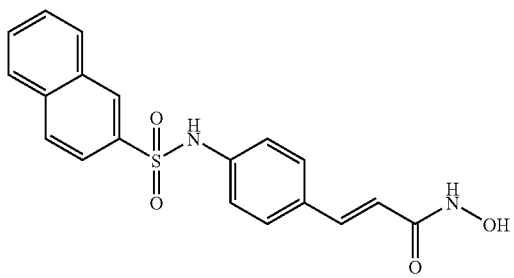

¹H NMR: (300 MHz, DMSO d₆): δ=10.65 (2H, s broad), 8.48 (1H, s), 8.15-8.08 (2H, m), 8.00 (1H, d, J=7.5 Hz), 7.77 (1H, d, J=9 Hz), 7.70-7.62 (2H, m), 7.39 (2H, d, J=8.4 Hz), 7.28 (1H, d, J=15.6 Hz), 7.15 (2H, d, J=8.4 Hz), 6.26 (1H, d, J=15.6 Hz).

Analysis: $C_{19}H_{16}N_2O_4S$ X 0.2H₂O, X 0.5 TFA Found: C=56.01%, H=3.94%, N=6.60%, S=7.41%. Calc.: C=55.99%, H=3.97%, N=6.53%, S=7.47%.

95

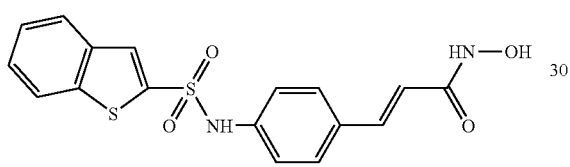

¹H NMR: (300 MHz, DMSO d₆): δ=10.91 (1H, s), 10.69 (1H, s br), 8.06-7.98 (3H, m), 7.57-7.46 (4H, m), 7.34 (1H, d, J=15.9 Hz), 7.21 (2H, d, J=8.4 Hz), 6.33 (1H, d, J=15.9 Hz).

96

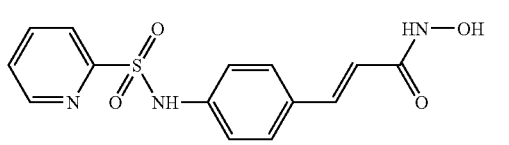

¹H NMR: (300 MHz, DMSO d₆): δ=8.69-8.8 (1H, m), 8.02-8.01 (2H, m), 7.61-7.59 (1H, m), 7.52-7.43 (3H, m), 7.25 (2H, d, J=7.5 Hz), 6.37 (1H, d, J=15.9 Hz).

Analysis: $C_{14}H_{13}N_3O_4S$ X 0.9 TFA Found: C=45.36%, H=3.51%, N=9.77%, S=7.09%. Calc.: C=44.97%, H=3.32%, N=9.96%, S=7.60%.

97

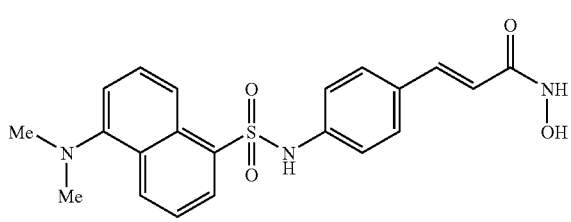

94

¹H NMR: (300 MHz, DMSO d₆): δ=10.91 (1H, s), 10.62 (1H, s br), 8.45 (1H, 8.1 Hz), 8.36 (1H, d, J=8.7 Hz), 8.25 (1H, d, J=6.9 Hz), 7.65-7.59 (2H, m), 7.37-7.34 (2H, m), 7.29-7.23 (2H, m), 7.06 (2H, d, J=8.7 Hz), 6.25 (1H, d, J=15.9 Hz) 2.80 (6H, s).

98

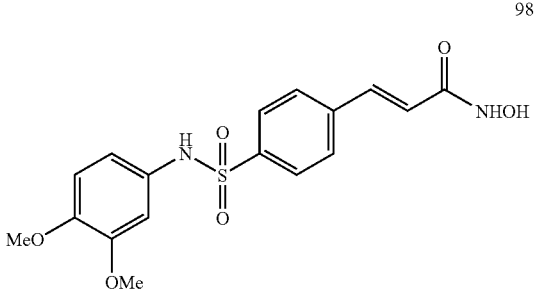

¹H NMR: (300 MHz, DMSO d₆): δ=10.82 (1H, s br), 9.95 (1H, s br), 9.12 (1H, s br), 7.70 (4H, s), 7.46 (1H, d, J=15.9 Hz), 6.79 (1H, d, J=8.7 Hz), 6.68 (1H, s), 6.56-6.51 (2H, m), 3.65 (3H, s), 3.62 (3H, s).

99

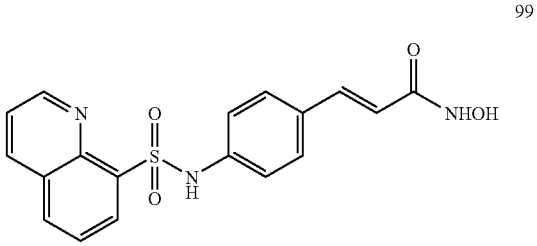

¹H NMR: (300 MHz, DMSO d₆): δ=10.63 (1H, s), 10.36 (1H, s br), 9.13-9.12 (1H, m), 8.93 (1H, s br), 8.51 (1H, d, J=8.1 Hz), 8.40 (1H, d, J=7.2 Hz), 8.28 (1H, d, J=8.4 Hz), 7.75-7.70 (2H, m), 7.30-720 (3H, m), 7.09 (2H, d, J=8.4 Hz) 6.21 (1H, d, J=15.9 Hz).

Analysis: $C_{18}H_{15}N_3O_4S$ X 1.1H₂O Found: C=55.72%, H=4.45%, N=10.64%, S=6.93%. Calc.: C=55.55%, H=4.45%, N=10.80%, S=8.24%.

100

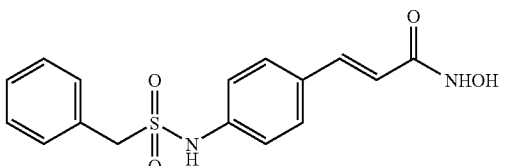

¹H NMR: (300 MHz, DMSO d₆): δ=10.72 (1H, s br), 10.07 (1H, s), 7.53-7.51 (2H, m), 7.43-7.34 (4H, m), 7.26-7.19 (4H, m), 6.38 (1H, d, J=15.6 Hz), 4.51 (2H, s).

Analysis: $C_{16}H_{16}N_2O_4S$ X 0.4 TFA Found: C=53.60%, H=4.46%, N=7.36%, S=7.81%. Calc.: C=53.38%, H=4.37%, N=7.41%, O=20.32%, S=8.48%, F=6.03%.

101

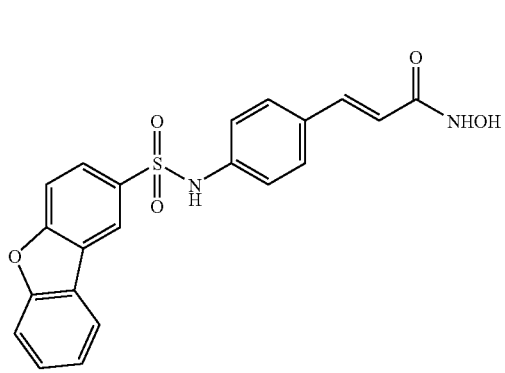

$^1$H NMR: (300 MHz, DMSO d$_6$): δ=10.63 (1H, s br), 10.56 (1H, s), 8.67 (1H, s), 8.29 (1H, d, J=6.9 Hz), 7.89-7.85 (2H, m), 7.75 (1H, d, J=8.4 Hz), 7.59 (1H, t, J=7.2 Hz), 7.47-7.38 (3H, m), 7.27 (1H, d, J=15.6 Hz), 7.15 (2H, d, J=8.7 Hz), 6.25 (1H, d, J=15.9 Hz).

102

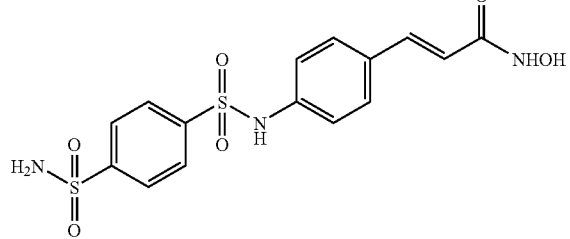

$^1$H NMR: (300 MHz, DMSO d$_6$): δ=10.72 (2H, s), 8.98 (1H, s br), 7.97 (4H, s), 7.55 (2H, s), 7.45 (2H, d, J=8.7 Hz), 7.33 (1H, d, J=15.9 Hz), 7.13 (2H, d, J=8.7 Hz), 6.32 (1H, d, J=15.9 Hz).

103

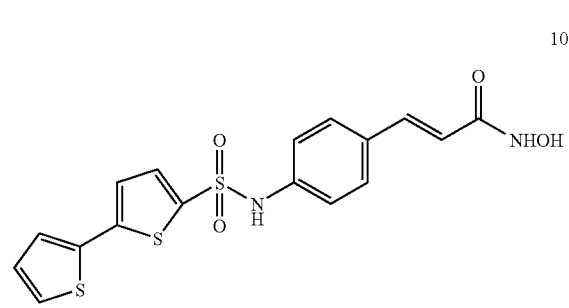

1H NMR: (300 MHz, DMSO d$_6$): δ=10.75 (2H, m), 7.65-7.64 (1H, m), 7.53-7.45 (4H, m), 7.35 (1H, d, J=16.2 Hz), 7.29 (1H, d, J=3.9 Hz), 7.20 (2H, d, J=8.7 Hz), 7.12 (1H, t, J=3.6 Hz), 6.34 (1H, d, J=15.6 Hz).

Analysis: C$_{17}$H$_{14}$N$_2$O$_4$S$_3$ X 0.1H$_2$O, X 1.0 TFA Found: C=43.83%, H=3.26%, N=5.73%, S=18.15%. Calc.: C=43.69%, H=2.93%, N=5.36%, S=18.42%.

104

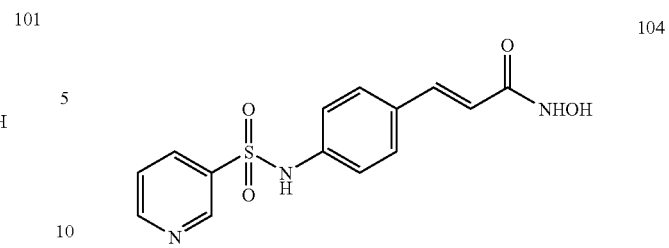

$^1$H NMR: (300 MHz, DMSO d$_6$): δ=10.72 (1H, s), 8.91 (1H, d, J=1.8 Hz), 8.80-8.78 (1H, m), 8.13 (1H, d, J=7.8 Hz), 7.63-7.59 (1H, m), 7.46 (2H, d, J=8.7 Hz), 7.33 (1H, d, J=15.6 Hz), 7.14 (2H, d, J=8.7 Hz), 6.32 (1H, d, J=15.9 Hz).

105

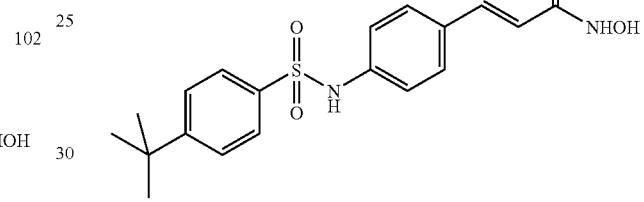

$^1$H NMR: (300 MHz, DMSO d$_6$): δ=10.54 (1H, s), 7.73 (2H, d, J=8.4 Hz), 7.58 (2H, d, 8.4 Hz), 7.43 (2H, d, J=8.4 Hz), 7.32 (1H, d, J=15.6 Hz), 7.15 (2H, d, J=8.4 Hz), 6.30 (1H, d, J=15.9 Hz), 1.25 (9H, s).

Analysis: C$_{19}$H$_{22}$N$_2$O$_4$S X 0.3H$_2$O, 0.6 TFA Found: C=54.17%, H=5.25%, N=6.32%, S=6.85%. Calc.: C=54.12%, H=5.22%, N=6.25%, S=7.15%.

106

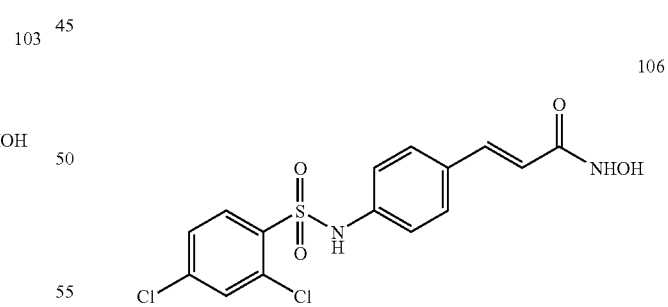

$^1$H NMR: (300 MHz, DMSO d$_6$): δ=11.02 (1H, s), 10.70 (1H, s), 8.99 (1H, s br), 8.03 (1H, d, J=1.8 Hz), 7.76-7.67 (2H, m), 7.45 (2H, d, J=8.1 Hz), 7.33 (1H, d, J=15.6 Hz), 7.13 (2H, d, J=8.4 Hz), 6.31 (1H, d, J=16.2 Hz).

Analysis: C$_{15}$H$_{12}$N$_2$O$_4$SCl$_2$ X 0.3H$_2$O Found: C=45.96%, H=3.11%, N=7.21%, S=8.06%. Calc.: C=45.89%, H=3.23%, N=7.13%, S=8.17%.

107

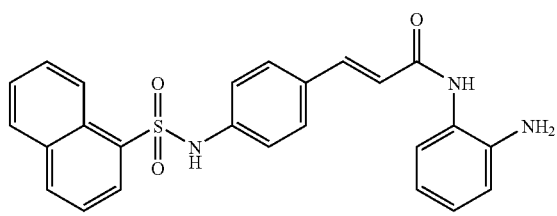

¹H NMR: (300 MHz, Acetone d₆): δ=8.81 (1H, d, J=8.4 Hz), 8.34 (2H, d, J=7.2 Hz), 8.20 (1H, d, J=8.1 Hz), 8.05 (1H, d, J=7.5 Hz), 7.75-7.59 (4H, m), 7.53-7.41 (4H, m), 7.23-7.07 (4H, m), 6.89-6.86 (2H, m), 6.75 (1H, d, J=15.3 Hz).

Analysis: $C_{25}H_{21}N_3O_3S \times 0.4H_2O$, 0.6 TFA Found: C=60.68%, H=4.36%, N=8.11%, S=6.15%. Calc.: C=60.62%, H=4.35%, N=8.09%, S=6.18%.

108

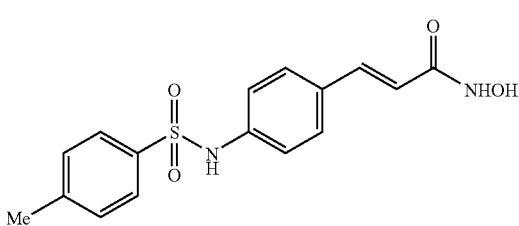

¹H NMR: (300 MHz, DMSO d₆): δ=10.7 (1H, s br), 10.45 (1H, s br), 8.96 (1H, s br), 7.64 (2H, d, J=8.1 Hz), 7.38 (2H, d, J=8.4 Hz), 7.32-7.29 (3H, m), 7.09 (2H, d, J=8.4 Hz), 6.29 (1H, d, J=16.2 Hz), 2.30 (3H, s).

Analysis: $C_{16}H_{16}N_2O_4S \times 1.6H_2O \times 1.6$ TFA Found: C=42.26%, H=3.62%, N=5.45%, S=6.09%. Calc.: C=42.42%, H=3.86%, N=5.15%, S=5.9%.

109

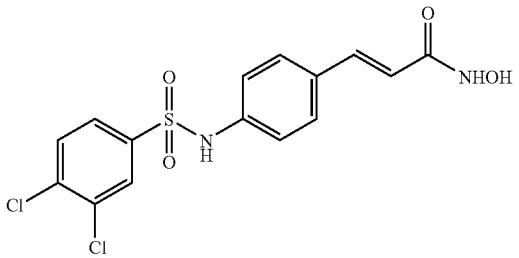

¹H NMR: (300 MHz, DMSO d₆): δ=10.71 (1H, s), 10.67 (1H, s), 9.00 (1H, s br), 7.96 (1H, d, J=2.4 Hz), 7.85 (1H, d, J=8.4 Hz), 7.69 (1H, dd, J=8.4 Hz and 2.1 Hz), 7.47 (2H, d, J=8.4 Hz) 7.35 (1H, d, J=15.9 Hz), 7.13 (2H, d, J=8.7 Hz), 6.33 (1H, d, J=15.9 Hz).

Analysis: $C_{15}H_{12}N_2O_4SCl_2 \times 0.3H_2O \times 0.3$ AcOEt Found: C=46.30%, H=3.27%, N=6.56%, S=7.57%. Calc.: C=46.43%, H=3.61%, N=6.68%, S=7.65%.

110

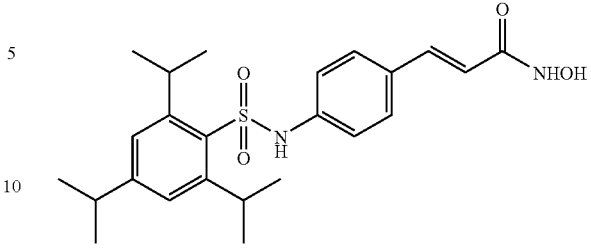

¹H NMR: (300 MHz, DMSO d₆): δ=1.65 (1H, s br), 10.45 (1H, s br), 8.96 (1H, s br), 7.42 (2H, d, J=8.1 Hz), 7.31 (1H, d, J=15.6 Hz), 7.22 (2H, s), 7.01 (2H, d, J=8.1 Hz), 6.30 (1H, d, J=15.9 Hz), 4.24-4.16 (2H, m), 2.93-2.84 (1H, m), 1.18-1.14 (18H, m).

Analysis: $C_{24}H_{32}N_2O_4S \times 1.10H_2O$ Found: C=62.14%, H=7.17%, N=6.20%, S=6.71%. Calc.: C=62.07%, H=7.42%, N=6.03%, S=6.9%.

111

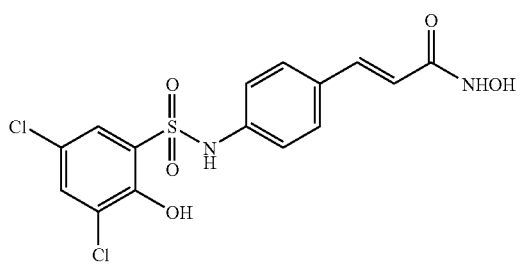

¹H NMR: (300 MHz, DMSO d₆): δ=11.18 (1H, s br), 10.69 (2H, m), 7.83-7.82 (1H, m), 7.68 (1H, m), 7.43 (2H, d, J=8.1 Hz), 7.32 (1H, d, J=15.3 Hz), 7.13 (2H, d, J=8.1 Hz), 6.31 (1H, d, J=15.9 Hz).

Analysis: $C_{15}H_{12}N_2O_5SCl_2 \times 0.2H_2O \times 0.2$ TFA Found: C=43.14%, H=3.04%, N=6.54%, S=7.19%. Calc.: C=43.05%, H=2.96%, N=6.52%, S=7.46%.

112

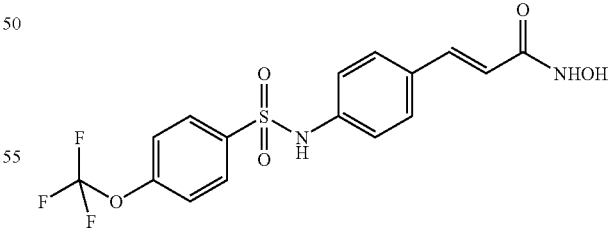

¹H NMR: (300 MHz, DMSO d₆): δ=10.70 (1H, s), 10.65 (1H, s), 9.01 (1H, s br), 7.91 (2H, d, J=8.4 Hz), 7.56 (2H, d, J=8.4 Hz), 7.45 (2H, d, J=8.1 Hz), 7.33 (1H, d, J=15.6 Hz), 7.13 (2H, d, J=8.1 Hz), 6.31 (1H, J=15.6 Hz).

Analysis: $C_{16}H_{13}N_2O_5SF_3 \times 0.2$ TFA Found: C=46.43%, H=3.33%, N=6.22%, S=7.25%. Calc.: C=46.33%, H=3.13%, N=6.59%, S=7.54%.

113

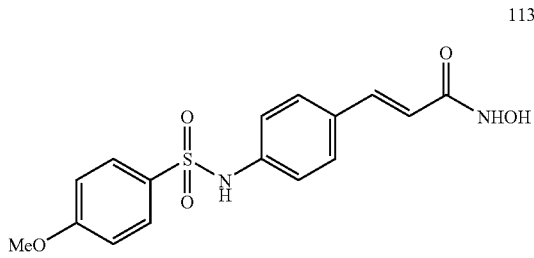

¹H NMR: (300 MHz, DMSO d₆): δ=10.66 (1H, s br), 10.37 (1H, s br), 8.56 (1H, s br), 7.69 (2H, d, J=8.7 Hz), 7.39 (2H, d, J=8.1 Hz), 7.30 (1H, d, J=16.2 Hz), 7.10-7.03 (4H, m), 6.27 (1H, d, J=15.9 Hz), 3.77 (3H, s).

Analysis: C₁₆H₁₆N₂O₅S X 0.7H₂O Found: C=53.32%, H=5.05%, N=7.98%, S=7.78%. Calc.: C=53.24%, H=4.86%, N=7.76%, S=8.88%.

114

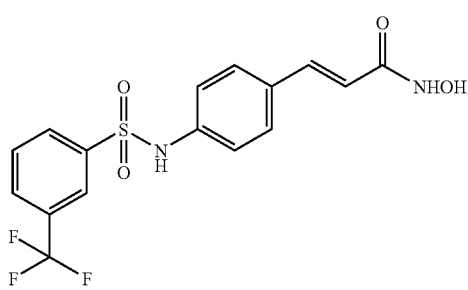

¹H NMR: (300 MHz, DMSO d₆): δ=10.70 (1H, s), 10.66 (1H, s), 8.99 (1H, s), 8.06-7.98 (3H, m), 7.84-7.79 (1H, m), 7.45 (2H, d, J=8.4 Hz), 7.33 (1H, d, J=15.6 Hz), 7.12 (2H, d, J=8.7 Hz), 6.32 (1H, d, J=15.9 Hz).

Analysis: C₁₆H₁₃F₃N₂O₄S Found: C=49.64%, H=3.30%, N=7.18%. Calc.: C=49.74%, H=3.39%, N=7.25%

115

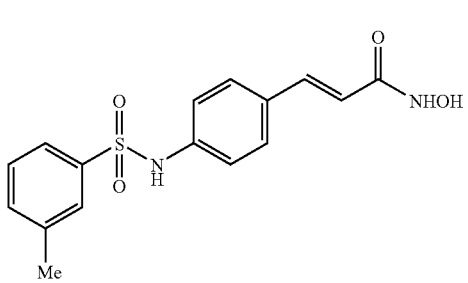

¹H NMR: (300 MHz, DMSO d₆): δ=10.69 (1H, s, br), 10.47 (1H, s, br), 8.98 (1H, s, br), 7.62 (1H, s), 7.58-7.56 (1H, m), 7.44-7.41 (4H, m), 7.32 (1H, d, J=16.2 Hz), 7.11 (2H, d, J=8.1 Hz), 6.30 (1H, d, J=15.6 Hz), 2.34 (3H, s).

Analysis: C₁₆H₁₆N₂O₄S X 0.3 TFA Found: C=54.64%, H=4.75%, N=7.92%. Calc.: C=54.66%, H=4.59%, N=7.82%

116

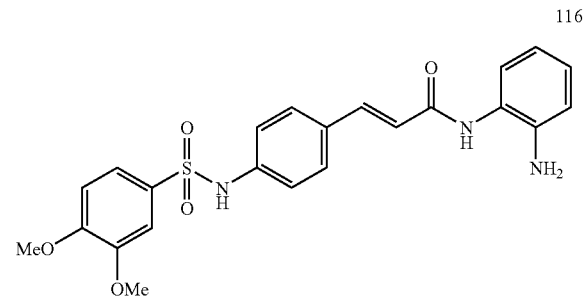 [SMILES: COc1ccc(S(=O)(=O)Nc2ccc(/C=C/C(=O)Nc3ccccc3N)cc2)cc1OC]

¹H NMR: (300 MHz, MeOD d₄): 7.62-6.61 (m, 13H); 3.81 (broad s, 3H, OCH₃), 3.80 (broad s, 3H, OCH₃), 3.26 (broad s, 4H, NH).
¹³C NMR: (75 MHz, MeOD d₄): 167.0 (C=O); 154.4; 150.5; 143.1; 141.9; 141.0; 132.5; 132.3; 129.9; 128.2; 126.7; 125.2; 122.4; 121.8; 120.8; 119.6; 118.7; 111.9; 110.9; 56.6 (2C, OCH₃).
Combustion analysis: Calc: 60.91% C, 5.11% H, 9.27% N, 7.07% S
Found: 60.40% C, 5.21% H, 9.16% N, 6.47% S
HRMS: Calc: 453.1358; Found: 453.1351

117

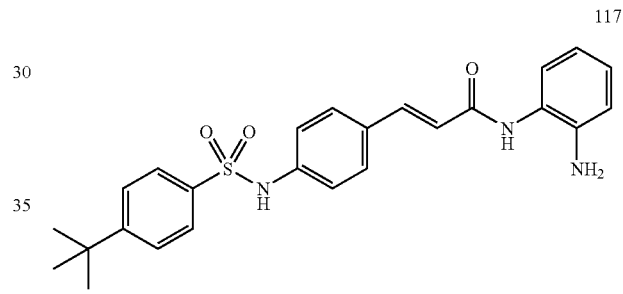

¹H NMR: (Acetone-d₆): δ (ppm): 9.25 (bs, 1H), 8.77 (bs, 1H), 7.79 (d, J=8.5 Hz, 2H), 7.61-7.51 (m, 5H), 7.36-7.28 (m, 3H), 6.99-6.93 (m, 1H), 6.86-6.82 (m, 2H), 6.68-6.62 (m, 1H), 4.63 (bs, 2H).
HRMS: 449.1773 (calc.): 449.1767±0.0013 (found)

118

¹H NMR: (300 MHz, MeOD d₄): 8.00-6.56 (m, 13H); 3.77 (broad s, 3H, OCH₃), 3.74 (broad s, 3H, OCH₃), 3.33 (broad s, 2H, NH), 3.00 (broad s, 1H, NH), 2.88 (broad s, 1H, NH).
¹³C NMR: (75 MHz, MeOD d₄): 166.2 (C=O); 150.7; 148.5; 143.2; 141.7; 140.6; 140.5; 131.9; 129.2; 128.9; 128.4; 126.7; 124.9; 119.5; 118.6; 116.4; 113.2; 108.9; 56.6 (OCH₃); 56.4 (OCH₃).
MS: Calc: 453.1358: Found: 453.1351

119

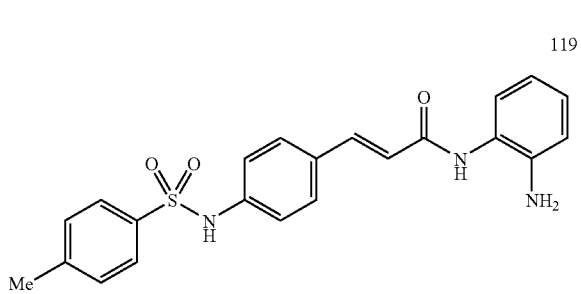 [SMILES: Cc1ccc(S(=O)(=O)Nc2ccc(/C=C/C(=O)Nc3ccccc3N)cc2)cc1]

¹H NMR: (CD₃OD) δ (ppm): 7.68 (d, J=8.2 Hz, 2H), 7.55 (d, J=15.9 Hz, 1H), 7.47 (d, J=8.5 Hz, 2H), 7.30 (d, J=8.0 Hz, 2H), 7.19-7.12 (m, 3H), 7.03 (t, J=7.1 Hz, 1H), 6.86 (d, J=8.0 Hz, 1H), 6.75-6.69 (m, 2H), 2.37 (s, 3H).

HRMS: 407.1304 (calc.): 407.1293±0.0012 (found)

120

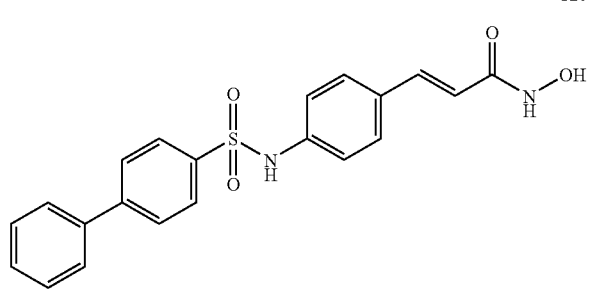

¹H NMR: (300 MHz, DMSO-d₆) δ 10.6 (s, OH); 9 (s, NH); 7.1-7.8 (m, 14H, CH Ar); 6.2 (d, 1H, J=15 Hz)

121

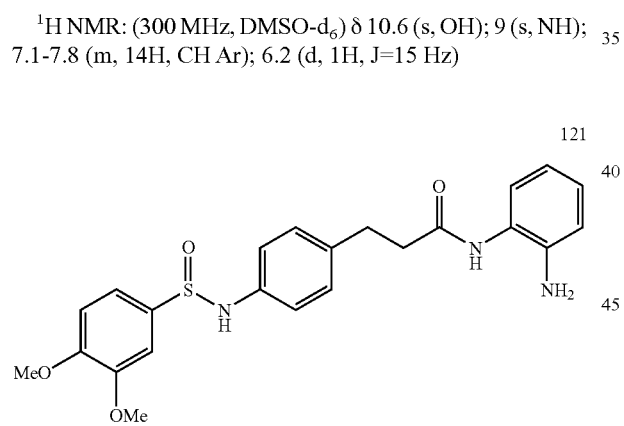

¹H NMR: (300 MHz, MeOD-d₄): 7.31-6.62 (m, 11H); 3.72 (broad s, 3H); 3.70 (broad s, 3H); 2.91 (t, 2H; J=7.1 Hz); 2.65 (broad t, 2H, J=7.4 Hz)

¹³C NMR: (75 MHz, MeOD-d₄): 173.9; 154.0; 150.3; 143.4; 138.6; 137.4; 132.6; 130.2; 128.4; 127.4; 124.6; 123.1; 122.3; 119.3; 118.1; 111.7; 110.9; 56.5 (2C); 38.8; 32.2.

HRMS: calc: 455.1515: Found: 455.1521

122

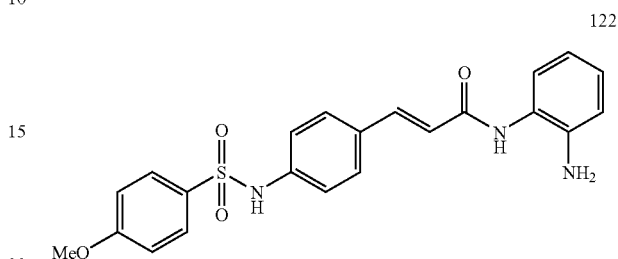

¹H NMR: (300 MHz, DMSO d₆): 7.77 (d, 2H, J=8.8 Hz); 7.51 (d, 2H, J=8.5 Hz); 7.34 (d, 2H, J=8.8 Hz); 7.18 (d, 2H, J=8.5 Hz); 7.11 (d, 2H, 8.8 Hz); 6.94 (t, 1H, J=7.4 Hz); 6.77 (broad d, 2H, J=7.9 Hz); 6.6 (t, 1H, J=7.4 Hz), 4.95 (broad s, 1H), 3.83 (s, 3H).

¹³C NMR: (75 MHz, DMSO d₆): 162.5; 141.5; 139.2; 138.8; 130.9; 130.2; 128.9; 128.6; 125.7; 124.7; 119.4; 116.2; 115.9; 114.5; 55.6.

HRMS: Calc: 423.1253: Found: 423.1235

123

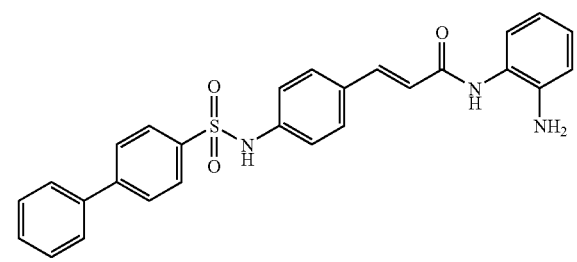

¹H NMR: (300 MHz, DMSO-d₆) δ 7.1-7.8 (m, 14H, CH Ar); 6.8-6.9 (m, 4H, CH Ar); 6.3 (d, 1H, J=15 Hz)

Example 32

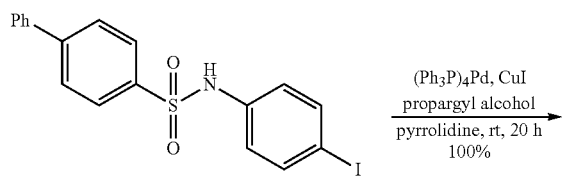

124

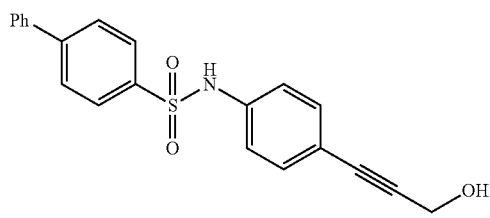

125

Dess-Martin.MeCN
rt, 16 h

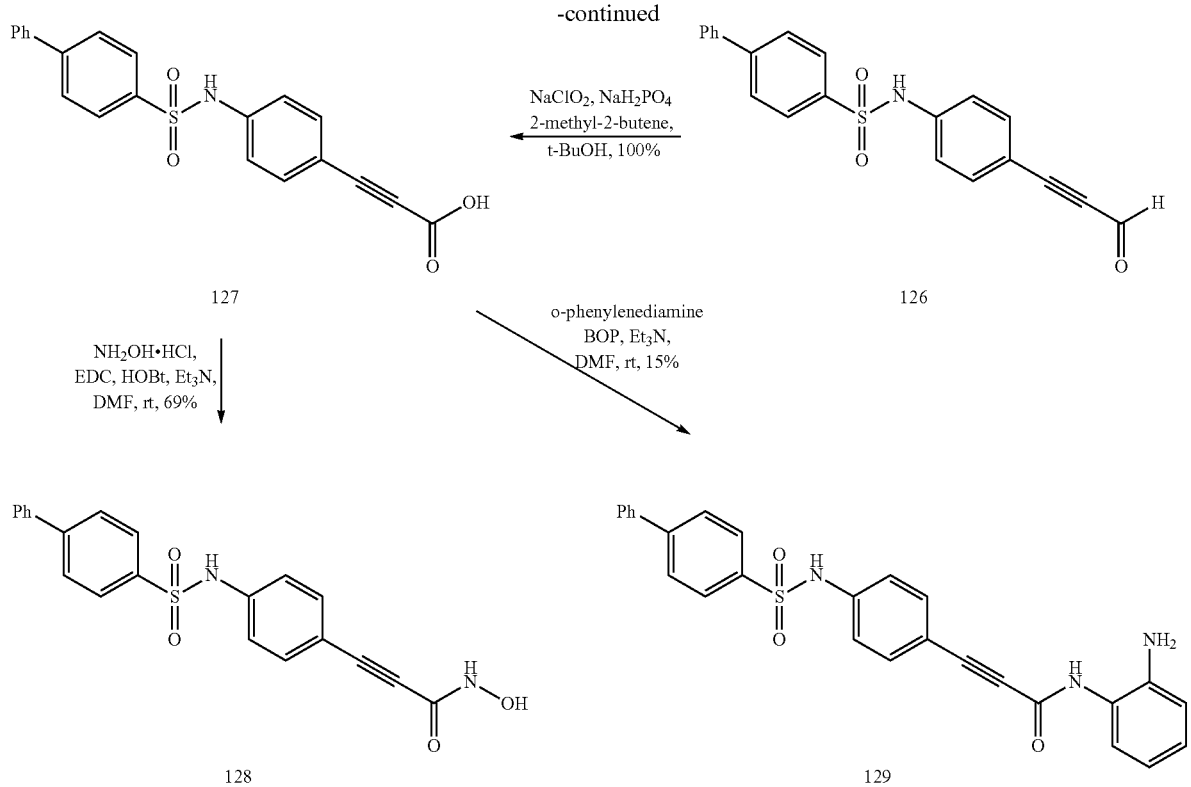

Sulfonamide 124 was prepared by condensation of 4-iodoaniline with benzenesulfonyl chloride. Compound 125 was quantitatively furnished by a Pd—Cu catalyzed coupling reaction of 124 with propargyl alcohol in basic solvent. Primary alcohol 125 was oxidized to the corresponding carboxylic acid 127 in two steps, including Dess-Martin periodinane oxidation to afford aldehyde 126, followed by treatment with sodium chlorite in buffered aqueous media in the presence of a chlorine scavenger. Acid 127 was derivatized to the hydroxamic acid 128 by treatment with hydroxylamine hydrochloride and the coupling reagent EDC in the presence of N-hydroxybenzotriazole in basic, aprotic media. Compound 129 was prepared by coupling acid 130 with o-phenylenediamine as described in Example 31 for compound 86.

Data for 128:
$^1$H NMR: (300.07 MHz; acetone-$d_6$) δ (ppm): 9.4 (bs, 2H); 7.93 (dd, J=1.9, 6.6; 2H); 7.82 (dd, J=1.9, 6.6; 2H); 7.68 (dd, J=1.4, 8.2; 2H); 7.48-741 (m, 5H); 7.35-7.32 (m, 2H); 2.90 (bs, 1H)

$^{13}$C NMR: (75.5 MHz; acetone-$d_6$) δ (ppm): 153.5; 147.2; 141.3; 140.3; 139.5; 134.6; 130.1; 129.5; 128.8; 128.6; 128.3; 120.8; 116.5; 87.7; 81.0.

MS: calc for $C_{21}H_{16}O_4N_2S$: 392.438; found: 393.4 for [M+H] (low resolution MS).

Data for 129:
$^1$H NMR: (300.07 MHz; acetone-$d_6$) δ (ppm): 9.43 (bs, 1H); 8.02 (d, J=8.5 Hz; 2H); 7.93 (d, J=8.5 Hz; 2H); 7.90 (d, J=8.5 Hz; 2H); 7.65 (d, J=8.5 Hz; 2H); 7.47-7.34 (m, 7H); 7.21-7.17 (m, 2H); 2.80 (bs, 3H)

$^{13}$C NMR: (75.5 MHz; acetone-$d_6$) δ (ppm): 167.2; 158.6; 146.3; 141.3; 140.9; 139.8; 139.5; 134.2; 131.0; 129.9; 129.8; 129.3; 128.7; 128.6; 128.4; 128.0; 126.8; 125.1; 122.7; 122.6; 120.1

MS: calc for $C_{27}H_{21}O_3N_3S$: 467.552; found: 468.5 for [M+H] (low resolution MS).

Example 33

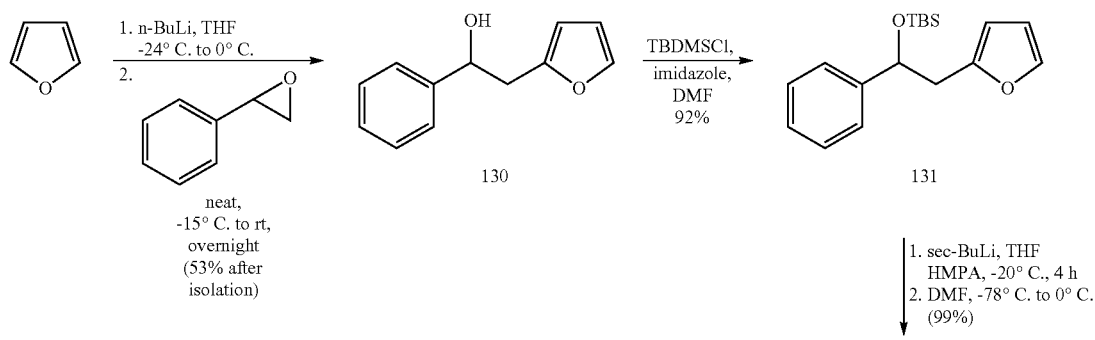

-continued

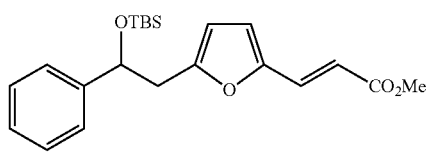

133

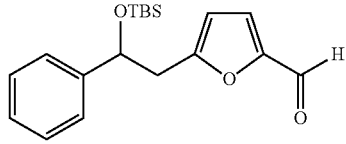

132

1. LiOH (2 eq) MeOH, THF, H₂O 60° C., 60 min
2. KHSO₄ (2 eq) (99%)

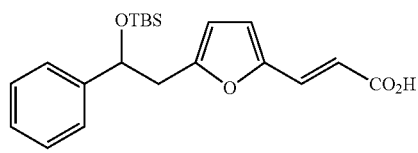

134

1. HOBt, EDC, CH₂Cl
2. NH₂OH·HCl, DMF
(51%; 33% recovered S.M.)

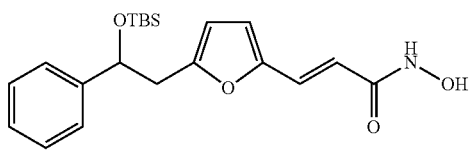

135

TBAF, THF
4A mol. sieves
(67%)

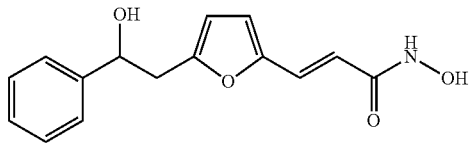

136

Benzylic alcohol 130 was prepared in 53% yield by addition of 2-lithiofuran to styrene oxide. After protection of the resulting hydroxyl group with tert-butyldimethylsilyl chloride, the lithiated species of compound 131 was treated with DMF to afford the formyl derivative 132. Wadsworth-Horner-Emmons olefination was effected by treatment of 132 with the sodium enolate of trimethylphosphonoacetate to afford the key intermediate 133 in 90% overall yield for the last three steps. Saponification of the methyl ester with LiOH yielded the acid 134, which in turn was converted into its hydroxamic acid form 135 by conventional activation with HOBt/EDC, followed by reaction with hydroxylamine. Fluoride-promoted cleavage of silylated ether gave alcohol 136 in 67% yield.

Data for 136:
$^{1}$H NMR: (300.07 MHz; acetone-d6) δ (ppm): 9.35 (bs, 1H); 7.40-7.15 (m; 6H); 6.56 (d, J=2.9 Hz, 1H); 6.24 (d, J=15.3 Hz, 1H); 4.96 (t, J=6.2 Hz, 1 H); 3.00 (d, J=6.2 Hz, 2H)
$^{13}$C NMR: (75.5 MHz; CD₃OD) δ (ppm): 166.6; 156.6; 151.3; 145.2; 129.3; 128.5; 126.9; 116.2; 114.5; 111.0; 73.6; 39.1

Example 34

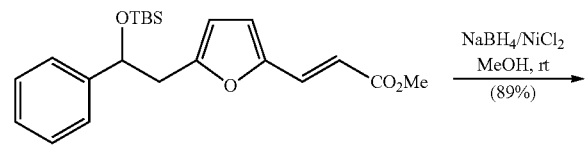

133

NaBH₄/NiCl₂
MeOH, rt
(89%)

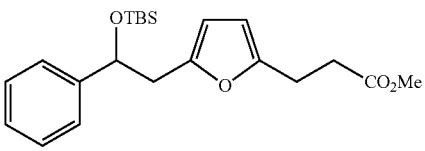

140

1. LiOH (2 eq), THF MeOH, H₂O, 60° C., 60 min then KHSO₄ (2 eq) (99%)
2. TBAF, THF, rt (82%)

1. LiOH (2 eq), THF MeOH, H₂O, 60° C., 60 min then KHSO₄ (2 eq) (72%)
2. TBAF, THF, rt (79%)

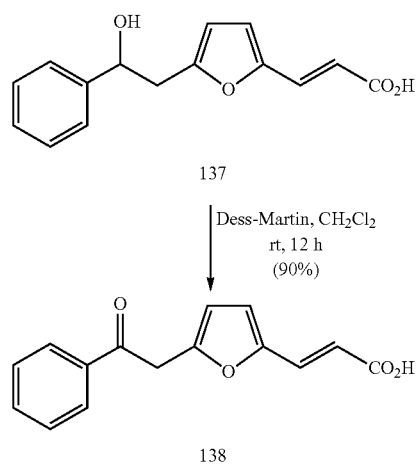

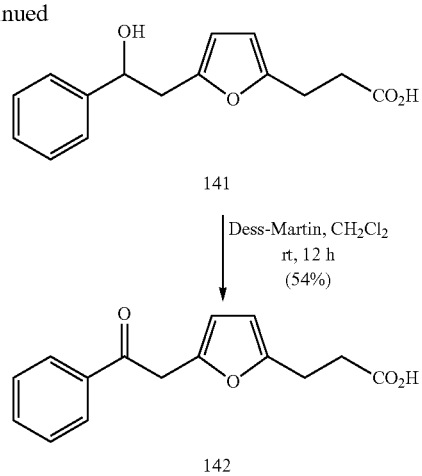

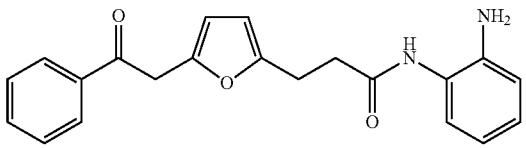

Unsaturated ketoacid 138 was obtained from ester 133 in 73% overall yield after three consecutive steps, including saponification (LiOH/H$_2$O/MeOH/THF), desilylation (TBAF/THF), and oxidation of benzylic alcohol 137 using Dess-Martin periodinane. Anilide 139 was obtained by BOP-mediated condensation of compound 138 with o-phenylenediamine in 83% yield.

Regioselective hydrogenation of the acrylate moiety in 133 was accomplished by treatment with NaBH$_4$ in the presence of NiCl$_2$, to afford the propionate 140 in high yield. Ketoacid 142 was then obtained in 31% overall yield from 140 by an identical procedure to that followed in the synthesis of 138 from 133. With compound 142 in hand, anilide 144 was obtained as described above (BOP/o-phenylendiamine). The low yield was due to a difficult purification process. To avoid oxime formation, hydroxamic acid 143 was synthesized from 142 in 73% overall yield over two steps, including BOP-mediated coupling with N,O-bistrimethylsilylhydroxy-lamine, followed by cleavage of silylated groups under acidic conditions (citric acid/MeOH).

Data for 139:
$^1$H NMR: (300.07 MHz; CDCl$_3$) δ (ppm): 8.02-7.42 (series of multiplets, 7H); 7.34 (bs, 1H); 7.06 (m, 1H); 6.80 (d, J=7.8; 1H); 6.79 (d, J=8.1; 1H); 6.54 (d, J=3.0 Hz, 1H); 6.38 (m, 1H); 6.34 (d, J=3.0 Hz, 1H); 4.37 (s, 2H); 3.90 (bs, 2H)
$^{13}$C NMR: (75.5 MHz; CDCl$_3$) δ (ppm): 194.5; 164.4; 150.9; 150.8; 150.5; 140.5; 135.9; 133.7; 128.7; 128.5; 126.9; 125.0; 124.4; 119.4; 118.0; 117.5; 115.7; 111.3; 38.5

Data for 143:
$^1$H NMR: (300.07 MHz; CDCl$_3$) δ (ppm): 8.99 (bs, 1H); 8.09-7.42 (series of multiplets, 5H); 6.09 (d, J=3.0 Hz, 1H); 6.00 (d, J=3.0 Hz, 1H); 4.35 (s, 2H); 2.95 (t, J=6.60 Hz, 2H); 2.50 (t, J=3.0 Hz, 1H).
$^{13}$C NMR: (75.5 MHz; CDCl$_3$) δ (ppm): 196.2; 162.8; 153.2; 146.8; 134.9; 133.7; 128.7; 128.5; 109.3; 107.1; 38.2; 31.7; 24.2

Data for 144:
$^1$H NMR: (300.07 MHz; CDCl$_3$) δ (ppm): 7.99-7.42 (series of multiplets, 5H); 7.36 (bs, 1H); 7.02 (d, J=7.8, 2H); 6.73 (d, J=7.8 Hz, 2H); 6.13 (d, J=3.0 Hz, 1H); 6.04 (d, J=3.0 Hz, 1H); 4.30 (s, 2H); 3.70 (bs, 2H); 3.03 (t, J=6.9 Hz, 2H); 2.69 (t, J=6.9 Hz, 2H).

$^{13}$C NMR: (75.5 MHz; CDCl$_3$) δ (ppm): 195.4; 170.7; 153.6; 147.1; 140.9; 136.1; 133.5; 128.7; 128.5; 127.1; 125.7; 124.0; 119.2; 117.8; 109.1; 107.2; 38.4; 35.7; 24.7

Example 35

General Procedure for Synthesis of Urea Compounds

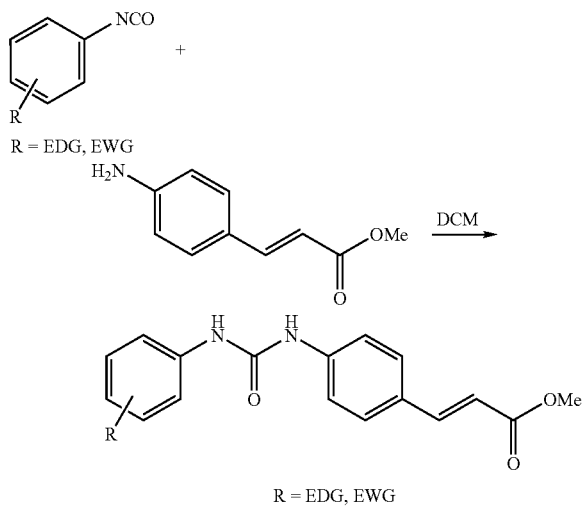

To a solution of isocyanate (1.5 mmol) in 15 mL of anhydrous dichloromethane, was added a solution of 4-anilinylmethylacrylate (1.5 mmol) in dichloromethane (10 mL). The mixture was stirred at room temperature for 15 hours. After addition of ammonium chloride solution the new mixture was extracted from dichloromethane. The organic layers were combined and washed with ammonium chloride solution, water, brine and dried over magnesium sulfate. The crude was then flashed over silica gel using CH$_2$Cl$_2$:MeOH (9.5:0.5) as eluent.

The following compounds were synthesized according to the general procedure:

145

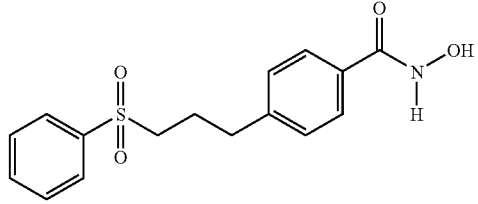

$^1$H NMR: (300 MHz, DMSO-d$_6$) δ 7.5-7.7 (m, 4H, CH Ar); 7.5 (d, 2H, J=6.6 Hz); 7.3 (d, 2H, J=6.6 Hz); 6.3 (d, 1H, J=15 Hz)

146

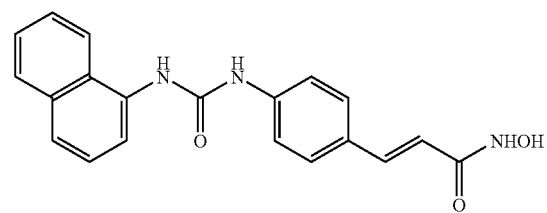

$^1$H NMR: (300 MHz, DMSO-d$_6$) δ 7.5-8.2 (m, 7H, CH Ar); 7.5 (d, 2H, J=6.6 Hz); 7.3 (d, 2H, J=6.6 Hz); 6.3 (d, 1H, J=15 Hz)

147

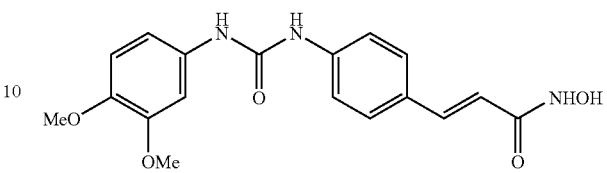

$^1$H NMR: (300 MHz, DMSO-d$_6$) δ 7.5-7.7 (m, 3H, CH Ar); 7.5 (d, 2H, J=6.6 Hz); 7.3 (d, 2H, J=6.6 Hz); 6.3 (d, 1H, J=15 Hz)

Example 36

The following additional compounds were prepared by procedures analogous to those described in the foregoing Examples:

148

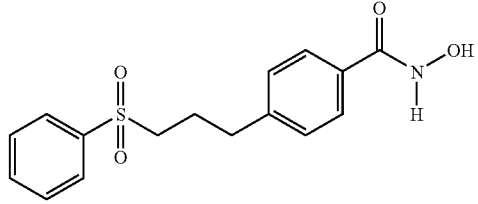

$^1$H NMR (300.072 MHz, (CD$_3$)$_2$CO): δ 1.99 (m, 2H), 2.79 (t, 2H, J=7.2 Hz), 3.21 (dd, 2H, J=6.8, 7.8 Hz), 7.27 (d, 2H, J=8.1 Hz), 7.65 (t, 2H, J=7.8 Hz), 7.72-7.77 (m, 3H), 7.90 (d, 2H, J=7.2 Hz), 10.77 (broad s, 1H).

$^{13}$C NMR (75.46 MHz, (CD$_3$)$_2$CO): δ 25.2 (t), 34.3 (t), 55.6 (t), 128.0 (d), 2×128.8 (d), 129.4 (d), 2×130.2 (d), 131.1 (s), 134.5 (d), 140.7 (s), 145.5 (s), 165.8 (s).

149

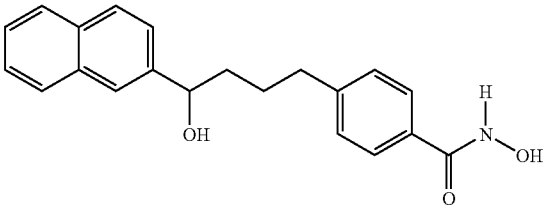

$^1$H NMR (300.072 MHz, (CD$_3$)$_2$CO): δ 1.66-1.88 (m, 4H), 2.71 (t, 2H, J=6.3 Hz), 4.34 (d, 1H, J=303 Hz), 4.87 (m, 1H), 7.27 (d, 2H, J=7.8 Hz), 7.44-7.48 (m, 2H), 7.52 (dd, 1H, J=1.5, 9.4 Hz), 7.73 (d, 2H, J=7.8 Hz), 7.83 (s, 1H), 7.83-7.88 (m, 3H), 8.16 (broad s, 1H), 10.67 (broad s, 1H).

$^{13}$C NMR (75.46 MHz, (CD$_3$)$_2$CO): δ 28.3 (t), 36.2 (t), 39.8 (t), 74.0 (d), 125.0 (d), 125.3 (d), 126.2 (d), 126.7 (d), 2×127.8 (d), 128.4 (d), 128.5 (d), 128.6 (d), 2×129.3 (d), 130.6 (s), 133.7 (s), 134.3 (s), 144.7 (s), 147.4 (s), 165.9 (s).

150

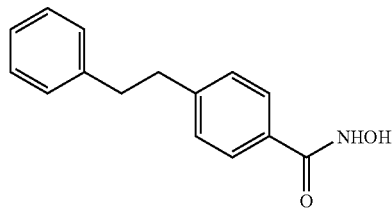

¹H NMR: (300 MHz, DMSO-d6) δ 11.2 (s, OH); 9 (s, NH); 7.6-7.8 (m, 4H, CH Ar); 7-7.4 (m, 5H, CH Ar); 2.8 (m, 4H, CH₂).

151

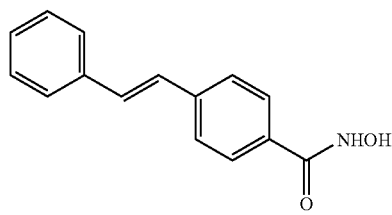

¹H NMR: (300 MHz, DMSO-d$_6$) δ 11.2 (s, 1H); 9.0 (s, 1H); 7.7 (m, 6H); 7.34 (m, 5H).

152

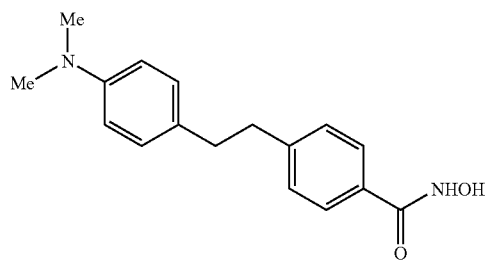

¹H NMR: (300 MHz, DMSO-d$_6$) δ 11.2 (s, OH); 9 (s, NH); 7.6-7.8 (m, 4H, CH Ar); 7-6.8 (m, 4H, CH Ar); 2.9 (s, 6H, 2CH₃); 2.8 (m, 4H, CH₂).

153

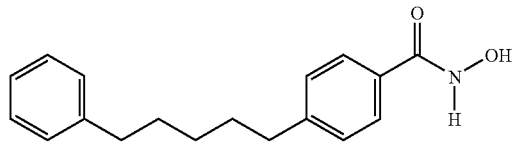

¹H NMR (300.072 MHz, (CD$_3$)$_2$CO): δ 1.38 (quintuplet, 2H, J=7.5 Hz), 1.60-1.72 (m, 4H), 2.60 (t, 2H, J=7.8 Hz), 2.67 (t, 2H, J=7.5 Hz), 7.15-7.31 (m, 7H), 7.75 (d, 2H, J=8.1 Hz), 8.11 (broad s, 1H), 10.68 (broad s, 1H).

¹³C NMR (75.46 MHz, (CD$_3$)$_2$CO): δ 31.8 (t), 32.1 (t), 36.2 (t), 36.4 (t), 126.4 (d), 127.8 (d), 2×129.0 (d), 2×129.2 (d), 2×129.3 (d), 143.3 (s).

154

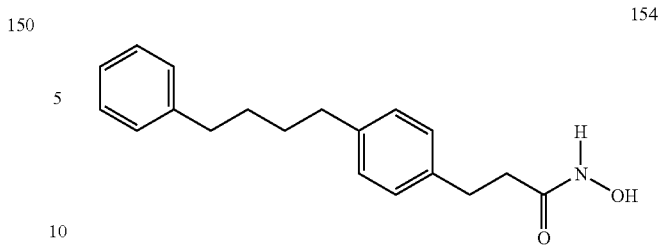

¹H NMR (300.072 MHz, (CD$_3$)$_2$CO): δ 1.63 (m, 4H, J=4.5 Hz), 2.37 (t, 2H, J=7.8 Hz), 2.57-2.66 (m, 4H), 2.86 (t, 2H, J=7.5 Hz), 7.10-7.28 (m, 9H), 8.01 (broad s, 1H), 9.98 (broad s, 1H).

¹³C NMR (75.46 MHz, (CD$_3$)$_2$CO): δ 31.0 (t), 2×31.9 (t), 35.1 (t), 35.8 (t), 36.2 (t), 126.4 (d), 2×129.0 (d), 2×129.1 (d), 2×129.1 (d), 129.2 (d), 138.8 (s), 141.2 (s), 143.4 (s), 164.1 (s).

155

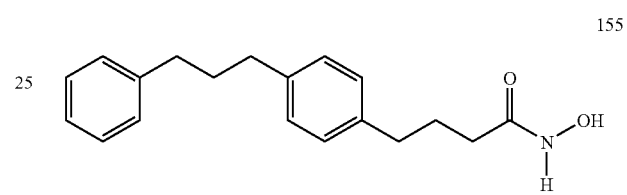

¹H NMR (300.072 MHz, (CD$_3$)$_2$CO): δ 1.83-1.98 (m, 4H), 2.08-2.14 (m, 2H), 2.56-2.67 (m, 6H), 7.12-7.30 (m, 9H), 9.98 (broad s, 1H).

156

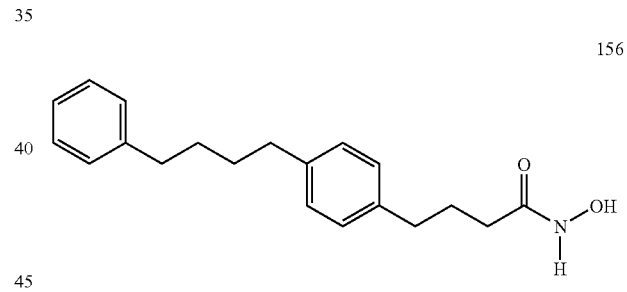

¹H NMR (300.072 MHz, (CD$_3$)$_2$CO): δ 1.60-1.68 (m, 4H), 1.87 (quintuplet, 2H, J=7.5 Hz), 2.03-2.14 (m, 2H), 2.55-2.67 (m, 6H), 7.09-7.28 (m, 9H).

157

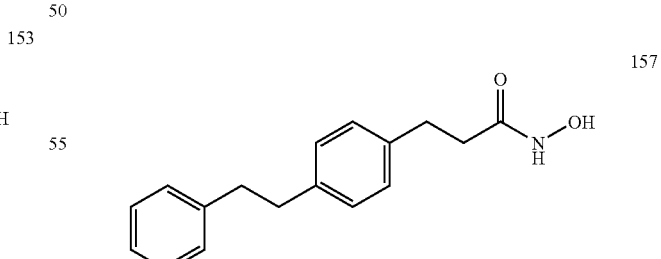

¹H NMR (300.072 MHz, (CD$_3$)$_2$CO): δ 2.37 (t, 2H, J=7.2 Hz), 2.78-2.89 (m, 6H), 7.13-7.29 (m, 9H), 7.84 (broad s, 1H), 9.90 (broad s, 1H).

¹³C NMR (75.46 MHz, (CD$_3$)$_2$CO): δ 31.6 (t), 35.1 (t), 38.2 (t), 38.6 (t), 2×126.6 (d), 2×129.1 (d), 2×129.2 (d), 2×129.3 (d), 139.4 (s), 140.4 (s), 142.8 (s), 170.1 (s).

158

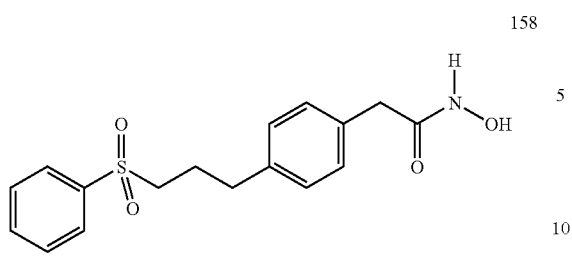

¹H NMR (300.072 MHz, (CD₃)₂CO): δ 1.96 (quintuplet, 2H, J=6.0 Hz), 2.69 (t, 2H, J=8.0 Hz), 3.19 (dd, 2H, J=6.0, 9.0 Hz), 3.38 (s, 2H), 7.09 (d, 2H, J=7.5 Hz), 7.21 (d, 2H, J=7.5 Hz), 7.66 (t, 2H, J=8.1 Hz), 7.747 (t, 1H, J=6.9 Hz), 7.90 (d, 2H, J=6.6 Hz), 10.08 (broad s, 1H).

¹³C NMR (75.46 MHz, (CD₃)₂CO): δ 25.5 (t), 34.1 (t), 39.9 (t), 55.7 (t), 2×128.8 (d), 130.0 (d), 2×130.2 (d), 134.4 (s), 139.9 (s), 140.7 (s), 168.5 (s).

159

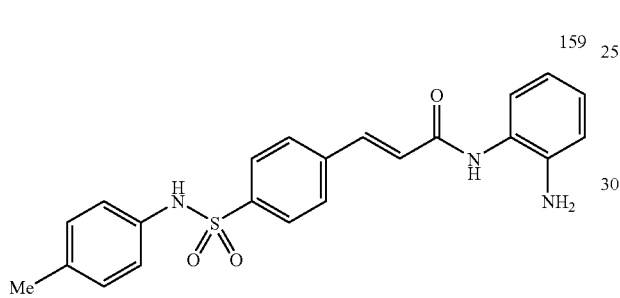

¹H NMR: (300 MHz, DMSO d₆): δ 7.77 (broad s, 4H); 7.57 (d, 1H, J=15.7 Hz); 7.35 (d, 1H, J=6.9 Hz); 7.03-6.94 (m, 6H); 6.76 (d, 1H, J=7.1 Hz); 6.59 (d, 1H, J=6.9 Hz); 4.98 (broad s, 2H); 2.19 (s, 3H).

¹³C NMR: (75 MHz, DMSO d₆): δ 162.9; 141.6; 139.8; 139.0; 137.6; 134.8; 133.6; 129.6; 128.1; 127.3; 125.9; 125.4; 124.7; 123.2; 120.7; 116.2; 115.9; 20.3.

160

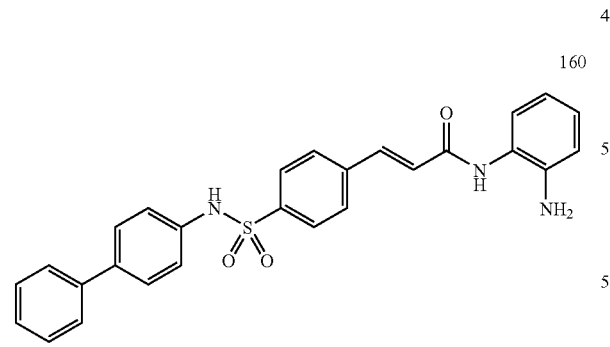

¹H NMR: (300 MHz, DMSO d₆): δ 7.91-7.81 (m, 4H); 7.63-7.58 (m, 5H); 7.48-7.43 (m, 2H); 7.39-7.33 (m, 2H); 7.24 (d, 2H, J=8.5 Hz); 6.97 (dd, 2H, J=9.9, 7.1 Hz); 6.79 (d, 1H, J=7.7 Hz) 6.61 (dd, 1H, J=7.7, 7.1 Hz); 5.01 (broad s, 2H).

¹³C NMR: (75 MHz, DMSO d₆): δ 162.9; 141.9; 141.6; 139.8; 139.2; 137.6; 136.9; 135.8; 128.9; 128.3; 127.4; 127.3; 127.2; 126.3; 126.0; 125.5; 124.8; 123.2; 120.4; 116.2; 115.9.

161

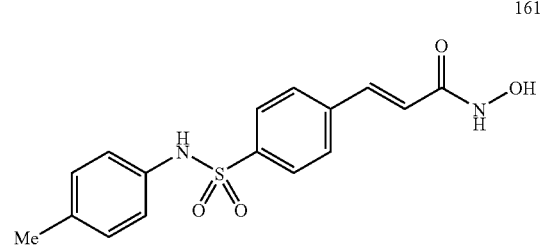 [SMILES: Cc1ccc(NS(=O)(=O)c2ccc(/C=C/C(=O)NO)cc2)cc1]

¹H NMR: (300 MHz, MeOD d₄): δ 7.74-7.54 (m, 5H); 7.07-6.96 (m, 4H); 6.55 (d, 1H, J=15.7); 2.25 (s, 3H).

¹³C NMR: (75 MHz, MeOD d₄): δ 163.5; 141.6; 140.4; 139.5; 136.1; 135.9; 130.6; 129.0; 128.8; 123.1; 121.7; 20.8

162

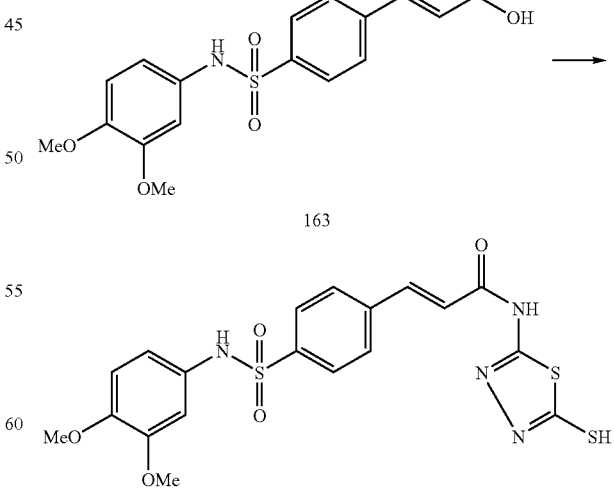

¹H NMR: (300 MHz, MeOD d₄): δ 7.83-7.19 (m, 14H); 6.56 (d, 1H, J=15.7 Hz).

¹³C NMR: (75 MHz, MeOD d₄): δ 165.4; 141.6; 141.4; 140.5; 139.5; 139.0; 137.9; 129.8; 129.2; 128.7; 128.6; 128.2; 127.6; 122.7; 121.7.

Example 37

To a solution of carboxylic acid 163 (131 mg, 0.36 mmol), prepared according to procedures described above, in 6 mL of dry DMF was added Et₃N (190 µl, 1.37 mmol), followed by the addition of solid BOP (259 mg; 0.59 mmol). The reaction mixture was stirred for 10 min. at room temperature and then solid 5-amino-1,3,4-thiadiazole-2-thiol (58 mg, 0.43 mmol) was added. After being stirred for 12 h, the mixture was diluted with methanol and concentrated under vacuum. Upon dilution with CH₂Cl₂/MeOH, crystallization of 164 (150 mg, 87%) from the crude oil took place.

¹H NMR: (300 MHz, DMSO d₆): δ 7.85 (broad s, 5H); 7.04-6.58 (m, 4H); 3.69 (s, 3H); 3.67 (s, 3H); 3.38 (broad s, 3H).

¹³C NMR: (75 MHz, DMSO d₆): 163.3; 161.7; 158.7; 148.7; 146.2; 142.0; 140.7; 137.9; 130.1; 128.7; 127.5; 121.4; 113.7; 112.0; 106.6; 55.5; 55.4.

Following this general procedure, the following thiadiazole derivatives were prepared from the corresponding carboxylic acids:

165

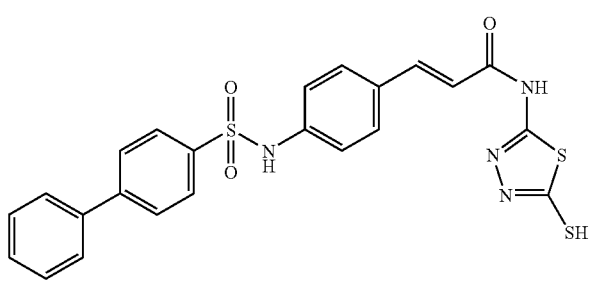

¹H NMR: (300 MHz, DMSO-d₆); δ (ppm): 7.89-7.72 (series of multiplets, 7H); 7.50-7.05 (series of multiplets, 6H); 3.32 (broad singlet, 3H)

¹³C NMR: (75 MHz, DMSO-d6); d (ppm): 162.6; 162.3; 144.5; 138.3; 138.3; 138.2; 132.5; 130.1; 129.7; 129.1; 128.6; 127.6; 127.3; 127.1; 120.9; 118.7; 116.8.

MS: calc. for M+H, 493.6. obs. for M+H, 496.3

166

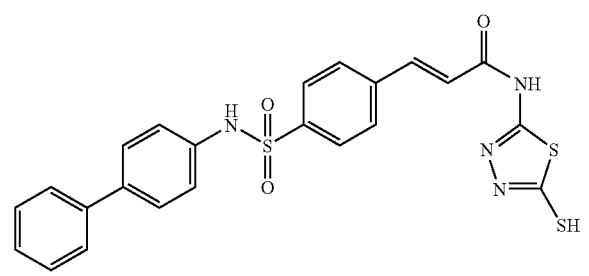

¹H NMR: (300 MHz, DMSO d₆): 7.87-7.72 (m, 5 H), 7.57-7.53 (m, 4 H), 7.39 (dd, 2H, J=6.9, 7.7 Hz), 7.30 (d, 1 H, J=7.1 Hz), 7.17 (d, 2 H, J=8.5 Hz), 6.85 (d, 1 H, J=15.9 Hz).

MS: cal: 495.61; found: 496.6

Following an analogous procedure, but substituting 2-amino-5-trifluoro-methyl-1,3,4-thiadiazole for 5-amino-1,3,4,-thiadiazol-2-thiol, the following compound was prepared:

167

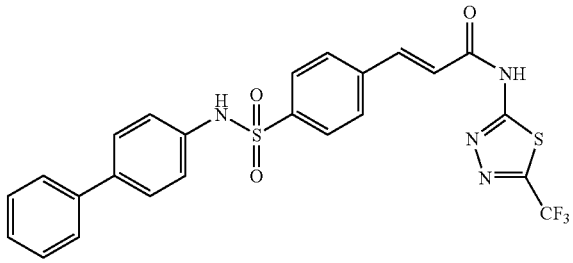

¹H NMR: (300 MHz, DMSO d₆): δ 7.96-7.81 (m, 5H); 7.71-7.48 (m, 4H); 7.38 (dd, 2H, J=7.1, 7.41 Hz); 7.28 (d, 1H, J=7.1 Hz); 7.19 (d, 2H, J=8.5 Hz); 6.98 (d, 1H, J=15.7 Hz).

¹³C NMR: (75 MHz, DMSO d₆): 192.3; 163.6; 161.6; 142.4; 140.9; 139.2; 138.0; 136.8; 135.9; 129.0; 128.8; 127.4; 127.2; 126.2; 121.2; 120.4.

MS: cal: 530.55 found: 531.5

Example 38

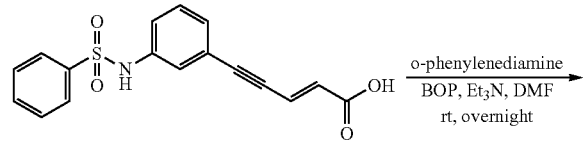

24

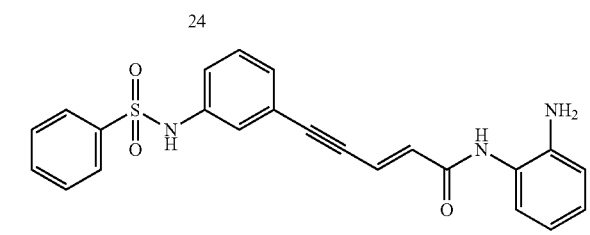

168

Coupling of 24 (from Example 15) with o-phenylenediamine in the presence of benzotriazol-1-yloxytris(dimethylamino)phosphonium hexafluorophosphate (BOP) afforded the anilide 168.

By an analogous procedure, the corresponding para-substituted compound is prepared from 32 (from Example 16).

Example 39

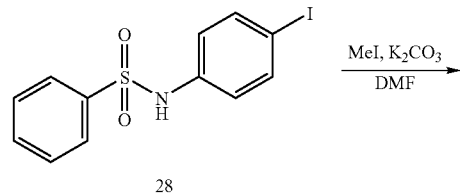

28

-continued

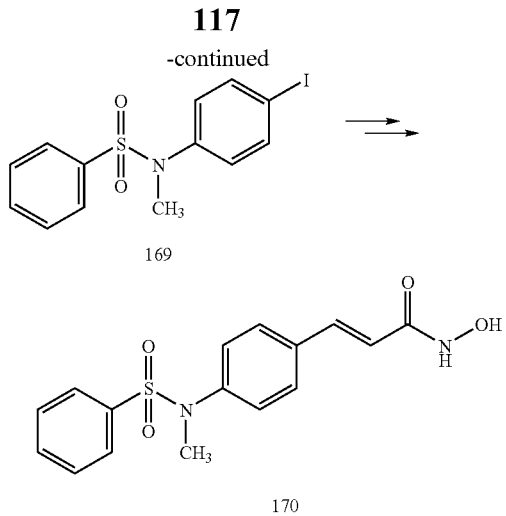

Step 1: N-Methyl-4-iodophenylbenzenesulfonamide (169)

To compound 28 (from Example 18) (500 mg, 1.39 mmol) in DMF (10 mL) were added at room temperature $K_2CO_3$ (962 mg, 6.96 mmol), followed by methyl iodide (395 mg, 2.78 mmol). The resulting reaction mixture was stirred at room temperature for 16 hours. The solvent is then removed and water was added. The resulting mixture was extracted with ethyl acetate, and the combined organic phases were dried and concentrated. Purification by flash chromatography using hexane:ethyl acetate (8:2) afforded 510 mg (98%) of the title compound as a white solid.

Compound 169 was converted to the hydroxamic acid 170 according to the procedures described in Example 18 for the preparation of compound 36.

Data for 170:
$^1$H NMR: (300 MHz, DMSO $d_6$): δ=10.76 (1H, s), 9.04 (1H, s), 7.73-7.68 (1H, m), 7.61-7.51 (6H, m), 7.43 (1H, d, J=15.9 Hz), 7.15 (2H, d, J=8.7 Hz), 6.43 (1H, d, J=16.2 Hz), 3.15 (3H, s).

Analysis: $C_{16}H_{16}N_2O_4S$ X $0.5H_2O$ Found: C=56.36%, H=5.09%, N=8.69%, S=8.33%. Calc.: C=56.29%, H=5.02%, N=8.21%, S=9.39%.

Example 40

N-hydroxy-2-(4-(4-phenylbutyl)phenyl)acetamide (174)

Step 1: Methyl 2-(4-iodophenyl)acetate

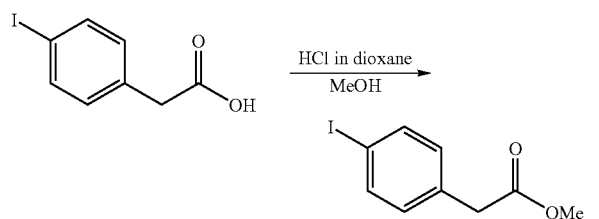

A 4M solution of HCl in dioxane (50 mL) was added to 2-(4-iodophenyl)acetic acid (10 g, 38.2 mmol) in MeOH (100 mL) and the reaction stirred overnight. The solvent was evaporated under reduced pressure. The residue was purified by silica gel column chromatography eluting with 0-30% EtOAc in hexanes to afford methyl 2-(4-iodophenyl)acetate in 10.42 g (99%). LRMS: 276.0 (calc) 277.1 (found)(MH$^+$)$^+$.

Step 2: Methyl 2-(4-(4-phenylbut-1-ynyl)phenyl)acetate

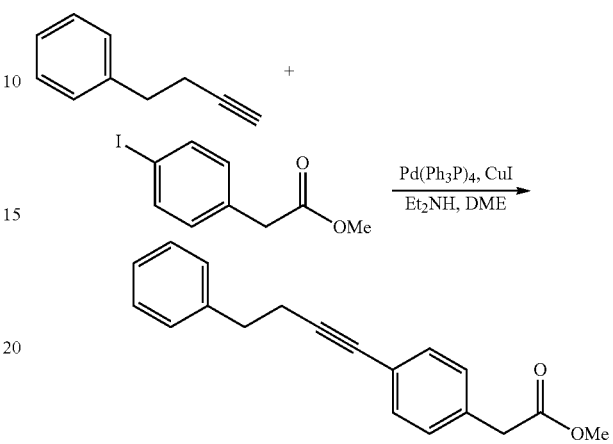

CuI (0.06 equiv, 207 mg, 1.1 mmol) was added to a solution of Pd(Ph$_3$P)$_4$ (0.03 equiv, 628 mg, 0.54 mmol) and aromatic iodide (1 equiv, 5 g, 18 mmol) in Et$_2$NH:DME (30 mL: 30 mL) and the reaction stirred for 20 min. 4-phenyl-1-butyne (3 equiv, 7.1 g, 54 mmol) was then added dropwise and the reaction stirred for 3 h. The reaction was concentrated under reduced pressure and then the residue partitioned between EtOAc (50 mL) and H$_2$O (50 mL). The organic phase was separated, dried over Na$_2$SO$_4$ filtered and concentrated. The compound was purified by silica gel flash column chromatography: 20%-100% EtOAc in hexanes to afford methyl 2-(4-(4-phenylbut-1-ynyl)phenyl)acetate in 4.95 g (98%). LRMS: 278.3 (calc) 279.2 (found)(MH)$^+$.

Step 3: Methyl 2-(4-(4-phenylbutyl)phenyl)acetate

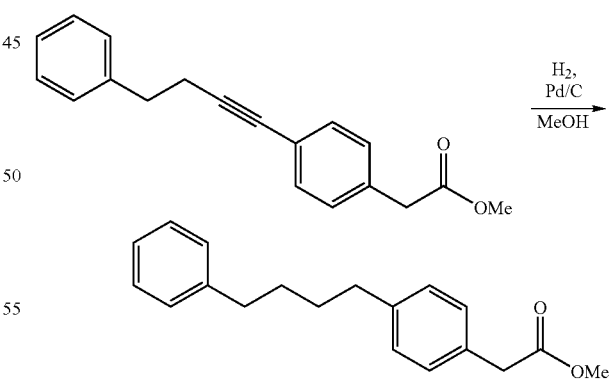

10% Pd/C (20% w/w, 1 g) was added to a solution of the acetylene (4.9 g, 18 mmol) in MeOH (30 mL). The reaction was then purged with H$_2$ and stirred overnight. The solvent was evaporated and the residue was purified by a silica plug eluting with 30% EtOAc in hexanes to afford methyl 2-(4-(4-phenylbutyl)phenyl)acetate in 4.99 g (99%). LRMS: 282.3 (calc) 283.1 (found)(MH)$^+$.

Step 4: N-hydroxy-2-(4-(4-phenylbutyl)phenyl)acetamide (174)

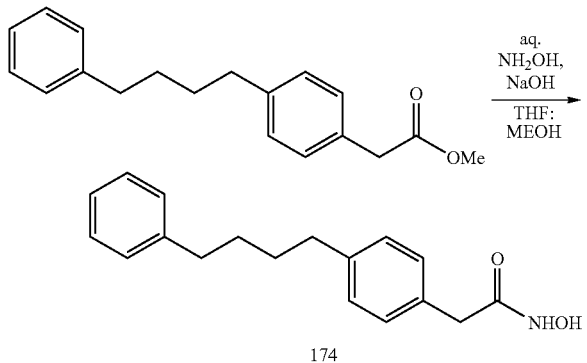

174

NaOH (6 equiv, 4.2 g, 106 mmol) was added to a solution of the methyl ester (1 equiv, 4.9 g, 18 mmol) and aq. NH₂OH (50 equiv, 58 g, 884 mmol) in MeOH (100 mL) and THF (100 mL) at 23° C. After stirring the reaction overnight, the reaction was adjusted to pH=7. The solvent was evaporated and the residue was purified by trituration with hexanes and water to afford N-hydroxy-2-(4-(4-phenylbutyl)phenyl)acetamide 174 in 4.66 g (93%).

(dDMSO) δ(ppm) ¹H, 10.59(s, 1H), 8.77(s, 1H), 7.25-7.06 (m, 9H), 3.19(s, 2H), 2.58-2.53(m, 4H), 1.54-1.52(m, 4H). LRMS: 283.1 (calc) 282.0 (MH)⁻.

Example 41

N-hydroxy-2-(4-(4-(2,4,5-trifluorophenyl)butyl)phenyl)acetamide (179)

Step 1: Methyl 2-(4-(3-hydroxyprop-1-ynyl)phenyl)acetate

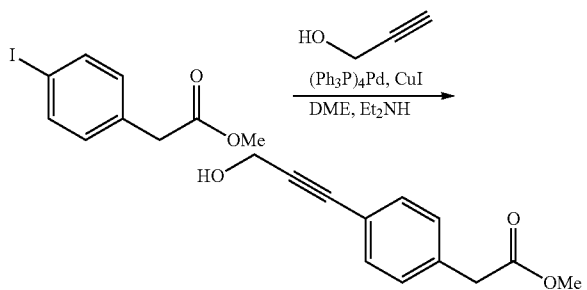

Following the procedure of Step 2 of Example 40 above afforded methyl 2-(4-(3-hydroxyprop-1-ynyl)phenyl)acetate in 1.17 g (79%) as a thick yellow oil. (MeOD-d4) δ(ppm) ¹H, 7.36 (d, J=8.4 Hz, 2H), 7.24 (d, J=8.0 Hz, 2H), 4.38 (s, 2H), 3.67 (s, 3H), 3.65 (s, 2H).

Step 2: Methyl 2-(4-(3-hydroxypropyl)phenyl)acetate

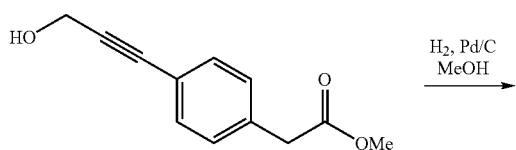

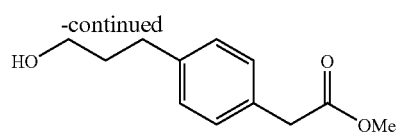

Following the procedure of Step 3 of Example 40 above afforded methyl 2-(4-(3-hydroxypropyl)phenyl)acetate in 1.18 g (99%) a clear translucent oil. (MeOD-d4) δ(ppm) ¹H, 7.15 (d, J=1.6 Hz, 4H), 3.66 (s, 3H), 3.59 (s, 2H), 3.55 (t, J=6.4 Hz, 2H), 2.65 (t, J=7.6 Hz, 2H), 1.82 (m, 2H).

Step 3: Methyl 2-(4-(3-oxopropyl)phenyl)acetate

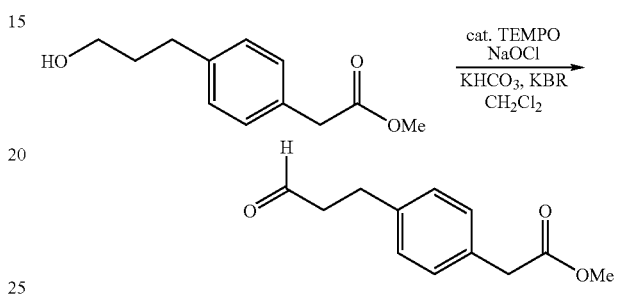

TEMPO (0.02 equiv, 6 mg, 0.038 mmol) was added to a solution of methyl 2-(4-(3-hydroxypropyl)phenyl)acetate in CH₂Cl₂ (5 mL) and cooled to 0° C. KBr (2.2 equiv, 1.6 mL, 2.7M) and KHCO₃ (5.5 equiv, 6.6 mL, 1.6M) solutions were then added followed by the dropwise addition of 10% aq. NaOCl (1.34 equiv, 1.9 g, 2.6 mmol). Once the addition was complete, the reaction was stirred for an additional 10 min. at 0° C. The reaction was quenched with sat. aq. sodium thiosulfate solution (3 mL) and then partitioned between H₂O (10 mL) and CH₂Cl₂ (10 mL). The organic phase was separated and the remaining aqueous phase was extracted with EtOAc (2×2 mL). The organic layers were combined, dried over Na₂SO₄, filtered and concentrated under reduced pressure. The resulting aldehyde was carried forward to the subsequent reaction without further purification. LRMS: 206.1 (calc) 207.2 (found)(MH)⁺.

Step 4: Methyl 2-(4-(but-3-ynyl)phenyl)acetate

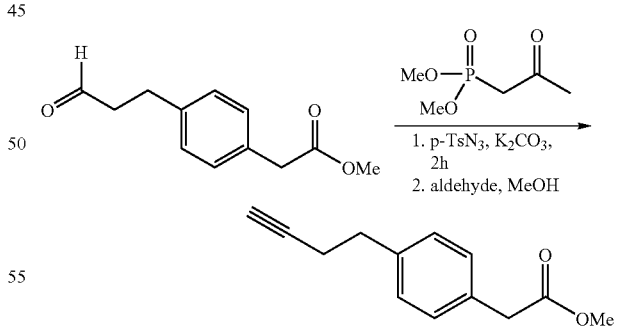

Dimethyl-2-oxopropylphosphonate (1.2 equiv, 1.5 g, 9.1 mmol) was added to a suspension of K₂CO₃ (3 equiv, 3.1 g, 23 mmol) and p-TsN₃ (1.2 equiv, 1.8 g, 9.1 mmol) in MeCN (144 mL). The mixture was then stirred for 2 h. A solution of the methyl 2-(4-(3-oxopropyl)phenyl)acetate (1 equiv, 1.56 g, 7.6 mmol) in MeOH was then added in one portion and the reaction was stirred overnight. The solvent was evaporated under reduced pressure. The residue was partitioned between Et₂O (100 mL) and water (100 mL). The aqueous phase was separated and extracted with Et₂O (25 mL) twice. The organic phases were combined, dried over Na₂SO₄, filtered and concentrated. The residue was purified by silica gel flash column eluting with 0-30% EtOAc in hexanes to afford methyl 2-(4-(but-3-ynyl)phenyl)acetate in 980 mg (64%). LRMS: 202.5 (calc) 225.1 (found)(MNa)⁺.

Step 5: Methyl 2-(4-(4-(2,4,5-trifluorophenyl)but-3-ynyl)phenyl)acetate

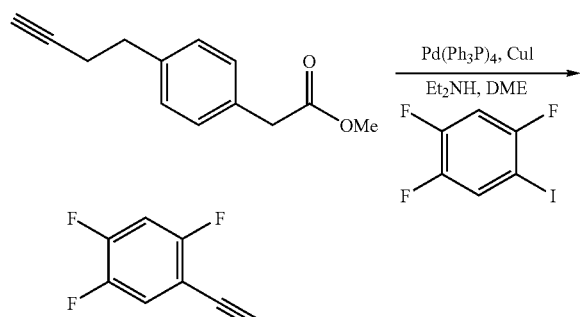

Following the procedure of Step 2 of Example 40 above afforded methyl 2-(4-(4-(2,4,5-trifluorophenyl)but-3-ynyl)phenyl)acetate in 95 mg (39%) as a yellow oil. LRMS: 332.3 (calc) 355.3 (found)(MNa)⁺.

Step 6: Methyl 2-(4-(4-(2,4,5-trifluorophenyl)butyl)phenyl)acetate

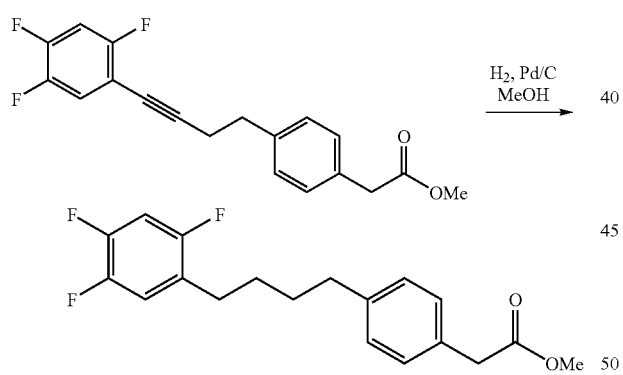

Following the procedure of Step 3 of Example 40 above afforded methyl 2-(4-(4-(2,4,5-trifluorophenyl)butyl)phenyl)acetate in 91 mg (95%) as a clear translucent oil.

LRMS: 336.3 (calc) 359.2 (found)(MNa)⁺.

Step 7: N-hydroxy-2-(4-(4-(2,4,5-trifluorophenyl)butyl)phenyl)acetamide (179)

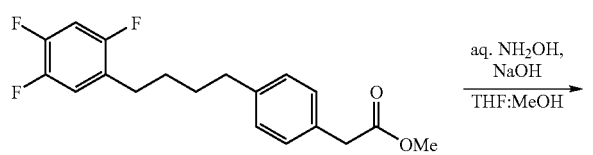

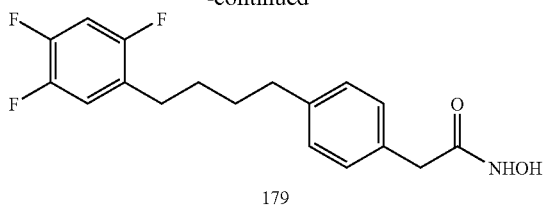

Following the procedure of Step 4 of Example 40 above afforded N-hydroxy-2-(4-(4-(2,4,5-trifluorophenyl)butyl)phenyl)acetamide 179 in 52 mg (57%) as a white powder. (MeOD-d4) δ(ppm) ¹H, 7.15 (m, 6H), 3.35 (s, 2H), 2.61 (m, 4H), 1.60 (m, 4H). LRMS: 337.3 (calc) 338.3 (found)(MH)⁺.

Example 42

2-(4-(4-(benzo[c][1,2,5]oxadiazol-5-yl)but-3-ynyl)phenyl)-N-hydroxyacetamide (180)

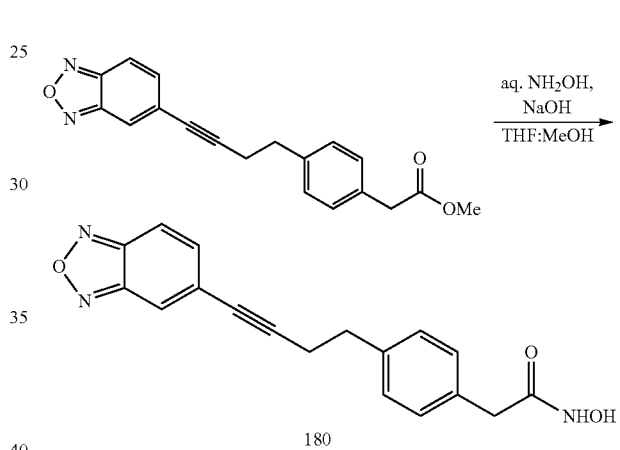

Following the procedure of Step 4 of Example 40 above afforded 2-(4-(4-(benzo[c][1,2,5]oxadiazol-5-yl)but-3-ynyl)phenyl)-N-hydroxyacetamide 180 in 8 mg (57%) as a yellowish orange powder. (MeOD-d4) δ(ppm) ¹H, 10.62 (s, 1H), 8.79 (s, 1H), 8.07 (s, 1H), 8.03 (d, J=9.2 Hz, 1H), 7.40 (d, J=9.6 Hz, 1H), 7.24 (d, J=8.4 Hz, 2H), 7.18 (d, J=8.0 hz, 2H), 3.23 (s, 3H), 2.83 (m, 2H), 2.77 (m, 2H) LRMS: 321.1 (calc) 320.3 (found)(MH)⁻.

Example 43

N-Hydroxy-2-(3-(4-phenylbutyl)phenyl)acetamide (181)

Step 1: Methyl 2-(3-(4-hydroxybut-1-ynyl)phenyl)acetate

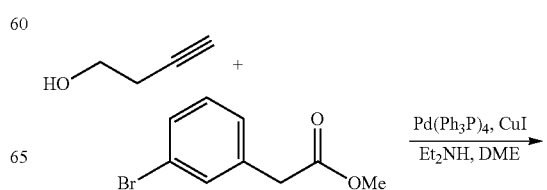

-continued

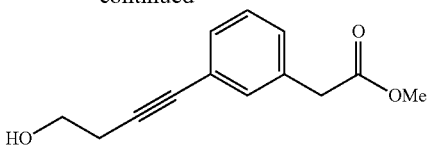

Following the procedure of Step 2 of Example 40 above afforded methyl 2-(3-(4-hydroxybut-1-ynyl)phenyl)acetate in 227 mg (34%) as a yellow oil. LRMS: 218.2 (calc) 219.1 (found)(MH)+.

Step 2: Methyl 2-(3-(4-hydroxybutyl)phenyl)acetate

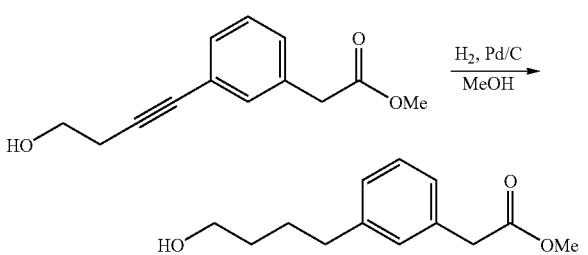

Following the procedure of Step 3 of Example 40 above afforded methyl 2-(3-(4-hydroxybutyl)phenyl)acetate in 181 mg (78%) as a clear translucent oil. LRMS: 222.3 (calc) 223.1 (found)(MH)+.

Step 3: Methyl 2-(3-(4-oxobutyl)phenyl)acetate

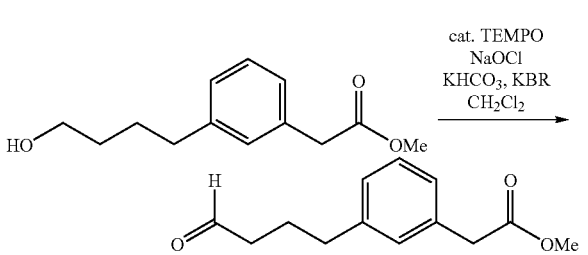

Following the procedure of Step 3 of Example 41 above afforded methyl 2-(3-(4-oxobutyl)phenyl)acetate in 178 mg (99%) as a clear translucent oil. LRMS: 220.3 (calc) 221.4 (found)(MH)+.

Step 4: Methyl 2-(3-(4-hydroxy-4-phenylbutyl)phenyl)acetate

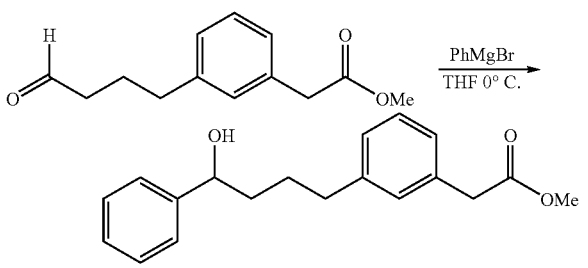

A 1.0 M solution of PhMgBr (1 equiv, 0.45 mmol) was added dropwise to a solution of methyl 2-(3-(4-oxobutyl)phenyl)acetate (1 equiv, 100 mg, 0.45 mmol) in THF (2 mL) at 0° C. The reaction was then allowed to warm to 23° C. over 1 h. The reaction was quenched by the addition on sat. aq. NH$_4$Cl (10 mL). The aqueous phase was separated and extracted with EtOAc (2×5 mL). The organic layers were then combined, dried over Na$_2$SO$_4$, filtered and concentrated under reduced pressure. The crude product was purified by silica gel column chromatography eluting with 0-50% EtOAc in hexanes to afford methyl 2-(3-(4-hydroxy-4-phenylbutyl)phenyl)acetate in 78 mg (58%) as a clear translucent oil. LRMS: 298.4 (calc) 321.2 (found)(MH)+.

Step 5: Methyl 2-(3-(4-phenylbutyl)phenyl)acetate

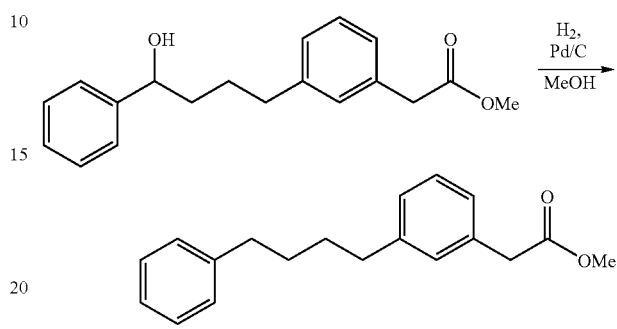

Following the procedure of Step 3 of Example 40 above afforded methyl 2-(3-(4-phenylbutyl)phenyl)acetate in 15 mg (20%) as a clear translucent oil. LRMS: 282.4 (calc) 283.2 (found)(MH)+.

Step 6: N-Hydroxy-2-(3-(4-phenylbutyl)phenyl)acetamide (181)

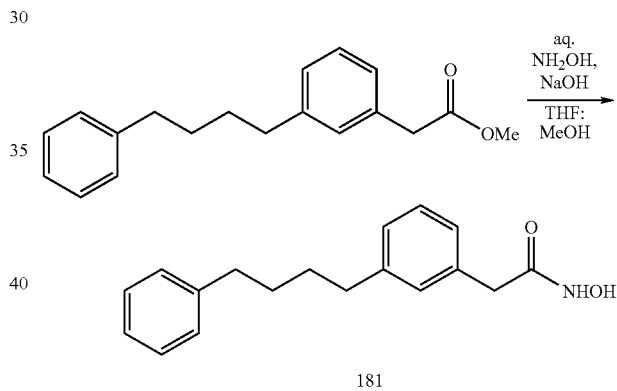

181

Following the procedure of Step 4 of Example 40 above afforded N-Hydroxy-2-(3-(4-phenylbutyl)phenyl)acetamide (181) in 5 mg (33%) as a white powder. (CD$_3$OD) δ (ppm) 1H, 7.23 (m, 9H), 3.36 (s, 2H), 2.61 (m, 4H), 1.63 (m, 4H) LRMS (ESI): (calc.) 283.1 (found) 282.2 (MH)−

Example 44

The following additional compounds were prepared by procedures analogous to those described in the Examples 40-43:

a) N-hydroxy-2-(4-(4-(4-(trifluoromethyl)phenyl)butyl)phenyl)acetamide (182)

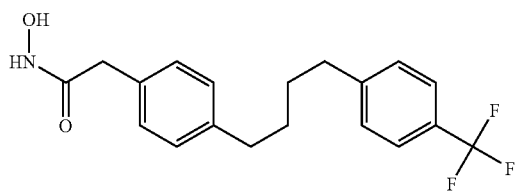 [SMILES: O=C(Cc1ccc(CCCCc2ccc(C(F)(F)F)cc2)cc1)NO]

(CD3OD) δ(ppm) 1H, 7.53 (d, J=8.4 Hz, 2H), 7.33 (d, J=8.0 Hz, 2H), 7.18 (d, J=8.0 Hz, 2H), 7.10 (d, J=8.0 Hz, 2H), (s, 2H), 2.70 (t, J=7.2 Hz, 2H), 2.61 (t, J=7.2 Hz, 2H), 1.63 (m, 4H). LRMS(ESI): (calc.) 351.14 (found) 350.24(MH)⁻.

b) 2-(4-(4-(1H-indol-5-yl)butyl)phenyl)-N-hydroxy-acetamide (183)

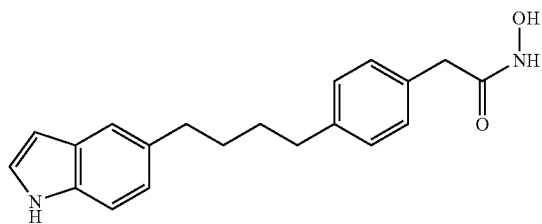 [SMILES: O=C(Cc1ccc(CCCCc2ccc3[nH]ccc3c2)cc1)NO]

(CD3OD) d(ppm) 1H, 7.29 (m, 1H), 7.24 (d, J=8.8 Hz, 1H), 7.18-7.16 (m, 3H), 7.11-7.09 (m, 2H), 6.90 (dd, J=8.4 Hz, 1.6 Hz, 1H), 6.34 (d, J=4 Hz, 1H), 3.35 (s, 2H), 2.68 (t, J=7.2 Hz, 2H), 2.61 (t, J=7.2 Hz, 2H), 1.64 (m, 4H) LRMS (ESI): (calc.) 322.17 (found) 323.421 (MH)+.

c) N-hydroxy-2-(4-(4-(3-(trifluoromethyl)phenyl) butyl)phenyl)acetamide (184)

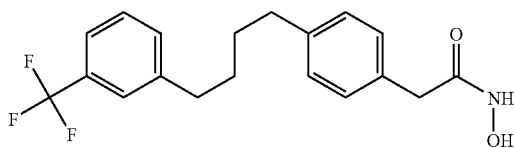 [SMILES: O=C(Cc1ccc(CCCCc2cccc(C(F)(F)F)c2)cc1)NO]

(dDMSO) δ(ppm) 1H: 10.60 (s, 1H), 8.77 (s, 1H), 7.50 (m, 4H), 7.12 (d, J=8.0 Hz, 2H), 7.07 (d, J=8.0 Hz, 2H), 3.19 (s, 2H), 2.68 (t, J=7.2 Hz, 2H), 2.54 (t, J=7.2 Hz, 2H), 1.55 (m, 4H). LRMS(ESI): (calc.) 351.1 (found) 350.3 (MH)⁻.

d) N-hydroxy-2-(4-(4-(2-(trifluoromethyl)phenyl) butyl)phenyl)acetamide (185)

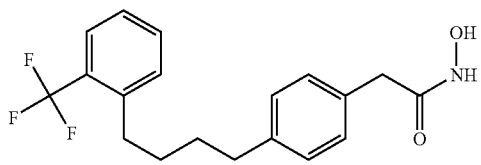

(dDMSO) d(ppm) 1H: 10.60 (s, 1H), 8.77 (s, 1H), 7.63 (d, J=8.0 Hz, 1H), 7.57 (t, J=7.2 Hz, 1H), 7.43 (d, J=7.6 Hz, 1H), 7.37 (t, J=8.0 Hz, 1H), 7.13 (d, J=8.0 Hz, 2H), 7.09 d, J=8.0 Hz, 2H), 3.20 (s, 2H), 2.73 (t, J=7.2 Hz, 2H), 1.58 (m, 4H). LRMS(ESI): (calc.) 351.1 (found) 350.3 (MH)⁻.

e) N-hydroxy-2-(4-(4-(imidazo[1,2-a]pyridin-6-yl) butyl)phenyl)acetamide (186)

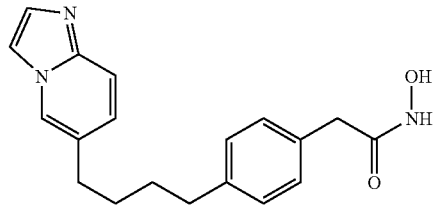 [SMILES: O=C(Cc1ccc(CCCCc2ccc3nccn3c2)cc1)NO]

(CD3OD) d(ppm) 1H, 8.19 (s, 1H), 7.73 (s, 1H), 7.49 (s, 1H), 7.43 (d, J=9.2 Hz, 1H), 7.15 (m, 5H), 3.34 (s, 2H), 2.63 (m, 4H), 1.66 (m, 4H). LRMS(ESI): (calc.) 323.1 (found) 324.3 (MH)+.

f) 2-(4-(4-(benzo[d][1,3]dioxol-5-yl)butyl)phenyl)-N-hydroxyacetamide (187)

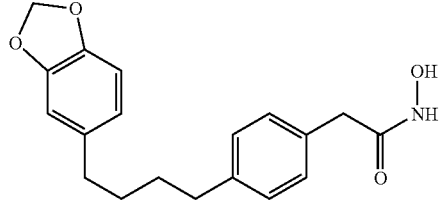 [SMILES: O=C(Cc1ccc(CCCCc2ccc3c(c2)OCO3)cc1)NO]

(dDMSO) d(ppm) 1H: 10.60 (s, 1H), 8.78 (s, 1H), 7.12 (d, J=8.0 Hz, 2H), 7.07 (d, J=8.0 Hz, 2H), 6.75 (m, 2H), 6.60 (d, J=8.0 Hz, 1H), 5.92 (s, 2H), 3.19 (s, 2H), 2.52 (m, 4H), 1.50 (m, 4H). LRMS(ESI): (calc.) 327.1 (found) 326.4 (MH)-.

g) 2-(4-(4-(benzo[d][1,3]dioxol-5-yl)but-3-ynyl) phenyl)-N-hydroxyacetamide (188)

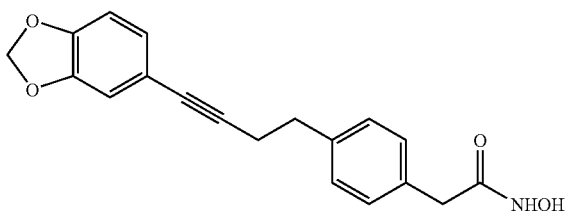

(dDMSO) d(ppm) 1H: 10.61 (s, 1H), 8.78 (s, 1H), 7.20 (d, J=8.4 Hz, 2H), 7.16 (d, J=8.4 Hz, 2H), 6.85 (m, 3H), 6.01 (s, 2H), 3.22 (s, 2H), 2.77 (t, J=7.6 Hz, 2H), 2.61 (t, J=6.8 Hz, 2H). LRMS(ESI): (calc.) 323.1 (found) 322.2 (MH)-.

i) N-hydroxy-2-(4-(2-phenoxyethoxy)phenyl)aceta-mide (190)

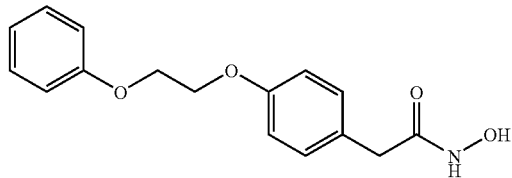 [SMILES: O=C(Cc1ccc(OCCOc2ccccc2)cc1)NO]

(DMSO) d(ppm) 1H, 10.58 (bs, 1H), 8.77 (bs, 1H), 7.28 (t, J=7.6 Hz<2H), 7.15 (d, J=8.8 Hz, 2H), 6.93 (m, 5H), 4.26 (s, 4H), 3.18 (s, 2H). LRMS(ESI): (calc.) 287.3 (found) 310.0 (MH)+.

j) N-hydroxy-2-(4-(3-phenoxypropyl)phenyl)acetamide (191)

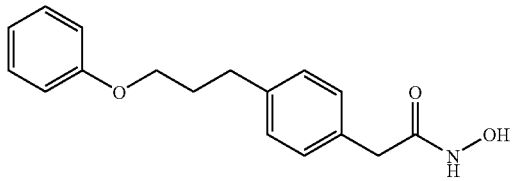 [SMILES: O=C(Cc1ccc(CCCOc2ccccc2)cc1)NO]

(CD3OD) d(ppm) 1H, 7.21 (m, 6H), 6.88 (m, 6H), 3.92 (t, J=8 Hz, 2H), 3.35 (s, 2H), 2.77 (t, J=7.2 Hz, 2H), 2.04 (m, 2H). LRMS(ESI): (calc.) 285.3 (found) 286.2 (MH)+.

k) 2-(4-butylphenyl)-N-hydroxyacetamide (192)

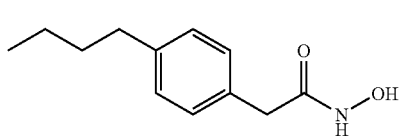

(CD3OD) d(ppm) 1H, 7.18 (d, J=8 Hz, 2H), 7.11 (d, J=8 Hz, 2H), 3.35 (s, 2H), 2.57 (T, J=7.6 Hz, 2H), 1.56 (m, 2H), 1.33 (m, 2H), 0.92 (t, J=7.2 Hz, 2H). LRMS(ESI): (calc.) 207.2 (found) 208.1 (ES+;Na+).

l) N-hydroxy-2-(4-(5-phenylpentyl)phenyl)acetamide (193)

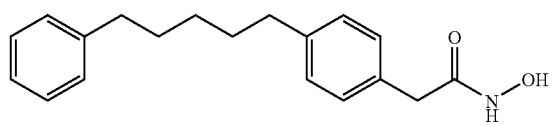 [SMILES: O=C(Cc1ccc(CCCCCc2ccccc2)cc1)NO]

(CD3OD) d(ppm) 1H, 7.22-7.08(m, 9H), 3.34 (s, 2H), 2.56 (m, 4H), 1.61 (m, 4H), 1.34 (m, 2H). LRMS(ESI): (calc.) 297.4 (found) 298.3 (MH)+.

m) N-hydroxy-2-(4-(4-hydroxy-4-(pyridin-4-yl)butyl)phenyl)acetamide (194)

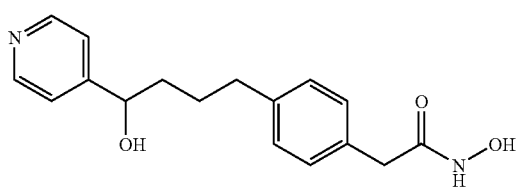 [SMILES: O=C(Cc1ccc(CCCC(O)c2ccncc2)cc1)NO]

(CD3OD) d(ppm) 1H, 8.44 (d, J=6.0 Hz, 2H), 7.36 (d, J=6.4 Hz, 2H), 7.18 (d, J=8.4 Hz, 2H), 7.09 (d, J=8.0 Hz, 2H), 4.65 (m, 1H), 3.34 s, 2H), 2.60 (m, 2H), 1.69 (m, 4H). LRMS (ESI): (calc.) 300.3 (found) 301.3 (MH)+.

n) N-hydroxy-2-(4-(4-hydroxy-4-(pyridin-3-yl)butyl)phenyl)acetamide (195)

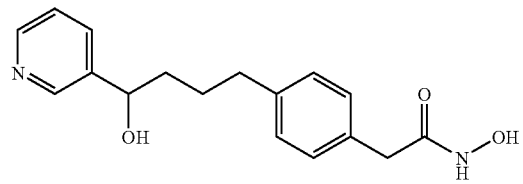 [SMILES: O=C(Cc1ccc(CCCC(O)c2cccnc2)cc1)NO]

(CD3OD) d(ppm) 1H, 8.46 (s, 1H), 8.41 (d, J=4.8 Hz, 1H), 7.78 (d, J=8.0 Hz, 1H), 7.39 (t, J=5.6 Hz, 1H), 7.18 (d, J=8.0 Hz, 2H), 7.09 (d, J=8.0 Hz, 2H), 4.69 (m, 1H), 3.34 (s, 2H), 2.61 ((t, J=6.4 Hz, 2H), 1.79-1.58 (m, 4H). LRMS(ESI): (calc.) 300.5 (found) 301.4 (MH)+.

o) N-hydroxy-2-(4-(4-hydroxy-4-(pyridin-2-yl)butyl)phenyl)acetamide (196)

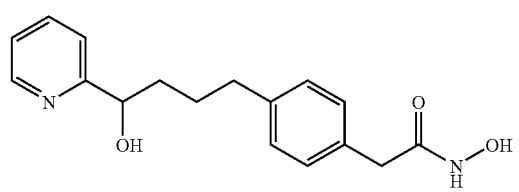 [SMILES: O=C(Cc1ccc(CCCC(O)c2ccccn2)cc1)NO]

(CD3OD) d(ppm) 1H, 8.42 (m, 1H), 7.81 (m, 1H), 7.51 (d, J=7.2 Hz, 1H), 7.26 (d, J=4.8 Hz, 1H), 7.16 (m, 1H), 7.08 (m, 2H), 4.69 (m, 1H), 3.34 (s, 2H), 2.59 (m, 2H), 1.76-1.69 (m, 4H). LRMS(ESI): (calc.) 300.3 (found) 301.4 (MH)+.

p) N-hydroxy-2-(4-(4-(pyridin-4-yl)butyl)phenyl)acetamide (197)

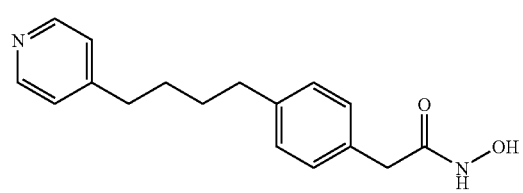 [SMILES: O=C(Cc1ccc(CCCCc2ccncc2)cc1)NO]

(CD3OD) d(ppm) 1H, 8.37 (d, J=6.0 Hz, 2H), 7.24 (d, J=5.6 Hz, 2H), 7.18 (d, J=8.0 Hz, 2H), 7.10 (d, J=8.0 Hz, 2H), 3.35 (s, 2H), 2.67(t, J=6.4 Hz, 2H), 2.62 (t, J=7.2 Hz, 2H), 1.65 (m, 4H). LRMS(ESI): (calc.) 284.1 (found) 285.3 (MH)+.

q) N-hydroxy-2-(4-(4-(pyridin-3-yl)butyl)phenyl)acetamide (198)

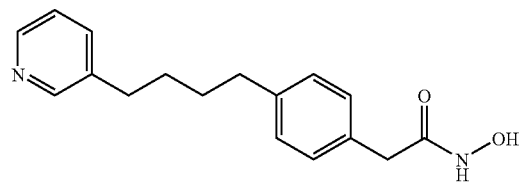 [SMILES: O=C(Cc1ccc(CCCCc2cccnc2)cc1)NO]

(CD3OD) d(ppm) 1H, 8.24 (m, 2H), 7.65 (d, J=8.0 Hz, 1H), 7.33 (m, 1H), 7.18 (d, J=7.6 Hz, 2H), 7.10 (d, J=7.6 Hz, 2H), 3.35 (s, 2H), 2.64 (m, 4H), 1.64 (m, 4H). LRMS(ESI): (calc.) 284.1 (found) 285.3 (MH)+.

r) N-hydroxy-2-(4-(4-(pyridin-2-yl)butyl)phenyl)acetamide (199)

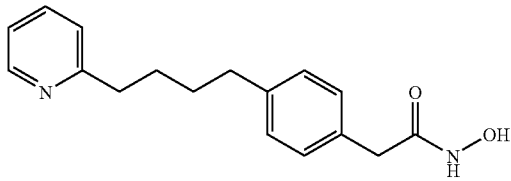 [SMILES: O=C(Cc1ccc(CCCCc2ccccn2)cc1)NO]

(CD3OD) d(ppm) 1H, 8.39 (d, J=6.0 Hz), 7.75 (t, J=8.0 Hz, 1H), 7.23 (m, 4H), 7.10 (d, J=8.0 Hz, 2H), 3.34 (s, 2H), 2.78 (t, J=7.6 Hz, 2H), 2.61 (t, J=7.6 Hz, 2H), 1.67 (m, 4H). LRMS(ESI): (calc.) 284.1 (found) 285.4 (MH)+.

s) N-hydroxy-2-(4-(3-phenylpropyl)phenyl)acetamide (200)

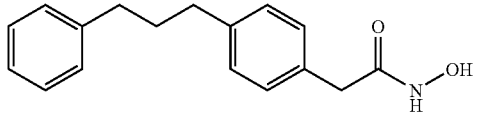 [SMILES: O=C(Cc1ccc(CCCc2ccccc2)cc1)NO]

(CD3OD) d (ppm): 7.24-7.11 (m, 9H), 3.35 (s, 2H), 2.60 (t, 4H, J=7.6 Hz), 1.89 (m, 2H). LRMS: 269.1 (calc) 270.1 (found).

t) N-hydroxy-4-(5-phenylpentyl)benzamide (201)

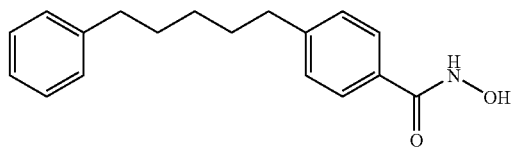 [SMILES: O=C(NO)c1ccc(CCCCCc2ccccc2)cc1]

(CD3OD) d(ppm) 1H, 7.64 (d, J=7.6 Hz, 2H), 7.22 (m, 4H), 7.12 (m, 3H), 2.63 (t, J=7.6 Hz, 2H), 2.57 (t, J=7.2 Hz, 2H), 1.63 (m, 4H), 1.35 (m, 2H). LRMS(ESI): (calc.) 283.4 (found) 284.3 (MH)+.

Example 45

N-(1-aminocyclopropanecarbonyloxy)-2-(4-(4-phenylbutyl)phenyl)acetamide hydrochloride (174a)

Step 1: tert-butyl-1-((2-(4-(4-phenylbutyl)phenyl)acetamidooxy)carbonyl)cyclopropylcarbamate

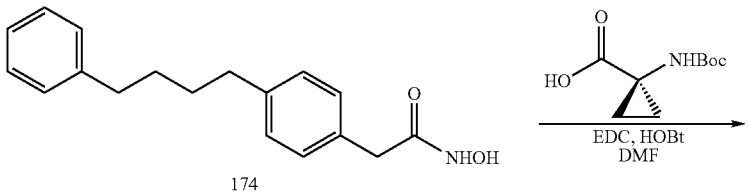

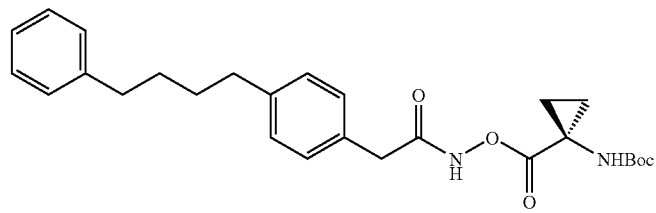

N-hydroxy-2-(4-(4-phenylbutyl)phenyl)acetamide 174 (1 equiv, 156 mg, 0.55 mmol) was dissolved in DMF (3 mL). 1-(tert-butoxycarbonylamino)cyclopropanecarboxylic acid (1.5 equiv, 166 mg, 0.83 mmol) was then added followed by the sequential addition of HOBt (1 equiv, 74 mg, 0.55 mmol) and EDC (1.5 equiv, 158 mg, 0.83 mmol). The reaction was then stirred overnight. The reaction was then partitioned between EtOAc (5 mL) and H$_2$O (5 mL). The organic phase was separated, dried over Na$_2$SO$_4$, filtered and concentrated. The residue was purified by trituration with Et$_2$O to afford tert-butyl-1-((2-(4-(4-phenylbutyl)phenyl)acetamidooxy)carbonyl)cyclopropylcarbamate in 166 mg (65%). LRMS: 466.5 (calc) 489.3 (MNa)$^+$.

Step 2: N-(1-aminocyclopropanecarbonyloxy)-2-(4-(4-phenylbutyl)phenyl)acetamide hydrochloride (174a)

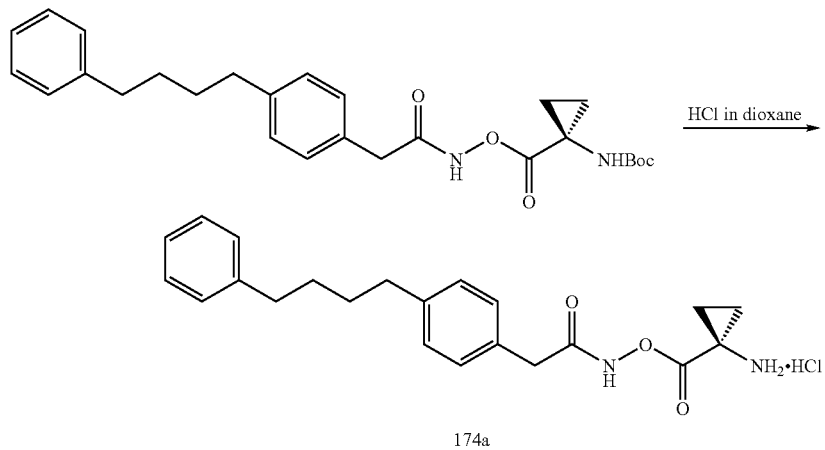

A 4M solution of HCl in dioxane (3 mL) was added to tert-butyl-1-((2-(4-(4-phenylbutyl)phenyl)acetamidooxy)carbonyl)cyclopropylcarbamate (166 mg, 0.36 mmol). The reaction was stirred for 1 h. The solvent was evaporated under reduced pressure. The compound was triturated with Et₂O to afford N-(1-aminocyclopropanecarbonyloxy)-2-(4-(4-phenylbutyl)phenyl)acetamide hydrochloride (174a) in 142 mg (99%). (dDMSO) δ(ppm) ¹H, 12.36 (bs, 1H), 8.82 (bs, 3H), 7.26-7.08 (m, 9H), 3.43 (s, 2H), 2.55 (m, 4H), 1.55-1.49 (m, 8H). LRMS: 366.1 (calc) 365.4 (MH)⁻.

Example 46

The following additional compounds were prepared by procedures analogous to those described in the Examples 40-43 and 45:

a) (S)—N-(2-amino-3-phenylpropanoyloxy)-2-(4-(4-phenylbutyl)phenyl)acetamide hydrochloride (174b)

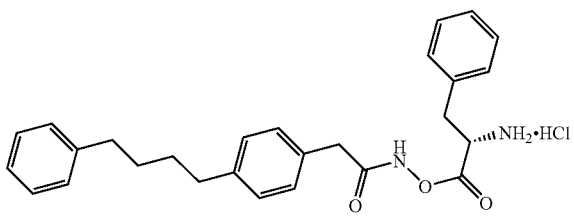

(DMSO) δ(ppm) 1H, 12.39 (bs, 1H), 8.47 (bs, 3H), 7.31-6.96 (m, 1H), 4.54 (m, 1H), 3.46 (s, 2H), 3.15 (m, 2H), 2.56 (q, J=6.8, 13.6 Hz, 4H), 1.54 (m, 4H). LRMS(ESI): (calc.) 430.2 (found) 431.4 (MH)⁺.

b) (S)—N-(2-amino-3-methylbutanoyloxy)-2-(4-(4-phenylbutyl)phenyl)acetamide hydrochloride (174c)

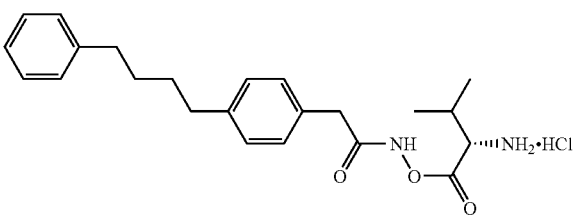

(DMSO) δ(ppm) 1H, 12.32 (bs, 1H), 8.33 (bs, 3H), 7.24-7.09 (m, 9H), 4.13 (m, 1H), 3.45 (s, 2H), 2.57 (m, 4H), 2.18 (m, 1H), 1.55 (m, 4H), 1.03-0.94 (m, 6H). LRMS(ESI): (calc.) 382.2 (found) 383.1 (MH)⁺.

c) (S)—N-(2-amino-3,3-dimethylbutanoyloxy)-2-(4-(4-phenylbutyl)phenyl)acetamide hydrochloride (174d)

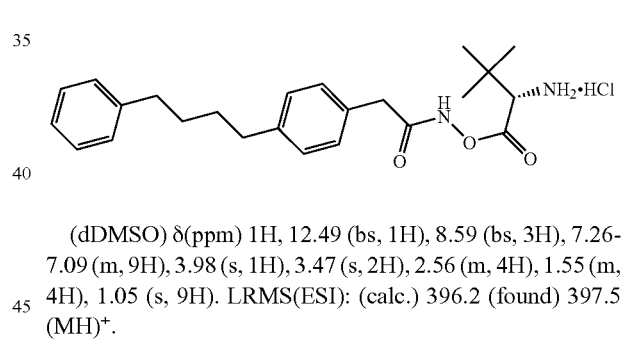

(dDMSO) δ(ppm) 1H, 12.49 (bs, 1H), 8.59 (bs, 3H), 7.26-7.09 (m, 9H), 3.98 (s, 1H), 3.47 (s, 2H), 2.56 (m, 4H), 1.55 (m, 4H), 1.05 (s, 9H). LRMS(ESI): (calc.) 396.2 (found) 397.5 (MH)⁺.

d) N-(1-aminocyclobutanecarbonyloxy)-2-(4-(4-phenylbutyl)phenyl)acetamide hydrochloride (174e)

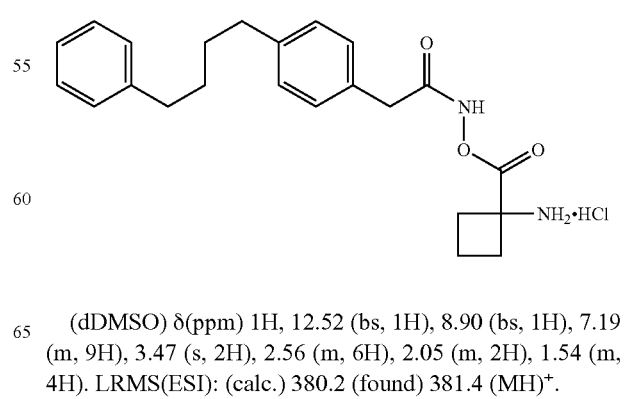

(dDMSO) δ(ppm) 1H, 12.52 (bs, 1H), 8.90 (bs, 1H), 7.19 (m, 9H), 3.47 (s, 2H), 2.56 (m, 6H), 2.05 (m, 2H), 1.54 (m, 4H). LRMS(ESI): (calc.) 380.2 (found) 381.4 (MH)⁺.

e) N-(2-amino-2-methylpropanoyloxy)-2-(4-(4-phenylbutyl)phenyl)acetamide hydrochloride (174f)

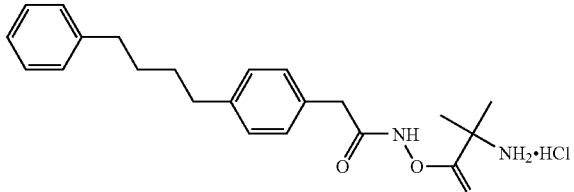

(dDMSO) δ(ppm) 1H, 12.45 (bs, 1H), 8.77 (bs, 3H), 7.16 (m, 9H), 3.45 (s, 2H), 2.56 (m, 4H), 1.54 (m, 10H). LRMS (ESI): (calc.) 368.2 (found) 369.4 (MH)+.

f) N-(1-(aminomethyl)cyclopropanecarbonyloxy)-2-(4-(4-phenylbutyl)phenyl)acetamide hydrochloride (174 g)

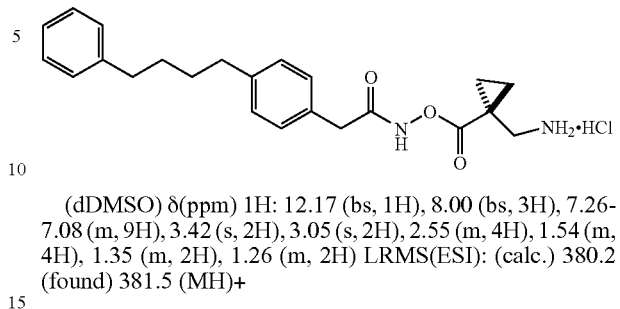

(dDMSO) δ(ppm) 1H: 12.17 (bs, 1H), 8.00 (bs, 3H), 7.26-7.08 (m, 9H), 3.42 (s, 2H), 3.05 (s, 2H), 2.55 (m, 4H), 1.54 (m, 4H), 1.35 (m, 2H), 1.26 (m, 2H) LRMS(ESI): (calc.) 380.2 (found) 381.5 (MH)+

Example 47

The following additional prodrugs according to the present invention were also prepared.

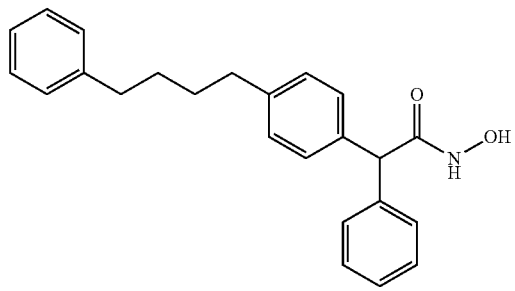

LRMS(ESI): (calc.) 359.2 (found) 360.4 (MH)+
(CD3OD) d(ppm) 1H: 7.30-7.11 (m, 14H), 4.73 (s, 1H), 2.60 (m, 4H), 1.61 (m, 4H)

1-methyl-3-(3-oxo-3-(2-(4-(4-phenylbutyl)phenyl)acetamidooxy)propyl)pyridinium

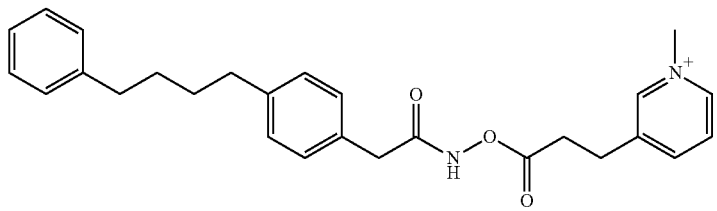

LRMS(ESI): (calc.) 431.5 (found) 431.5 (M)+
(CD3OD) d(ppm) 1H: 8.84 (s, 1H), 8.71 (d, J = 6.0 Hz, 1H), 8.49 (d, J = 8.0 Hz, 1H), 7.96 (t, J = 6.8 Hz, 1H), 7.24-7.10 (m, 9H), 4.30 (s, 3H), 3.47 (s, 2H), 3.22 (t, J = 7.2 Hz, 2H), 2.97 (t, J = 6.8 Hz, 2H), 2.61 (m, 4H), 1.62 (m, 4H)

2-(4-(4-(4-fluorophenyl)butyl)phenyl)-N-hydroxyacetamide

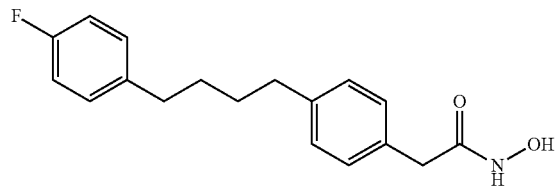

LRMS(ESI): (calc.) 301.1 (found) 302.3 (MH)+
(dDMSO) d(ppm) 1H: 7.19 (m, 2H), 7.11-6.98 (m, 6H), 3.02 (s, 2H), 2.54 (m, 4H), 1.53 (m, 4H)

1-methyl-4-(3-oxo-3-(2-(4-(4-phenylbutyl)phenyl)acetamidooxy)propyl)-4H-1,2,4-triazol-1-ium

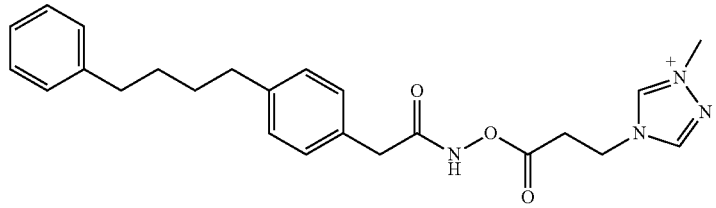

LRMS(ESI): (calc.) 421.2 (found) 421.5 (MH)+
(CD3OD) d(ppm) 1H: 12.13 (bs, 1H), 10.11 (s, 1H), 9.14 (s, 1H), 7.27-7.09 (m, 9H), 4.67 (t, J = 6.0 Hz, 2H), 3.86 (s, 3H), 3.39 (s, 2H), 3.17 (t, J = 6.0 Hz, 2H), 2.56 (m, 4H), 1.55 (m, 4H)

1-methyl-3-((2-(4-(4-phenylbutyl)phenyl)acetamidooxy)carbonyl)pyridinium

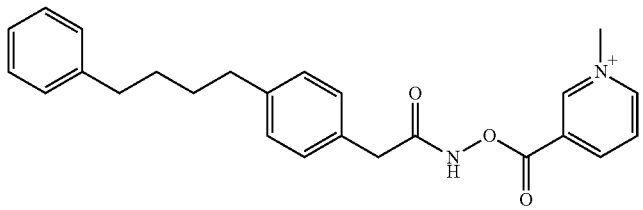

Example 48

Inhibition of Histone Deacetylase Enzymatic Activity

HDAC inhibitors are screened against histone deacetylase enzyme in nuclear extracts prepared from the human small cell lung cancer cell line H446 (ATTC HTB-171) and against a cloned recombinant human (e.g., HDAC-1) enzyme expressed and purified from a Baculovirus insect cell expression system.

For deacetylase assays, 20,000 cpm of the [$^3$H]-metabolically labeled acetylated histone substrate (M. Yoshida et al., *J. Biol. Chem.* 265(28): 17174-17179 (1990)) is incubated with 30 μg of H446 nuclear extract or an equivalent amount of the cloned recombinant hHDAC-1 for 10 minutes at 37° C. The reaction is stopped by adding acetic acid (0.04 M, final concentration) and HCl (250 mM, final concentration). The mixture is extracted with ethyl acetate and the released [$^3$H]-acetic acid was quantified by scintillation counting. For inhibition studies, the enzyme is preincubated with compounds at 4° C. for 30 minutes prior to initiation of the enzymatic assay. IC$_{50}$ values for HDAC enzyme inhibitors are determined by performing dose response curves with individual compounds and determining the concentration of inhibitor producing fifty percent of the maximal inhibition.

Alternatively (Table 4a), the following protocol is used to assay the compounds of the invention. In the assay, the buffer used is 25 mM HEPES, pH 8.0, 137 mM NaCl, 2.7 mM KCl, 1 mM MgCl$_2$ and the substrate is Boc-Lys(Ac)-AMC in a 50 mM stock solution in DMSO. The enzyme stock solution is 4.08 μg/mL in buffer. The compounds are pre-incubated (2 μl in DMSO diluted to 13 μl in buffer for transfer to assay plate) with enzyme (20 μl of 4.08 μg/ml) for 10 minutes at room temperature (35 μl pre-incubation volume). The mixture is pre-incubated for 5 minutes at room temperature. The reaction is started by bringing the temperature to 37° C. and adding 16 μl substrate. Total reaction volume is 50 μl. The reaction is stopped after 20 minutes by addition of 50 μl developer, prepared as directed by Biomol (Fluor-de-Lys developer, Cat. # KI-105). A plate is incubated in the dark for 10 minutes at room temperature before reading ($\lambda_{Ex}$=360 nm, $\lambda_{Em}$=470 nm, Cutoff filter at 435 nm).

Representative data are presented in Tables 4 and 4a. In the first column of Table 4 are reported IC$_{50}$ values determined against histone deacetylase in nuclear extracts from H446 cells (pooled HDACs). In the second column of Table 4 are reported IC$_{50}$ values determined against recombinant human HDAC-1 enzyme (rHDAC-1). For less active compounds, the data are expressed as the percent inhibition at the specified concentration.

TABLE 4

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 1 | 4 | 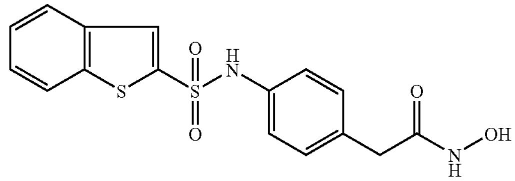 [SMILES: O=C(Cc1ccc(NS(=O)(=O)c2cc3ccccc3s2)cc1)NO] | 7 | |

TABLE 4-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 2 | 7 | 2-nitrobenzenesulfonamide of 4-(hydroxycarbamoylmethyl)aniline | 70 | |
| Ex. 3 | 8 | 2,5-dichlorobenzenesulfonamide of 4-(hydroxycarbamoylmethyl)aniline | 15 | |
| Ex. 4 | 9 | 4-methylbenzenesulfonamide of 4-(hydroxycarbamoylmethyl)aniline | 9 | |
| Ex. 5 | 10 | 3-(trifluoromethyl)benzenesulfonamide of 4-(hydroxycarbamoylmethyl)aniline | 30 | |
| Ex. 6 | 11 | 4-tert-butylbenzenesulfonamide of 4-(hydroxycarbamoylmethyl)aniline | 10 | |
| Ex. 7 | 12 | naphthalene-2-sulfonamide of 4-(hydroxycarbamoylmethyl)aniline | 3 | |
| Ex. 8 | 13 | benzo[b]thiophene-2-sulfonamide of 4-(hydroxycarbamoyl)aniline | 0.9 | |

TABLE 4-continued

Inhibition of Histone Deacetylase

| Example | Cpd. | Structure | pooled HDACs IC$_{50}$ (μM) | rHDAC-1 IC$_{50}$ (μM) |
|---------|------|-----------|------------------------------|-------------------------|
| Ex. 9 | 14 | 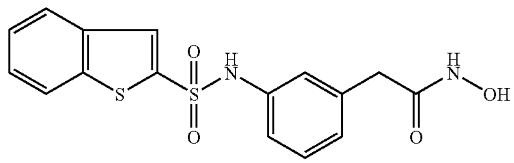 [SMILES: O=C(Cc1cccc(NS(=O)(=O)c2cc3ccccc3s2)c1)NO] | 36% @ 100 μM | |
| Ex. 10 | 15 | 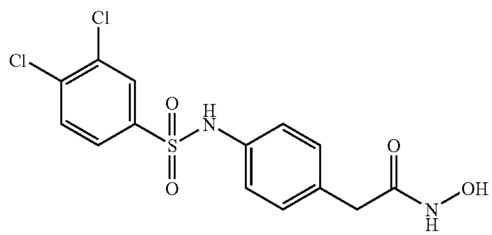 [SMILES: O=C(Cc1ccc(NS(=O)(=O)c2ccc(Cl)c(Cl)c2)cc1)NO] | 25 | |
| Ex. 11 | 16 | 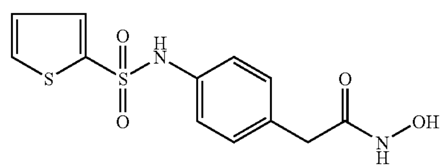 [SMILES: O=C(Cc1ccc(NS(=O)(=O)c2cccs2)cc1)NO] | 38% 100 μM | |
| Ex. 12 | 17 | 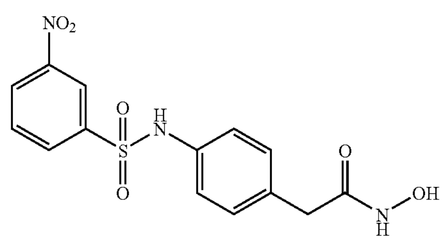 [SMILES: O=C(Cc1ccc(NS(=O)(=O)c2cccc([N+](=O)[O-])c2)cc1)NO] | 47% 100 μM | |
| Ex. 13 | 18 | 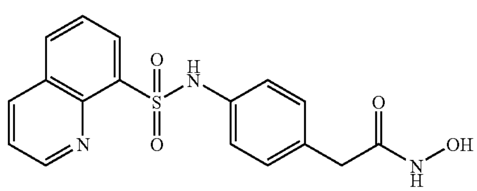 [SMILES: O=C(Cc1ccc(NS(=O)(=O)c2cccc3cccnc23)cc1)NO] | 160 | |
| Ex. 14 | 19 | 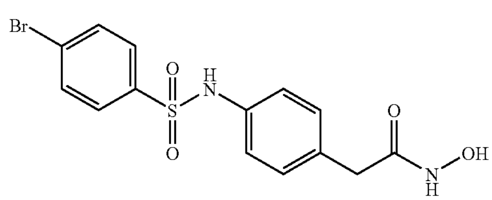 [SMILES: O=C(Cc1ccc(NS(=O)(=O)c2ccc(Br)cc2)cc1)NO] | 20 | |
| Ex. 15 | 26 | 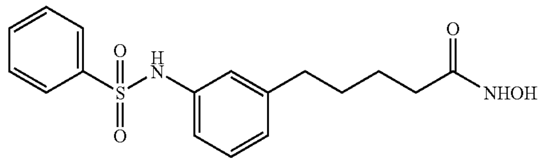 | <20 | |

TABLE 4-continued

Inhibition of Histone Deacetylase

| Example | Cpd. | Structure | pooled HDACs IC$_{50}$ (μM) | rHDAC-1 IC$_{50}$ (μM) |
|---------|------|-----------|------------------------------|------------------------|
| Ex. 16 | 32 | PhSO$_2$NH-C$_6$H$_4$-C≡C-CH=CH-C(O)NHOH | <20 | |
| Ex. 17 | 34 | PhSO$_2$NH-C$_6$H$_4$-(CH$_2$)$_4$-C(O)NHOH | 2 | 0.3 |
| Ex. 18 | 36 | PhSO$_2$NH-C$_6$H$_4$-CH=CH-C(O)NHOH | 0.5 | 0.2 |
| Ex. 19 | 38 | PhSO$_2$NH-C$_6$H$_4$-(CH$_2$)$_2$-C(O)NHOH | 0.75 | 0.1 |
| Ex. 20 | 42 | PhSO$_2$NH-C$_6$H$_4$-(CH$_2$)$_3$-C(O)NHOH | 5 | 1.0 |
| Ex. 21 | 45 | PhC(O)-CH=CH-C$_6$H$_4$-C(O)NHOH | 4 | |
| Ex. 22 | 50 | PhC(O)-CH$_2$CH$_2$-C$_6$H$_4$-C(O)NHOH | 5 | |

TABLE 4-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 23 | 53 | *1-phenyl-3-hydroxy-3-(4-(N-hydroxycarbamoyl)phenyl)propan-1-one* | 25 | |
| Ex. 24 | 56 | *N-hydroxy-4-(3-phenylpropyl)benzamide* | 15 | |
| Ex. 25 | 61 | *N-hydroxy-4-(4-phenylbutyl)benzamide* | 4 | |
| Ex. 26 | 64 | *N-hydroxy-3-(3-phenylpropyl)benzamide* | 12% @ 100 μM | |
| Ex. 27 | 68 | *N-hydroxy-3-(2-phenylethyl)benzamide* | 3% @ 20 μM | |
| Ex. 28 | 70 | *N-hydroxy-4-(2-(phenylthio)ethyl)benzamide* | 5.5 | 0.9 |
| Ex. 28 | 71 | *N-hydroxy-4-(2-(phenylsulfinyl)ethyl)benzamide* | 44% @ 20 μM | |
| Ex. 28 | 73 | *N-hydroxy-4-(2-(phenylsulfonyl)ethyl)benzamide* | 35% @ 20 μM | |

TABLE 4-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 29 | 77 | 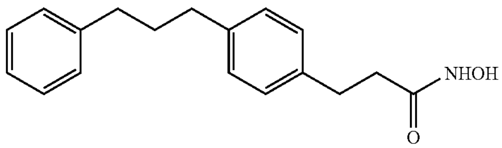 | ☐ | 0.65 |
| Ex. 30 | 81 | 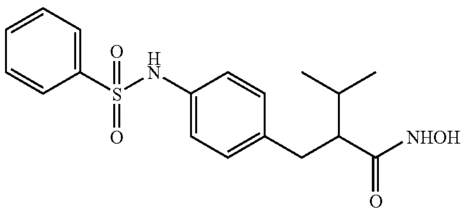 | >50 | >25 |
| Ex. 31 | 86 | | | 3.8 |
| Ex. 31 | 87 | | 3 | 0.6 |
| Ex. 31 | 88 | | 0.6 | 0.075 |
| Ex. 31 | 89 | | 3 | 0.9 |

TABLE 4-continued

Inhibition of Histone Deacetylase

| Example | Cpd. | Structure | pooled HDACs IC$_{50}$ (μM) | rHDAC-1 IC$_{50}$ (μM) |
| --- | --- | --- | --- | --- |
| Ex. 31 | 90 | *[3,4-dimethoxyphenylsulfonylamino-phenyl cinnamic hydroxamic acid]* | 0.4 | 0.09 |
| Ex. 31 | 91 | *[phenylsulfonylamino-phenyl α-methyl cinnamic hydroxamic acid]* | 5 | 2 |
| Ex. 31 | 92 | *[phenylsulfonylamino-phenyl methyl propanoic hydroxamic acid]* | >20 | 17 |
| Ex. 31 | 93 | *[naphthalene-1-sulfonylamino-phenyl cinnamic hydroxamic acid]* | 0.35 | 0.05 |
| Ex. 31 | 94 | *[naphthalene-2-sulfonylamino-phenyl cinnamic hydroxamic acid]* | 0.4 | 0.03 |
| Ex. 31 | 95 | *[benzothiophene-2-sulfonylamino-phenyl cinnamic hydroxamic acid]* | 0.8 | 0.2 |

TABLE 4-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 31 | 96 | (pyridine-2-sulfonyl)-NH-C$_6$H$_4$-CH=CH-C(O)NHOH | 33% @ 5 μM | |
| Ex. 31 | 97 | (5-(dimethylamino)naphthalen-1-sulfonyl)-NH-C$_6$H$_4$-CH=CH-C(O)NHOH | 0.8 | 0.28 |
| Ex. 31 | 98 | (3,4-dimethoxyphenyl)-NH-SO$_2$-C$_6$H$_4$-CH=CH-C(O)NHOH | 0.55 | 0.06 |
| Ex. 31 | 99 | (quinolin-8-sulfonyl)-NH-C$_6$H$_4$-CH=CH-C(O)NHOH | 0.9 | 0.05 |
| Ex. 31 | 100 | (benzylsulfonyl)-NH-C$_6$H$_4$-CH=CH-C(O)NHOH | 0.8 | 0.75 |
| Ex. 31 | 101 | (dibenzofuran-2-sulfonyl)-NH-C$_6$H$_4$-CH=CH-C(O)NHOH | 0.3 | 0.04 |

TABLE 4-continued

Inhibition of Histone Deacetylase

| Example | Cpd. | Structure | pooled HDACs IC$_{50}$ (μM) | rHDAC-1 IC$_{50}$ (μM) |
| --- | --- | --- | --- | --- |
| Ex. 31 | 102 | (4-sulfamoylphenyl)sulfonyl-NH-C6H4-CH=CH-C(O)NHOH | 5.5 | 0.8 |
| Ex. 31 | 103 | 5-(thiophen-2-yl)thiophene-2-sulfonyl-NH-C6H4-CH=CH-C(O)NHOH | 0.7 | 0.05 |
| Ex. 31 | 104 | pyridin-3-ylsulfonyl-NH-C6H4-CH=CH-C(O)NHOH | 21% @ 5 μM | |
| Ex. 31 | 105 | 4-tert-butylphenylsulfonyl-NH-C6H4-CH=CH-C(O)NHOH | 0.55 | 0.2 |
| Ex. 31 | 106 | 2,4-dichlorophenylsulfonyl-NH-C6H4-CH=CH-C(O)NHOH | 0.8 | 0.3 |
| Ex. 31 | 107 | naphthalen-1-ylsulfonyl-NH-C6H4-CH=CH-C(O)NH-C6H4-2-NH2 | 0% @ 1 μM | 5 |

TABLE 4-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 31 | 108 | | 10% @ 1 µM | 0.3 |
| Ex. 31 | 109 | | 32% @ 1 µM | 0.12 |
| Ex. 31 | 110 | | 0.7 | 0.55 |
| Ex. 31 | 111 | | 0.4 | 0.095 |
| Ex. 31 | 112 | | 1.2 | 0.6 |
| Ex. 31 | 113 | | 46% @ 1 µM | 0.2 |

TABLE 4-continued

Inhibition of Histone Deacetylase

| Example | Cpd. | Structure | pooled HDACs IC$_{50}$ (μM) | rHDAC-1 IC$_{50}$ (μM) |
| --- | --- | --- | --- | --- |
| Ex. 31 | 114 | 3-CF$_3$-C$_6$H$_4$-SO$_2$-NH-C$_6$H$_4$-CH=CH-C(O)-NHOH | 40% @ 1 μM | 0.1 |
| Ex. 31 | 115 | 3-CH$_3$-C$_6$H$_4$-SO$_2$-NH-C$_6$H$_4$-CH=CH-C(O)-NHOH | 53% @ 1 μM | 0.1 |
| Ex. 31 | 116 | 3,4-(MeO)$_2$-C$_6$H$_3$-SO$_2$-NH-C$_6$H$_4$-CH=CH-C(O)-NH-C$_6$H$_4$-2-NH$_2$ | | 4 |
| Ex. 31 | 117 | 4-tBu-C$_6$H$_4$-SO$_2$-NH-C$_6$H$_4$-CH=CH-C(O)-NH-C$_6$H$_4$-2-NH$_2$ | 0% @ 20 μM | 1.9 |
| Ex. 31 | 118 | 3,4-(MeO)$_2$-C$_6$H$_3$-NH-SO$_2$-C$_6$H$_4$-CH=CH-C(O)-NH-C$_6$H$_4$-2-NH$_2$ | 0% @ 20 μM | 2.3 |
| Ex. 31 | 119 | 4-CH$_3$-C$_6$H$_4$-SO$_2$-NH-C$_6$H$_4$-CH=CH-C(O)-NH-C$_6$H$_4$-2-NH$_2$ | | 3 |

TABLE 4-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 31 | 120 | (biphenyl-SO$_2$-NH-C$_6$H$_4$-CH=CH-C(O)NHOH) | 0.12 | 0.01 |
| Ex. 31 | 121 | (3,4-dimethoxyphenyl-SO$_2$-NH-C$_6$H$_4$-CH$_2$CH$_2$-C(O)NH-C$_6$H$_4$-NH$_2$) | | 23 |
| Ex. 31 | 122 | (4-MeO-C$_6$H$_4$-SO$_2$-NH-C$_6$H$_4$-CH=CH-C(O)NH-C$_6$H$_4$-NH$_2$) | | 2.3 |
| Ex. 31 | 123 | (biphenyl-SO$_2$-NH-C$_6$H$_4$-CH=CH-C(O)NH-C$_6$H$_4$-NH$_2$) | | 1 |
| Ex. 32 | 128 | (biphenyl-SO$_2$-NH-C$_6$H$_4$-C≡C-C(O)NHOH) | | 0.3 |

TABLE 4-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 32 | 129 | 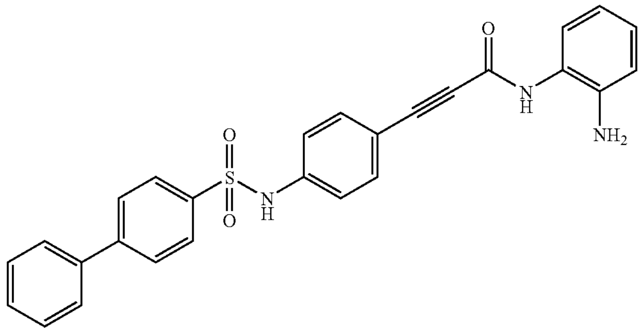 [SMILES: Nc1ccccc1NC(=O)C#Cc1ccc(NS(=O)(=O)c2ccc(-c3ccccc3)cc2)cc1] | | 3.0 |
| Ex. 33 | 136 | 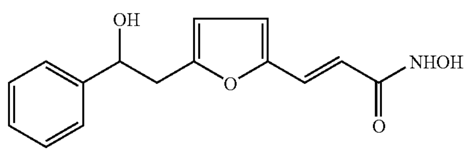 | 9 | 0.5 |
| Ex. 34 | 139 | | 44% @ 20 μM | |
| Ex. 34 | 143 | | 55% @ 20 μM | 2.4 |
| Ex. 34 | 144 | | 6% @ 20 μM | 6.9 |
| Ex. 35 | 145 | | 3.8 | 0.84 |
| Ex. 35 | 146 | | 2.9 | 0.91 |

TABLE 4-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 35 | 147 | 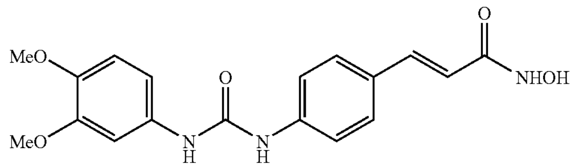 | 1.9 | 0.48 |
| Ex. 36 | 148 | | 5 | 2.0 |
| Ex. 36 | 149 | | 8% @ 20 µM | 0.1 |
| Ex. 36 | 150 | | 10 | 1.0 |
| Ex. 36 | 151 | | 7.5 | 2.3 |
| Ex. 36 | 152 | | 35% @ 20 µM | |
| Ex. 36 | 153 | | 5 | 4.8 |

TABLE 4-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 36 | 154 | | ⊔ | 0.9 |
| Ex. 36 | 155 | | 39% @ 20 μM | |
| Ex. 36 | 156 | | 5 | 0.75 |
| Ex. 36 | 157 | | 6 | 2.4 |
| Ex. 36 | 158 | | >20 | |
| Ex. 36 | 159 | | | 1.5 |
| Ex. 36 | 160 | | | 1.2 |

TABLE 4-continued

| | | Inhibition of Histone Deacetylase | | |
|---|---|---|---|---|
| Example | Cpd. | Structure | pooled HDACs IC$_{50}$ (µM) | rHDAC-1 IC$_{50}$ (µM) |
| Ex. 36 | 161 | | | 0.05 |
| Ex. 36 | 162 | | | 0.04 |
| Ex. 37 | 164 | | | 5.0 |
| Ex. 37 | 165 | | | 2.0 |
| Ex. 37 | 166 | | | |

US 8,796,330 B2
167                                                                                              168
TABLE 4-continued
Inhibition of Histone Deacetylase
| Example | Cpd. | Structure | pooled HDACs IC$_{50}$ (μM) | rHDAC-1 IC$_{50}$ (μM) |
|---------|------|-----------|------------------------------|------------------------|
| Ex. 37  | 167  | 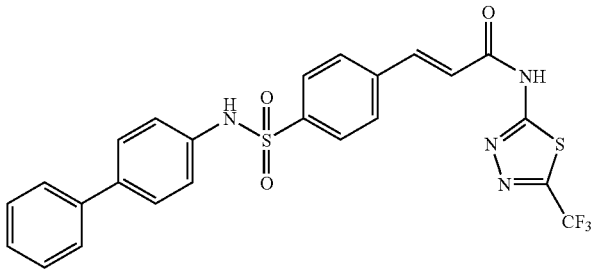 [SMILES: O=C(/C=C/c1ccc(S(=O)(=O)Nc2ccc(-c3ccccc3)cc2)cc1)Nc1nnc(C(F)(F)F)s1] |  |  |
| Ex. 38  | 168  | 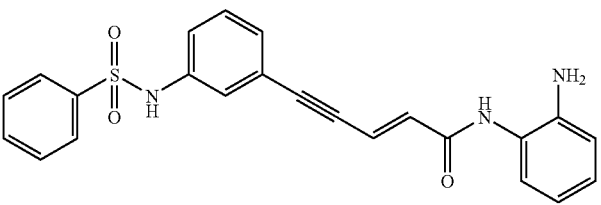 [SMILES: Nc1ccccc1NC(=O)/C=C/C#Cc1cccc(NS(=O)(=O)c2ccccc2)c1] | 0% @ 20 μM | 3 |
| Ex. 39  | 170  | 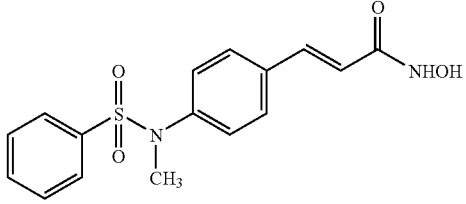 | 48% @ 2 μM | 0.57 |
|         | 171  | 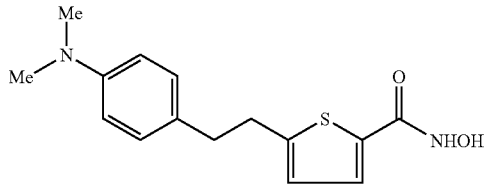 | 20 |  |
|         | 172  | 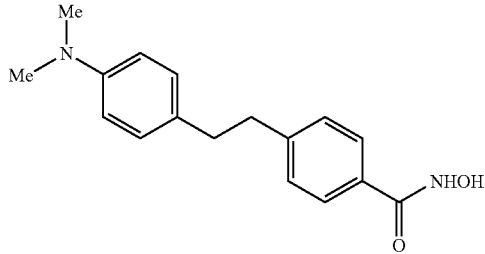 | 10 |  |
|         | 173  | 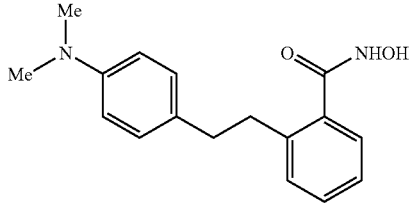 | 35% @ 20 μM |  |

TABLE 4-continued
Inhibition of Histone Deacetylase
| Example | Cpd. | Structure | pooled HDACs IC$_{50}$ (μM) | rHDAC-1 IC$_{50}$ (μM) |
|---|---|---|---|---|
| | 174 | 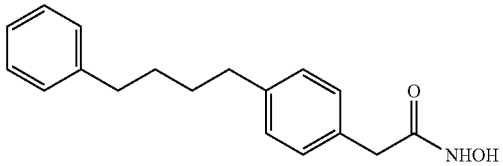 | >20 | |
| | 175 | 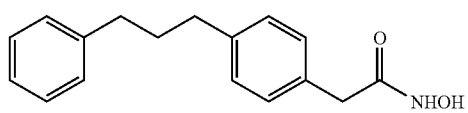 | >2 | |
| | 176 | 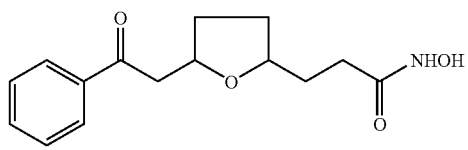 | 20% @ 20 μM | |
| | 177 | 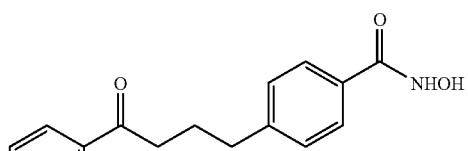 | 10% @ 20 μM | |
| | 178 | 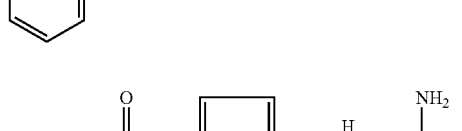 | 2% @ 20 μM | >20 |
TABLE 4a
| Cpd. | Structure | rHDAC-1 IC$_{50}$ (μM) | rHDAC-8 IC$_{50}$ (μM) |
|---|---|---|---|
| 182 | 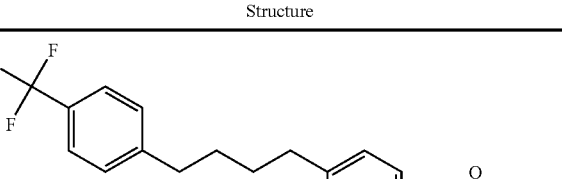 | 0.7 PI (64%) | 1.3 PI (74%) |
| 179 | 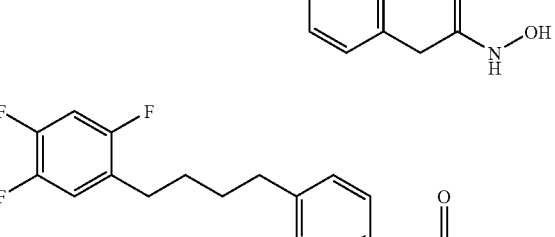 | 0.5 | 0.53 |

TABLE 4a-continued

| Cpd. | Structure | rHDAC-1 IC$_{50}$ (µM) | rHDAC-8 IC$_{50}$ (µM) |
|---|---|---|---|
| 183 | 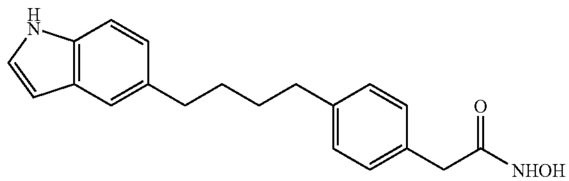 | 0.38 | 0.41 |
| 184 | 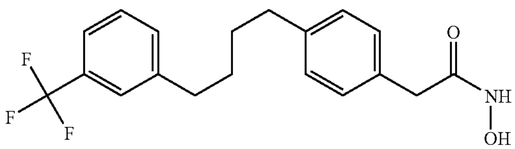 [SMILES: O=C(Cc1ccc(CCCCc2cccc(C(F)(F)F)c2)cc1)NO] | 0.93 | 0.4 PI (79%) |
| 185 | 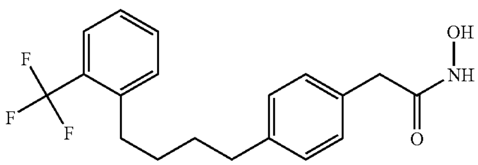 [SMILES: O=C(Cc1ccc(CCCCc2ccccc2C(F)(F)F)cc1)NO] | 0.84 | 0.61 |
| 187 | 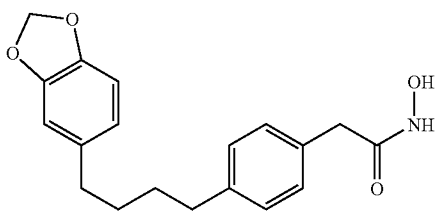 [SMILES: O=C(Cc1ccc(CCCCc2ccc3c(c2)OCO3)cc1)NO] | 0.2 PI (62%) | 0.21 |

PI = partial inhibition (100% inhibition not reached-PI value indicates IC$_{50}$ (at maximum % inhibition reached))

Example 49

Inhibition of Histone Deacetylase in Whole Cells

1. Histone H4 Acetylation in Whole Cells by Immunoblots

T24 human bladder cancer cells growing in culture are incubated with HDAC inhibitors for 16 hours. Histones are extracted from the cells after the culture period as described by M. Yoshida et al. (*J. Biol. Chem.* 265(28): 17174-17179 (1990)). 20 µµg of total histone protein are loaded onto SDS/PAGE and transferred to nitrocellulose membranes. Membranes are probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection is performed using Kodak films (Eastman Kodak). Acetylated H-4 signal is quantified by densitometry.

Data for selected compounds are presented in Table 5. Data are presented as the concentration effective for reducing the acetylated H-4 signal by 50% (EC$_{50}$).

TABLE 5

Inhibibition of Histone Acetylation in Cells

| Cpd. | Structure | EC$_{50}$ (µM) |
|---|---|---|
| 36 | 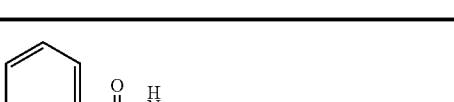 | 5 |

TABLE 5-continued

Inhibition of Histone Acetylation in Cells

| Cpd. | Structure | EC$_{50}$ (μM) |
|---|---|---|
| 90 | 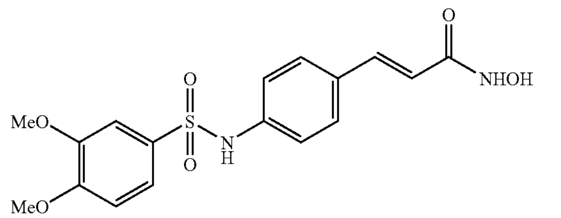 | 1 |
| 98 | 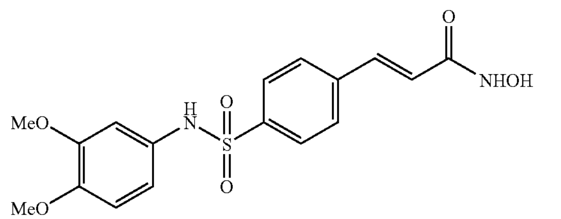 | 1 |
| 107 | 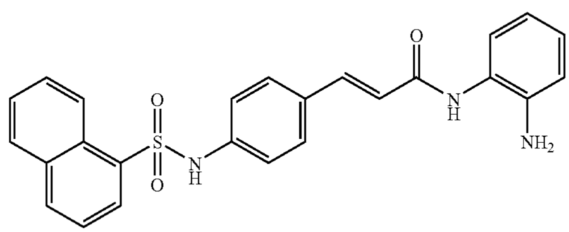 [SMILES: Nc1ccccc1NC(=O)/C=C/c1ccc(NS(=O)(=O)c2cccc3ccccc23)cc1] | 5 |
| 118 | 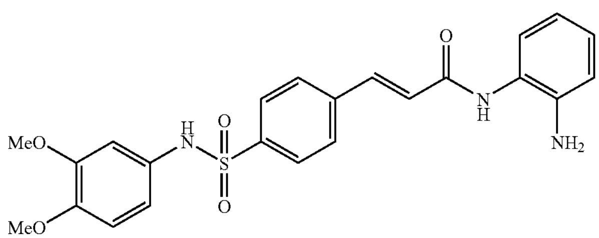 [SMILES: COc1ccc(NS(=O)(=O)c2ccc(/C=C/C(=O)Nc3ccccc3N)cc2)cc1OC] | 3 |
| 120 | 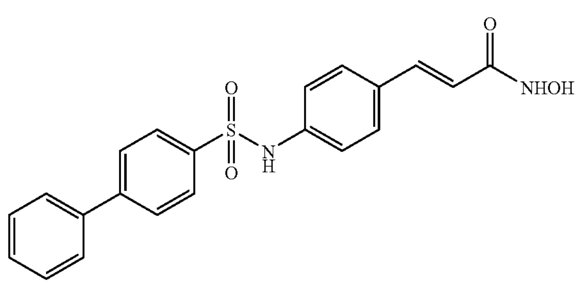 | 1 |
| 122 | 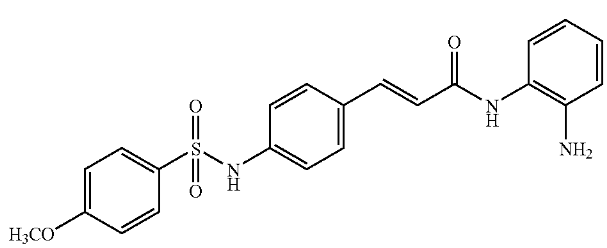 [SMILES: COc1ccc(S(=O)(=O)Nc2ccc(/C=C/C(=O)Nc3ccccc3N)cc2)cc1] | 2 |

2. Acid Urea Triton (AUT) Gel Analysis of Histone Acetylation.

Human cancer cells (T24, 293T or Jurkat cells) growing in culture are incubated with HDAC inhibitors for 24 h. Histones are extracted from the cells as described by M. Yoshida et al. (*J. Biol. Chem.* 265(28): 17174-17179 (1990)). Acid urea triton (AUT) gel electrophoresis is used for detection of acetylated histone molecules. Histones (150 μμg of total protein) are electrophoresed at 80 V for 16 h at room temperature as described by M. Yoshida et al., supra. Gels are stained with Coomassie brilliant blue to visualize histones, dried and scanned by densitometry to quantified acetylation of histones.

Example 50

Antineoplastic Effect of Histone Deacetylase Inhibitors on Tumor Cells In Vivo

Eight to ten week old female BALB/c nude mice (Taconic Labs, Great Barrington, N.Y.) are injected subcutaneously in the flank area with $2 \times 10^6$ preconditioned A549 human lung carcinoma cells. Preconditioning of these cells is done by a minimum of three consecutive tumor transplantations in the same strain of nude mice. Subsequently, tumor fragments of approximately 30 mgs are excised and implanted subcutaneously in mice, in the left flank area, under Forene anesthesia (Abbott Labs, Geneve, Switzerland). When the tumors reach a mean volume of 100 mm³, the mice are treated intravenously, subcutaneously, or intraperitoneally by daily injection, with a solution of the histone deacetylase inhibitor in an appropriate vehicle, such as PBS, DMSO/water, or Tween 80/water, at a starting dose of 10 mg/kg. The optimal dose of the HDAC inhibitor is established by dose response experiments according to standard protocols. Tumor volume is calculated every second day post infusion according to standard methods (e.g., Meyer et al., *Int. J. Cancer* 43: 851-856 (1989)). Treatment with the HDAC inhibitors according to the invention causes a significant reduction in tumor weight and volume relative to controls treated with saline only (i.e., no HDAC inhibitor). In addition, the activity of histone deacetylase when measured is expected to be significantly reduced relative to saline treated controls.

Example 51

Synergistic Antineoplastic Effect of Histone Deacetylase Inhibitors and Histone Deacetylase Antisense Oligonucleotides on Tumor Cells In Vivo The purpose of this example is to illustrate the ability of the histone deacetylase inhibitor of the invention and a histone deacetylase antisense oligonucleotide to synergistically inhibit tumor growth in a mammal. Preferably, the antisense oligonucleotide and the HDAC inhibitor inhibit the expression and activity of the same histone deacetylase.

As described in Example 10, mice bearing implanted A549 tumors (mean volume 100 mm³) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitor according to the invention causes a significant reduction in tumor weight and volume relative to controls.

Example 52

Solubility

The solubility of several compounds according to the invention was measured, and the results are displayed in the table below.

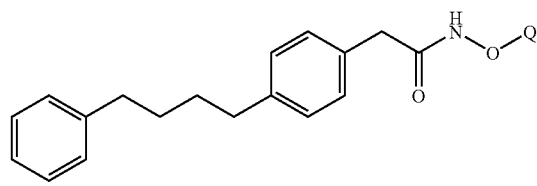

| Q | Solubility (μM) pH 2 | Water* |
|---|---|---|
| H | 3 | 3 |
| ![structure with NH3+ and tBu] | 4 | 5 |
| ![cyclopropyl CH2NH3+] | 132 | 195 |
| ![OH] | 10 | 9 |
| ![lysine-like with NH3+] | >250 | >250 |
| ![valine cyclopropyl NH3+] | 142 | 136 |

What is claimed is:

1. A compound selected from the group consisting of
N-(1-aminocyclopropanecarbonyloxy)-2-(4-(4-phenylbutyl)phenyl)acetamide hydrochloride;
(S)-N-(2-amino-3-phenylpropanoyloxy)-2-(4-(4-phenylbutyl)phenyl)acetamide hydrochloride;
(S)-N-(2-amino-3-methylbutanoyloxy)-2-(4-(4-phenylbutyl)phenyl)acetamide hydrochloride;
(S)-N-(2-amino-3,3-dimethylbutanoyloxy)-2-(4-(4-phenylbutyl)phenyl)acetamide hydrochloride;
N-(1-aminocyclobutanecarbonyloxy)-2-(4-(4-phenylbutyl)phenyl)acetamide hydrochloride;
N-(2-amino-2-methylpropanoyloxy)-2-(4-(4-phenylbutyl)phenyl)acetamide hydrochloride;
N-(1-(aminomethyl)cyclopropanecarbonyloxy)-2-(4-(4-phenylbutyl)phenyl)acetamide hydrochloride;
(S)-N-(2,6-diaminohexanoyloxy)-2-(4-(4-phenylbutyl)phenyl)acetamide;
N-(2-hydroxyacetoxy)-2-(4-(4-phenylbutyl)phenyl)acetamide;
(S)-N-(2-amino-5-guanidinopentanoyloxy)-2-(4-(4-phenylbutyl)phenyl)acetamide;
(S)-2,6-diamino-N-(1-((2-(4-(4-phenylbutyl)phenyl)acetamidooxy)carbonyl)cyclopropyl)hexanamide;
N-(1-((2-(4-(4-phenylbutyl)phenyl)acetamidooxy)carbonyl)cyclopropyl)nicotinamide;
(S)-2-amino-3-methyl-N-(1-((2-(4-(4-phenylbutyl)phenyl)acetamidooxy)carbonyl)cyclopropyl)butanamide;
(S)-2-amino-3-phenyl-N-(1-((2-(4-(4-phenylbutyl)phenyl)acetamidooxy)carbonyl)cyclopropyl)propanamide;
2-(4-(4-phenylbutyl)phenyl)-N-((2S,3R,4S,5S,6R)-3,4,5-trihydroxy-6-(hydroxymethyl)tetrahydro-2H-pyran-2-yloxy)acetamide; and
N-(2,3-dihydroxypropanoyloxy)-2-(4-(4-phenylbutyl)phenyl)acetamide.

2. A pharmaceutically acceptable salt of a species selected from the group consisting of
1-methyl-3-(3-oxo-3-(2-(4-(4-phenylbutyl)phenyl)acetamidooxy)propyl)pyridinium, 1-methyl-4-(3-oxo-3-(2-(4-(4-phenylbutyl)phenyl)acetamidooxy)propyl)-4H-1,2,4-triazol-1-ium, and
1-methyl-3-((2-(4-(4-phenylbutyl)phenyl)acetamidooxy)carbonyl)pyridinium.

3. A composition comprising a pharmaceutically acceptable salt of claim 1.

* * * * *

UNITED STATES PATENT AND TRADEMARK OFFICE
CERTIFICATE OF CORRECTION

| | | |
|---|---|---|
| PATENT NO. | : 8,796,330 B2 | Page 1 of 1 |
| APPLICATION NO. | : 11/959204 | |
| DATED | : August 5, 2014 | |
| INVENTOR(S) | : Deziel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 883 days.

Signed and Sealed this
Twentieth Day of October, 2015

Michelle K. Lee
*Director of the United States Patent and Trademark Office*

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 1
gagacagcag caccagcggg                                              20

<210> SEQ ID NO 2
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 2
atgaccgagt gggagacagc                                              20

<210> SEQ ID NO 3
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1
```

```
<400> SEQUENCE: 3
ggatgaccga gtgggagaca                                                    20

<210> SEQ ID NO 4
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 4
caggatgacc gagtgggaga                                                    20

<210> SEQ ID NO 5
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 5
tgtgttctca ggatgaccga                                                    20

<210> SEQ ID NO 6
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 6
gagtgacaga gacgctcagg                                                    20

<210> SEQ ID NO 7
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 7
ttctggcttc tcctccttgg                                                    20

<210> SEQ ID NO 8
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 8
cttgacctcc tccttgaccc                                                    20

<210> SEQ ID NO 9
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1
```

-continued

```
<400> SEQUENCE: 9
ggaagccaga gctggagagg                                              20

<210> SEQ ID NO 10
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 10
gaaacgtgag ggactcagca                                              20

<210> SEQ ID NO 11
<211> LENGTH: 23
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 11
ccgtcgtagt agtaacagac ttt                                          23

<210> SEQ ID NO 12
<211> LENGTH: 22
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 12
tgtccataat agtaatttcc aa                                           22

<210> SEQ ID NO 13
<211> LENGTH: 26
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 13 cagcaaaatta tgagtcatgc ggattc                                      26

<210> SEQ ID NO 14
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 14
ctccttgact gtacgccatg                                              20

<210> SEQ ID NO 15
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-2
```

```
<400> SEQUENCE: 15
tgctgctgct gctgctgccg                                               20

<210> SEQ ID NO 16
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 16
cctcctgctg ctgctgctgc                                               20

<210> SEQ ID NO 17
<211> LENGTH: 23
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 17
ccgtcgtagt agtagcagac ttt                                           23

<210> SEQ ID NO 18
<211> LENGTH: 22
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 18
tgtccataat aataatttcc aa                                            22

<210> SEQ ID NO 19
<211> LENGTH: 26
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 19
cagcaagtta tgggtcatgc ggattc                                        26

<210> SEQ ID NO 20
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 20
ggttcctttg gtatctgttt                                               20

<210> SEQ ID NO 21
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-4
```

```
<400> SEQUENCE: 21
gctgcctgcc gtgcccaccc                                                         20
```